(12) United States Patent
Kester

(10) Patent No.: US 10,375,327 B2
(45) Date of Patent: Aug. 6, 2019

(54) MOBILE GAS AND CHEMICAL IMAGING CAMERA

(71) Applicant: REBELLION PHOTONICS, INC., Houston, TX (US)

(72) Inventor: Robert Timothy Kester, Friendswood, TX (US)

(73) Assignee: Rebellion Photonics, Inc., Houston, TX (US)

( * ) Notice: Subject to any disclaimer, the term of this patent is extended or adjusted under 35 U.S.C. 154(b) by 0 days.

(21) Appl. No.: 15/789,811

(22) Filed: Oct. 20, 2017

(65) Prior Publication Data

US 2018/0191967 A1 Jul. 5, 2018

Related U.S. Application Data

(60) Provisional application No. 62/411,480, filed on Oct. 21, 2016.

(51) Int. Cl.
*H04N 5/33* (2006.01)
*G01J 3/02* (2006.01)
(Continued)

(52) U.S. Cl.
CPC .............. *H04N 5/33* (2013.01); *G01J 3/02* (2013.01); *G01J 3/0232* (2013.01);
(Continued)

(58) Field of Classification Search
CPC .......... G01J 3/02; G01J 3/0232; G01J 3/0256; G01J 3/28; G01J 3/2803; G01J 5/0014;
(Continued)

(56) References Cited

U.S. PATENT DOCUMENTS 3,841,763 A 10/1974 Lewis
3,849,005 A 11/1974 Girard et al.
(Continued)

FOREIGN PATENT DOCUMENTS

CA 2 365 866 9/2000
CA 2 787 303 7/2011
(Continued)

OTHER PUBLICATIONS

US 10,113,914 B2, 10/2018, Kester et al. (withdrawn)
(Continued)

*Primary Examiner* — Marcus H Taningco
(74) *Attorney, Agent, or Firm* — Knobbe, Martens, Olson & Bear LLP

(57) ABSTRACT

In one embodiment, an infrared (IR) imaging system for determining a concentration of a target species in an object is disclosed. The imaging system can include an optical system including an optical focal plane array (FPA) unit. The optical system can have components defining at least two optical channels thereof, said at least two optical channels being spatially and spectrally different from one another. Each of the at least two optical channels can be positioned to transfer IR radiation incident on the optical system towards the optical FPA. The system can include a processing unit containing a processor that can be configured to acquire multispectral optical data representing said target species from the IR radiation received at the optical FPA. Said optical system and said processing unit can be contained together in a data acquisition and processing module configured to be worn or carried by a person.

6 Claims, 57 Drawing Sheets

(51) Int. Cl.
  *G01J 3/28* (2006.01)
  *G01J 5/00* (2006.01)
  *H04N 5/225* (2006.01)
  *G01N 21/3504* (2014.01)
  *G02B 5/20* (2006.01)
  *G06K 9/00* (2006.01)
  *G06K 9/20* (2006.01)
  *G01J 5/08* (2006.01)
  *G01J 5/02* (2006.01)

(52) U.S. Cl.
  CPC .............. *G01J 3/0256* (2013.01); *G01J 3/28* (2013.01); *G01J 3/2803* (2013.01); *G01J 5/0014* (2013.01); *G01J 5/02* (2013.01); *G01J 5/0834* (2013.01); *G01N 21/3504* (2013.01); *G02B 5/201* (2013.01); *G02B 5/208* (2013.01); *G06K 9/00624* (2013.01); *G06K 9/209* (2013.01); *H04N 5/2258* (2013.01)

(58) Field of Classification Search
  CPC ...... G01J 5/02; G01J 5/0834; G01N 21/3504; G02B 5/201; G02B 5/208; G06K 9/00624; G06K 9/209; H04N 5/2258; H04N 5/33
  See application file for complete search history.

(56) References Cited

U.S. PATENT DOCUMENTS

| | | | |
|---|---|---|---|
| 4,134,683 A | 1/1979 | Goetz et al. | |
| 4,464,789 A | 8/1984 | Sternberg | |
| 4,933,555 A | 6/1990 | Smith | |
| 4,963,963 A | 10/1990 | Dorman | |
| 5,127,742 A | 7/1992 | Fraden | |
| 5,136,421 A | 8/1992 | Sagan | |
| 5,157,258 A | 10/1992 | Gunning, III et al. | |
| 5,354,987 A | 10/1994 | MacPherson | |
| 5,550,373 A | 8/1996 | Cole et al. | |
| 5,559,336 A | 9/1996 | Kosai et al. | |
| 5,604,346 A | 2/1997 | Hamrelius et al. | |
| 5,822,222 A | 10/1998 | Kaplinsky et al. | |
| 5,877,500 A | 3/1999 | Braig et al. | |
| 5,920,066 A | 7/1999 | DiRenzo et al. | |
| 5,926,283 A | 7/1999 | Hopkins | |
| 5,973,844 A * | 10/1999 | Burger | G02B 3/0056 359/621 |
| 5,994,701 A | 11/1999 | Tsuchimoto et al. | |
| 6,023,061 A | 2/2000 | Bodkin | |
| 6,184,529 B1 | 2/2001 | Contini | |
| 6,268,883 B1 | 7/2001 | Zehnder et al. | |
| 6,456,261 B1 | 9/2002 | Zhang | |
| 6,465,785 B1 | 10/2002 | McManus | |
| 6,556,853 B1 | 4/2003 | Cabib et al. | |
| 6,680,778 B2 | 1/2004 | Hinnrichs et al. | |
| 6,700,527 B1 | 3/2004 | Martin et al. | |
| 7,109,488 B2 | 9/2006 | Milton | |
| 7,119,337 B1 | 10/2006 | Johnson et al. | |
| 7,242,478 B1 | 7/2007 | Dombrowski et al. | |
| 7,315,377 B2 | 1/2008 | Holland et al. | |
| 7,321,119 B2 | 1/2008 | King | |
| 7,364,697 B2 | 4/2008 | McFarland et al. | |
| 7,433,042 B1 | 10/2008 | Cavanaugh et al. | |
| 7,606,484 B1 | 10/2009 | Richards et al. | |
| 7,634,157 B1 | 12/2009 | Richards et al. | |
| 7,750,802 B1 | 7/2010 | Parish et al. | |
| 7,835,002 B2 | 11/2010 | Muhammed et al. | |
| 7,888,624 B1 | 2/2011 | Murguia et al. | |
| 8,027,041 B1 | 9/2011 | Mitchell et al. | |
| 8,153,980 B1 | 4/2012 | Brady et al. | |
| 8,159,568 B2 | 4/2012 | Ahdoot | |
| 8,212,213 B2 | 7/2012 | Myrick et al. | |
| 8,373,757 B1 | 2/2013 | Nguyen | |
| 8,629,930 B2 * | 1/2014 | Brueckner | H04N 5/3572 348/335 |
| 8,653,461 B1 | 2/2014 | Benson et al. | |
| 8,654,328 B2 | 2/2014 | Tkaczyk et al. | |
| 9,395,516 B2 | 7/2016 | Katsunuma et al. | |
| 9,562,849 B2 | 2/2017 | Kester et al. | |
| 9,599,508 B2 | 3/2017 | Kester et al. | |
| 9,625,318 B2 | 4/2017 | Kester et al. | |
| 9,641,772 B2 | 5/2017 | Yujiri | |
| 9,644,562 B2 | 5/2017 | Fujita | |
| 9,756,263 B2 | 9/2017 | Kester et al. | |
| 10,084,975 B2 | 9/2018 | Kester et al. | |
| 2001/0040216 A1 | 11/2001 | Knauth et al. | |
| 2002/0015151 A1 | 2/2002 | Gorin | |
| 2002/0121370 A1 | 9/2002 | Kurkjian et al. | |
| 2002/0159101 A1 | 10/2002 | Alderson et al. | |
| 2003/0102435 A1 | 6/2003 | Myers et al. | |
| 2003/0134426 A1 | 7/2003 | Jiang et al. | |
| 2003/0183756 A1 | 10/2003 | Huniu | |
| 2004/0093167 A1 | 5/2004 | Braig et al. | |
| 2004/0111232 A1 | 6/2004 | Butler et al. | |
| 2004/0252300 A1 | 12/2004 | Slater | |
| 2005/0029453 A1 | 2/2005 | Allen et al. | |
| 2005/0103989 A1 | 5/2005 | Watson et al. | |
| 2006/0044562 A1 | 3/2006 | Hagene et al. | |
| 2006/0183241 A1 | 8/2006 | Lehmann et al. | |
| 2006/0232675 A1 | 10/2006 | Chamberlain et al. | |
| 2006/0279632 A1 | 12/2006 | Anderson | |
| 2007/0018105 A1 | 1/2007 | Grimberg | |
| 2007/0075888 A1 | 4/2007 | Kelly et al. | |
| 2007/0108385 A1 | 5/2007 | Mantese et al. | |
| 2007/0170359 A1 | 7/2007 | Syllaios et al. | |
| 2007/0170363 A1 | 7/2007 | Schimert et al. | |
| 2008/0170140 A1 | 7/2008 | Silver et al. | |
| 2008/0204744 A1 | 8/2008 | Mir et al. | |
| 2008/0231719 A1 | 9/2008 | Benson et al. | |
| 2008/0251724 A1 | 10/2008 | Baliga et al. | |
| 2009/0252650 A1 | 10/2009 | Lakshmanan | |
| 2010/0162206 A1 | 6/2010 | Roth et al. | |
| 2010/0171866 A1 | 7/2010 | Brady et al. | |
| 2010/0211333 A1 | 8/2010 | Pruet et al. | |
| 2010/0309467 A1 | 12/2010 | Fox et al. | |
| 2011/0176577 A1 | 7/2011 | Bandara et al. | |
| 2011/0185048 A1 | 7/2011 | Yew et al. | |
| 2011/0261321 A1 | 10/2011 | Ramella-Roman et al. | |
| 2012/0273680 A1 | 11/2012 | Furry | |
| 2013/0181836 A1 | 7/2013 | Cardoso et al. | |
| 2013/0206990 A1 | 8/2013 | Hsu et al. | |
| 2013/0228887 A1 | 9/2013 | Wehner et al. | |
| 2013/0235256 A1 | 9/2013 | Kodama | |
| 2013/0250124 A1 | 9/2013 | Furry | |
| 2013/0307991 A1 | 11/2013 | Olsen et al. | |
| 2013/0321806 A1 | 12/2013 | Kester et al. | |
| 2013/0341509 A1 | 12/2013 | Nelson et al. | |
| 2013/0342680 A1 | 12/2013 | Zeng et al. | |
| 2014/0002639 A1 | 1/2014 | Cheben et al. | |
| 2014/0139643 A1 | 5/2014 | Högasten et al. | |
| 2014/0320843 A1* | 10/2014 | Streuber | F41G 7/008 356/4.01 |
| 2015/0069239 A1* | 3/2015 | Kester | G01J 3/36 250/332 |
| 2015/0136981 A1* | 5/2015 | Kester | G01N 21/3504 250/330 |
| 2015/0136982 A1* | 5/2015 | Kester | G01J 3/2823 250/332 |
| 2015/0138534 A1 | 5/2015 | Tidhar | |
| 2015/0144770 A1 | 5/2015 | Choi | |
| 2015/0226613 A1* | 8/2015 | Bauer | G01J 5/061 250/349 |
| 2015/0288894 A1 | 10/2015 | Geelen et al. | |
| 2015/0316473 A1* | 11/2015 | Kester | G06K 9/22 250/339.02 |
| 2016/0037089 A1 | 2/2016 | Silny et al. | |
| 2016/0041095 A1 | 2/2016 | Rothberg et al. | |
| 2016/0097713 A1 | 4/2016 | Kester et al. | |
| 2016/0097714 A1 | 4/2016 | Zeng et al. | |
| 2016/0238454 A1 | 8/2016 | Pillans | |
| 2016/0245698 A1 | 8/2016 | Pau et al. | |
| 2016/0313181 A1 | 10/2016 | Golub et al. | |
| 2016/0349228 A1 | 12/2016 | Kester et al. | |
| 2016/0356702 A1 | 12/2016 | Hinnrichs | |

(56) References Cited

U.S. PATENT DOCUMENTS

| | | | |
|---|---|---|---|
| 2016/0380014 | A1 | 12/2016 | Ganapathi et al. |
| 2017/0026588 | A1 | 1/2017 | Kester et al. |
| 2017/0205290 | A1 | 7/2017 | Kester et al. |
| 2017/0234761 | A1 | 8/2017 | Augusto |
| 2017/0248517 | A1 | 8/2017 | Scherer et al. |
| 2017/0350758 | A1 | 12/2017 | Kester et al. |
| 2017/0356802 | A1 | 12/2017 | Kester et al. |
| 2018/0077363 | A1 | 3/2018 | Kester et al. |
| 2018/0188163 | A1 | 7/2018 | Kester et al. |
| 2019/0003984 | A1 | 1/2019 | Kester et al. |

FOREIGN PATENT DOCUMENTS

| | | |
|---|---|---|
| EP | 0 837 600 | 4/1998 |
| EP | 2 871 452 | 5/2015 |
| EP | 2 942 615 | 11/2015 |
| EP | 2 955 496 | 12/2015 |
| EP | 3 040 706 | 7/2016 |
| GB | 1014769 | 12/1965 |
| GB | 2518224 | 3/2015 |
| JP | 2013-128185 | 6/2013 |
| WO | WO 2004/097389 | 11/2004 |
| WO | WO 2007/008826 | 1/2007 |
| WO | WO 2008/109183 | 9/2008 |
| WO | WO 2009/094782 | 8/2009 |
| WO | WO 2010/053979 | 5/2010 |
| WO | WO 2012/078417 | 6/2012 |
| WO | WO 2012/082366 | 6/2012 |
| WO | WO 2013/173541 | 11/2013 |
| WO | WO 2015/108236 | 7/2015 |
| WO | WO 2016/196224 | 12/2016 |
| WO | WO 2017/201194 | 11/2017 |
| WO | WO 2018/075957 | 4/2018 |
| WO | WO 2018/075964 | 4/2018 |
| WO | WO 2018/156795 | 8/2018 |

OTHER PUBLICATIONS

Adams, et al., "Advances in Detectors: Hot IR sensors improve IR camera size, weight, and power", Laser Focus World, vol. 50, Issue 1, Jan. 17, 2014, 6 pages. Also available at http://www.ircameras.com/articles/advances-detectors-hot-ir-sensors-improve-ir-camera-size-weight-power/.

Allen et al., "Measurements of Methane Emissions at Natural Gas Production Sites in the United States", PNAS, Oct. 29, 2013, vol. 110, No. 44, pp. 7.

Alvarez et al., "Greater Focus Needed on Methane Leakage from Natural Gas Infrastructure", PNAS, Apr. 24, 2012, vol. 109, No. 17, pp. 12.

Bedard et al., "Image Mapping Spectrometry: Calibration and Characterization", Optical Engineering, Nov. 2012, vol. 51, No. 11, pp. 111711-1-111711-13.

Ben-David et al., "Probability Theory for 3-Layer Remote Sensing Radiative Transfer Model: Univariate Case," Optics Express, Apr. 2012, vol. 20, No. 9, pp. 10004-10033.

Ben-David et al., "Probability Theory for 3-Layer Remote Sensing Radiative Transfer Model: Errata," Optics Express, May 20, 2013, vol. 21, No. 10, pp. 11852.

Brady et al., "Multiscale Lens Design", Optics Express, Jun. 22, 2009, vol. 17, No. 13, pp. 10659-10674.

Brochure provided by Lofty Designs to Rebellion Photonics on Oct. 31, 2012 as noted from the email. Subsequent to that date brochure was used in connection with potential customers.

Caulton et al., "Toward a Better Understanding and Quantification of Methane Emissions from Shale Gas Development", PNAS, Apr. 29, 2014, vol. 111, No. 17, pp. 7.

Chen et al., "Quantitative Sectioning and Noise Analysis for Structured Illumination Microscopy: Erratum", Optics Express, Oct. 19, 2015, vol. 23, No. 21, pp. 27633-27634.

Chidley et al., "Flow-Induced Birefringence: The Hidden PSF Killer in High Performance Injection-Molded Plastic Optics", Endoscopic Microscopy, Proceedings of SPIE vol. 6082, 2006, pp. 11.

Chu et al., "The NIST Quantitative Infrared Database", Journal of Research of the National Institute of Standards and Technology, Jan.-Feb. 1999, vol. 104, No. 1, pp. 59-81.

DiPietro et al., "Hyperspectral Matched Filter with False-Alarm Mitigation", Optical Engineering, Jan. 2012, vol. 51, No. 1, pp. 016202-1-016202-7.

"Directed Inspection and Maintenance at Gas Processing Plants and Booster Stations," United States Environmental Protection Agency Air and Radiation (6202J), EPA430-B-03-018, Oct. 2003 available at https://www3.epa.gov/gasstar/documents/II_dimgasproc.pdf.

Eriksson et al., "Radiative Cooling Computed for Model Atmospheres", Applied Optics, Dec. 1, 1982, vol. 21, No. 23, pp. 4381-4388.

Flanigan, "Detection of Organic Vapors with Active and Passive Sensors: A Comparison," Applied Optics, 1986, vol. 25, No. 23, pp. 4253-4260.

Gålfalk et al., "Making Methane Visible", Nature Climate Change, Apr. 2016, vol. 6, pp. 426-430.

Gålfalk et al., "Making Methane Visible", Supplementary Information, Nature Climate Change, 2015, pp. 1-14.

Gallagher et al., "Error Analysis for Estimation of Trace Vapor Concentration Pathlength in Stack Plumes", Applied Spectroscopy, 2003, vol. 57, No. 6, pp. 614-621.

Gallagher et al., "Estimation of Trace Vapor Concentration-Pathlength in Plumes for Remote Sensing Applications from Hyperspectral Images", Analytica Chimica Acta, 2003, vol. 490, pp. 139-152.

Gao et al., "Compact Image Slicing Spectrometer (ISS) for Hyperspectral Fluorescence Microscopy", Optics Express, Jul. 20, 2009, vol. 17, No. 15, pp. 12293-12308.

Gao et al., "Depth-Resolved Image Mapping Spectrometer (IMS) with Structured Illumination", Optics Express, Aug. 29, 2011, vol. 19, No. 18, pp. 17439-17452.

Gao et al., "Optical Design of a Snapshot High-Sampling Image Mapping Spectrometer (IMS) for Hyperspectral Microscopy", Three-Dimensional and Multidimensional Microscopy: Image Acquisition and Processing XVII, Proceedings of SPIE vol. 7570, 2010, pp. 1-7.

Gao et al., "Quantitative Comparison Between Full-Spectrum and Filter-Based Imaging in Hyperspectral Fluorescence Microscopy", Journal of Microscopy, 2012, vol. 246, No. 2, pp. 113-123.

Gao et al., "Snapshot Image-Mapping Spectrometer for Hyperspectral Fluorescence Microscopy", Optics and Photonics News, Nov. 2010, vol. 21, No. 12, p. 50.

Gao et al., "Snapshot Image Mapping Spectrometer (IMS) with High Sampling Density for Hyperspectral Microscopy", Optics Express, Jul. 5, 2010, vol. 18, No. 4, pp. 14330-14344.

Gerhart et al., "Detection and Tracking of Gas Plumes in LWIR Hyperspectral Video Sequence Data," Algorithms and Technologies for Multispectral, Hyperspectral, and Ultraspectral Imagery XIX, 2013, SPIE Proceedings vol. 8743, pp. 1-14.

Gittins, Christopher M., "Detection and Characterization of Chemical Vapor Fugitive Emissions by Nonlinear Optimal Estimation: Theory and Simulation", Applied Optics, Aug. 10, 2009, vol. 48, No. 23, pp. 4545-4561.

Goldberg et al., "Dual Band MWIR/LWIR Focal Plane Array Test Results," Army Research Lab, Adelphi, MD, Aug. 1999, pp. 18.

Golowich et al., "Performance Limits of LWIR Gaseous Plume Quantification", Algorithms and Technologies for Multispectral, Hyperspectral, and Ultraspectral Imagery XVII, 2011, Proceedings of SPIE vol. 8048, pp. 1-12.

Griffin et al., "The Herschel—SPIRE 1-15 Instrument and its In-Flight Performance," Astronomy and Astrophysics, Jul. 1, 2010, vol. 518, pp. 7.

Gross et al., "Remote Identification and Quantification of Industrial Smokestack Effluents via Imaging Fourier-Transform Spectroscopy", Environmental Science & Technology, 2010, vol. 44, No. 24, pp. 9390-9397.

Gupta et al., "Miniature Snapshot Multispectral Imager," Optical Engineering, 2011, vol. 50, pp. 033203-1-033203-9.

Hadlington, Simon, "New Camera Makes Methane Visible", Chemistry World, http://web.archive.org/web/20160305234907/http://www.rsc.org/chemistryworld/2015/12/methane-camera-infrared-greenhouse-gas, Dec. 14, 2015, pp. 2.

(56) References Cited

OTHER PUBLICATIONS

Hagen et al., "Analysis of Computed Tomographic Imaging Spectrometers. I. Spatial and Spectral Resolution", Applied Optics, Oct. 1, 2008, vol. 47, No. 28, pp. F85-F95.
Hagen et al., "Coded Aperture DUV Spectrometer for Standoff Raman Spectroscopy", Next-Generation Spectroscopic Technologies II, Proceedings of SPIE vol. 7319, 2009, pp. 1-10.
Hagen et al., "Compound Prism Design Principles, I", Applied Optics, Sep. 1, 2011, vol. 50, No. 25, pp. 4998-5011.
Hagen et al., "Compound Prism Design Principles, II: Triplet and Janssen Prisms", Applied Optics, Sep. 1, 2011, vol. 50, No. 25, pp. 5012-5022.
Hagen et al., "Compound Prism Design Principles, III: Linear-in-Wavenumber and Optical Coherence Tomography Prisms", Applied Optics, Sep. 1, 2011, vol. 50, No. 25, pp. 5023-5030.
Hagen et al., "Fourier Methods of Improving Reconstruction Speed for CTIS Imaging Spectrometers", Imaging Spectrometry XII, Proceedings of SPIE vol. 6661, 2007, pp. 11.
Hagen et al., "Foveated Endoscopic Lens", Journal of Biomedical Optics, Feb. 2012, vol. 17, No. 2, pp. 021104-1-021104-6.
Hagen et al., "Gaussian Profile Estimation in One Dimension", Applied Optics, Aug. 1, 2007, vol. 46, No. 22, pp. 5374-5383.
Hagen et al., "Gaussian Profile Estimation in Two Dimensions", Applied Optics, Dec. 20, 2008, vol. 47, No. 36, pp. 6842-6851.
Hagen et al., "Quantitative Sectioning and Noise Analysis for Structured Illumination Microscopy", Optics Express, Jan. 2, 2012, vol. 20, No. 1, pp. 403-413.
Hagen et al., "Quantitative Sectioning and Noise Analysis for Structured Illumination Microscopy: Errata", Optics Express, Feb. 27, 2012, vol. 20, No. 5, pp. 5343.
Hagen et al., "Real-Time Quantitative Hydrocarbon Gas Imaging with the Gas Cloud Imager (GCI)", Proceedings of SPIE, vol. 8358, Chemical, Biological, Radiological, Nuclear, and Explosives (CBRNE) Sensing XIII, May 1, 2012, pp. 7.
Hagen et al., "Review of Snapshot Spectral Imaging Technologies", Optical Engineering, Sep. 2013, vol. 52, No. 9, pp. 090901-1-090901-23.
Hagen et al., "Snapshot Advantage: A Review of the Light Collection Improvement for Parallel High-Dimensional Measurement Systems," Optical Engineering, Jun. 13, 2012, vol. 51, No. 11, p. 111702-1-111702-7.
Hagen et al., "Snapshot Mueller Matrix Spectropolarimeter" Optics Letters, Aug. 1, 2007, vol. 32, No. 15, pp. 2100-2102.
Hagen et al., "Spectrally-Resolved Imaging of Dynamic Turbid Media", Multimodal Biomedical Imaging VI, Proceedings of SPIE vol. 7892, 2011, pp. 1-7.
Hagen et al., "Video-Rate Spectral Imaging of Gas Leaks in the Longwave Infrared," Chemical, Biological, Radiological, Nuclear, and Explosives (CBRNE) Sensing XIV, May 29, 2013, SPIE Proceedings vol. 8710, pp. 7.
Harley et al., "Remote Quantification of Smokestack Effluent Mass Flow Rates Using Imaging Fourier Transform Spectrometry," Chemical, Biological, Radiological, Nuclear, and Explosives (CBRNE) Sensing XII, Apr. 25-29, 2011, SPIE Proceedings vol. 8018, pp. 1-13.
Hayden et al., "Determination of Trace-Gas Amounts in Plumes by the Use of Orthogonal Digital Filtering of Thermal-Emission Spectra", Applied Optics, Jun. 1, 1996, vol. 35, No. 16, pp. 2802-2809.
Hirsch et al., "Detection of Gaseous Plumes in IR Hyperspectral Images Using Hierarchical Clustering", Applied Optics, Sep. 1, 2007, vol. 46, No. 25, pp. 6368-6374.
Johnston et al., "A Real-Time FPGA Implementation of a Barrel Distortion Correction Algorithm", Projects, 2003, vol. 10, pp. 91-96.
Karion et al., "Methane Emissions Estimate from Airborne Measurements Over a Western United States Natural Gas Field", Geophysical Research Letters, 2013, vol. 40, pp. 4393-4397.
Keshava et al., "A Survey of Spectral Unmixing Algorithms", Lincoln Laboratory Journal, 2003, vol. 14, No. 1, pp. 55-78.
Kester et al., "A Real-Time Gas Cloud Imaging Camera for Fugitive Emission Detection and Monitoring", Imaging and Applied Optics Technical Digest, 2012, pp. 3.
Kester et al., "Development of Image Mappers for Hyperspectral Biomedical Imaging Applications", Applied Optics, Apr. 1, 2010, vol. 49, No. 10, pp. 1886-1899.
Kester et al., "High Numerical Aperture Microendoscope Objective for a Fiber Confocal Reflectance Microscope", Optics Express, Mar. 5, 2007, vol. 15. No. 5, pp. 2409-2420.
Kester et al., "Low Cost, High Performance, Self-Aligning Miniature Optical Systems", Applied Optics, Jun. 20, 2009, vol. 48, No. 18, pp. 3375-3384.
Kester et al., "Real-Time Snapshot Hyperspectral Imaging Endoscope", Journal of Biomedical Optics, May 2011, vol. 16, No. 5, pp. 056005-1-056005-12.
Kudenov et al., "Fourier Transform Channeled Spectropolarimetry in the MWIR", Optics Express, Oct. 1, 2007, vol. 15, No. 20, pp. 12792-12805.
Kudenov et al., "Snapshot Imaging Mueller Matrix Polarimeter Using Polarization Gratings", Optics Letters, Apr. 15, 2012, vol. 37, No. 8, pp. 1367-1369.
Landau et al., "Design and Evaluation of an Ultra-Slim Objective for in-vivo Deep Optical Biopsy", Optics Express, Mar. 1, 2010, vol. 18, No. 5, pp. 4758-4775.
Levi, Michael A., "Comment on 'Hydrocarbon Emissions Characterization in the Colorado Front Range: A Pilot Study' by Gabrielle Pétron et al.", Journal of Geophysical Research, 2012, vol. 117, No. D21203, pp. 1-5.
Levi, Michael A., "Reply to "'Reply to 'Comment on Hydrocarbon Emissions Characterization in the Colorado Front Range—A Pilot Study' by Michael A. Levi'" by Gabrielle Pétron et al.", Journal of Geophysical Research: Atmospheres, 2013, vol. 118, pp. 3044-3046.
Low et al., "Remote Sensing and Characterization of Stack Gases by Infrared Spectroscopy. An Approach by Using Multiple-Scan Interferometry", Environmental Science & Technology, Jan. 1967, vol. 1, No. 1, pp. 73-74.
Luo et al., "Fast Processing of Imaging Spectrometer Data Cube Based on FPGA Design", MIPPR 2007: Multispectral Image Processing, Proceedings of SPIE vol. 6787, pp. 7.
Manolakis et al., "Long-Wave Infrared Hyperspectral Remote Sensing of Chemical Clouds", IEEE Signal Processing Magazine, Jul. 2014, vol. 31, No. 4, pp. 120-141.
Mathews, "Design and Fabrication of a Low-Cost, Multispectral Imaging System," Applied Optics, 2008, pp. F71-F76, vol. 47.
Naranjo et al., "IR Gas Imaging in an Industrial Setting," Thermosense XXXII, Published in SPIE Proceedings vol. 7661, May 4, 2010, pp. 1-8.
Nguyen et al., "Snapshot 3D Optical Coherence Tomography System using Image Mapping Spectrometer", Biomedical Optics and 3D Imaging OSA, 2012, pp. 3.
Niu et al., "New Approach to Remote Gas-Phase Chemical Quantification: Selected-Band Algorithm", Optical Engineering, Feb. 2014, vol. 53, No. 2, pp. 021111-1-021111-10.
"Oil and Natural Gas Sector Leaks", U.S. EPA Office of Air Quality Planning and Standards (OAQPS), Review Panel, Apr. 2014, pp. 63.
Pétron et al., "Hydrocarbon Emissions Characterization in the Colorado Front Range: A Pilot Study", Journal of Geophysical Research, 2012, vol. 117, No. D04304, pp. 1-19.
Pétron et al., "Reply to Comment on 'Hydrocarbon Emissions Characterization in the Colorado Front Range—A Pilot Study' by Michael A. Levi", Journal of Geophysical Research: Atmospheres, 2013, vol. 118, pp. 236-242.
Pisano et al., "Thermal Illuminators for Far-Infrared and Submillimeter Astronomical Instruments," Applied Optics, Jun. 1, 2005, vol. 44, No. 16, pp. 3208-3217.
Polak et al., "Passive Fourier-Transform Infrared Spectroscopy of Chemical Plumes: An Algorithm for Quantitative Interpretation and Real-Time Background Removal", Applied Optics, Aug. 20, 1995, vol. 34, No. 24, pp. 5406-5412.

(56) References Cited

OTHER PUBLICATIONS

Rebellion Photonics, "Gas Cloud Imaging Camera: A Breakthrough in Leak Monitoring for the Rig & Refinery Safety Market", Presentation at SPIE Defense Security and Sensing, 28 pages, Apr. 29-May 3, 2013.
Sandsten et al., "Development of Infrared Spectroscopy Techniques for Environmental Monitoring", Doctoral Thesis, Aug. 2000, pp. 123.
Sandsten et al., "Real-Time Gas-Correlation Imaging Employing Thermal Background Radiation", Optics Express, Feb. 14, 2000, vol. 6, No. 4, pp. 92-103.
Sandsten et al., "Volume Flow Calculations on Gas Leaks Imaged with Infrared Gas-Correlation," Optics Express, 2012, vol. 20, No. 18, pp. 20318-20329.
Shogenji et al., "Multispectral Imaging Using Compact Compound Optics," Optics Express, Apr. 19, 2004, vol. 12, No. 8, pp. 1643-1655.
Telops, "Hyper-Cam", http://web.archive.org/web/20160608180941/ http://www.telops.com/en/hyperspectral-cameras/hyper-cam as archived Jun. 8, 2016 in 2 pages.
Telops, "Innovative Infrared Imaging", http://web.archive.org/web/2016060321729/http://www.telops.com/en/ as archived Jun. 3, 2016 in 2 pages.
Walter Jr., et al., "Detection of Atmospheric Pollutants: a Correlation Technique", Applied Optics, Jun. 1975, vol. 14, No. 6, pp. 1423-1428.
Wikipedia entry https://en.wikipedia.org/wiki/Mobile_computing last modified on Dec. 30, 2016; retrieved from the internet on Feb. 2, 2017 in 6 pages.
Williams et al., "Dual-Band MWIR/LWIR Radiometer for Absolute Temperature Measurements," SPIE Thermosense Conference XXVIII—Manuscript 6205-23, Apr. 18, 2006, pp. 13.
Young et al., "An In-Scene Method for Atmospheric Compensation of Thermal Hyperspectral Data", Journal of Geophysical Research, 2002, vol. 107, No. D24, pp. 14-1-14-20.
Zheng et al., "A Static Multiplex Fabry-Perot Spectrometer", Sensors, Cameras, and Systems for Industrial/Scientific Applications X, Proceedings of SPIE-IS&T Electronic Imaging, SPIE vol. 7249, 2009, pp. 8.
Zheng et al., "Analytic-Domain Lens Design with Proximate Ray Tracing", Journal of the Optical Society of America A, Aug. 2010, vol. 27, No. 8, pp. 1791-1802.
Preliminary Amendment as filed in U.S. Appl. No. 14/538,827 dated Jan. 28, 2015 in 6 pages.
Office Action received in U.S. Appl. No. 14/538,827 dated Jun. 30, 2015 in 8 pages.
Non-Final Office Action Response as filed in U.S. Appl. No. 14/538,827 dated Dec. 28, 2015 in 11 pages.
Notice of Allowance received in U.S. Appl. No. 14/538,827 dated Feb. 1, 2016 in 18 pages.
Corrected Notice of Allowance received in U.S. Appl. No. 14/538,827 dated Feb. 10, 2016 in 4 pages.
Corrected Notice of Allowance received in U.S. Appl. No. 14/538,827 dated Feb. 22, 2016 in 4 pages.
Request for Continued Examination and Response to Correct Application Papers as filed in U.S. Appl. No. 14/538,827 dated Apr. 29, 2016 in 14 pages.
Notice of Allowance received in U.S. Appl. No. 14/538,827 dated May 26, 2016 in 9 pages.
Notice of Allowance received in U.S. Appl. No. 14/538,827 dated Sep. 19, 2016 in 9 pages.
Amendment as filed in U.S. Appl. No. 14/538,827 dated Dec. 16, 2016 in 9 pages.
Official Communication received in U.S. Patent Application No. 15/418,532 dated Jun. 23, 2017 in 7 pages.
Amendment as filed in U.S. Appl. No. 15/418,532 dated Nov. 22, 2017 in 8 pages.
Official Communication received in U.S. Appl. No. 15/418,532 dated Dec. 11, 2017 in 21 pages.
Office Action received in U.S. Appl. No. 14/543,692 dated Nov. 3, 2015 in 7 pages.
Interview Summary received in U.S. Appl. No. 14/543,692 dated Feb. 17, 2016 in 5 pages.
Response to Office Action as filed in U.S. Appl. No. 14/543,692 dated May 2, 2016 in 9 pages.
Office Action received in U.S. Appl. No. 14/543,692 dated Jun. 1, 2016 in 18 pages.
Response to Final Action as filed in U.S. Appl. No. 14/543,692 dated Nov. 30, 2016 in 12 pages.
Notice of Allowance received in U.S. Appl. No. 14/543,692 dated Dec. 9, 2016 in 12 pages.
Amendment after Allowance as filed in U.S. Appl. No. 14/543,692 dated Mar. 3, 2017 in 6 pages.
Notice of Allowance received in U.S. Appl. No. 14/543,692 dated Mar. 17, 2017 in 4 pages.
Preliminary Amendment as filed in U.S. Appl. No. 15/471,398 dated Oct. 6, 2017 in 6 pages.
Notice of Allowance received in U.S. Appl. No. 14/571,398 dated Oct. 18, 2017 in 8 pages.
Notice of Allowance received in U.S. Appl. No. 14/571,398 dated Feb. 7, 2018 in 20 pages.
Office Action received in U.S. Appl. No. 14/539,899 dated Mar. 26, 2015 in 6 pages.
Non-Final Office Action Response as filed in U.S. Appl. No. 14/539,899 dated Aug. 26, 2015 in 8 pages.
Final Office Action received in U.S. Appl. No. 14/539,899 dated Dec. 11, 2015 in 9 pages.
Amendment as filed in U.S. Appl. No. 14/539,899 dated Jun. 9, 2016 in 6 pages.
Notice of Allowance received in U.S. Appl. No. 14/539,899 dated Jun. 21, 2016 in 17 pages.
Notice of Allowance received in U.S. Appl. No. 14/539,899 dated Oct. 31, 2016 in 10 pages.
Amendment as filed in U.S. Appl. No. 14/539,899 dated Jan. 27, 2017 in 5 pages.
Official Communication received in U.S. Appl. No. 15/462,352 dated Sep. 28, 2017 in 6 pages.
Amendment as filed in U.S. Appl. No. 15/462,352 dated Feb. 28, 2018 in 5 pages.
Extended European Search Report received in European Application No. 14192862.2 dated Mar. 30, 2015 in 10 pages.
Official Communication received in European Application No. 14192862.2 dated Apr. 19, 2016 in 6 pages.
International Search Report in PCT Application No. PCT/US2013/041278 dated Aug. 27, 2013 in 4 pages.
International Preliminary Report on Patentability in PCT Application No. PCT/US2013/041278 dated Nov. 27, 2014 in 10 pages.
Preliminary Amendment as filed in U.S. Appl. No. 14/700,791 dated Jul. 13, 2015 in 8 pages.
Notice of Allowance received in U.S. Appl. No. 14/700,791 dated Jun. 9, 2016 in 11 pages.
Notice of Allowance received in U.S. Appl. No. 14/700,791 dated Sep. 30, 2016 in 19 pages.
Notice of Allowance received in U.S. Appl. No. 14/700,791 dated Feb. 21, 2017 in 20 pages.
Comments on Allowance received in U.S. Appl. No. 14/700,791 dated May 19, 2017 in 2 pages.
Notice of Allowance received in U.S. Appl. No. 14/700,791 dated Jul. 10, 2017 in 24 pages.
Preliminary Amendment as filed in U.S. Appl. No. 15/623,942 dated Dec. 7, 2017 in 6 pages.
Notice of Allowance received in U.S. Appl. No. 15/623,942 dated Jan. 24, 2018 in 22 pages.
Extended European Search Report received in European Application No. 15165877.0 dated Oct. 8, 2015 in 12 pages.
Official Communication received in European Application No. 15165877.0 dated Jan. 3, 2017 in 9 pages.
Preliminary Amendment as filed in U.S. Appl. No. 14/700,567 dated Jul. 10, 2015 in 6 pages.
Publication Request as filed in U.S. Appl. No. 14/700,567 dated Aug. 24, 2016 in 237 pages.

(56) References Cited

OTHER PUBLICATIONS

Official Communication received in U.S. Appl. No. 14/700,567 dated Jun. 14, 2017 in 29 pages.
Amendment as filed in U.S. Appl. No. 14/700,567 dated Dec. 13, 2017 in 12 pages.
Official Communication received in U.S. Appl. No. 14/700,567 dated Mar. 5, 2018 in 38 pages.
Extended European Search Report received in European Application No. EP 15165880.4 dated Nov. 24, 2015 in 8 pages.
Preliminary Amendment as filed in U.S. Appl. No. 14/792,477 dated Dec. 21, 2015 in 7 pages.
Official Communication received in U.S. Appl. No. 14/792,477 dated Jan. 27, 2017 in 10 pages.
Response to Restriction Requirement submitted in U.S. Appl. No. 14/792,477 dated May 8, 2017 in 6 pages.
Official Communication received in U.S. Appl. No. 14/792,477 dated Jul. 19, 2017 in 20 pages.
Amendment as filed in U.S. Appl. No. 14/792,477 dated Jan. 18, 2018 in 10 pages.
Preliminary Amendment as filed in U.S. Appl. No. 15/166,092 dated Aug. 15, 2016 in 7 pages.
International Search Report in PCT Application No. PCT/US2016/034455 dated Oct. 24, 2016 in 12 pages.
International Preliminary Report on Patentability in PCT Application No. PCT/US2016/034455 Dec. 5, 2017 in 8 pages.
Preliminary Amendment as filed in U.S. Appl. No. 15/789,811 dated Mar. 20, 2018 in 6 pages.
Invitation to Pay Additional Fees in PCT Application No. PCT/US2017/057725 dated Dec. 14, 2017 in 3 pages.
International Search Report in PCT Application No. PCT/US2017/057725 dated Feb. 14, 2018 in 14 pages.
Preliminary Amendment as filed in U.S. Appl. No. 15/789,829 dated Mar. 20, 2018 in 8 pages.
Invitation to Pay Additional Fees in PCT Application No. PCT/US2017/057712 dated Jan. 10, 2018 in 2 pages.
International Search Report in PCT Application No. PCT/US2017/057712 dated Mar. 6, 2018 in 12 pages.
Cossel et al., "Analysis of Trace Impurities in Semiconductor Gas Via Cavity-Enhanced Direct Frequency Comb Spectroscopy", Applied Physics B, Sep. 2010, vol. 100, No. 4, pp. 917-924.
Notice of Allowance received in U.S. Appl. No. 15/418,532 dated Jun. 15, 2018 in 12 pages.
Corrected Notice of Allowance received in U.S. Appl. No. 15/418,532 dated Jul. 6, 2018 in 3 pages.
Amendment after Allowance as filed in U.S. Appl. No. 15/418,532 dated Sep. 14, 2018 in 6 pages.
Notice of Allowance received in U.S. Appl. No. 15/418,532 dated Dec. 5, 2018 in 11 pages.
Notice of Allowance received in U.S. Appl. No. 14/571,398 dated Jul. 2, 2018 in 8 pages.
Notice of Allowance received in U.S. Appl. No. 14/571,398 dated Oct. 24, 2018 in 7 pages.
Notice of Allowance received in U.S. Appl. No. 15/462,352 dated Jul. 17, 2018 in 25 pages.
Notice to File Corrected Application Papers received in U.S. Appl. No. 15/462,352 dated Aug. 8, 2018 in 3 pages.
Response to Notice to File Corrected Application Papers filed in U.S. Appl. No. 15/462,352 dated Oct. 8, 2018 in 3 pages.
Notice of Allowance received in U.S. Appl. No. 15/462,352 dated Oct. 31, 2018 in 9 pages.
Official Communication received in European Application No. 13732285.5 dated Jul. 26, 2018 in 6 pages.
Official Communication received in European Application No. 14192862.2 dated May 2, 2018 in 3 pages.
Notice of Allowance received in U.S. Appl. No. 15/623,942 dated May 24, 2018 in 23 pages.
Comments on Allowance filed in U.S. Appl. No. 15/623,942 dated Aug. 23, 2018 in 2 pages.
Amendment as filed in U.S. Appl. No. 14/700,567 dated Jul. 5, 2018 in 10 pages.
Office Action as filed in U.S. Appl. No. 14/700,567 dated Aug. 27, 2018 in 36 pages.
Notice of Allowance received in U.S. Appl. No. 14/792,477 dated Apr. 19, 2018 in 13 pages.
Notice of Allowance received in U.S. Appl. No. 14/792,477 dated Sep. 20, 2018 in 14 pages.
Official Communication received in U.S. Appl. No. 15/166,092 dated May 15, 2018 in 30 pages.
Amendment as filed in U.S. Appl. No. 15/166,092 dated Nov. 15, 2018 in 11 pages.
Official Communication received in U.S. Appl. No. 15/789,829 dated Jun. 5, 2018 in 16 pages.
Amendment as filed in U.S. Appl. No. 15/789,829 dated Dec. 4, 2018 in 9 pages.
Preliminary Amendment as filed in U.S. Appl. No. 15/902,336 dated Sep. 20, 2018 in 9 pages.
International Search Report in PCT Application No. PCT/US2018/019271 dated Jun. 27, 2018 in 15 pages.

* cited by examiner

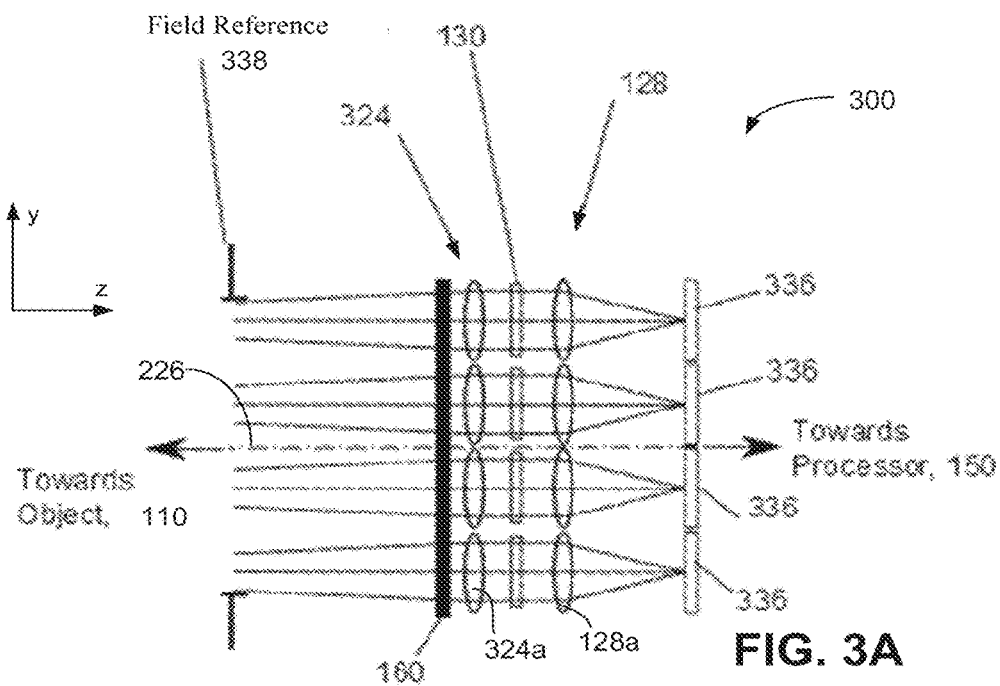
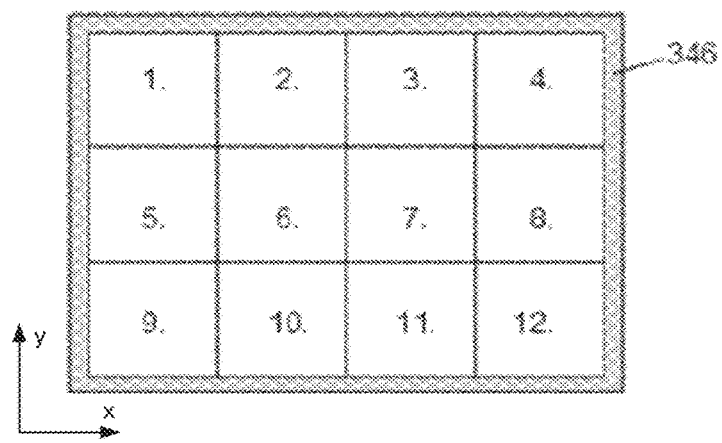
FIG. 3B

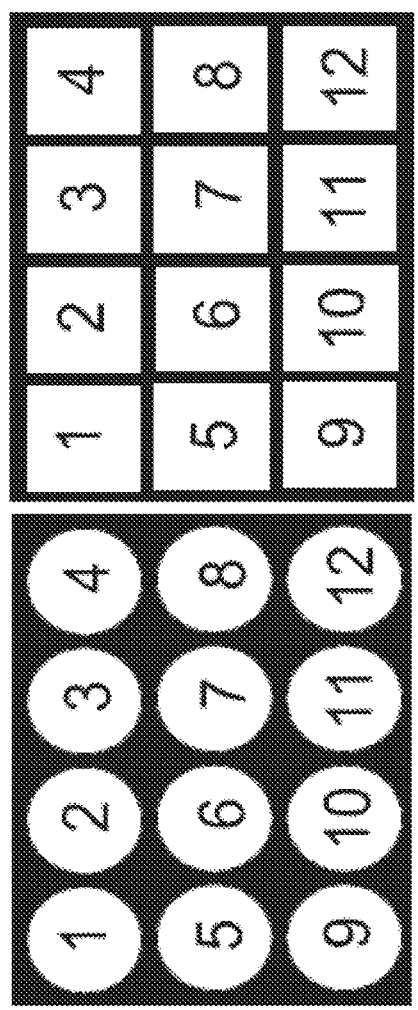

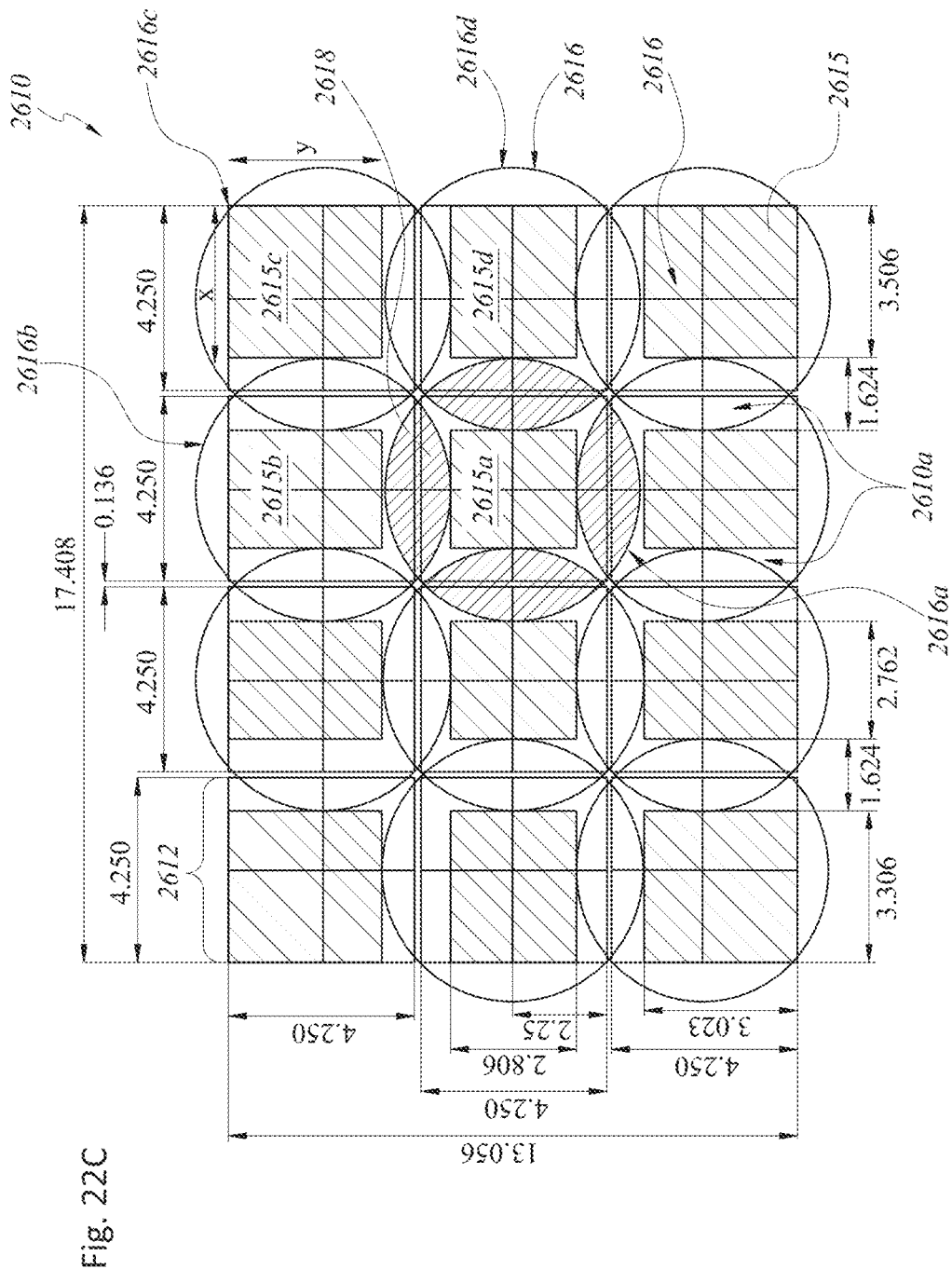

MOBILE GAS AND CHEMICAL IMAGING CAMERA

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application claims priority to U.S. Provisional Patent Application No. 62/411,480, filed Oct. 21, 2016, entitled "MOBILE GAS AND CHEMICAL IMAGING CAMERA," the contents of which is hereby incorporated by reference herein in its entirety and for all purposes.

STATEMENT REGARDING FEDERALLY SPONSORED R&D

Funding for some portions of the technology disclosed in this application was provided by the Advanced Research Projects Agency—Energy (ARPA-E) under Contract Number DE-AR0000541. The government may have certain rights in these portions of the technology.

FIELD OF THE INVENTION

The present invention generally relates to a system and method for gas cloud detection and, in particular, to a system and method of detecting spectral signatures of chemical compositions in infrared spectral regions.

DESCRIPTION OF THE RELATED TECHNOLOGY

Spectral imaging systems and methods have applications in a variety of fields. Spectral imaging systems and methods obtain a spectral image of a scene in one or more regions of the electromagnetic spectrum to detect phenomena, identify material compositions or characterize processes. The spectral image of the scene can be represented as a three-dimensional data cube where two axes of the cube represent two spatial dimensions of the scene and a third axis of the data cube represents spectral information of the scene in different wavelength regions. The data cube can be processed using mathematical methods to obtain information about the scene. Some of the existing spectral imaging systems generate the data cube by scanning the scene in the spatial domain (e.g., by moving a slit across the horizontal dimensions of the scene) and/or spectral domain (e.g., by scanning a wavelength dispersive element to obtain images of the scene in different spectral regions). Such scanning approaches acquire only a portion of the full data cube at a time. These portions of the full data cube are stored and then later processed to generate a full data cube.

SUMMARY

The systems, methods and devices of this disclosure each have several innovative aspects, no single one of which is solely responsible for the desirable attributes disclosed herein.

In one embodiment, an infrared (IR) imaging system for determining a concentration of a target species in an object is disclosed. The imaging system can include an optical system including an optical focal plane array (FPA) unit. The optical system can have components defining at least two optical channels thereof, said at least two optical channels being spatially and spectrally different from one another. Each of the at least two optical channels can be positioned to transfer IR radiation incident on the optical system towards the optical FPA. The system can include a processing unit containing a processor that can be configured to acquire multispectral optical data representing said target species from the IR radiation received at the optical FPA. Said optical system and said processing unit can be contained together in a data acquisition and processing module configured to be worn or carried by a person.

In another embodiment, an infrared (IR) imaging system for determining a concentration of a target species in an object is disclosed. The imaging system can comprise an optical system including an optical focal plane array (FPA) unit. The optical system can have components defining at least two optical channels thereof, said at least two optical channels being spatially and spectrally different from one another. Each of the at least two optical channels can be positioned to transfer IR radiation incident on the optical system towards the optical FPA. The system can include a processing unit containing a processor that can be configured to acquire multispectral optical data representing said target species from the IR radiation received at the optical FPA. Said data acquisition and processing module can have dimensions less than 8 inches×6 inches×6 inches.

In another embodiment, an infrared (IR) imaging system for determining a concentration of a target species in an object is disclosed. The imaging system can include an optical system including an optical focal plane array (FPA) unit. The optical system can have components defining at least two optical channels thereof, said at least two optical channels being spatially and spectrally different from one another. Each of the at least two optical channels can be positioned to transfer IR radiation incident on the optical system towards the optical FPA. The system can include a processing unit containing a processor that can be configured to acquire multispectral optical data representing said target species from the IR radiation received at the optical FPA. Said data acquisition and processing module can have a volume of less than 300 cubic inches.

In yet another embodiment, a method of identifying a target species or quantifying or characterizing a parameter of the target species in an object is disclosed. The method can include wearing or carrying a data acquisition and processing module. The data acquisition and processing module can comprise an optical system and a processing unit in communication with the optical system, the optical system including an optical focal plane array (FPA) unit. The method can include capturing multispectral infrared (IR) image data at the FPA unit from at least two optical channels that are spatially and spectrally different from one another. The method can include acquiring multispectral optical data representing the target species from the IR radiation received at the FPA.

In another embodiment, a system for monitoring the presence of one or more target gases at one or more installation sites is disclosed. The system can include a plurality of infrared (IR) imaging systems, each imaging system comprising a data acquisition and processing module. The data acquisition and processing module can be configured to capture infrared images of the one or more target gases in real-time. The data acquisition and processing module can be configured to associate each captured infrared image with a location at which the one or more target gases are present. The data acquisition and processing module can be configured to transmit image data associated with the one or more target gases and location data associated with the location of the one or more target gases to a central server.

In yet another embodiment, a method for monitoring the presence of one or more target gases at one or more installation sites is disclosed. The method can comprise receiving image data from a plurality of IR imaging systems located at a plurality of installation sites and configured to be worn or carried by a person. Each IR imaging system can be configured to capture infrared images of the one or more target gases in real-time and to associate each captured infrared image with a location at which the one or more target gases are present. The method can include processing the received image data to identify the installation sites at which the one or more target gases is detected.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale.

BRIEF DESCRIPTION OF THE DRAWINGS

FIG. 3A represents an embodiment employing an array of front objective lenses operably matched with the re-imaging lens array. FIG. 3B illustrates a two-dimensional array of optical components corresponding to the embodiment of FIG. 3A.

FIG. 5A is a diagram of a 4-by-3 pupil array comprising circular optical filters (and IR blocking material between the optical filters) used to spectrally divide an optical wavefront imaged with an embodiment of the system.

FIG. 5B is a diagram of a 4-by-3 pupil array comprising rectangular optical filters (and IR blocking material between the optical filters) used to spectrally divide an optical wavefront imaged with an embodiment of the system.

FIG. 22C is a forward facing schematic diagram of the optical detector depicting another example of optical crosstalk between neighboring optical channels, and the resulting non-uniformity in usable image size due to the crosstalk, according to various embodiments.

Like reference numbers and designations in the various drawings indicate like elements.

DETAILED DESCRIPTION

I. Overview of Various Embodiments

Figure 1:
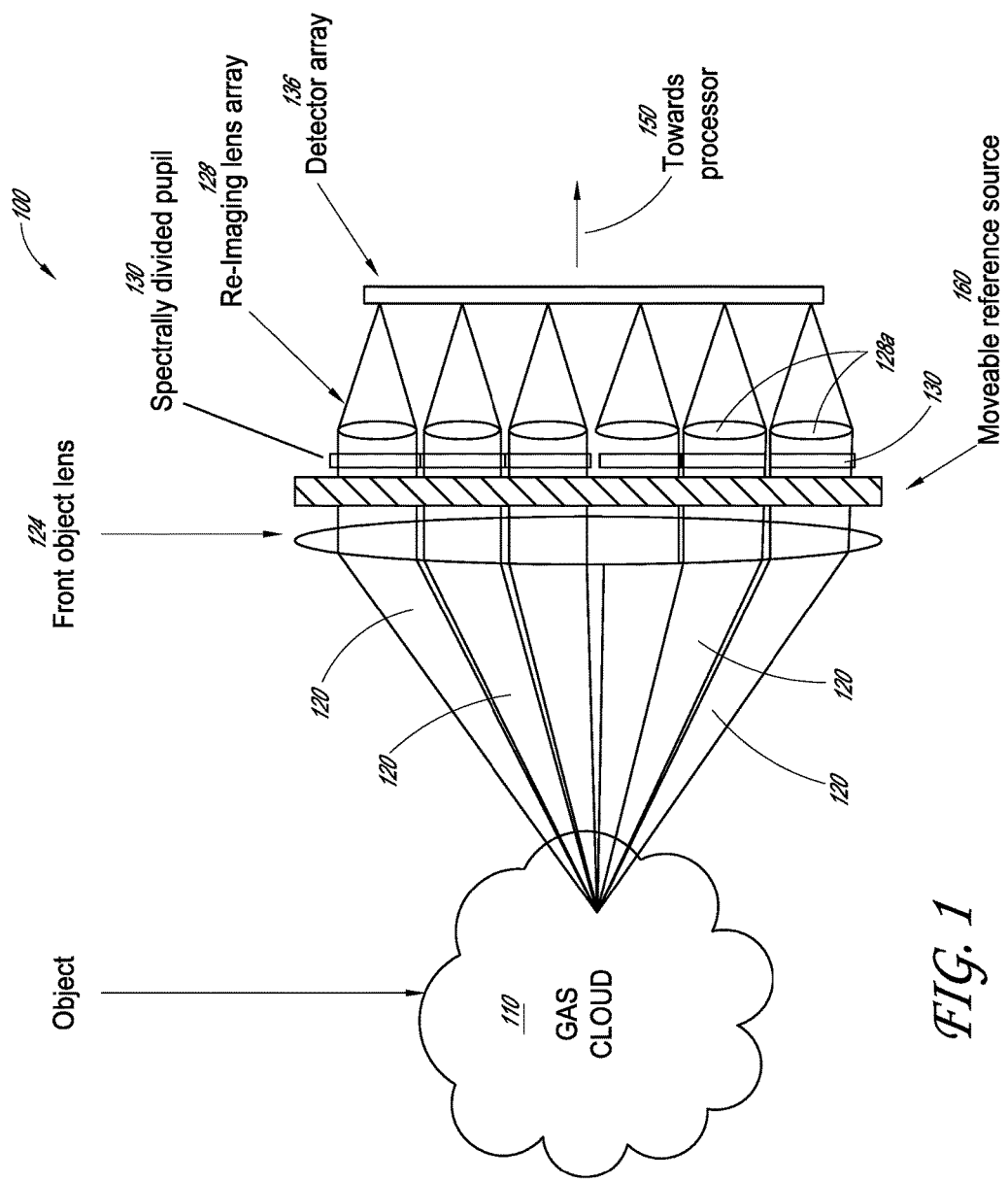
FIG. 1 shows an embodiment of an imaging system including a common front objective lens that has a pupil divided spectrally and re-imaged with a plurality of lenses onto an infrared FPA.

The following description is directed to certain implementations for the purposes of describing the innovative aspects of this disclosure. However, a person having ordinary skill in the art will readily recognize that the teachings herein can be applied in a multitude of different ways. The described implementations may be implemented in any device, apparatus, or system that can be configured to operate as an imaging system such as in an infra-red imaging system. The methods and systems described herein can be included in or associated with a variety of devices such as, but not limited to devices used for visible and infrared spectroscopy, multispectral and hyperspectral imaging devices used in oil and gas exploration, refining, and transportation, agriculture, remote sensing, defense and homeland security, surveillance, astronomy, environmental monitoring, etc. The methods and systems described herein have applications in a variety of fields including but not limited to agriculture, biology, physics, chemistry, defense and homeland security, environment, oil and gas industry, etc. The teachings are not intended to be limited to the implementations depicted solely in the Figures, but instead have wide applicability as will be readily apparent to one having ordinary skill in the art.

The spectral image of the scene can be represented as a three-dimensional data cube where two axes of the cube represent two spatial dimensions of the scene and a third axes of the data cube represents spectral information of the scene in different wavelength regions. The data cube can be processed using mathematical methods to obtain information about the scene. Some of the existing spectral imaging systems generate the data cube by scanning the scene in the spatial domain (e.g., by moving a slit across the horizontal and vertical dimensions of the scene) and/or spectral domain. Such scanning approaches acquire only a portion of the full data cube at a time. These portions of the full data cube are stored and then later processed to generate a full data cube.

Various embodiments disclosed herein describe a divided-aperture infrared spectral imaging (DAISI) system that is structured and adapted to provide identification of target chemical contents of the imaged scene. The system is based on spectrally-resolved imaging and can provide such identification with a single-shot (also referred to as a snapshot) comprising a plurality of images having different wavelength compositions that are obtained generally simultaneously. Without any loss of generality, snapshot refers to a system in which most of the data elements that are collected are continuously viewing the light emitted from the scene. In contrast in scanning systems, at any given time only a minority of data elements are continuously viewing a scene, followed by a different set of data elements, and so on, until the full dataset is collected. Relatively fast operation can be achieved in a snapshot system because it does not need to use spectral or spatial scanning for the acquisition of infrared (IR) spectral signatures of the target chemical contents. Instead, IR detectors (such as, for example, infrared focal plane arrays or FPAs) associated with a plurality of different optical channels having different wavelength profiles can be used to form a spectral cube of imaging data. Although spectral data can be obtained from a single snapshot comprising multiple simultaneously acquired images corresponding to different wavelength ranges, in various embodiments, multiple snap shots may be obtained. In various embodiments, these multiple snapshots can be averaged. Similarly, in certain embodiments multiple snap shots may be obtained and a portion of these can be selected and possibly averaged. Also, in contrast to commonly used IR spectral imaging systems, the DAISI system does not require cooling. Accordingly, it can advantageously use uncooled infrared detectors. For example, in various implementations, the imaging systems disclosed herein do not include detectors configured to be cooled to a temperature below 300 Kelvin. As another example, in various implementations, the imaging systems disclosed herein do not include detectors configured to be cooled to a temperature below 273 Kelvin. As yet another example, in various implementations, the imaging systems disclosed herein do not include detectors configured to be cooled to a temperature below 250 Kelvin. As another example, in various implementations, the imaging systems disclosed herein do not include detectors configured to be cooled to a temperature below 200 Kelvin.

Implementations disclosed herein provide several advantages over existing IR spectral imaging systems, most if not all of which may require FPAs that are highly sensitive and cooled in order to compensate, during the optical detection, for the reduction of the photon flux caused by spectrum-scanning operation. The highly sensitive and cooled FPA systems are expensive and require a great deal of maintenance. Since various embodiments disclosed herein are configured to operate in single-shot acquisition mode without spatial and/or spectral scanning, the instrument can receive photons from a plurality of points (e.g., every point) of the object substantially simultaneously, during the single reading. Accordingly, the embodiments of imaging system described herein can collect a substantially greater amount of optical power from the imaged scene (for example, an order of magnitude more photons) at any given moment in time especially in comparison with spatial and/or spectral scanning systems. Consequently, various embodiments of the imaging systems disclosed herein can be operated using uncooled detectors (for example, FPA unit including an array of microbolometers) that are less sensitive to photons in the IR but are well fit for continuous monitoring applications. For example, in various implementations, the imaging systems disclosed herein do not include detectors configured to be cooled to a temperature below 300 Kelvin. As another example, in various implementations, the imaging systems disclosed herein do not include detectors configured to be cooled to a temperature below 273 Kelvin. As yet another example, in various implementations, the imaging systems disclosed herein do not include detectors configured to be cooled to a temperature below 250 Kelvin. As another example, in various implementations, the imaging systems disclosed herein do not include detectors configured to be cooled to a temperature below 200 Kelvin. Imaging systems including uncooled detectors can be capable of operating in extreme weather conditions, require less power, are capable of operation during day and night, and are less expensive. Some embodiments described herein can also be less susceptible to motion artifacts in comparison with spatially and/or spectrally scanning systems which can cause errors in either the spectral data, spatial data, or both.

In various embodiments disclosed herein, the DAISI system can be mobile. For example, the DAISI system can be configured to be worn or carried by a person, e.g., the DAISI system can be miniaturized to fit in a relatively small housing or compartment. For example, the components of the DAISI system can be sized and shaped to fit within small dimensions and can have a mass sufficiently small to enable the human user to carry or wear the system without undue exertion. As explained herein, in some embodiments, the DAISI system can be sized and shaped to fit within a volume of less than about 300 cubic inches, or in some embodiments, less than about 200 cubic inches. In still other embodiments, the DAISI system can be sized and shaped to fit within a volume less than about 100 cubic inches. For example, in some arrangements, the DAISI system can be sized and shaped to fit within a volume in a range of about 50 cubic inches to about 300 cubic inches. In other arrangements, the DAISI system can be sized and shaped to fit within a volume in a range of about 80 cubic inches to about 200 cubic inches.

Advantageously, such a portable and/or wearable DAISI system can enable the user to monitor installations in remote locations and to detect the presence of various gases (e.g., poisonous gases) in real-time. Further, the portable DAISI system can enable the user to travel to different installations to monitor the presence of gases or chemicals in multiple locations. For example, the user may travel to an oil drilling installation in which oil is pumped from the ground. The user can carry or attach the portable DAISI system to his or her clothing or body (e.g., by way of a clip, hat, etc.) and can activate the system while he or she is on-site. Optical components on board the portable DAISI system can capture one or more snapshot multispectral images of portions of the installation susceptible to gas or chemical leaks. Computing units on board the portable DAISI system can process the captured multispectral image data to detect and/or classify gases or chemicals present at the site. A communications module can notify the user of the detected gases. For example, in various embodiments, the communications module can send a notification to a user interface (such as a set of computing eyeglasses, a mobile computing device such as a mobile smartphone, a tablet computing device, a laptop computing device, or any other suitable interface), and the user interface can display information about the detected gases to the user in real-time, e.g., at the oil drilling installation.

II. Examples of Divided Aperture Infrared Spectral Imagers Systems

FIG. 1 provides a diagram schematically illustrating spatial and spectral division of incoming light by an embodiment 100 of a divided aperture infrared spectral imager (DAISI) system that can image an object 110 possessing IR spectral signature(s). The system 100 includes a front objective lens 124, an array of optical filters 130, an array of reimaging lenses 128 and a detector array 136. In various embodiments, the detector array 136 can include a single FPA or an array of FPAs. Each detector in the detector array 136 can be disposed at the focus of each of the lenses in the array of reimaging lenses 128. In various embodiments, the detector array 136 can include a plurality of photo-sensitive devices. In some embodiments, the plurality of photo-sensitive devices may comprise a two-dimensional imaging sensor array that is sensitive to radiation having wavelengths between 1 μm and 20 μm (for example, in near infra-red wavelength range, mid infra-red wavelength range, or long infra-red wavelength range,). In various embodiments, the plurality of photo-sensitive devices can include CCD or CMOS sensors, bolometers, microbolometers or other detectors that are sensitive to infra-red radiation.

An aperture of the system 100 associated with the front objective lens system 124 is spatially and spectrally divided by the combination of the array of optical filters 130 and the array of reimaging lenses 128. In various embodiments, the combination of the array of optical filters 130 and the array of reimaging lenses 128 can be considered to form a spectrally divided pupil that is disposed forward of the optical detector array 136. The spatial and spectral division of the aperture into distinct aperture portions forms a plurality of optical channels 120 along which light propagates. In various embodiments, the array 128 of re-imaging lenses 128a and the array of spectral filters 130 which respectively correspond to the distinct optical channels 120. The plurality of optical channels 120 can be spatially and/or spectrally distinct. The plurality of optical channels 120 can be formed in the object space and/or image space. In one implementation, the distinct channels 120 may include optical channels that are separated angularly in space. The array of spectral filters 130 may additionally include a filter-holding aperture mask (comprising, for example, IR light-blocking materials such as ceramic, metal, or plastic). Light from the object 110 (for example a cloud of gas), the optical properties of which in the IR are described by a unique absorption, reflection and/or emission spectrum, is received by the aperture of the system 100. This light propagates through each of the plurality of optical channels 120 and is further imaged onto the optical detector array 136. In various implementations, the detector array 136 can include at least one FPA. In various embodiments, each of the re-imaging lenses 128a can be spatially aligned with a respectively-corresponding spectral region. In the illustrated implementation, each filter element from the array of spectral filters 130 corresponds to a different spectral region. Each re-imaging lens 128a and the corresponding filter element of the array of spectral filter 130 can coincide with (or form) a portion of the divided aperture and therefore with respectively-corresponding spatial channel 120. Accordingly, in various embodiment an imaging lens 128a and a corresponding spectral filter can be disposed in the optical path of one of the plurality of optical channels 120. Radiation from the object 110 propagating through each of the plurality of optical channels 120 travels along the optical path of each re-imaging lens 128a and the corresponding filter element of the array of spectral filter 130 and is incident on the detector array (e.g., FPA component) 136 to form a single image (e.g., sub-image) of the object 110. The image formed by the detector array 136 generally includes a plurality of sub-images formed by each of the optical channels 120. Each of the plurality of sub-images can provide different spatial and spectral information of the object 110. The different spatial information results from some parallax because of the different spatial locations of the smaller apertures of the divided aperture. In various embodiments, adjacent sub-images can be characterized by close or substantially equal spectral signatures. The detector array (e.g., FPA component) 136 is further operably connected with a processor 150 (not shown). The processor 150 can be programmed to aggregate the data acquired with the system 100 into a spectral data cube. The data cube represents, in spatial (x, y) and spectral (λ) coordinates, an overall spectral image of the object 110 within the spectral region defined by the combination of the filter elements in the array of spectral filters 130. Additionally, in various embodiments, the processor or processing electronics 150 may be programmed to determine the unique absorption characteristic of the object 110. Also, the processor/processing electronics 150 can, alternatively or in addition, map the overall image data cube into a cube of data representing, for example, spatial distribution of concentrations, c, of targeted chemical components within the field of view associated with the object 110.

Various implementations of the embodiment 100 can include an optional moveable temperature-controlled reference source 160 including, for example, a shutter system comprising one or more reference shutters maintained at different temperatures. The reference source 160 can include a heater, a cooler or a temperature-controlled element configured to maintain the reference source 160 at a desired temperature. For example, in various implementations, the embodiment 100 can include two reference shutters maintained at different temperatures. The reference source 160 is removably and, in one implementation, periodically inserted into an optical path of light traversing the system 100 from the object 110 to the detector array (e.g., FPA component) 136 along at least one of the channels 120. The removable reference source 160 thus can block such optical path. Moreover, this reference source 160 can provide a reference IR spectrum to recalibrate various components including the detector array 136 of the system 100 in real time. The configuration of the moveable reference source 160 is further discussed below.

In the embodiment 100, the front objective lens system 124 is shown to include a single front objective lens positioned to establish a common field-of-view (FOV) for the reimaging lenses 128a and to define an aperture stop for the whole system. In this specific case, the aperture stop substantially spatially coincides with and/or is about the same size as or slightly larger than the plurality of smaller limiting apertures corresponding to different optical channels 120. As a result, the positions for spectral filters of the different optical channels 120 coincide with the position of the aperture stop of the whole system, which in this example is shown as a surface between the lens system 124 and the array 128 of the reimaging lenses 128a. In various implementations, the lens system 124 can be an objective lens 124. However, the objective lens 124 is optional and various embodiments of the system 100 need not include the objective lens 124. In various embodiments, the objective lens 124 can slightly shift the images obtained by the different detectors in the array 136 spatially along a direction perpendicular to optical axis of the lens 124, thus the functionality of the system 100 is not necessarily compromised when the objective lens 124 is not included. Generally, however, the field apertures corresponding to different optical channels may be located in the same or different planes. These field apertures may be defined by the aperture of the reimaging lens 128a and/or filters in the divided aperture 130 in certain implementations. In one implementation, the field apertures corresponding to different optical channels can be located in different planes and the different planes can be optical conjugates of one another. Similarly, while all of the filter elements in the array of spectral filters 130 of the embodiment 100 are shown to lie in one plane, generally different filter elements of the array of spectral filter 130 can be disposed in different planes. For example, different filter elements of the array of spectral filters 130 can be disposed in different planes that are optically conjugate to one another. However, in other embodiments, the different filter elements can be disposed in non-conjugate planes.

Figure 2:
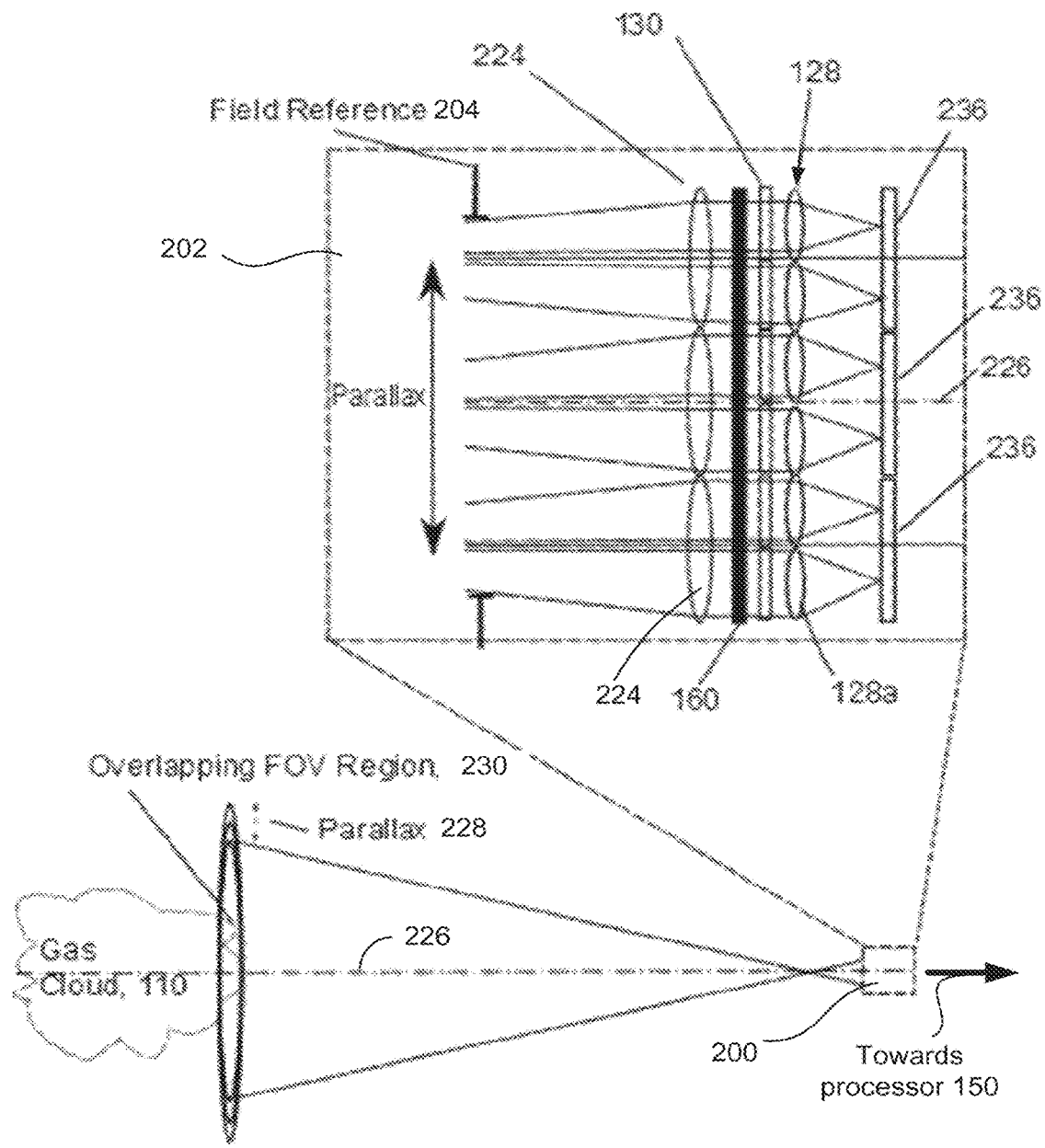
FIG. 2 shows an embodiment with a divided front objective lens and an array of infrared sensing FPAs.

In contrast to the embodiment 100, the front objective lens 124 need not be a single optical element, but instead can include a plurality of lenses 224 as shown in an embodiment 200 of the DAISI imaging system in FIG. 2. These lenses 224 are configured to divide an incoming optical wavefront from the object 110. For example, the array of front objective lenses 224 can be disposed so as to receive an IR wavefront emitted by the object that is directed toward the DAISI system. The plurality of front objective lenses 224 divide the wavefront spatially into non-overlapping sections. FIG. 2 shows three objective lenses 224 in a front optical portion of the optical system contributing to the spatial division of the aperture of the system in this example. The plurality of objective lenses 224, however, can be configured as a two-dimensional (2D) array of lenses. FIG. 2 presents a general view of the imaging system 200 and the resultant field of view of the imaging system 200. An exploded view 202 of the imaging system 200 is also depicted in greater detail in a figure inset of FIG. 2. As illustrated in the detailed view 202, the embodiment of the imaging system 200 includes a field reference 204 at the front end of the system. The field reference 204 can be used to truncate the field of view. The configuration illustrated in FIG. 2 has an operational advantage over embodiment 100 of FIG. 1 in that the overall size and/or weight and/or cost of manufacture of the embodiment 200 can be greatly reduced because the objective lens is smaller. Each pair of the lenses in the array 224 and the array 128 is associated with a field of view (FOV). Each pair of lenses in the array 224 and the array 128 receives light from the object from a different angle. Accordingly, the FOV of the different pairs of lenses in the array 224 and the array 128 do not completely overlap as a result of parallax. As the distance between the imaging system 200 (portion 202) and the object 110 increases, the overlapping region 230 between the FOVs of the individual lenses 224 increases while the amount of parallax 228 remains approximately the same, thereby reducing its effect on the system 200. When the ratio of the parallax-to-object-distance is substantially equal to the pixel-size-to-system-focal-length ratio then the parallax effect may be considered to be negligible and, for practical purposes, no longer distinguishable. While the lenses 224 are shown to be disposed substantially in the same plane, optionally different objective lenses in the array of front objective lenses 224 can be disposed in more than one plane. For example, some of the individual lenses 224 can be displaced with respect to some other individual lenses 224 along the axis 226 (not shown) and/or have different focal lengths as compared to some other lenses 224. As discussed below, the field reference 204 can be useful in calibrating the multiple detectors 236.

In one implementation, the front objective lens system such as the array of lenses 224 is configured as an array of lenses integrated or molded in association with a monolithic substrate. Such an arrangement can reduce the costs and complexity otherwise accompanying the optical adjustment of individual lenses within the system. An individual lens 224 can optionally include a lens with varying magnification. As one example, a pair of thin and large diameter Alvarez plates can be used in at least a portion of the front objective lens system. Without any loss of generality, the Alvarez plates can produce a change in focal length when translated orthogonally with respect to the optical beam.

In further reference to FIG. 1, the detector array 136 (e.g., FPA component) configured to receive the optical data representing spectral signature(s) of the imaged object 110 can be configured as a single imaging array (e.g., FPA) 136. This single array may be adapted to acquire more than one image (formed by more than one optical channel 120) simultaneously. Alternatively, the detector array 136 may include a FPA unit. In various implementations, the FPA unit can include a plurality of optical FPAs. At least one of these plurality of FPAs can be configured to acquire more than one spectrally distinct image of the imaged object. For example, as shown in the embodiment 200 of FIG. 2, in various embodiments, the number of FPAs included in the FPA unit may correspond to the number of the front objective lenses 224. In the embodiment 200 of FIG. 2, for example, three FPAs 236 are provided corresponding to the three objective lenses 224. In one implementation of the system, the FPA unit can include an array of microbolometers. The use of multiple microbolometers advantageously allows for an inexpensive way to increase the total number of detection elements (i.e. pixels) for recording of the three-dimensional data cube in a single acquisition event (i.e. one snapshot). In various embodiments, an array of microbolometers more efficiently utilizes the detector pixels of the array of FPAs (e.g., each FPA) as the number of unused pixels is reduced, minimized and/or eliminated between the images that may exist when using a single microbolometer.

FIG. 3A illustrates schematically an embodiment 300 of the imaging system in which the number of the front objective lenses 324a in the lens array 324, the number of re-imaging lenses 128a in the lens array 128, and the number of FPAs 336 are the same. So configured, each combination of respectively corresponding front objective lens 324, re-imaging lens 128a, and FPAs 336 constitutes an individual imaging channel. Such a channel is associated with acquisition of the IR light transmitted from the object 110 through an individual filter element of the array of optical filters 130. A field reference 338 of the system 300 is configured to have a uniform temperature across its surface and be characterized by a predetermined spectral curve of radiation emanating therefrom. In various implementations, the field reference 338 can be used as a calibration target to assist in calibrating or maintaining calibration of the FPA. Accordingly, in various implementations, the field reference 338 is used for dynamically adjusting the data output from each FPA 336 after acquisition of light from the object 110. This dynamic calibration process helps provide that output of the different (e.g., most, or each of the) FPA 336 represents correct acquired data, with respect to the other FPAs 336 for analysis, as discussed below in more detail.

FIG. 3B illustrates the plan view perpendicular to the axis 226 of an embodiment 300 of the imaging system illustrated in FIG. 3A. For the embodiment shown in FIG. 3B, the optical components (e.g., objective lenses 324a, filter elements of the array of spectral filters 130, re-imaging lenses 128a and FPA units 336) are arranged as a 4×3 array. In one implementation, the 4×3 array 340 of optical components (lenses 324a, 128a; detector elements 336) is used behind the temperature controlled reference target 160. The field reference aperture 338 can be adapted to obscure and/or block a peripheral portion of the bundle of light propagating from the object 110 towards the FPA units 336. As a result, the field reference 338 obscures and/or blocks the border or peripheral portion(s) of the images of the object 110 formed on the FPA elements located along the perimeter 346 of the detector system. Generally, two elements of the FPA unit will produce substantially equal values of digital counts when they are used to observe the same portion of the scene in the same spectral region using the same optical train. If any of these input parameters (for example, scene to be observed, spectral content of light from the scene, or optical elements delivering light from the scene to the two detector elements) differ, the counts associated with the elements of the FPA unit will differ as well. Accordingly, and as an example, in a case when the two FPAs of the FPA unit 336 (such as those denoted as #6 and #7 in FIG. 3B) remain substantially un-obscured by the field reference 338, the outputs from these FPAs can be dynamically adjusted to the output from one of the FPAs located along perimeter 346 (such as, for example, the FPA element #2 or FPA element #11) that processes light having similar spectral characteristics.

Figure 4:
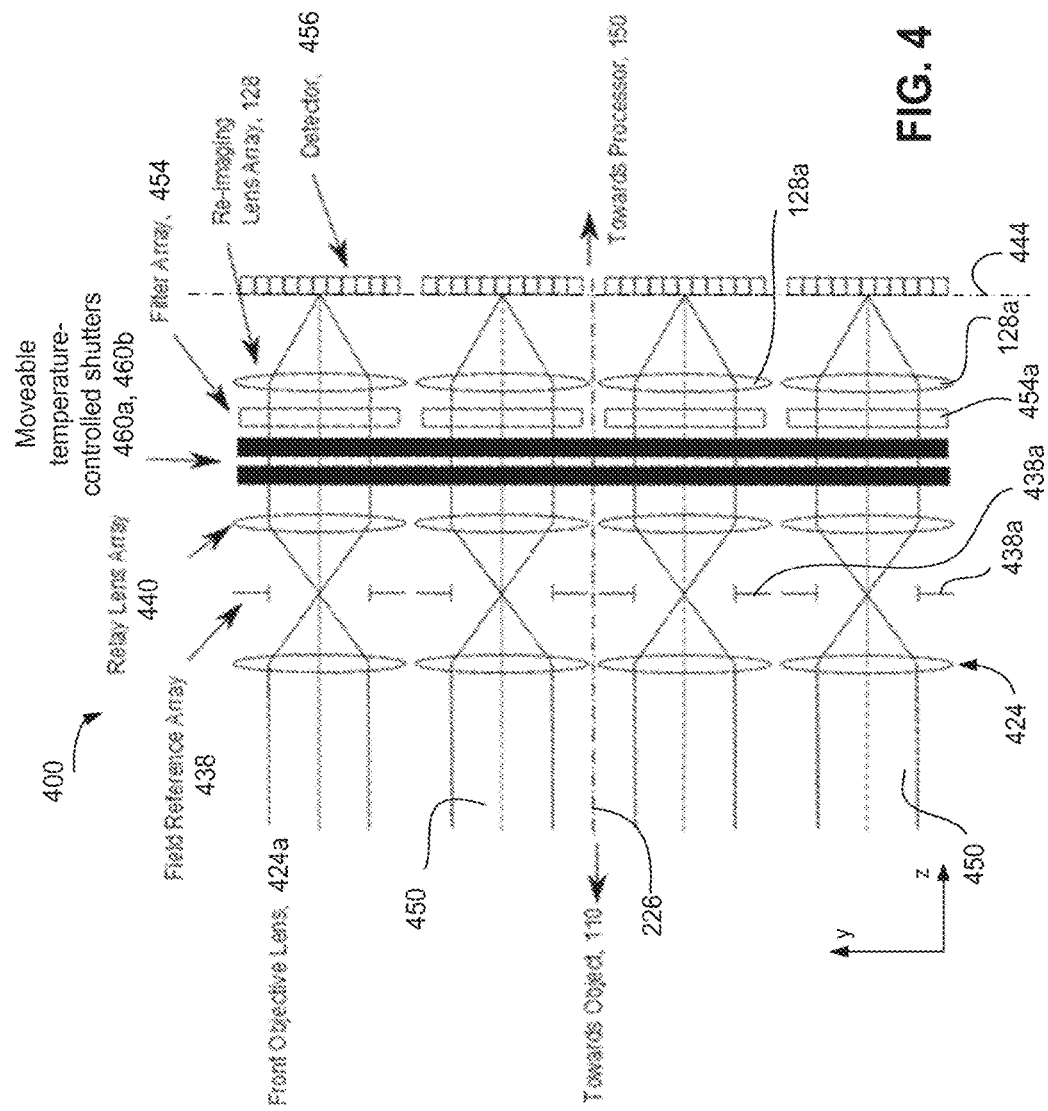
FIG. 4 is a diagram of the embodiment employing an array of field references (e.g., field stops that can be used as references for calibration) and an array of respectively corresponding relay lenses.

FIG. 4 illustrates schematically a portion of another embodiment of an imaging system 400 that contains an array 424 of front objective lenses 424a. The array 424 of lenses 424a adapted to receive light from the object 110 and relay the received light to the array 128 of re-imaging lenses 128a through an array 438 of field references (or field stops) 438a, and through an array 440 of the relay lenses. The spectral characteristics of the field references/field stops 438a can be known. The field references 438a are disposed at corresponding intermediate image planes defined, with respect to the object 110, by respectively corresponding front objective lenses 424a. When refractive characteristics of all of the front objective lenses 424a are substantially the same, all of the field references 438a are disposed in the same plane. A field reference 438a of the array 438 obscures (or casts a shadow on) a peripheral region of a corresponding image (e.g., sub-image) formed at the detector plane 444 through a respectively corresponding spatial imaging channel 450 of the system 400 prior to such image being spectrally processed by the processor 150. The array 440 of relay lenses then transmits light along each of the imaging channels 450 through different spectral filters 454a of the filter array 454, past the calibration apparatus that includes two temperature controlled shutters 460a, 460b, and then onto the detector module 456. In various embodiments, the detector module 456 can include a microbolometer array or some other IR FPA.

The embodiment 400 has several operational advantages. It is configured to provide a spectrally known object within every image (e.g., sub-image) and for every snapshot acquisition which can be calibrated against. Such spectral certainty can be advantageous when using an array of IR FPAs like microbolometers, the detection characteristics of which can change from one imaging frame to the next due to, in part, changes in the scene being imaged as well as the thermal effects caused by neighboring FPAs. In various embodiments, the field reference array 438 of the embodiment 400—can be disposed within the Rayleigh range (approximately corresponding to the depth of focus) associated with the front objective lenses 424, thereby removing unusable blurred pixels due to having the field reference outside of this range. Additionally, the embodiment 400 of FIG. 4 can be more compact than, for example, the configuration 300 of FIG. 3A. In the system shown in FIG. 3A, for example, the field reference 338 may be separated from the lens array 324 by a distance greater than several (for example, five) focal lengths to minimize/reduce blur contributed by the field reference to an image formed at a detector plane.

In various embodiments, the multi-optical FPA unit of the IR imaging system can additionally include an FPA configured to operate in a visible portion of the spectrum. In reference to FIG. 1, for example, an image of the scene of interest formed by such visible-light FPA may be used as a background to form a composite image by overlapping an IR image with the visible-light image. The IR image may be overlapped virtually, with the use of a processor and specifically-designed computer program product enabling such data processing, or actually, by a viewer. The IR image may be created based on the image data acquired by the individual FPAs 136. The so-formed composite image facilitates the identification of the precise spatial location of the target species, the spectral signatures of which the system is able to detect/recognize.

Optical Filters.

The optical filters, used with an embodiment of the system, that define spectrally-distinct IR image (e.g., sub-image) of the object can employ absorption filters, interference filters, and Fabry-Perot etalon based filters, to name just a few. When interference filters are used, the image acquisition through an individual imaging channel defined by an individual re-imaging lens (such as a lens 128a of FIGS. 1, 2, 3, and 4) may be carried out in a single spectral bandwidth or multiple spectral bandwidths. Referring again to the embodiments 100, 200, 300, 400 of FIGS. 1 through 4, and in further reference to FIG. 3B, examples of a 4-by-3 array of spectral filters 130 is shown in FIGS. 5A and 5B. Individual filters 1 through 12 are juxtaposed with a supporting opto-mechanical element (not shown) to define a filter-array plane that is oriented, in operation, substantially perpendicularly to the general optical axis 226 of the imaging system. In various implementations, the individual filters 1 through 12 need not be discrete optical components. Instead, the individual filters 1 through 12 can comprise one or more coatings that are applied to one or more surfaces of the reimaging lenses (such as a lens 128a of FIGS. 1, 2, 3, and 4) or the surfaces of one or more detectors.

Figure 6A:
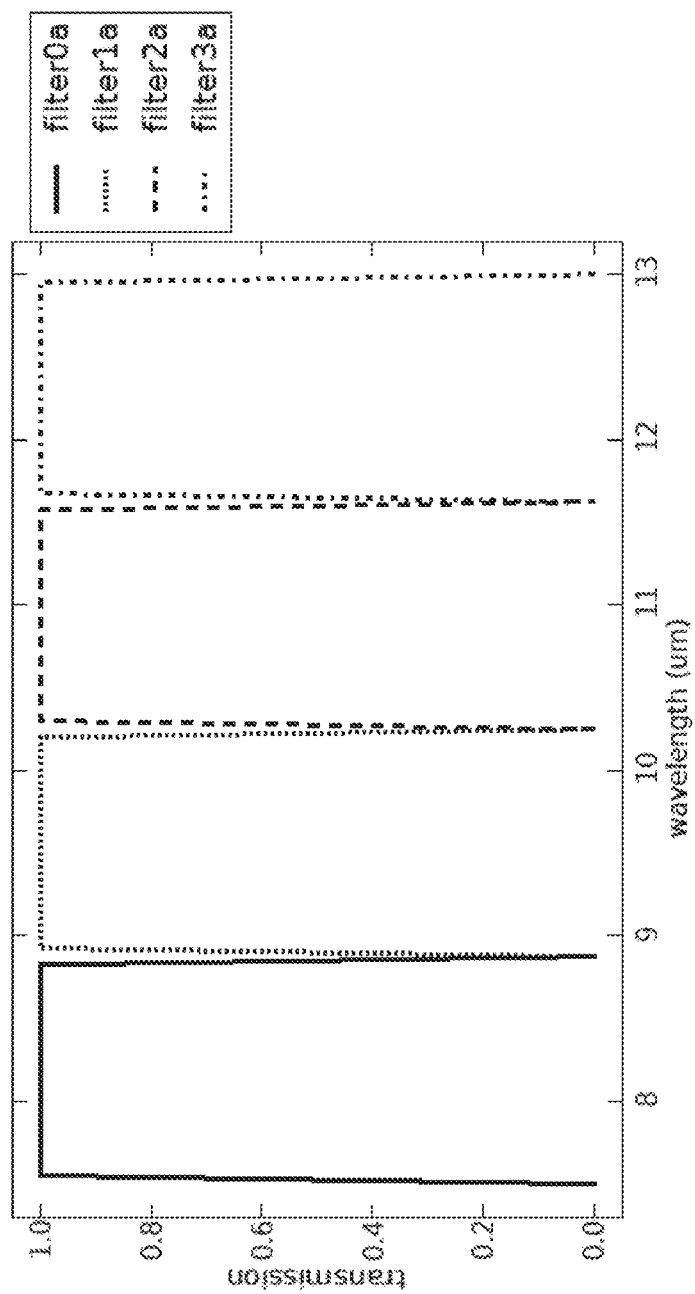
FIG. 6A depicts theoretical plots of transmission characteristics of a combination of band-pass filters used with an embodiment of the system.
Figure 6B:
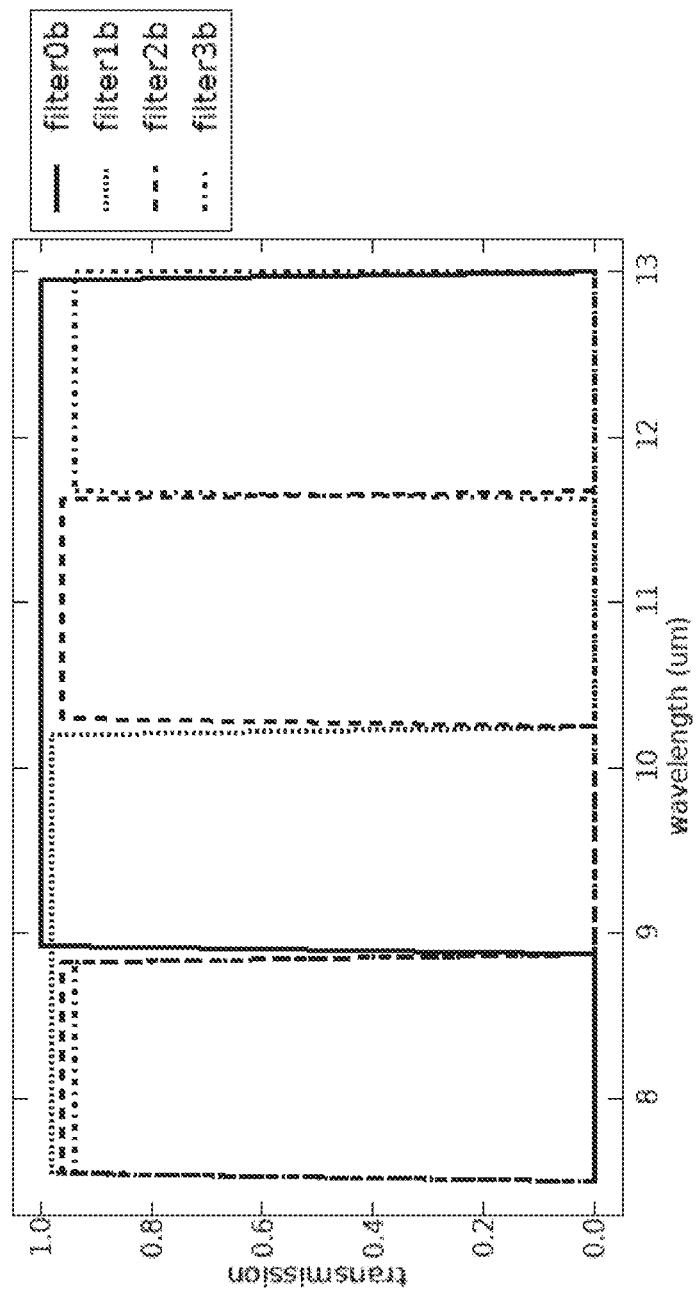
FIG. 6B depicts theoretical plots of transmission characteristics of a spectrally multiplexed notch-pass filter combination used in an embodiment of the system.

The optical filtering configuration of various embodiments disclosed herein may advantageously use a bandpass filter defining a specified spectral band. Any of the filters $0a$ through $3a$, the transmission curves of which are shown in FIG. 6A may, for example, be used. The filters may be placed in front of the optical FPA (or generally, between the optical FPA and the object). In particular, and in further reference to FIGS. 1, 2 3, and 4, when optical detector arrays 136, 236, 336, 456 include microbolometers, the predominant contribution to noise associated with image acquisition is due to detector noise. To compensate and/or reduce the noise, various embodiments disclosed herein utilize spectrally-multiplexed filters. In various implementations, the spectrally-multiplexed filters can comprise a plurality of long pass filters, a plurality long pass filters, a plurality of band pass filters and any combinations thereof. An example of the spectral transmission characteristics of spectrally-multiplexed filters $0b$ through $3d$ for use with various embodiments of imaging systems disclosed herein is depicted in FIG. 6B. Filters of FIG. 6C can be referred to as long-wavelength pass, LP filters. An LP filter generally attenuates shorter wavelengths and transmits (passes) longer wavelengths (e.g., over the active range of the target IR portion of the spectrum). In various embodiments, short-wavelength-pass filters, SP, may also be used. An SP filter generally attenuates longer wavelengths and transmits (passes) shorter wavelengths (e.g., over the active range of the target IR portion of the spectrum). At least in part due to the snap-shot/non-scanning mode of operation, embodiments of the imaging system described herein can use less sensitive microbolometers without compromising the SNR. The use of microbolometers, as detector-noise-limited devices, in turn not only benefits from the use of spectrally multiplexed filters, but also does not require cooling of the imaging system during normal operation.

Referring again to FIGS. 6A, 6B, 6C, and 6D, each of the filters ($0b$ . . . $3d$) transmits light in a substantially wider region of the electromagnetic spectrum as compared to those of the filters ($0a$ . . . $3a$). Accordingly, when the spectrally-multiplexed set of filters ($0b$ . . . $0d$) is used with an embodiment of the imaging system, the overall amount of light received by the FPAs (for example, 236, 336) is larger than would be received when using the bandpass filters ($0a$ . . . $4a$). This "added" transmission of light defined by the use of the spectrally-multiplexed LP (or SP) filters facilitates an increase of the signal on the FPAs above the level of the detector noise. Additionally, by using, in an embodiment of the imaging system, filters having spectral bandwidths greater than those of band-pass filters, the uncooled FPAs of the embodiment of the imaging system experience less heating from radiation incident thereon from the imaged scene and from radiation emanating from the FPA in question itself. This reduced heating is due to a reduction in the back-reflected thermal emission(s) coming from the FPA and reflecting off of the filter from the non-band-pass regions. As the transmission region of the multiplexed LP (or SP) filters is wider, such parasitic effects are reduced thereby improving the overall performance of the FPA unit.

In one implementation, the LP and SP filters can be combined, in a spectrally-multiplexed fashion, in order to increase or maximize the spectral extent of the transmission region of the filter system of the embodiment.

The advantage of using spectrally multiplexed filters is appreciated based on the following derivation, in which a system of M filters is examined (although it is understood that in practice an embodiment of the invention can employ any number of filters). As an illustrative example, the case of M=7 is considered. Analysis presented below relates to one spatial location in each of the images (e.g., sub-images) formed by the differing imaging channels (e.g., different optical channels 120) in the system. A similar analysis can be performed for each point at an image (e.g., sub-image), and thus the analysis can be appropriately extended as required.

The unknown amount of light within each of the M spectral channels (corresponding to these M filters) is denoted with $f_1$, $f_2$, $f_3$, $f_3$ . . . $f_M$, and readings from corresponding detector elements receiving light transmitted by each filter is denoted as $g_1$, $g_2$, $g_3$ . . . $g_M$, while measurement errors are represented by $n_1$, $n_2$, $n_3$, . . . $n_M$. Then, the readings at the seven FPA pixels each of which is optically filtered by a corresponding band-pass filter of FIG. 6A can be represented by:

$$g_1 = f_1 + n_1,$$

$$g_2 = f_2 + n_2,$$

$$g_3 = f_3 + n_3,$$

$$g_4 = f_4 + n_4,$$

$$g_5 = f_5 + n_5,$$

$$g_6 = f_6 + n_6,$$

$$g_7 = f_7 + n_7,$$

These readings (pixel measurements) $g_i$ are estimates of the spectral intensities $f_i$. The estimates $g_i$ are not equal to the corresponding $f_i$ values because of the measurement errors $n_i$. However, if the measurement noise distribution has zero mean, then the ensemble mean of each individual measurement can be considered to be equal to the true value, i.e. $\langle g_i \rangle = f_i$. Here, the angle brackets indicate the operation of calculating the ensemble mean of a stochastic variable. The variance of the measurement can, therefore, be represented as:

$$\langle (g_i - f_i)^2 \rangle = \langle n_i^2 \rangle = \sigma^2$$

In embodiments utilizing spectrally-multiplexed filters, in comparison with the embodiments utilizing band-pass filters, the amount of radiant energy transmitted by each of the spectrally-multiplexed LP or SP filters towards a given detector element can exceed that transmitted through a spectral band of a band-pass filter. In this case, the intensities of light corresponding to the independent spectral bands can be reconstructed by computational means. Such embodiments can be referred to as a "multiplex design".

One matrix of such "multiplexed filter" measurements includes a Hadamard matrix requiring "negative" filters that may not be necessarily appropriate for the optical embodiments disclosed herein. An S-matrix approach (which is restricted to having a number of filters equal to an integer that is multiple of four minus one) or a row-doubled Hadamard matrix (requiring a number of filters to be equal to an integer multiple of eight) can be used in various embodiments. Here, possible numbers of filters using an S-matrix setup are 3, 7, 11, etc. and, if a row-doubled Hadamard matrix setup is used, then the possible number of filters is 8, 16, 24, etc. For example, the goal of the measurement may be to measure seven spectral band $f_i$ intensities using seven measurements $g_i$ as follows:

$$g_1 = f_1 + 0 + f_3 + 0 + f_5 + 0 + f_7 + n_1,$$

$$g_2 = 0 + f_2 + f_3 + 0 + 0 + f_5 + f_7 + n_2,$$

$$g_3 = f_1 + f_2 + 0 + 0 + f_5 + 0 + f_7 + n_3,$$

$$g_4 = 0 + 0 + 0 + f_4 + f_5 + f_7 + f_8 + n_4,$$

$$g_5 = f_1 + 0 + f_3 + f_4 + 0 + f_6 + 0 + n_5,$$

$$g_6 = 0 + f_2 + f_3 + f_4 + f_5 + 0 + 0 + n_6,$$

$$g_7 = f_1 + f_2 + 0 + f_4 + 0 + 0 + f_7 + n_7,$$

Optical transmission characteristics of the filters described above are depicted in FIG. 6B. Here, a direct estimate of the $f_i$ is no longer provided through a relationship similar to $\langle g_i \rangle = f_i$. Instead, if a "hat" notation is used to denote an estimate of a given value, then a linear combination of the measurements can be used such as, for example, $$\hat{f}_1 = \frac{1}{4}(+g_1 - g_2 + g_3 - g_4 + g_5 - g_6 + g_7),$$

$$\hat{f}_2 = \frac{1}{4}(-g_1 + g_2 + g_3 - g_4 - g_5 + g_6 + g_7),$$

$$\hat{f}_3 = \frac{1}{4}(+g_1 + g_2 - g_3 - g_4 + g_5 + g_6 - g_7),$$

$$\hat{f}_4 = \frac{1}{4}(-g_1 - g_2 - g_3 + g_4 + g_5 + g_6 + g_7),$$

$$\hat{f}_5 = \frac{1}{4}(+g_1 - g_2 + g_3 + g_4 - g_5 + g_6 - g_7),$$

$$\hat{f}_6 = \frac{1}{4}(-g_1 + g_2 + g_3 + g_4 + g_5 - g_6 + g_7),$$

$$\hat{f}_7 = \frac{1}{4}(+g_1 + g_2 - g_3 + g_4 - g_5 - g_6 + g_7),$$

These $\hat{f}_i$ are unbiased estimates when the $n_i$ are zero mean stochastic variables, so that $\langle \hat{f}_i - f_i \rangle = 0$. The measurement variance corresponding to $i^{th}$ measurement is given by the equation below:

$$\langle (\hat{f}_i - f_i)^2 \rangle = \frac{7}{16}\sigma^2$$

From the above equation, it is observed that by employing spectrally-multiplexed system the signal-to-noise ratio (SNR) of a measurement is improved by a factor of $\sqrt{16/7} = 1.51\sqrt{7/16} = 0.66$.

For N channels, the SNR improvement achieved with a spectrally-multiplexed system can be expressed as $(N+1)/(2\sqrt{N})$. For example, an embodiment employing 12 spectral channels (N=12) is characterized by a SNR improvement, over a non-spectrally-multiplexed system, comprising a factor of up to 1.88.

Figure 6C:
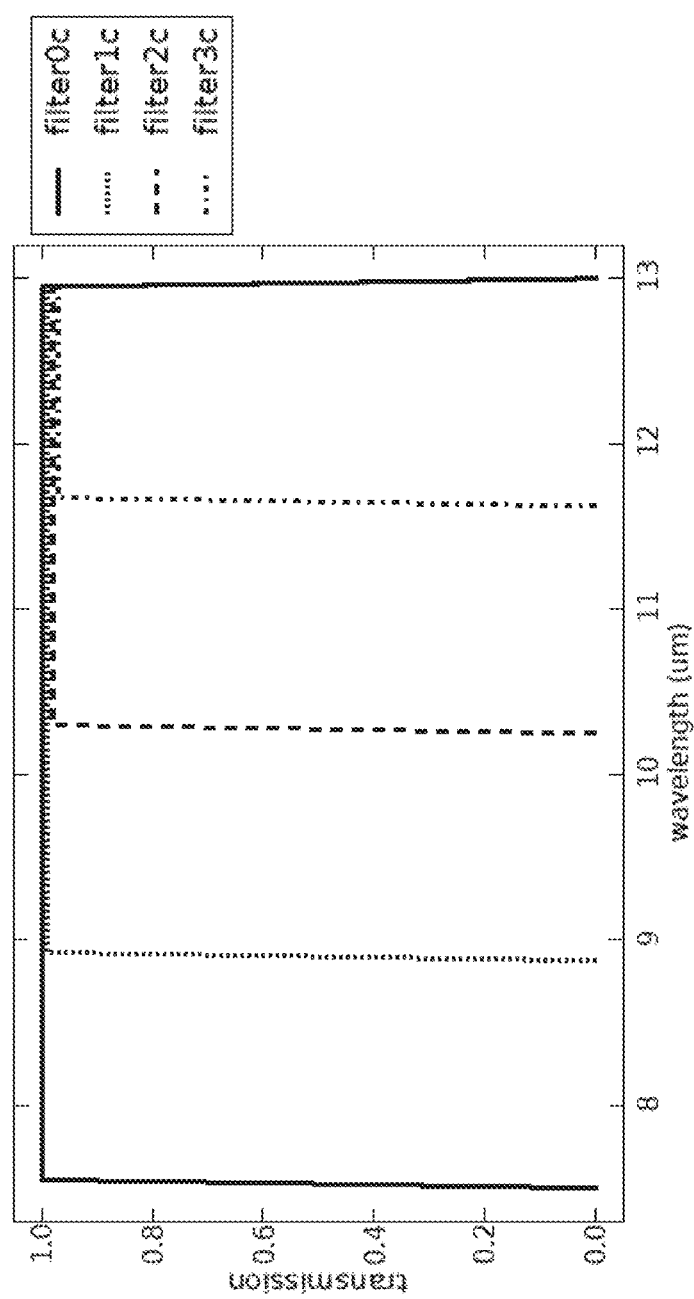
FIG. 6C shows theoretical plots of transmission characteristics of spectrally multiplexed long-pass filter combination used in an embodiment of the system.
Figure 6D:
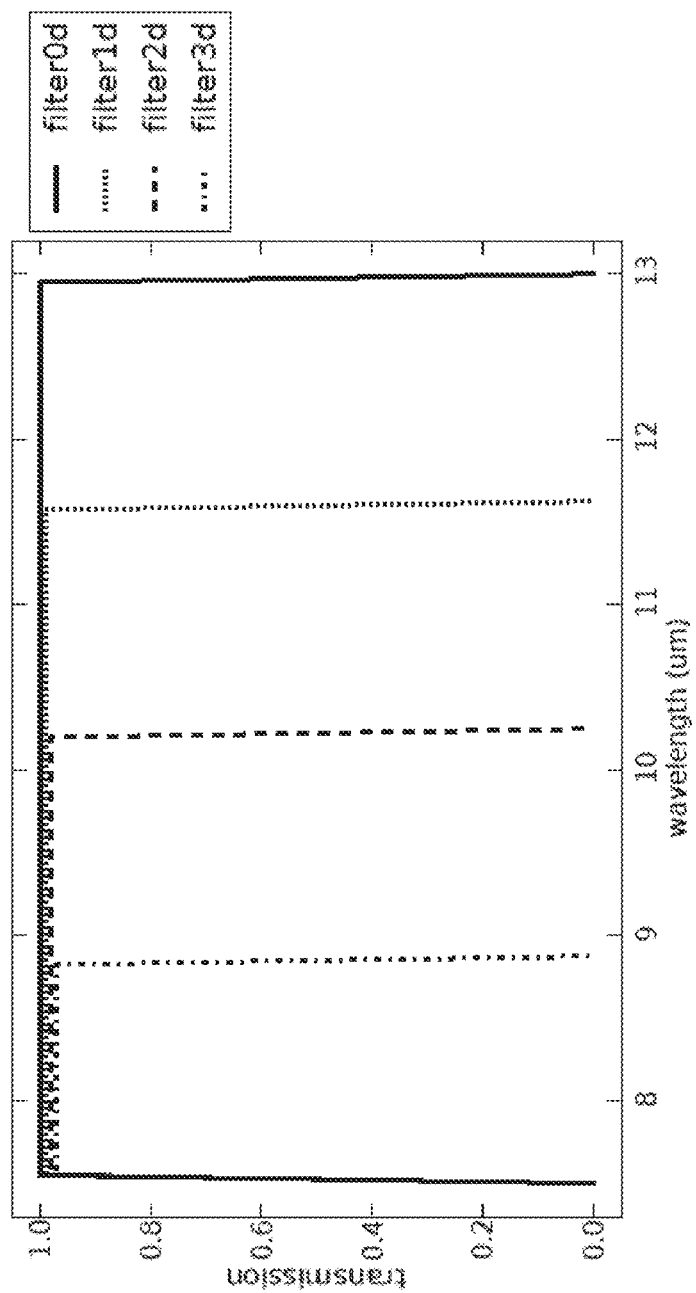
FIG. 6D shows theoretical plots of transmission characteristics of spectrally multiplexed short-pass filter combination used in an embodiment of the system.

Two additional examples of related spectrally-multiplexed filter arrangements 0c through 3c and 0d through 3d that can be used in various embodiments of the imaging systems described herein are shown in FIGS. 6C and 6D, respectively. The spectrally-multiplexed filters shown in FIGS. 6C and 6D can be used in embodiments of imaging systems employing uncooled FPAs (such as microbolometers). FIG. 6C illustrates a set of spectrally-multiplexed long-wavelength pass (LP) filters used in the system. An LP filter generally attenuates shorter wavelengths and transmits (passes) longer wavelengths (e.g., over the active range of the target IR portion of the spectrum). A single spectral channel having a transmission characteristic corresponding to the difference between the spectral transmission curves of at least two of these LP filters can be used to procure imaging data for the data cube using an embodiment of the system described herein. In various implementations, the spectral filters disposed with respect to the different FPAs can have different spectral characteristics. In various implementations, the spectral filters may be disposed in front of only some of the FPAs while the remaining FPAs may be configured to receive unfiltered light. For example, in some implementations, only 9 of the 12 detectors in the 4×3 array of detectors described above may be associated with a spectral filter while the other 3 detectors may be configured to receive unfiltered light. Such a system may be configured to acquire spectral data in 10 different spectral channels in a single data acquisition event.

The use of microbolometers, as detector-noise-limited devices, in turn not only can benefit from the use of spectrally multiplexed filters, but also does not require cooling of the imaging system during normal operation. In contrast to imaging systems that include highly sensitive FPA units with reduced noise characteristics, the embodiments of imaging systems described herein can employ less sensitive microbolometers without compromising the SNR. This result is at least in part due to the snap-shot/non-scanning mode of operation.

As discussed above, an embodiment may optionally, and in addition to a temperature-controlled reference unit (for example temperature controlled shutters such as shutters 160, 460a, 460b), employ a field reference component (e.g., field reference aperture 338 in FIG. 3A), or an array of field reference components (e.g., filed reference apertures 438 in FIG. 4), to enable dynamic calibration. Such dynamic calibration can be used for spectral acquisition of one or more or every data cube. Such dynamic calibration can also be used for a spectrally-neutral camera-to-camera combination to enable dynamic compensation of parallax artifacts. The use of the temperature-controlled reference unit (for example, temperature-controlled shutter system 160) and field-reference component(s) facilitates maintenance of proper calibration of each of the FPAs individually and the entire FPA unit as a whole.

In particular, and in further reference to FIGS. 1, 2, 3, and 4, the temperature-controlled unit generally employs a system having first and second temperature zones maintained at first and second different temperatures. For example, shutter system of each of the embodiments 100, 200, 300 and 400 can employ not one but at least two temperature-controlled shutters that are substantially parallel to one another and transverse to the general optical axis 226 of the embodiment(s) 100, 200, 300, 400. Two shutters at two different temperatures may be employed to provide more information for calibration; for example, the absolute value of the difference between FPAs at one temperature as well as the change in that difference with temperature change can be recorded. Referring, for example, to FIG. 4, in which such multi-shutter structure is shown, the use of multiple shutters enables the user to create a known reference temperature difference perceived by the FPAs 456. This reference temperature difference is provided by the IR radiation emitted by the shutter(s) 460a, 460b when these shutters are positioned to block the radiation from the object 110. As a result, not only the offset values corresponding to each of the individual FPAs pixels can be adjusted but also the gain values of these FPAs. In an alternative embodiment, the system having first and second temperature zones may include a single or multi-portion piece. This single or multi-portion piece may comprise for example a plate. This piece may be mechanically-movable across the optical axis with the use of appropriate guides and having a first portion at a first temperature and a second portion at a second temperature.

Indeed, the process of calibration of an embodiment of the imaging system starts with estimating gain and offset by performing measurements of radiation emanating, independently, from at least two temperature-controlled shutters of known and different radiances. The gain and offset can vary from detector pixel to detector pixel. Specifically, first the response of the detector unit 456 to radiation emanating from one shutter is carried out. For example, the first shutter 460a blocks the FOV of the detectors 456 and the temperature $T_1$ is measured directly and independently with thermistors. Following such initial measurement, the first shutter 460a is removed from the optical path of light traversing the embodiment and another second shutter (for example, 460b) is inserted in its place across the optical axis 226 to prevent the propagation of light through the system. The temperature of the second shutter 460b can be different than the first shutter ($T_2 \neq T_1$). The temperature of the second shutter 460b is also independently measured with thermistors placed in contact with this shutter, and the detector response to radiation emanating from the shutter 460b is also recorded. Denoting operational response of FPA pixels (expressed in digital numbers, or "counts") as $g_i$ to a source of radiance $L_i$, the readings corresponding to the measurements of the two shutters can be expressed as:

$$g_1 = \gamma L_1(T_1) + g_{offset}$$

$$g_2 = \gamma L_2(T_2) + g_{offset}$$

Here, $g_{offset}$ is the pixel offset value (in units of counts), and $\gamma$ is the pixel gain value (in units of counts per radiance unit). The solutions of these two equations with respect to the two unknowns $g_{offset}$ and $\gamma$ can be obtained if the values of $g_1$ and $g_2$ and the radiance values $L_1$ and $L_2$ are available. These values can, for example, be either measured by a reference instrument or calculated from the known temperatures $T_1$ and $T_2$ together with the known spectral response of the optical system and FPA. For any subsequent measurement, one can then invert the equation(s) above in order to estimate the radiance value of the object from the detector measurement, and this can be done for each pixel in each FPA within the system.

As already discussed, and in reference to FIGS. 1 through 4, the field-reference apertures may be disposed in an object space or image space of the optical system, and dimensioned to block a particular portion of the IR radiation received from the object. In various implementations, the field-reference aperture, the opening of which can be substantially similar in shape to the boundary of the filter array (for example, and in reference to a filter array of FIGS. 3B, 5B—e.g., rectangular). The field-reference aperture can be placed in front of the objective lens (124, 224, 324, 424) at a distance that is at least several times (in one implementation—at least five times) larger than the focal length of the lens such that the field-reference aperture is placed closer to the object. Placing the field-reference aperture closer to the object can reduce the blurriness of the image. In the embodiment 400 of FIG. 4, the field-reference aperture can be placed within the depth of focus of an image conjugate plane formed by the front objective lens 424. The field reference, generally, can facilitate, effectuates and/or enable dynamic compensation in the system by providing a spectrally known and temporally-stable object within every scene to reference and stabilize the output from the different FPAs in the array.

Because each FPA's offset value is generally adjusted from each frame to the next frame by the hardware, comparing the outputs of one FPA with another can have an error that is not compensated for by the static calibration parameters $g_{offset}$ and $\gamma$ established, for example, by the movable shutters 160. In order to ensure that FPAs operate in radiometric agreement over time, it is advantageous for a portion of each detector array to view a reference source (such as the field reference 338 in FIG. 3A, for example) over a plurality of frames obtained over time. If the reference source spectrum is known a priori (such as a blackbody source at a known temperature), one can measure the response of each FPA to the reference source in order to estimate changes to the pixel offset value. However, the temperature of the reference source need not be known. In such implementations, dynamic calibration of the different detectors can be performed by monitoring the change in the gain and the offset for the various detectors from the time the movable shutters used for static calibration are removed. An example calculation of the dynamic offset proceeds as follows.

Among the FPA elements in an array of FPAs in an embodiment of the imaging system, one FPA can be selected to be the "reference FPA". The field reference temperature measured by all the other FPAs can be adjusted to agree with the field reference temperature measured by the reference as discussed below. The image obtained by each FPA includes a set of pixels obscured by the field reference 338. Using the previously obtained calibration parameters $g_{offset}$ and $\gamma$ (the pixel offset and gain), the effective blackbody temperature $T_i$ of the field reference as measured by each FPA is estimated using the equation below:

$$T_i = \text{mean}\{(g + \Delta g_i + g_{offset})/\gamma\} = \text{mean}\{(g - g_{offset})/\gamma\} + \Delta T_i$$

Using the equation above, the mean value over all pixels that are obscured by the field reference is obtained. In the above equation $\Delta g_i$ is the difference in offset value of the current frame from $\Delta g_{offset}$ obtained during the calibration step. For the reference FPA, $\Delta g_i$ can be simply set to zero. Then, using the temperature differences measured by each FPA, one obtains $$T_i - T_{ref} = \text{mean}\{(g + \Delta g_i + g_{offset})/\gamma\} + \Delta T_i - \text{mean}\{(g - g_{offset})/\gamma\} + \Delta T_i$$

Once $\Delta T_i$ for each FPA is measured, its value can be subtracted from each image in order to force operational agreement between such FPA and the reference FPA. While the calibration procedure has been discussed above in reference to calibration of temperature, a procedurally similar methodology of calibration with respect to radiance value can also be implemented.

Examples of Methodology of Measurements.

Prior to optical data acquisition using an embodiment of the IR imaging system as described herein, one or more, most, or potentially all the FPAs of the system can be calibrated. For example, greater than 50%, 60%, 70%, 80% or 90% of the FPAs 336 can be initially calibrated. As shown in FIG. 3A, these FPAs 336 may form separate images of the object using light delivered in a corresponding optical channel that may include the combination of the corresponding front objective and re-imaging lenses 324, 128. The calibration procedure can allow formation of individual images in equivalent units (so that, for example, the reading from the FPA pixels can be re-calculated in units of temperature or radiance units, etc.). Moreover, the calibration process can also allow the FPAs (e.g., each of the FPAs) to be spatially co-registered with one another so that a given pixel of a particular FPA can be optically re-mapped through the optical system to the same location at the object as the corresponding pixel of another FPA.

To achieve at least some of these goals, a spectral differencing method may be employed. The method involves forming a difference image from various combinations of the images from different channels. In particular, the images used to form difference images can be registered by two or more different FPAs in spectrally distinct channels having different spectral filters with different spectral characteristics. Images from different channels having different spectral characteristics will provide different spectral information. Comparing (e.g., subtracting) these images, can therefore yield valuable spectral based information. For example, if the filter element of the array of spectral filters 130 corresponding to a particular FPA 336 transmits light from the object 110 including a cloud of gas, for example, with a certain spectrum that contains the gas absorption peak or a gas emission peak while another filter element of the array of spectral filters 130 corresponding to another FPA 336 does not transmit such spectrum, then the difference between the images formed by the two FPAs at issue will highlight the presence of gas in the difference image.

A shortcoming of the spectral differencing method is that contributions of some auxiliary features associated with imaging (not just the target species such as gas itself) can also be highlighted in and contribute to the difference image. Such contributing effects include, to name just a few, parallax-induced imaging of edges of the object, influence of magnification differences between the two or more optical channels, and differences in rotational positioning and orientation between the FPAs. While magnification-related errors and FPA-rotation-caused errors can be compensated for by increasing the accuracy of the instrument construction as well as by post-processing of the acquired imaging, parallax is scene-induced and is not so easily correctable. In addition, the spectral differencing method is vulnerable to radiance calibration errors. Specifically, if one FPA registers radiance of light from a given feature of the object as having a temperature of 40° C., for example, while the data from another FPA represents the temperature of the same object feature as being 39° C., then such feature of the object will be enhanced or highlighted in the difference image (formed at least in part based on the images provided by these two FPAs) due to such radiance-calibration error.

One solution to some of such problems is to compare (e.g., subtract) images from the same FPA obtained at different instances in time. For example, images can be compared to or subtracted from a reference image obtained at another time. Such reference image, which is subtracted from other later obtained images, may be referred to as a temporal reference image. This solution can be applied to spectral difference images as well. For example, the image data resulting from spectral difference images can be normalized by the data corresponding to a temporal reference image. For instance, the temporal reference images can be subtracted from the spectral difference image to obtain the temporal difference image. This process is referred to, for the purposes of this disclosure, as a temporal differencing algorithm or method and the resultant image from subtracting the temporal reference image from another image (such as the spectral difference image) is referred to as the temporal difference image. In some embodiments where spectral differencing is employed, a temporal reference image may be formed, for example, by creating a spectral difference image from the two or more images registered by the two or more FPAs at a single instance in time. This spectral difference image is then used as a temporal reference image. The temporal reference image can then be subtracted from other later obtained images to provide normalization that can be useful in subtracting out or removing various errors or deleterious effects. For example, the result of the algorithm is not affected by a prior knowledge of whether the object or scene contains a target species (such as gas of interest), because the algorithm can highlight changes in the scene characteristics. Thus, a spectral difference image can be calculated from multiple spectral channels as discussed above based on a snap-shot image acquisition at any later time and can be subtracted from the temporal reference image to form a temporal difference image. This temporal difference image is thus a normalized difference image. The difference between the two images (the temporal difference image) can highlight the target species (gas) within the normalized difference image, since this species was not present in the temporal reference frame. In various embodiments, more than two FPAs can be used both for registering the temporal reference image and a later-acquired difference image to obtain a better SNR figure of merit. For example, if two FPAs are associated with spectral filters having the same spectral characteristic, then the images obtained by the two FPAs can be combined after they have been registered to get a better SNR figure.

While the temporal differencing method can be used to reduce or eliminate some of the shortcomings of the spectral differencing, it can introduce unwanted problems of its own. For example, temporal differencing of imaging data is less sensitive to calibration and parallax induced errors than the spectral differencing of imaging data. However, any change in the imaged scene that is not related to the target species of interest (such as particular gas, for example) is highlighted in a temporally-differenced image. Thus such change in the imaged scene may be erroneously perceived as a location of the target species triggering, therefore, an error in detection of target species. For example, if the temperature of the background against which the gas is being detected changes (due to natural cooling down as the day progresses, or increases due to a person or animal or another object passing through the FOV of the IR imaging system), then such temperature change produces a signal difference as compared to the measurement taken earlier in time. Accordingly, the cause of the scenic temperature change (the cooling object, the person walking, etc.) may appear as the detected target species (such as gas). It follows, therefore, that an attempt to compensate for operational differences among the individual FPAs of a multi-FPA IR imaging system with the use of methods that turn on spectral or temporal differencing can cause additional problems leading to false detection of target species. Among these problems are scene-motion-induced detection errors and parallax-caused errors that are not readily correctable and/or compensatable. Accordingly, there is a need to compensate for image data acquisition and processing errors caused by motion of elements within the scene being imaged. Various embodiments of data processing algorithms described herein address and fulfill the need to compensate for such motion-induced and parallax-induced image detection errors.

In particular, to reduce or minimize parallax-induced differences between the images produced with two or more predetermined FPAs, another difference image can be used that is formed from the images of at least two different FPAs to estimate parallax effects. Parallax error can be determined by comparing the images from two different FPAs where the position between the FPAs is known. The parallax can be calculated from the known relative position difference. Differences between the images from these two FPAs can be attributed to parallax, especially, if the FPA have the same spectral characteristics, for example have the same spectral filter or both have no spectral filters. Parallax error correction, however, can still be obtained from two FPAs that have different spectral characteristics or spectral filters, especially if the different spectral characteristics, e.g., the transmission spectra of the respective filters are known and/or negligible. Use of more than two FPAs or FPAs of different locations such as FPAs spaced farther apart can be useful. For example, when the spectral differencing of the image data is performed with the use of the difference between the images collected by the outermost two cameras in the array (such as, for example, the FPAs corresponding to filters 2 and 3 of the array of filters of FIG. 5A), a difference image referred to as a "difference image 2-3" is formed. In this case, the alternative "difference image 1-4" is additionally formed from the image data acquired by, for example, the alternative FPAs corresponding to filters 1 and 4 of FIG. 5A. Assuming or ensuring that both of these two alternative FPAs have approximately the same spectral sensitivity to the target species, the alternative "difference image 1-4" will highlight pixels corresponding to parallax-induced features in the image. Accordingly, based on positive determination that the same pixels are highlighted in the spectral "difference image 2-3" used for target species detection, a conclusion can be made that the image features corresponding to these pixels are likely to be induced by parallax and not the presence of target species in the imaged scene. It should be noted that compensation of parallax can also be performed using images created by individual re-imaging lenses, 128a, when using a single FPA or multiple FPA's as discussed above. FPAs spaced apart from each other in different directions can also be useful. Greater than 2, for example, 3 or 4, or more FPAs can be used to establish parallax for parallax correction. In certain embodiments two central FPAs and one corner FPA are used for parallax correction. These FPA may, in certain embodiments, have substantially similar or the same spectral characteristics, for example, have filters having similar or the same transmission spectrum or have no filter at all.

Another capability of the embodiments described herein is the ability to perform the volumetric estimation of a gas cloud. This can be accomplished by using (instead of compensating or negating) the parallax induced effects described above. In this case, the measured parallax between two or more similar spectral response images (e.g., two or more channels or FPAs) can be used to estimate a distance between the imaging system and the gas cloud or between the imaging system and an object in the field of view of the system. The parallax induced transverse image shift, d, between two images is related to the distance, z, between the cloud or object 110 and the imaging system according to the equation $z=-sz'/d$. Here, s, is the separation between two similar spectral response images, and z' is the distance to the image plane from the back lens. The value for z' is typically approximately equal to the focal length f of the lens of the imaging system. Once the distance z between the cloud and the imaging system is calculated, the size of the gas cloud can be determined based on the magnification, $m=f/z$, where each image pixel on the gas cloud, $\Delta x'$, corresponds to a physical size in object space $\Delta x=\Delta x'/m$. To estimate the volume of the gas cloud, a particular symmetry in the thickness of the cloud based on the physical size of the cloud can be assumed. For example, the cloud image can be rotated about a central axis running through the cloud image to create a three dimensional volume estimate of the gas cloud size. It is worth noting that in the embodiments described herein only a single imaging system is required for such volume estimation. Indeed, due to the fact that the information about the angle at which the gas cloud is seen by the system is decoded in the parallax effect, the image data includes the information about the imaged scene viewed by the system in association with at least two angles.

When the temporal differencing algorithm is used for processing the acquired imaging data, a change in the scene that is not caused by the target species can inadvertently be highlighted in the resulting image. In various embodiments, compensation for this error makes use of the temporal differencing between two FPAs that are substantially equally spectrally sensitive to the target species. In this case, the temporal difference image will highlight those pixels the intensity of which have changed in time (and not in wavelength). Therefore, subtracting the data corresponding to these pixels on both FPAs, which are substantially equally spectrally sensitive to the target species, to form the resulting image, excludes the contribution of the target species to the resulting image. The differentiation between (i) changes in the scene due to the presence of target species and (ii) changes in the scene caused by changes in the background not associated with the target species is, therefore, possible. In some embodiments, these two channels having the same or substantially similar spectral response so as to be substantially equally spectrally sensitive to the target species may comprise FPAs that operate using visible light. It should also be noted that, the data acquired with a visible light FPA (when present as part of the otherwise IR imaging system) can also be used to facilitate such differentiation and compensation of the motion-caused imaging errors. Visible cameras generally have much lower noise figure than IR cameras (at least during daytime). Consequently, the temporal difference image obtained with the use of image data from the visible light FPA can be quite accurate. The visible FPA can be used to compensate for motion in the system as well as many potential false-alarms in the scene due to motion caused by people, vehicles, birds, and steam, for example, as long as the moving object can be observed in the visible region of the spectra. This has the added benefit of providing an additional level of false alarm suppression without reducing the sensitivity of the system since many targets such as gas clouds cannot be observed in the visible spectral region. In various implementations, an IR camera can be used to compensate for motion artifacts.

Another method for detection of the gases is to use a spectral unmixing approach. A spectral unmixing approach assumes that the spectrum measured at a detector pixel is composed of a sum of component spectra (e.g., methane and other gases). This approach attempts to estimate the relative weights of these components needed to derive the measurement spectrum. The component spectra are generally taken from a predetermined spectral library (for example, from data collection that has been empirically assembled), though sometimes one can use the scene to estimate these as well (often called "endmember determination"). In various embodiments, the image obtained by the detector pixel is a radiance spectrum and provides information about the brightness of the object. To identify the contents of a gas cloud in the scene and/or to estimate the concentration of the various gases in the gas cloud, an absorption/emission spectrum of the various gases of interest can be obtained by comparing the measured brightness with an estimate of the expected brightness. The spectral unmixing methodology can also benefit from temporal, parallax, and motion compensation techniques.

In various embodiments, a method of identifying the presence of a target species in the object includes obtaining the radiance spectrum (or the absorption spectrum) from the object in a spectral region indicative of the presence of the target species and calculating a correlation (e.g., a correlation coefficient) by correlating the obtained radiance spectrum (or the absorption spectrum) with a reference spectrum for the target species. The presence or absence of the target species can be determined based on an amount of correlation (e.g., a value of correlation coefficient). For example, the presence of the target species in the object can be confirmed if the amount of correlation or the value of correlation coefficient is greater than a threshold. In various implementations, the radiance spectrum (or the absorption spectrum) can be obtained by obtaining a spectral difference image between a filtered optical channel and/or another filtered optical channel/unfiltered optical channel or any combinations thereof.

For example, an embodiment of the system configured to detect the presence of methane in a gas cloud comprises optical components such that one or more of the plurality of optical channels is configured to collect IR radiation to provide spectral data corresponding to a discrete spectral band located in the wavelength range between about 7.9 µm and about 8.4 µm corresponding to an absorption peak of methane. The multispectral data obtained in the one or more optical channels can be correlated with a predetermined absorption spectrum of methane in the wavelength range between about 7.9 µm and 8.4 µm. In various implementations, the predetermined absorption spectrum of methane can be saved in a database or a reference library accessible by the system. Based on an amount of correlation (e.g., a value of correlation coefficient), the presence or absence of methane in the gas cloud can be detected.

Examples of Practical Embodiments and Operation

The embodiment 300 of FIG. 3 is configured to employ 12 optical channels and 12 corresponding microbolometer FPAs 336 to capture a video sequence substantially immediately after performing calibration measurements. The video sequence corresponds to images of a standard laboratory scene and the calibration measurements are performed with the use of a reference source including two shutters, as discussed above, one at room temperature and one 5° C. above room temperature. The use of 12 FPAs allows increased chance of simultaneous detection and estimation of the concentrations of about 8 or 9 gases present at the scene. In various embodiments, the number of FPAs 336 can vary, depending on the balance between the operational requirements and consideration of cost.

Due to the specifics of operation in the IR range of the spectrum, the use of the so-called noise-equivalent temperature difference (or NETD) is preferred and is analogous to the SNR commonly used in visible spectrum instruments. The array of microbolometer FPAs 336 is characterized to perform at NETD≤72 mK at an f-number of 1.2. Each measurement was carried out by summing four consecutive frames, and the reduction in the NETD value expected due to such summation would be described by corresponding factor of $\sqrt{4}=2$. Under ideal measurement conditions, therefore, the FPA NETD should be about 36 mK.

It is worth noting that the use of optically-filtered FPAs in various embodiments of the system described herein can provide a system with higher number of pixels. For example, embodiments including a single large format microbolometer FPA array can provide a system with large number of pixels. Various embodiments of the systems described herein can also offer a high optical throughput for a substantially low number of optical channels. For example, the systems described herein can provide a high optical throughput for a number of optical channels between 4 and 50. By having a lower number of optical channels (e.g., between 4 and 50 optical channels), the systems described herein have wider spectral bins which allows the signals acquired within each spectral bin to have a greater integrated intensity.

An advantage of the embodiments described herein over various scanning based hyperspectral systems that are configured for target species detection (for example, gas cloud detection) is that, the entire spectrum can be resolved in a snapshot mode (for example, during one image frame acquisition by the FPA array). This feature enables the embodiments of the imaging systems described herein to take advantage of the compensation algorithms such as the parallax and motion compensation algorithms mentioned above. Indeed, as the imaging data required to implement these algorithms are collected simultaneously with the target-species related data, the compensation algorithms are carried out with respect to target-species related data and not with respect to data acquired at another time interval. This rapid data collection thus improves the accuracy of the data compensation process. In addition, the frame rate of data acquisition is much higher. For example, embodiments of the imaging system described herein can operate at video rates from about 5 Hz and higher. For example, various embodiments described herein can operate at frame rates from about 5 Hz to about 60 Hz or 200 Hz. Thus, the user is able to recognize in the images the wisps and swirls typical of gas mixing without blurring out of these dynamic image features and other artifacts caused by the change of scene (whether spatial or spectral) during the lengthy measurements. In contradistinction, scanning based imaging systems involve image data acquisition over a period of time exceeding a single-snap-shot time and can, therefore, blur the target gas features in the image and inevitably reduce the otherwise achievable sensitivity of the detection. This result is in contrast to embodiments of the imaging system described herein that are capable of detecting the localized concentrations of gas without it being smeared out with the areas of thinner gas concentrations. In addition, the higher frame rate also enables a much faster response rate to a leak of gas (when detecting such leak is the goal). For example, an alarm can trigger within fractions of a second rather than several seconds.

Figure 7:
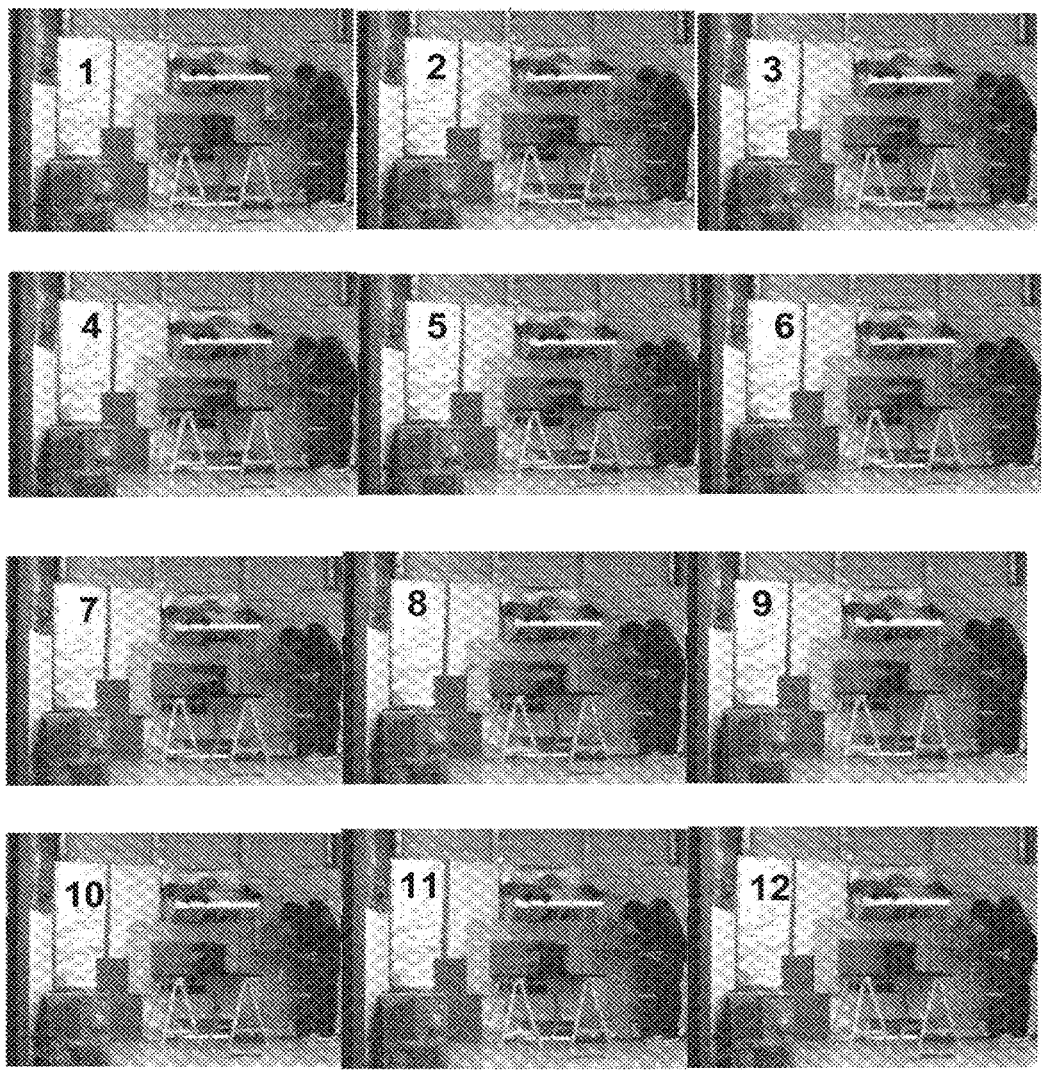
FIG. 7 is a set of video-frames illustrating operability of an embodiment of the system used for gas detection.

To demonstrate the operation and gas detection capability of the imaging systems described herein, a prototype was constructed in accordance with the embodiment 300 of FIG. 3A and used to detect a hydrocarbon gas cloud of propylene at a distance of approximately 10 feet. FIG. 7 illustrates video frames 1 through 12 representing gas-cloud-detection output 710 (seen as a streak of light) in a sequence from t=1 to t=12. The images 1 through 12 are selected frames taken from a video-data sequence captured at a video-rate of 15 frames/sec. The detected propylene gas is shown as a streak of light 710 (highlighted in red) near the center of each image. The first image is taken just prior to the gas emerging from the nozzle of a gas-contained, while the last image represents the system output shortly after the nozzle has been turned off.

Figure 8A:
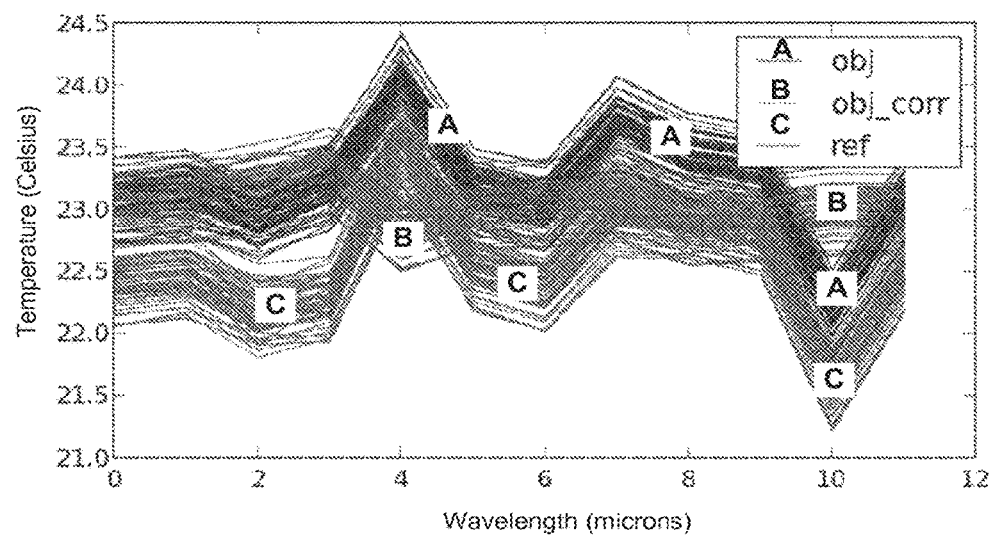
FIGS. 8A and 8B are plots (on axes of wavelength in microns versus the object temperature in Celsius representing effective optical intensity of the object) illustrating results of dynamic calibration of an embodiment of the system.
Figure 8B:
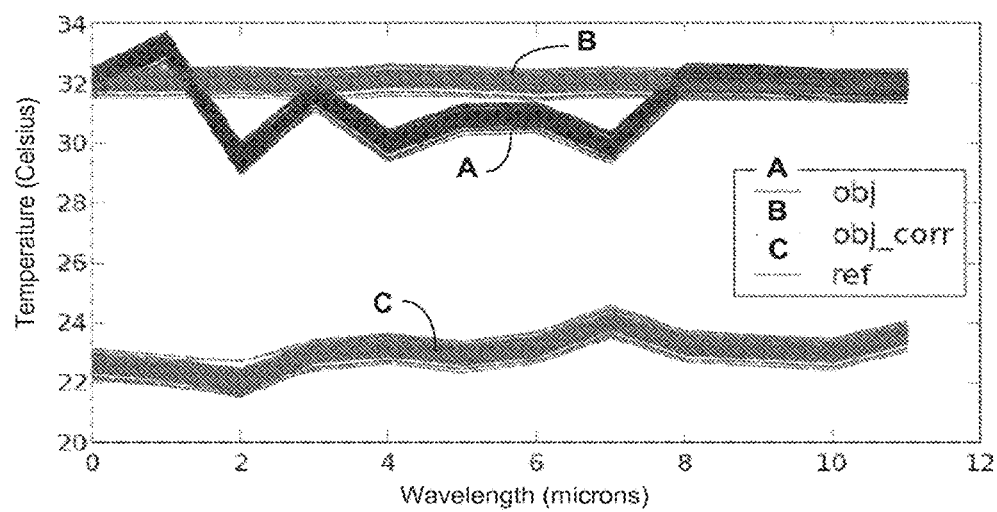

The same prototype of the system can also demonstrate the dynamic calibration improvement described above by imaging the scene surrounding the system (the laboratory) with known temperature differences. The result of implementing the dynamic correction procedure is shown in FIGS. 8A, 8B, where the curves labeled "obj" (or "A") represent temperature estimates of an identified region in the scene. The abscissa in each of the plots of FIGS. 8A, 8B indicates the number of a FPA, while the ordinate corresponds to temperature (in degrees C.). Accordingly, it is expected that when all detector elements receive radiant data that, when interpreted as the object's temperature, indicates that the object's temperature perceived by all detector elements is the same, any given curve would be a substantially flat line. Data corresponding to each of the multiple "obj" curves are taken from a stream of video frames separated from one another by about 0.5 seconds (for a total of 50 frames). The recorded "obj" curves shown in FIG. 8A indicate that the detector elements disagree about the object's temperature, and that difference in object's temperature perceived by different detector elements is as high as about 2.5° C. In addition, all of the temperature estimates are steadily drifting in time, from frame to frame. The curves labeled "ref" (or "C") correspond to the detectors' estimates of the temperature of the aperture 338 of the embodiment 300 of FIG. 3A. The results of detection of radiation carried out after each detector pixel has been subjected to the dynamic calibration procedure described above are expressed with the curved labeled "obj corr" (or "B"). Now, the difference in estimated temperature of the object among the detector elements is reduced to about 0.5° C. (thereby improving the original reading at least by a factor of 5).

FIG. 8B represents the results of similar measurements corresponding to a different location in the scene (a location which is at a temperature about 9° C. above the estimated temperature of the aperture 338 of FIG. 3A). As shown, the correction algorithm discussed above is operable and effective and applicable to objects kept at different temperature. Accordingly, the algorithm is substantially temperature independent.

Dynamic Calibration Elements and References

Figure 9A:
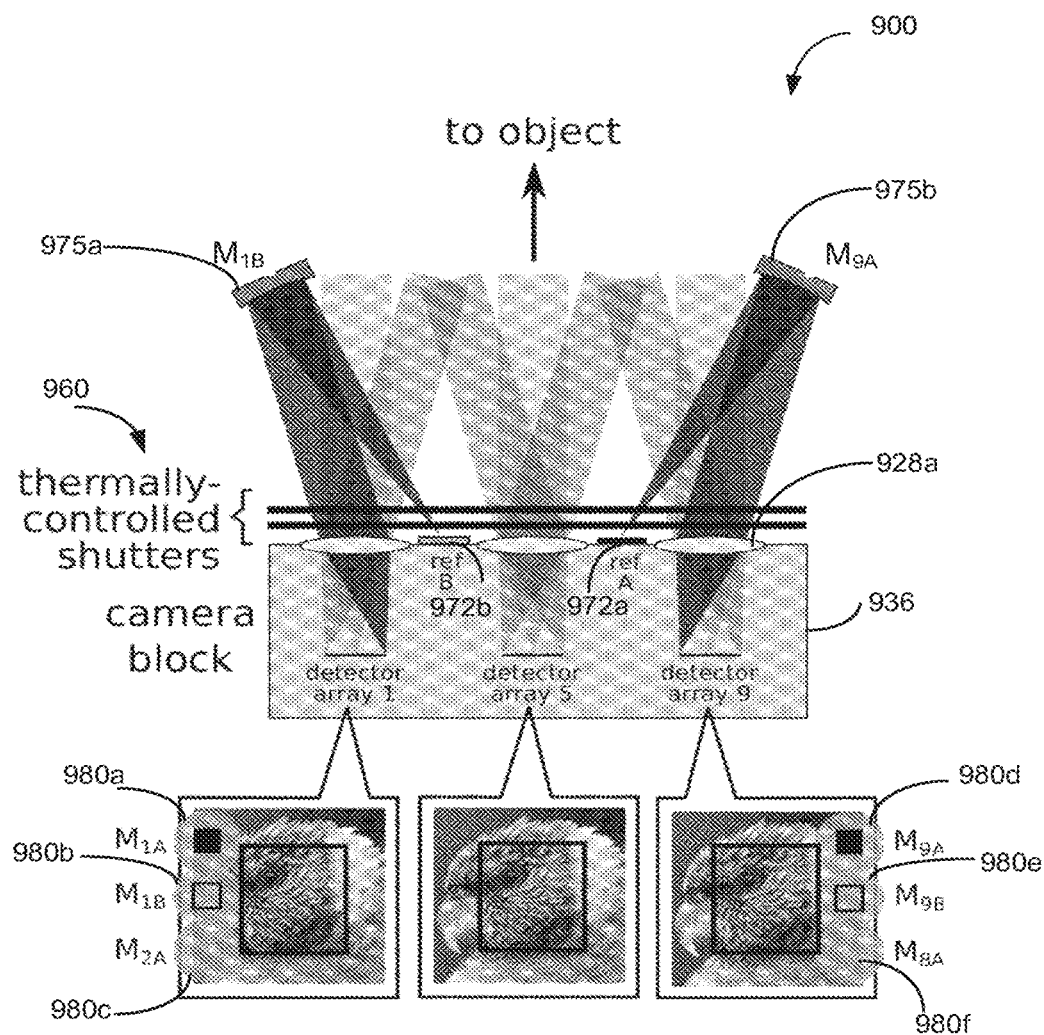
FIGS. 9A and 9B illustrate a cross-sectional view of different embodiments of an imaging system comprising an arrangement of reference sources and mirrors that can be used for dynamic calibration.
Figure 9B:
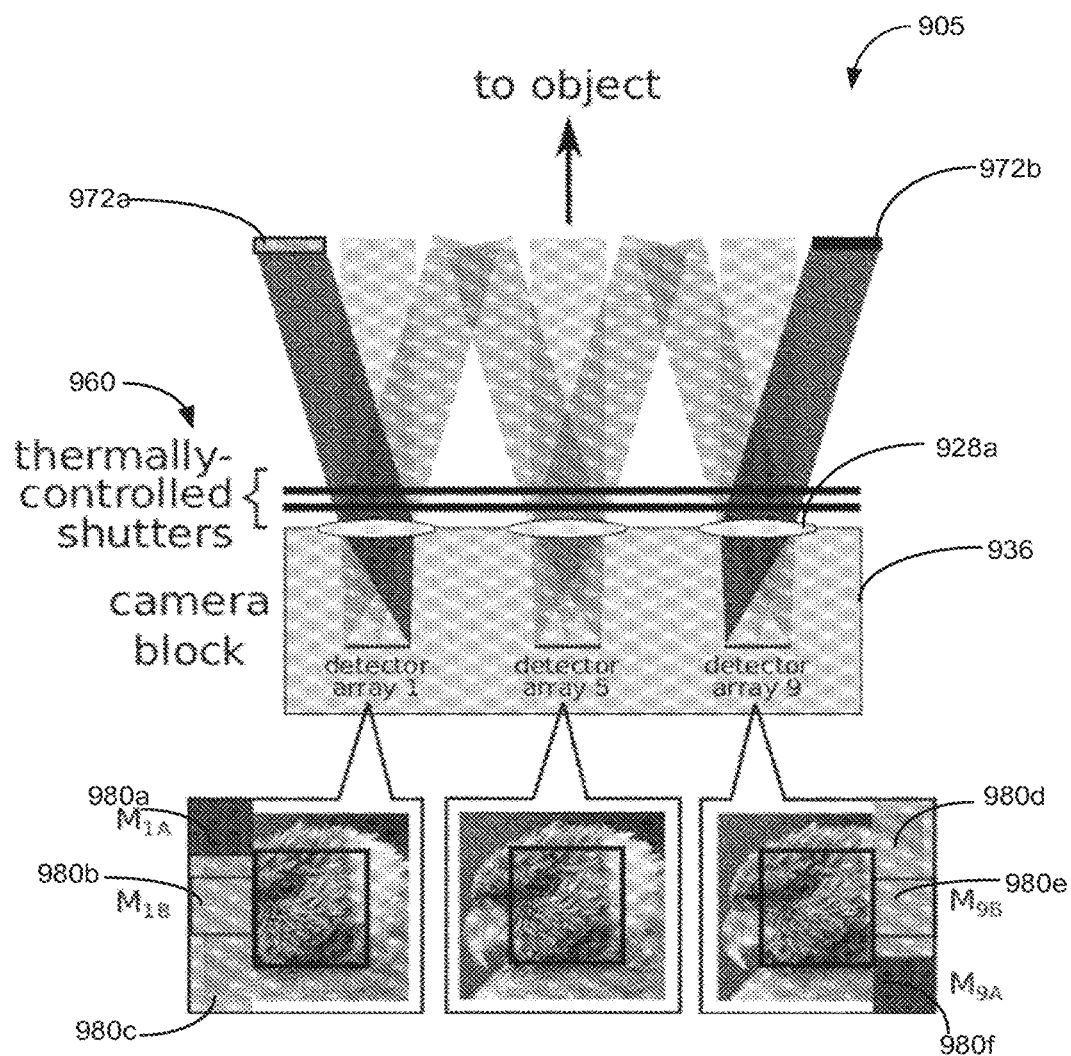

FIGS. 9A and 9B illustrates schematically different implementations 900 and 905 respectively of the imaging system that include a variety of temperature calibration elements to facilitate dynamic calibration of the FPAs. The temperature calibration elements can include mirrors 975a, 975b (represented as $M_{1A}$, $M_{9A}$, etc.) as well as reference sources 972a and 972b. The implementation 900 can be similarly configured as the embodiment 300 and include one or more front objective lens, a divided aperture, one or more spectral filters, an array of imaging lenses 928a and an imaging element 936. In various implementations, the imaging element 936 (e.g., camera block) can include an array of cameras. In various implementations, the array of cameras can comprise an optical FPA unit. The optical FPA unit can comprise a single FPA, an array of FPAs. In various implementations, the array of cameras can include one or more detector arrays represented as detector array 1, detector array 5, detector array 9 in FIGS. 9A and 9B. In various embodiments, the FOV of each of the detector arrays 1, 5, 9 can be divided into a central region and a peripheral region. Without any loss of generality, the central region of the FOV of each of the detector arrays 1, 5, 9 can include the region where the FOV of all the detector arrays 1, 5, 9 overlap. In the embodiment illustrated in FIG. 9A, the reference sources 972a and 972b are placed at a distance from the detector arrays 1, 5, 9, for example, and mirrors 975a and 975b that can image them onto the detector arrays are then placed at the location of the scene reference aperture (e.g., 338 of FIG. 3A).

In FIG. 9A, the mirrors 975a and 975b are configured to reflect radiation from the reference sources 972a and 972b (represented as ref A and ref B). The mirrors 975a and 975b can be disposed away from the central FOV of the detector arrays 1, 5, 9 such that the central FOV is not blocked or obscured by the image of the reference source 972a and 972b. In various implementations, the FOV of the detector array 5 could be greater than the FOV of the detector arrays 1 and 9. In such implementations, the mirrors 975a and 975b can be disposed away from the central FOV of the detector array 5 at a location such that the reference source 972a and 972b is imaged by the detector array 5. The mirrors 975a and 975b may comprise imaging optical elements having optical power that image the reference sources 972a and 972b onto the detector arrays 1 and 9. In this example, the reference sources 972a and 972b can be disposed in the same plane as the re-imaging lenses 928a, however, the reference sources 972a and 972b can be disposed in a different plane or in different locations. For example, the reference sources 972a and 972b can be disposed in a plane that is conjugate to the plane in which the detector array 1, detector array 5, and detector array 9 are disposed such that a focused image of the reference sources 972a and 972b is formed by the detector arrays. In some implementations, the reference sources 972a and 972b can be disposed in a plane that is spaced apart from the conjugate plane such that a defocused image of the reference sources 972a and 972b is formed by the detector arrays. In various implementations, the reference sources 972a and 972b need not be disposed in the same plane.

As discussed above, in some embodiments, the reference sources 972a and 972b are imaged onto the detector array 1 and detector array 9, without much blur such that the reference sources 972a and 972b are focused. In contrast, in other embodiments, the image of reference sources 972a and 972b formed on the detector array 1, and detector array 9 are blurred such that the reference sources 972a and 972b are defocused, and thereby provide some averaging, smoothing, and/or low pass filtering. The reference sources 972a and 972b may comprise a surface of known temperature and may or may not include a heater or cooler attached thereto or in thermal communication therewith. For example, the reference source 972a and 972b may comprises heaters and coolers respectively or may comprise a surface with a temperature sensor and a heater and sensor respectively in direct thermal communication therewith to control the temperature of the reference surface. In various implementations, the reference sources 972a and 972b can include a temperature controller configured to maintain the reference sources 972a and 972b at a known temperature. In some implementations, the reference sources 972a and 972b can be associated with one or more sensors that measure the temperature of the reference sources 972a and 972b and communicate the measured temperature to the temperature controller. In some implementations, the one or more sensors can communicate the measured temperature to the data-processing unit. In various implementations, the reference sources 972a and 972b may comprise a surface of unknown temperature. For example, the reference sources may comprise a wall of a housing comprising the imaging system. In some implementations, the reference sources 972a and 972b can comprise a surface that need not be associated with sensors, temperature controllers. However, in other implementations, the reference sources 972a and 972b can comprise a surface that can be associated with sensors, temperature controllers.

In FIG. 9B, the temperature-calibration elements comprise temperature-controlled elements 972a and 972b (e.g., a thermally controlled emitter, a heating strip, a heater or a cooler) disposed a distance from the detector arrays 1, 5, 9. In various embodiments, the temperature-controlled elements 972a and 972b can be disposed away from the central FOV of the detector arrays 1, 5, 9 such that the central FOV is not blocked or obscured by the image of the reference source 972a and 972b. The radiation emitted from the reference sources 972a and 972b is also imaged by the detector array 936 along with the radiation incident from the object. Depending on the position of the reference sources 972a and 972b the image obtained by the detector array of the reference sources can be blurred (or defocused) or sharp (or focused). The images 980a, 980b, 980c, 980d, 980e and 980f of the temperature-controlled elements 972a and 972b can be used as a reference to dynamically calibrate the one or more cameras in the array of cameras.

In the implementations depicted in FIGS. 9A and 9B, the detector arrays 1, 5 and 9 are configured to view (or image) both the reference sources 972a and 972b. Accordingly, multiple frames (e.g., every or substantially every frame) within a sequence of images contains one or more regions in the image in which the object image has known thermal and spectral properties. This allows multiple (e.g., most or each) cameras within the array of cameras to be calibrated to agree with other (e.g., most or every other) camera imaging the same reference source(s) or surface(s). For example, detector arrays 1 and 9 can be calibrated to agree with each other. As another example, detector arrays 1, 5 and 9 can be calibrated to agree with each other. In various embodiments, the lenses 928a provide blurred (or defocused) images of the reference sources 972a, 972b on the detector arrays 1 and 9 because the location of the reference sources are not exactly in a conjugate planes of the detector arrays 1 and 9. Although the lenses 928a are described as providing blurred or defocused images, in various embodiments, reference sources or surfaces are imaged on the detectors arrays 1, 5, 9 without such blur and defocus and instead are focused images. Additionally optical elements may be used, such as for example, the mirrors shown in FIG. 9A to provide such focused images.

The temperature of the reference sources 972b, 972a can be different. For example, the reference source 972a can be at a temperature $T_A$, and the reference source 972b can be at a temperature $T_B$ lower than the temperature $T_A$. A heater can be provided under the temperature-controlled element 972a to maintain it at a temperature $T_A$, and a cooler can be provided underneath the temperature-controlled element 972b to maintain it at a temperature $T_B$. In various implementations, the embodiments illustrated in FIGS. 9A and 9B can be configured to image a single reference source 972 instead of two references sources 972a and 972b maintained at different temperatures. It is understood that the single reference source need not be thermally controlled. For example, in various implementations, a plurality of detectors in the detector array can be configured to image a same surface of at least one calibration element whose thermal and spectral properties are unknown. In such implementations, one of the plurality of detectors can be configured as a reference detector and the temperature of the surface of the at least one calibration element imaged by the plurality of detectors can be estimated using the radiance spectrum obtained by the reference detector. The remaining plurality of detectors can be calibrated such that their temperature and/or spectral measurements agree with the reference detector. For example, detector arrays 1 and 9 can be calibrated to agree with each other. As another example, detector arrays 1, 5 and 9 can be calibrated to agree with each other.

The reference sources 972a and 972b can be coated with a material to make it behave substantially as a blackbody (for which the emission spectrum is known for any given temperature). If a temperature sensor is used at the location of each reference source, then the temperature can be tracked at these locations. As a result, the regions in the image of each camera (e.g., on the detector arrays 1 and 9) in which the object has such known temperature (and, therefore, spectrum) can be defined. A calibration procedure can thus be used so that most of the cameras (if not every camera) so operated agrees, operationally, with most or every other camera, for objects at the temperatures represented by those two sources. Calibrating infrared cameras using sources at two different temperatures is known as a "two-point" calibration, and assumes that the measured signal at a given pixel is linearly related to the incident irradiance. Since this calibration can be performed during multiple, more, or even every frame of a sequence, it is referred to as a "dynamic calibration".

An example of the dynamic calibration procedure is as follows. If there is a temperature sensor on the reference sources or reference surface, then the temperature measurements obtained by these temperature sensors can be used to determine their expected emission spectra. These temperature measurements are labeled as $T_A[R]$, $T_B[R]$, and $T_c[R]$ for the "reference temperatures" of sources/surfaces A, B, and C. These temperature measurements can be used as scalar correction factors to apply to the entire image of a given camera, forcing it to agree with the reference temperatures. Correcting the temperature estimate of a given pixel from T to T' can use formulae analogous to those discussed below in reference to FIGS. 10A, 10B, 10C. If no direct temperature sensor is used, then one of the cameras can be used instead. This camera can be referred to as the "reference camera". In this case, the same formulae as those provided in paragraph below can be used, but with $T_A[R]$ and $T_B[R]$ representing the temperatures of the reference sources/surfaces A and B as estimated by the reference camera. By applying the dynamic calibration correction formulae, all of the other cameras are forced to match the temperature estimates of the reference camera.

In the configuration illustrated in FIG. 9B, the reference sources 972a and 972b are placed such that the images of the sources on the detector arrays are blurred. The configuration illustrated in FIG. 9A is similar to the system 400 illustrated in FIG. 4 where the reference sources are placed at an intermediate image plane (e.g., a conjugate image plane). In this configuration, the array of reference apertures, similar to reference apertures 438a in FIG. 4, will have an accompanying array of reference sources or reference surfaces such that the reference sources or surfaces (e.g., each reference source or surface) are imaged onto a camera or a detector array such as FPAs 1, 5, 9. With this approach, the reference source or surface images are at a conjugate image plane and thus are not appreciably blurred, so that their images can be made to block a smaller portion of each camera's field of view.

A "static" calibration (a procedure in which the scene is largely blocked with a reference source such as the moving shutters 960 in FIGS. 9A and 9B, so that imaging of an unknown scene cannot be performed in parallel with calibration) allows a plurality of the cameras (for example, most or each camera) to accurately estimate the temperature of a plurality of elements (for example, most or each element in the scene) immediately after the calibration is complete. It cannot, however, prevent the cameras' estimates from drifting away from one another during the process of imaging an unknown scene. The dynamic calibration can be used to reduce or prevent this drift, so that all cameras imaging a scene can be forced to agree on the temperature estimate of the reference sources/surfaces, and adjust this correction during every frame.

Figure 10A:
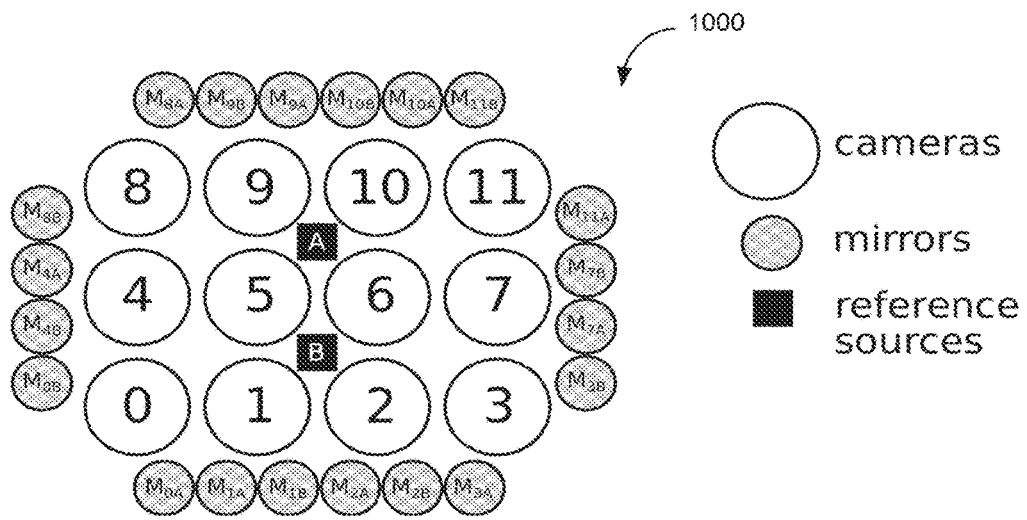
FIGS. 10A-10C illustrate a plan view of different embodiments of an imaging system comprising an arrangement of reference sources and mirrors that can be used for dynamic calibration.

FIG. 10A illustrates schematically a related embodiment 1000 of the imaging system, in which one or more mirrors $M_{0A}, \ldots M_{11A}$ and $M_{0B}, \ldots M_{11B}$ are placed within the fields of view of one or more cameras 0, ..., 11, partially blocking the field of view. The cameras 0, ..., 11 are arranged to form an outer ring of cameras including cameras 0, 1, 2, 3, 7, 11, 10, 9, 8 and 4 surrounding the central cameras 5 and 6. In various implementations, the FOV of the central cameras 5 and 6 can be less than or equal to the FOV of the outer ring of cameras 0, 1, 2, 3, 7, 11, 10, 9, 8 and 4. In such implementations, the one or more mirrors $M_{0A}, \ldots M_{11A}$ and $M_{0B}, \ldots M_{11B}$ can be placed outside the central FOV of the cameras 5 and 6 and is placed in a peripheral FOV of the cameras outer ring of cameras 0, 1, 2, 3, 7, 11, 10, 9, 8 and 4 which does not overlap with the central FOV of the cameras 5 and 6 such that the reference sources A and B are not imaged by the cameras 5 and 6. In various implementations, the FOV of the central cameras 5 and 6 can be greater than the FOV of the outer ring of cameras 0, 1, 2, 3, 7, 11, 10, 9, 8 and 4. In such implementations, the one or more mirrors $M_{0A}, \ldots M_{11A}$ and $M_{0B}, \ldots M_{11B}$ can be placed in a peripheral FOV of the cameras 5 and 6 which does overlap with the central FOV of the outer ring of cameras 0, 1, 2, 3, 7, 11, 10, 9, 8 and 4 such that the reference sources A and B are imaged by the cameras 5 and 6.

This design is an enhancement to the systems 300 and 400 shown in FIGS. 3A and 4A. In the system 1000 shown in FIG. 10A, an array of two or more imaging elements (curved mirrors, for example) is installed at a distance from the FPAs, for example, in the plane of the reference aperture 160 shown in FIG. 3A. These elements (mirror or imaging elements) are used to image one or more temperature-controlled reference sources A and B onto the detector elements of two or more of the cameras. The primary difference between embodiment 1000 and embodiment 300 or 400 is that now a plurality or most or all of the outer ring of cameras in the array can image both the reference sources A and B instead of imaging one of the two reference source A and B. Accordingly, most or all of the outer ring of cameras image an identical reference source or an identical set of reference sources (e.g., both the reference sources A and B) rather than using different reference sources for different cameras or imaging different portions of the reference sources as shown in FIGS. 3A and 4A. Thus, this approach improves the robustness of the calibration, as it eliminates potential failures and errors due to the having additional thermal sensors estimating each reference source.

Figure 10B:
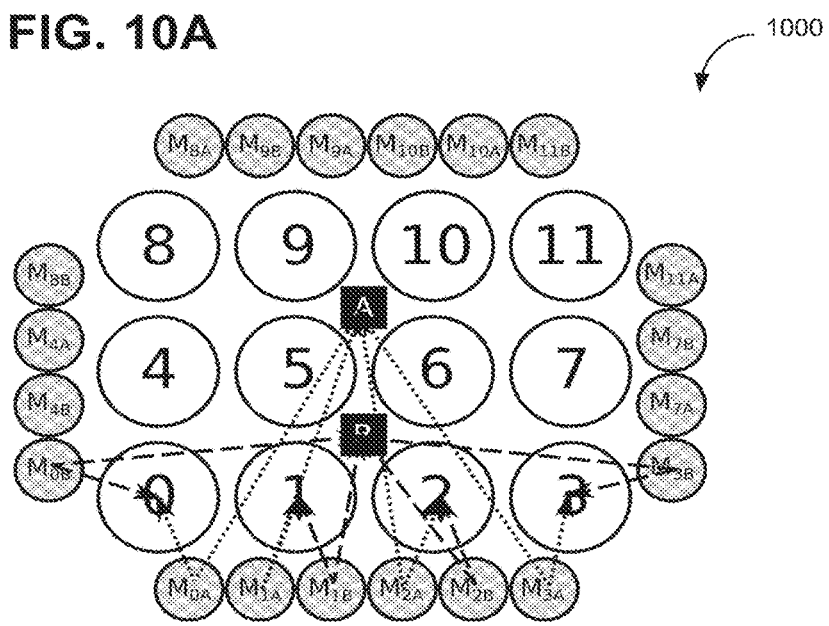

The imaging elements in the system 1000 (shown as mirrors in FIGS. 10A and 10B) image one or more controlled-temperature reference sources or a surface of a calibration element (shown as A and B in FIGS. 10A and 10B) into the blocked region of the cameras' fields of view. FIG. 10B shows an example in which mirror $M_{0A}$ images reference source/surface A onto camera 0, and mirror $M_{0B}$ images reference source/surface B onto camera 0, and likewise for cameras 1, 2, and 3. This way, each of the mirrors is used to image a reference source/surface onto a detector array of a camera, so that many, most, or every frame within a sequence of images contains one or more regions in the image in which the object image has known thermal and spectral properties. This approach allows most of the camera, if not each camera, within the array of cameras to be calibrated to agree with most or every other camera imaging the same reference source or sources. For example, cameras 0, 1, 2, 3, 7, 11, 10, 9, 8 and 4 can be calibrated to agree with each other. As another example, cameras 0, 1, 2 and 3 can be calibrated to agree with each other. As yet another example, cameras 0, 1, 2, 3, 7, 11, 10, 9, 8, 4, 5 and 6 can be calibrated to agree with each other. Accordingly, in various implementations, two, three, four, five, six, seven, eight, nine, ten, eleven or twelve cameras can be calibrated to agree with each other. In certain embodiments, however, not all the cameras are calibrated to agree with each other. For example, one, two, or more cameras may not be calibrated to agree with each other while others may be calibrated to agree with each other. In various embodiments, these mirrors may be configured to image the reference sources/surfaces A and B onto different respective pixels a given FPA. Without any loss of generality, FIGS. 10A and 10B represent a top view of the embodiment shown in FIG. 9A.

Figure 10C:
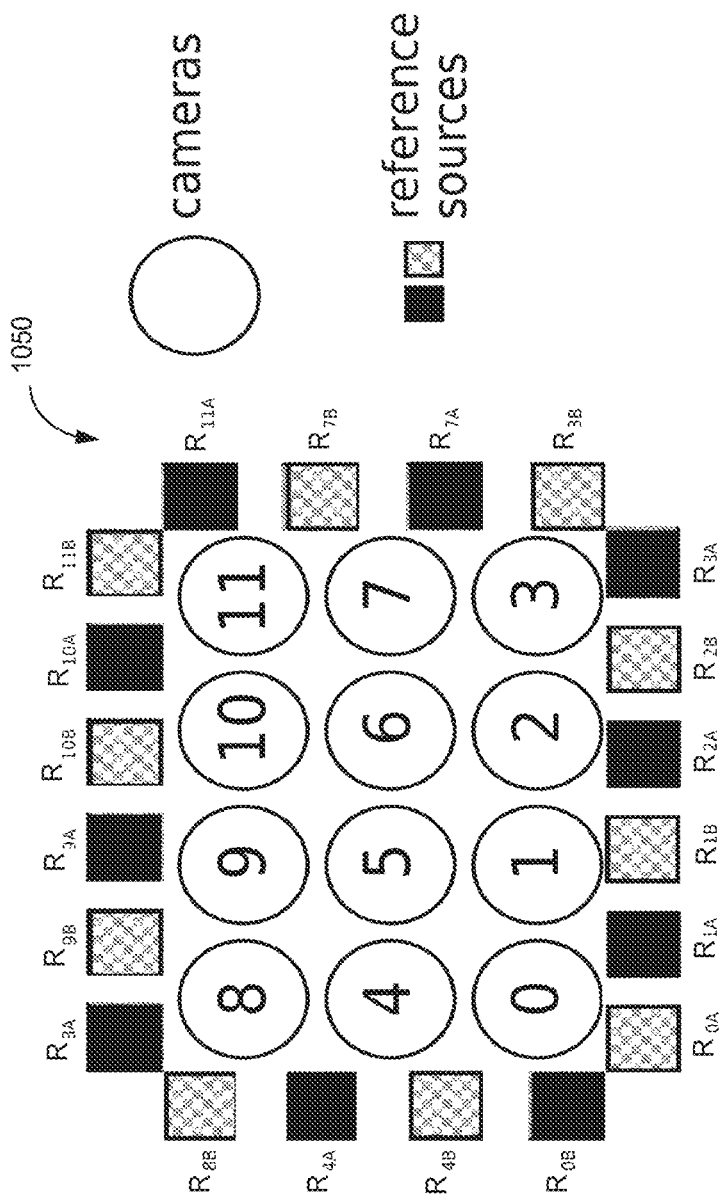

FIG. 10C illustrates schematically a related embodiment 1050 of the imaging system, in which one or more' reference sources $R_{0A}, \ldots, R_{11A}$ and $R_{0B}, \ldots, R_{11B}$ are disposed around the array of detectors 0, . . . , 11. In various implementations, the one or more reference sources $R_{0A}, \ldots, R_{11A}$ and $R_{0B}, \ldots, R_{11B}$ can be a single reference source that is imaged by the detectors 0, . . . , 11. In various implementations, central detector arrays 5 and 6 can have a FOV that is equal to or lesser than the FOV of the outer ring of the detectors 0, 1, 2, 3, 7, 11, 10, 9, 8 and 4. In such implementations, the reference sources $R_{0A}, \ldots, R_{11A}$ can be disposed away from the central FOV of the detector arrays 5 and 6 such that the radiation from the reference sources $R_{0A}, \ldots, R_{11A}$ is imaged only by the outer ring of detectors 0, 1, 2, 3, 7, 11, 10, 9, 8 and 4. In various implementations, central detector arrays 5 and 6 can have a FOV that is greater than the FOV of the outer ring of the detectors 0, 1, 2, 3, 7, 11, 10, 9, 8 and 4. In such implementations, the reference sources $R_{0A}, \ldots, R_{11A}$ can be disposed in the peripheral FOV of the detector arrays 5 and 6 such that the radiation from the reference sources $R_{0A}, \ldots, R_{11A}$ is imaged only by the outer ring of detectors 0, 1, 2, 3, 7, 11, 10, 9, 8 and 4. The radiation from the reference sources $R_{0A}, \ldots, R_{11A}$ is therefore imaged by the outer ring of detectors 0, 1, 2, 3, 7, 11, 10, 9, 8 and 4 as well as central cameras 5 and 6. Without any loss of generality, FIG. 10C represents a top view of the embodiment shown in FIG. 9B.

In various implementations, a heater can be provided underneath, adjacent to, or in thermal communication with reference source/surface A to give it a higher temperature $T_A$, and a cooler can be provided underneath, adjacent to, or in thermal communication with reference source B to give it a lower temperature $T_B$. In various implementations, the embodiments illustrated in FIGS. 10A, 10B and 10C can be configured to image a single reference source A instead of two references sources A and B maintained at different temperatures. As discussed above, the embodiments illustrated in FIGS. 10A, 10B and 10C can be configured to image a same surface of a calibration element. In such implementations, the temperature of the surface of the calibration element need not be known. Many, most or each reference source/surface can be coated with a material to make it behave approximately as a blackbody, for which the emission spectrum is known for any given temperature. If many, most, or each camera in the array of cameras images both of references A and B, so that there are known regions in the image of these cameras in which the object has a known temperature (and therefore spectrum), then one can perform a calibration procedure. This procedure can provide that many, most or every camera so operated agrees with various, most, or every other camera, for objects at the temperatures represented by those two sources. For example, two, three, four, five, six, seven, eight, nine, ten, eleven or twelve cameras can be calibrated to agree with each other. In certain embodiments, however, not all the cameras are calibrated to agree with each other. For example, one, two, or more cameras may not be calibrated to agree with each other while others may be calibrated to agree with each other. As discussed above, calibration of infrared cameras using sources at two different temperatures is known as a "two-point" calibration, and assumes that the measured signal at a given pixel is linearly related to the incident irradiance.

The dynamic calibration is used to obtain a corrected temperature T' from the initial temperature T estimated at each pixel in a camera using the following formulae:

$$T'[x,y,c] = (T[x,y,c] - T_A[R])G[c] + T_A[R]$$

where is $T_A[R]$ is a dynamic offset correction factor, and, $$G[c] = \frac{T_B[R] - T_A[R]}{T_B[c] - T_A[c]},$$

is a dynamic gain correction factor. The term c discussed above is a camera index that identifies the camera whose data is being corrected.

III. Examples of a Mobile DAISI System

The DAISI systems disclosed herein can be configured to be installed at a suitable location on a long-term basis, according to some embodiments. For example, the DAISI systems disclosed in Section II above can be affixed to a fixture mounted to the ground at a location to continuously or periodically monitor the presence of gases or chemicals at the location. In some embodiments, for example, the DAISI systems can be attached to a pole, post, or any suitable fixture at the location to be monitored. In such arrangements, the DAISI system can continuously or periodically capture multispectral, multiplexed image data of the scene, and an on-board or remote computing unit can process the captured image data to identify or characterize gases or chemicals at the location. A communications module can communicate data relating to the identified gases or chemicals to any suitable external system, such as a central computing server, etc. For such long-term installations of the DAISI system, the installation site may include a power source (e.g., electrical transmission lines connected to a junction box at the site) and network communications equipment (e.g., network wiring, routers, etc.) to provide network communication between the DAISI system and the external systems.

It can be advantageous to provide a mobile DAISI system configured to be worn or carried by a user. For example, it may be unsuitable or undesirable to install a DAISI system at some locations on a long-term basis. As an example, some oil well sites may not have sufficient infrastructure, such as power sources or network communication equipment, to support the DAISI system. In addition, it can be challenging to move the DAISI system from site to site to monitor different locations. For example, installing and removing the DAISI system from a site for transport may involve substantial effort and time for the user when the system is connected to infrastructure at the site to be monitored. Accordingly, it can be desirable to provide a DAISI system that can be used independently of the facilities or infrastructure at the site to be monitored. Furthermore, it can be advantageous to implement the DAISI system in a form factor and with a weight that can be carried or worn by a user. For example, a mobile DAISI system can enable the user to easily transport the system from site-to-site, while monitoring the presence of gases or chemicals in real-time.

It should be appreciated that each of the systems disclosed herein can be used to monitor potential gas leaks in any suitable installation site, including, without limitation, drilling rigs, refineries, pipelines, transportations systems, ships or other vessels (such as off-shore oil rigs, trains, tanker trucks, petro-chemical plants, chemical plants, etc. In addition, each of the embodiments and aspects disclosed and illustrated herein such as above, e.g., with respect to FIGS. 1-10C, can be used in combination with each of the embodiments disclosed and illustrated herein with respect to FIGS. 11A-14C.

Figure 11A:
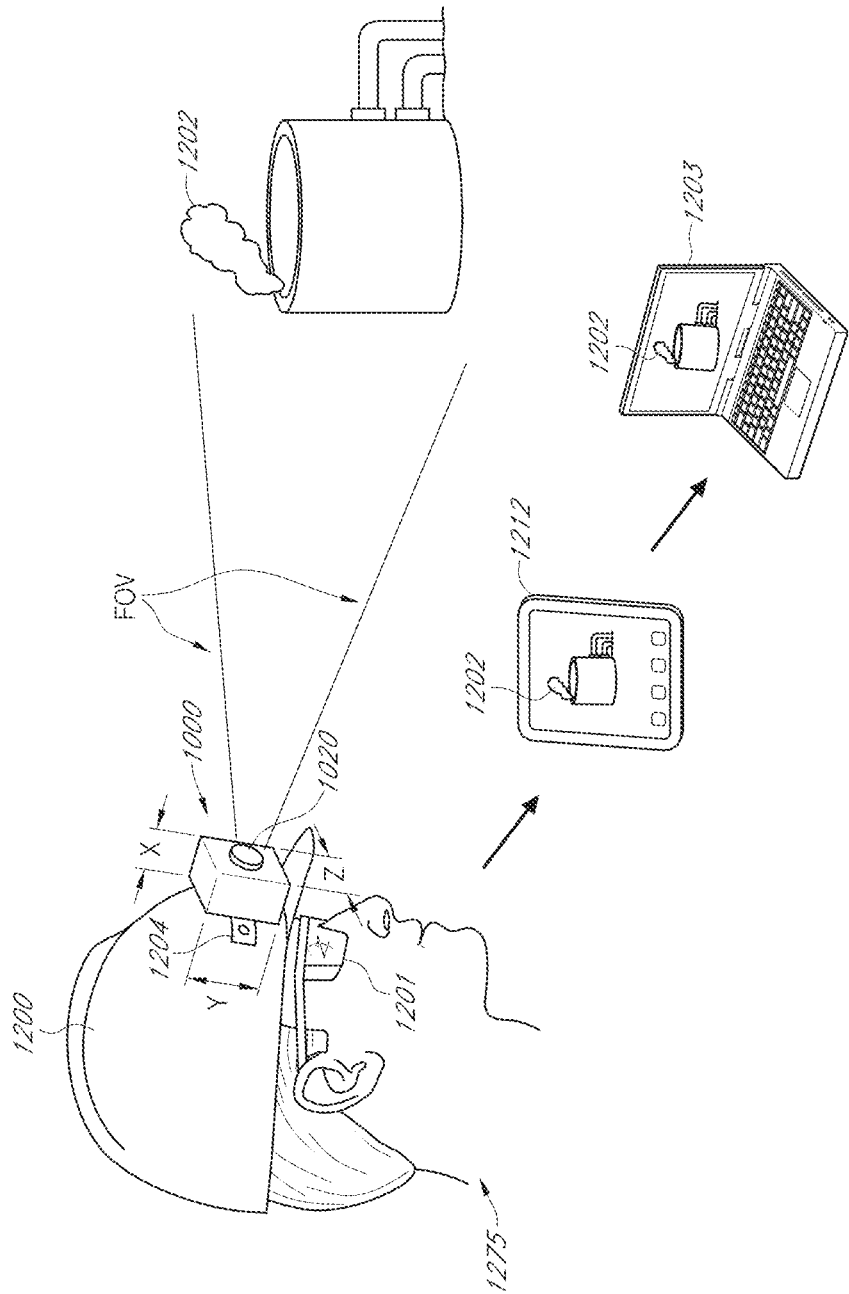
FIG. 11A is a schematic diagram illustrating a mobile infrared imaging system configured to be carried or worn by a human user.

FIG. 11A is a schematic diagram illustrating a mobile infrared imaging system 1000 (e.g., a mobile or portable DAISI system) configured to be carried or worn by a human user 1275. The user 1275 may wear a hat or helmet 1200 when he travels to a site to be monitored, such as an oil well site, a refinery, etc. The system 1000 shown in FIG. 11A is attached to the helmet 1200 by way of a support 1204 that securely mounts the system 1000 to the helmet 1200. For example, the support 1204 can comprise a fastener, a strap, or any other suitable structure. Advantageously, mounting the system 1000 to the helmet 1200 can enable the user 1275 to capture images within the system's field of view (FOV) by turning his head to face a particular location to be monitored. For example, the user 1275 can walk through the site and can capture video images of each portion of the site, e.g., various structures that may be susceptible to gas or chemical leaks, such as valves, fittings, etc. Thus, in the embodiment shown in FIG. 11A, the user 1275 can image each portion of the site by facing the area to be imaged and ensuring that the system 1000 is activated. In addition, by mounting the system 1000 to the user's helmet 1200, the user 1275 may use his hands for other tasks while the system 1000 images the site. Although the system 1000 of FIG. 11A is shown as being mounted to the user's helmet 1200, it should be appreciated that the system 1000 can instead be worn on other parts of the user's clothing or can be carried by the user, e.g., in a bag, case, or other suitable container. Furthermore, in some embodiments, a wind sensor can be provided to the user, e.g., on the user's clothing and/or on or near the system 1000. The wind sensor can be used to estimate wind conditions at the installation site, which can be used to improve the detection of gas leaks. In other embodiments, the system 1000 can be coupled to or formed with a housing that defines a "gun"-like structure which can be aimed or pointed by the user in a particular direction.

As explained herein, a gas cloud 1202 emitted from a structure at the site can be imaged by pointing the system 1000 towards the gas cloud 1202 and capturing an image of the gas cloud 1202 when the cloud 1202 is within the FOV of the system 1000. Unlike other systems, the system 1000 can capture multispectral image data of a single scene over a range of IR wavelengths with a single snapshot, as explained in further detail herein. The single snapshot can be captured in a short timeframe, e.g., less than about 3 seconds, less than about 2 seconds, or less than about 1.5 seconds (for example, in about 1 second, in some embodiments). The single snapshot can be captured in greater than about 5 milliseconds, greater than about 0.2 seconds, or greater than about 0.5 seconds. The captured image data can be processed on board the system 1000 by a processing unit, as explained in further detail herein. For example, the processing unit can process the image data from the different optical channels and can compare the captured spectral information with a database of known chemicals to identify and/or characterize the gases that are included in the gas cloud 1202.

A communications module on board the system 1000 can transmit information relating to the identified gases or chemicals to any suitable external device. For example, the communications module can wirelessly communicate (e.g., by Bluetooth, WiFi, etc.) the information to a suitable mobile computing device, such as an electronic eyewear apparatus 1201, a tablet computing device 1212, a mobile smartphone, a laptop or notebook computer 1203, or any other suitable mobile computing device. In some embodiments, if a gas cloud is detected, the system 1000 can warn the user by way of sending a signal to the mobile device (e.g., tablet computing device 1212 or a mobile smartphone. The mobile device can emit an audible ring and/or can vibrate to notify the user of a potential gas leak. In the embodiment of FIG. 11A, the electronic eyewear apparatus 1201 can include a user interface comprising a display that the user 1275 can view in real-time as he visits the site. In some embodiments, the electronic eyewear apparatus 1201 comprises eyewear that includes a display. The electronics eyewear apparatus 1201 can be further configured to present images from this display to the wearer. The electronics eyewear apparatus 1201 may for example include projection optics that projects the image into the eye. The electronic eyewear apparatus 1201 may comprise heads up display optics the presents the image on the lens portion(s) of the eyewear so that the wearer can view the image and also see through the eyewear and peer at objects in the distance. Other configurations are possible. In some arrangements, the eyewear apparatus 1201 can comprise a Google Glass device, sold by Google, Inc., of Mountain View, Calif.

The processing unit can configure the processed image data such that the types of identified gases are displayed to the user 1275 on the display of the eyewear apparatus 1201. For example, in some embodiments, color-coded data may represent different types of gases or concentrations of a particular gas, and may be overlaid on a visible light image of the scene. For example, the color-coded data and image of the gas cloud can be seen by the user on the electronic eyewear apparatus 1201. In various embodiments, text data and statistics about the composition of the gas cloud 1202 may also be displayed to the user 1275. Thus, the user 1275 can walk the site and can view the different types of gases in the gas cloud 1202 substantially in real-time. Advantageously, such real-time display of the composition of the gas cloud 1202 can enable the user 1275 to quickly report urgent events, such as the leakage of a toxic gas or chemical. In some embodiments, detection of a toxic leak can trigger an alarm, which may cause emergency personnel to help evacuate the site and/or fix the leak.

In some embodiments, the processed image data can be transmitted from the system 1000 to the tablet computing device 1212, laptop computer 1203, and/or smartphone. The user 1275 can interact with the table computing device 1212 or laptop computer 1203 to conduct additional analysis of the imaged and processed gas cloud 1202. Furthermore, information about the gas cloud (including the processed data and/or the raw image data) may also be transmitted to a central server for centralized collection, processing, and analysis. In various arrangements, a global positioning system (GPS) module can also be installed on board the system 1000 and/or on the mobile computing device (such as a tablet computing device, smartphone, etc.). The GPS module can identify the coordinates of the user 1275 when a particular image is captured. The location data for the captured image data can be stored on the central server for further analysis.

Thus, the system 1000 shown in FIG. 11A can enable the user 1275 to image multiple locations of a particular site to be monitored, such as an oil well site. Advantageously, the optical components, the processing components, and the communications components of the system 1000 can be integrated within a relatively small housing that can be carried or worn by the user 1275. For example, in various embodiments, the system 1000 does not include complex mechanical components for movement, such as gimbals, actuators, motors, etc. Without such components, the size of the system 1000 can be reduced relative to other systems.

Unlike other systems, in which the system components are bulky or are assembled over a large form factor, the mobile system 1000 can be sized and shaped in such a manner so as to be easily moved and manipulated when the user 1275 moves about the site. Indeed, it can be very challenging to integrate the various system components in a small form-factor. Advantageously, the systems 1000 can be worn or carried by a human user. For example, the components of the system 1000 can be contained together in a data acquisition and processing module 1020, which may include a housing to support the system components. The components of the system 1000 (including the optical or imaging components, the focal plane array, the on-board processing electronics, and the communications components) may be packaged or assembled in the data acquisition and processing module 1020 and may occupy a volume less than about 300 cubic inches, less than about 200 cubic inches, or less than about 100 cubic inches. In various embodiments, the components of the system 1000 (including the optical or imaging components, the focal plane array, the on-board processing electronics, and the communications components) may be packaged or assembled in the data acquisition and processing module 1020 and may occupy a volume greater than about 2 cubic inches, or greater than about 16 cubic inches.

The data acquisition and processing module 1020 (with the system components mounted therein or thereon) may be sized and shaped to fit within a box-shaped boundary having dimensions X×Y×Z. For example, the data acquisition and processing module 1020, including the imaging optics, focal plane array, and on board processing electronics, may be included in a package that is sized and shaped to fit within the box-shaped boundary having dimensions X×Y×Z. This package may also contain a power supply, such as a battery and/or solar module. In some embodiments, the data acquisition and processing module 1020 (including the imaging optics, focal plane array, and on board processing electronics may) can be sized and shaped to fit within a box-shaped boundary smaller than 8 inches×6 inches×6 inches. In some embodiments, the data acquisition and processing module 1020 (including the imaging optics, focal plane array, and on board processing electronics may) can be sized and shaped to fit within a box-shaped boundary smaller than 7 inches×5 inches×5 inches, e.g., a box-shaped boundary small than 7 inches×3 inches×3 inches. In some embodiments, the data acquisition and processing module 1020 (including the imaging optics, focal plane array, and on board processing electronics may) can be sized and shaped to fit within a box-shaped boundary smaller than 6 inches×4 inches×4 inches. In some embodiments, the data acquisition and processing module 1020 (including the imaging optics, focal plane array, and on board processing electronics may) can be sized and shaped to fit within a box-shaped boundary smaller than 2 inches×2 inches×6 inches. In some embodiments, the data acquisition and processing module 1020 (including the imaging optics, focal plane array, and on board processing electronics may) can be sized and shaped to fit within a box-shaped boundary having dimensions larger than 4 inches×2 inches×2 inches. In some embodiments, the data acquisition and processing module 1020 (including the imaging optics, focal plane array, and on board processing electronics may) can be sized and shaped to fit within a box-shaped boundary having dimensions larger than 3 inches×3 inches×7 inches. In some embodiments, the data acquisition and processing module 1020 (including the imaging optics, focal plane array, and on board processing electronics may) can be sized and shaped to fit within a box-shaped boundary having dimensions larger than 2 inches×1 inches×1 inches. The data acquisition and processing module 1020 (including the imaging optics, focal plane array, and on board processing electronics may) can have dimensions less than 2 inches×2 inches×6 inches. The data acquisition and processing module 1020 (including the imaging optics, focal plane array, and on board processing electronics may) can have dimensions greater than 1 inches×1 inches×3 inches. The data acquisition and processing module 1020 (including the imaging optics, focal plane array, and on board processing electronics may) can have dimensions greater than 2 inches×2 inches×4 inches. said data acquisition and processing module has dimensions less than 6 inches×3 inches×3 inches. The data acquisition and processing module 1020 (including the imaging optics, focal plane array, and on board processing electronics may) can have dimensions less than 4 inches×3 inches×3 inches. The data acquisition and processing module 1020 (including the imaging optics, focal plane array, and on board processing electronics may) can have dimensions less than 3 inches×2 inches×2 inches. The data acquisition and processing module 1020 (including the imaging optics, focal plane array, and on board processing electronics may) can have dimensions greater than 2 inches×1 inches×1 inches. The data acquisition and processing module 1020 (including the imaging optics, focal plane array, and on board processing electronics may) can have dimensions greater than 1 inches×0.5 inch×0.5 inch. The data acquisition and processing module 1020 (including the imaging optics, focal plane array, and on board processing electronics may) can have a volume less than 30 cubic inches. The data acquisition and processing module 1020 (including the imaging optics, focal plane array, and on board processing electronics may) can have a volume less than 20 cubic inches. The data acquisition and processing module 1020 (including the imaging optics, focal plane array, and on board processing electronics may) can have a volume less than 15 cubic inches. The data acquisition and processing module 1020 (including the imaging optics, focal plane array, and on board processing electronics may) can have a volume less than 10 cubic inches. The data acquisition and processing module 1020 (including the imaging optics, focal plane array, and on board processing electronics may) can have a volume more than 1 cubic inches. The data acquisition and processing module 1020 (including the imaging optics, focal plane array, and on board processing electronics may) can have a volume more than 4 cubic inches. The data acquisition and processing module 1020 (including the imaging optics, focal plane array, and on board processing electronics may) can have a volume more 5 cubic inches. The data acquisition and processing module 1020 (including the imaging optics, focal plane array, and on board processing electronics may) can have a volume more 10 cubic inches. This package may also contain a power supply, including a battery and/or solar module, a communications module, or both and fit into the above-referenced dimensions. It should be appreciated that the dimensions disclosed herein may not correspond to the directions shown in FIG. 11A with respect to X, Y, and Z.

Moreover, the system 1000 can have a mass and weight sufficiently small so as to enable the user 1275 to easily carry or wear the data acquisition and processing module 1020 at the site. Thus, the embodiment shown in FIG. 11A can be sized and shaped and configured to have a mass that enables a human user to easily and effectively manipulate the system 1000.

Figure 11B:
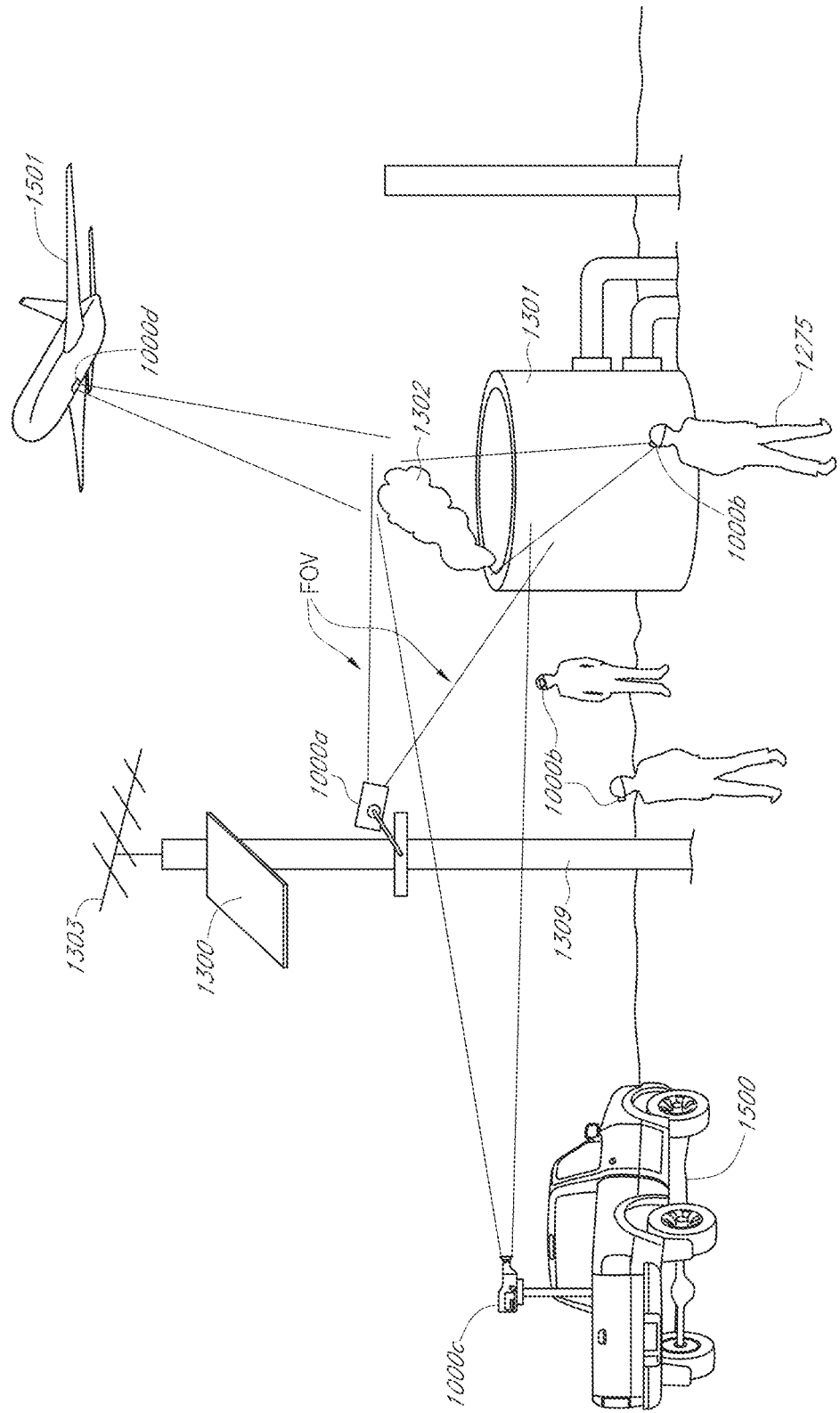
FIG. 11B is a schematic diagram illustrating an installation site that can be monitored by multiple infrared imaging systems.

FIG. 11B is a schematic diagram illustrating an installation site (e.g., an oil well site, etc.) that can be monitored by multiple infrared imaging systems 1000 (e.g., a DAISI system). For example, as shown in FIG. 11B, an imaging system 1000A can be mounted to a pole 1309 or other stationary structure at the site. An imaging system 1000B can be worn or carried by multiple users 1275, an imaging system 1000C can be mounted on a truck 1500, and/or an imaging system 1000D can be mounted on an aerial platform 1501, such as an unmanned aerial vehicle (UAV) or a piloted airplane. In some arrangements, the UAV can comprise an airplane, a helicopter (such as a quad helicopter), etc. The embodiments disclosed herein can utilize the image data captured by any combination of the systems 1000A-1000D at the installation site to image the entire installation site in an efficient manner. Indeed, each installation site can include any suitable number and type of system 1000A-1000D. For example, each installation site can include greater than two systems 1000A-1000D, greater than five systems 1000A-1000D, greater than ten systems 1000A-1000D, greater than twenty systems 1000A-1000D. Each installation site may include less than about 100 systems 1000A-1000D.

For example, the central server can track the real-time locations of each imaging system 1000A-1000D based on the GPS coordinates of the particular system or on predetermined knowledge about the system's stationary location. The distributed nature of the imaging systems 1000A-1000D can provide rich information to the central server about the types and locations of gas leaks or other problems throughout multiple installation sites. Although FIG. 11B illustrates a stationary system 1000A mounted to a fixture, a portable system 1000B to be worn or carried by a human, a truck-based system 1000C, and an aerial-based system 1000D, it should be appreciated that other types of systems may be suitable. For example, in some embodiments, a robotic vehicle or a walking robot can be used as a platform for the systems 1000 disclosed herein. In various embodiments, a floating platform (such as a boat) can be used as a platform for the systems 1000 disclosed herein. It should also be appreciated that the systems disclosed herein can utilize any combination of the platforms (e.g., stationary fixtures such as a pole, human user(s), truck(s) or other vehicle, aerial platform(s), floating platform(s), robotic platform(s), etc.) to support the systems 1000.

The systems 1000 shown in FIG. 11B can comprise a mobile DAISI system, similar to that illustrated in FIG. 11A. In other embodiments, the systems 1000 can comprise a larger DAISI system configured for use on a relatively long-term basis. For example, the stationary imaging system 1000A shown in FIG. 11B can be installed on a pole 1309 or other suitable structure for monitoring a storage tank 1301. A solar panel 1300 can be provided at or near the system 1000 to help provide power to the system 1000. An antenna 1303 can electrically couple to the system and can provide wireless communication between the system 1000 and any other external entity, such as a central server, for storing and/or processing the data captured by the system 1000.

A DAISI system such as system 1000 may, if desired, be coupled to a unit that adjusts the pan, tilt, rotation, height, or other position of the system 1000. As an example, system 1000 may be mounted to a pan and tilt unit. The pan and tilt unit may be able to rotate the front of system 1000 left and right (e.g., yaw system 1000 left and right) and able to rotate the front of system 1000 up and down (e.g., pitch system 1000 up and down), thereby enabling system 1000 to focus on a particular portion of the surrounding environment and, when desired, to scan different areas of the surrounding environment (i.e., to move through a desired scan path). The pan and tilt unit (or any other unit that adjusts the position of system 1000 may include motors, actuators, or other suitable mechanisms to drive movements of system 1000. The operation of a pan and tilt unit (or any other unit that adjusts the position of system 1000) may be controlled by system 1000, by the pan and tilt unit, by a remote system, by a control system capable of controlling one or more systems 1000 and/or corresponding pan and tilt units, or by any suitable and desired control system.

The stationary infrared imaging system 1000A can be programmed to continuously or periodically monitor the site. If a gas cloud 1302 escapes from the storage tank 1301, such as by leaking from a broken valve, then the system 1000A can capture a multispectral, snapshot image or series of images (e.g., a video stream) of the gas cloud 1302. As with the embodiment of FIG. 11A, the imaging system 1000A can include imaging, processing, and communications components on board the system 1000A to identify and characterize the types of gases in the cloud 1302 and to transmit the processed data to the central server, e.g., by way of the antenna 1303.

The imaging systems 1000B worn or carried by the multiple users 1275 can advantageously capture and process multispectral image data of the portions of the installation site that each user 1275 visits. It should be appreciated that the different users 1275 may work in or travel through different portions of the installation site (and also to a number of installation sites) over a period of time. When activated, the imaging systems 1000B worn or carried by the users 1275 can continuously or periodically capture multispectral image data of the different locations at the installation site(s) to which the user 1275 travels. As explained herein, the system 1000B can transmit the image data and the location at which the image was captured to the central server. If the system 1000B or the central server detects a problem (such as a gas leak), then the central server can associate that leak with a particular location and time.

Furthermore, because the central server can receive image data and location data from multiple users at different locations and viewing from different perspectives, the central server can create an organization-wide mapping of gas leaks that include, e.g., the locations of gas leaks in any of multiple installation sites, the type and concentrations and expanse or extent of each gas leaked, the particular user 1275 that captured the image data, and the time at which the image was taken. Thus, each user 1275 that carries or wears a portable imaging system 1000B can contribute information to the central server that, when aggregated by the central server, provides rich details on the status of any gas leaks at any installation sites across the organization.

The truck-mounted imaging system 1000C can be mounted to a truck or other type of vehicle (such as a car, van, all-terrain vehicle, etc.). As shown in FIG. 11B, the imaging system 1000C can be connected to an end of an extendable pole or extension member mounted to the truck 1500. The system 1000C can be raised and lowered by a control system to enable the system 1000C to image a wide area of the installation site. In some embodiments, actuators can be provided to change the angular orientation of the system 1000C, e.g., its pitch and yaw. A vibration isolation or reduction mechanism can also be provided to reduce vibrations, which may disturb the imaging process. The system 1000C can be battery powered and/or can be powered by the truck; in some embodiments, a generator can be used to supply power to the system 1000C. A user can drive the truck 1500 throughout the installation site to image various portions of the site to detect leaks. In addition, the user can drive the truck 1500 to other installation sites to detect gas leaks. As explained herein, the location of the truck 1500 can be communicated to the central server and the location of the truck 1500 can be associated with each captured image. The truck 1500 may include GPS electronics to assist in tracking the location of the truck 1500 and/or system 1000C over time as the user drives from place to place. Similarly, the aerial platform 1501 (such as an unmanned aerial vehicle, or UAV) can support the imaging system 1000D. The aerial platform 1501 can be piloted (either remotely or non-remotely) to numerous installation sites to capture multispectral image data to detect gas clouds.

Thus, the systems 1000A-1000D can provide extensive data regarding the existence of leaks at numerous installations across an organization. Monitoring numerous cameras simultaneously or concurrently across an organization, site, region, or the entire country can be enabled at least in part by providing wireless (or wired) communication between the systems 1000A-1000D and one or more central servers. Advantageously, the collection of image data from multiple sources and multiple platforms can enable the organization to create a real-time mapping of potential gas leaks, the types and amounts of gases being leaks, the locations of the leaks, and the time the image data of the leak was captured. In some arrangements, the aggregation of data about a site can improve the safety of installation sites. For example, if a gas leak is detected at a particular installation, the embodiments disclosed herein can alert the appropriate personnel, who can begin safety and/or evacuation procedures. Moreover, the aggregation of data across an organization (such as an oil service company) can provide site-wide, region-wide, and/or company-wide metrics for performance. For example, a given facility can monitor its total emissions over time and use the resulting data to help determine the facility's overall performance. A given region (such as a metropolitan area, a state, etc.) can monitor trends in emissions over time, providing a value on which to base decisions. Likewise, a company can look at the emissions performance at all of its facilities and can make decisions about whether some facilities should make new investments to improve performance, and/or whether the entire company should make various improvements. The mobile systems 1000 disclosed herein can thus provide a ubiquitous monitoring system for decision making In addition, the systems 1000 disclosed herein can be used in a feedback control process to improve various manufacturing procedures based on the gases detected by the system(s) 1000. Accordingly, a control module may be provided to adjust the manufacturing procedure and/or parameters according to the gases measured by the system 1000.

The embodiments of the mobile infrared imaging system 1000 disclosed herein provide various advantages over other systems. As explained above, aggregation of data about a site and its potential gas leaks can provide an organization- or system-wide mapping of potential problems. Furthermore, automatic detection of gas leaks (and identification of the gases in the gas cloud) can simplify operation of the system 1000 and can reduce the risk of user errors in attempting to detect or identify gas clouds manually. Moreover, the small size of the systems 1000 disclosed herein are more easily carried or worn by the user than other systems. In addition, the systems 1000 disclosed herein can overlay the identified gas clouds on a visible image of the scene and can color code the gas cloud according to, e.g., type of gas, concentration, etc.

Figure 12:
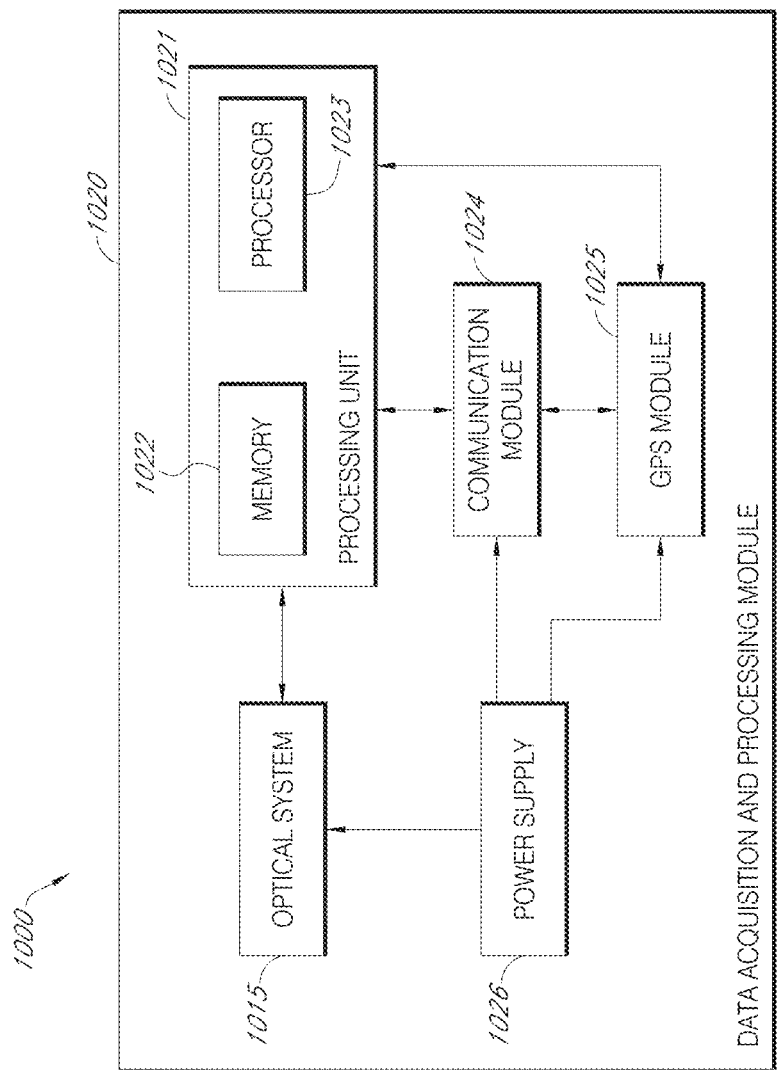
FIG. 12 is a schematic system block diagram showing a mobile infrared imaging system, according to one embodiment.

FIG. 12 is a schematic system block diagram showing a mobile infrared imaging system 1000 (e.g., a mobile DAISI system), according to one embodiment. The imaging system 1000 can include a data acquisition and processing module 1020 configured to be worn or carried by a person. The data acquisition and processing module 1020 can include, contain, or house an optical system 1015, a processing unit 1021, a power supply 1026, a communication module 1025, and GPS module 1025. In other embodiments, the data acquisition and processing module 1020 can be configured to be mounted to a structure at the site to be monitored, such as a post. The power unit 1026 can be provided on board the system 1000. The power unit 1026 can be configured to provide power to the various system components, such as the optical system 1015, the processing unit 1021, the communication module 1024, and/or the GPS module 1025. In some embodiments, the power unit 1026 can comprise one or more batteries (which may be rechargeable) to power the system components. In some embodiments, the power unit 1026 can include a solar power system including one or more solar panels for powering the system by sunlight. In some embodiments, the power unit 1026 can include various power electronics circuits for converting AC power supplied by standard power transmission lines to DC power for powering the system components. Other types of power supply may be suitable for the power unit 1026.

The system 1000 can include an optical system 1015 configured to capture multispectral image data in a single snapshot, as explained herein. The optical system 1015 can correspond to any suitable type of DAISI system, such as, but not limited to, the optical systems and apparatus illustrated in FIGS. 1-10C above and/or in the optical systems 1015 illustrated in FIGS. 13A-13B below. For example, the optical system 1015 can include an optical focal plane array (FPA) unit and components that define at least two optical channels that are spatially and spectrally different from one another. The two optical channels can be positioned to transfer IR radiation incident on the optical system towards the optical FPA. The multiple channels can be used to multiplex different spectral images of the same scene and to image the different spectral images on the FPA unit.

The processing unit 1021 can also be provided on board the data acquisition and processing module 1020. The processing unit 1021 can include a processor 1023 and a memory 1022. The processor 1023 can be in operable cooperation with the memory 1022, which can contain a computer-readable code that, when loaded onto the processor 1023, enables the processor 1023 to acquire multispectral optical data representing a target species of gas or chemical from IR radiation received at the optical FPA unit of the optical system 1015. The memory 1022 can be any suitable type of memory (such as a non-transitory computer-readable medium) that stores data captured by the optical system 1015 and/or processed by the processing unit 1021. The memory 1022 can also store the software that is executed on the processor 1023. The processor 1023 can be configured to execute software instructions that process the multispectral image data captured by the optical system 1015. For example, the processor 1023 can analyze the different images detected by the FPA and can compare the captured data with known signatures of various types of gases or chemicals. Based on the analysis of the captured image data, the processor can be programmed to determine the types and concentrations of gases in a gas cloud. Further, as explained herein, the processor 1023 can analyze calibration data provided by the optical system 1015 to improve the accuracy of the measurements.

Advantageously, the processor 1023 can comprise one or more field-programmable gate arrays (FPGA) configured to execute methods used in the analysis of the images captured by the optical system 1015. For example, the FPGA can include logic gates and read access memory (RAM) blocks that are designed to quickly implement the computations used to detect the types of gases in a gas cloud. The small size/weight, and high performance characteristics of the FPGA can enable on board computation and analysis within the data acquisition and detection unit 1020 worn or carried by the user. The use of FPGA (or similar electronics) on board the system 1000 can reduce costs associated with using an off-site central server or larger computing device to conduct the image analysis computations. In addition, enabling computation with one or more FPGA devices on board the wearable system can also prevent or reduce communication bottlenecks associated with wirelessly transmitting large amounts of raw data from the system 1000 to a remote server or computer, which can be used in some embodiments.

The communication module 1024 can be configured to communicate with at least one device physically separate from the data acquisition and processing module 1020. For example, the communication module 1024 can include a wireless communication module configured to wirelessly communicate with the at least one separate device. The wireless communication module can be configured to provide wireless communication over wireless networks (e.g., WiFi internet networks, Bluetooth networks, etc.) and/or over telecommunications networks (e.g., 3G networks, 4G networks, etc.).

In some embodiments, for example, the wireless communication module can provide data communication between the data acquisition and processing module 1020 and a mobile device such as an electronic eyewear apparatus, a tablet computing device, a mobile smartphone, a laptop or notebook computer, or any other suitable mobile computing device. As explained herein, the mobile device can include a display on which the processed image data can be displayed to the user. For example, the types (and/or concentrations) of gases in a gas cloud can be illustrated on the display, e.g., by color coding or other suitable illustration scheme. The processed data can overlie a visible image of the scene in some arrangements. In some embodiments, the wireless communication module can provide data communication between the system 1000 and an external device remote from the system 1000, such as a central server. For example, the processed image data and/or the raw image data may be transmitted over a telecommunications network to the central server for storage and/or further analysis. In some embodiments, the processed or raw image data can be uploaded to the mobile device (e.g., notebook computer, smartphone, tablet computing device, etc.), which can in turn communicate the image data to the central server.

The GPS module 1025 can be configured to determine the location of the data acquisition and processing module 1020 at a particular time. The processing unit 1021 can store the location data and can associate the location data with a particular image captured by the optical system 1015 in some arrangements. The location data associated with the captured images can be transmitted by the communication module 1024 (or by an external device) to a central server in some arrangements.

The optical system 1015, the processing unit 1021, the power supply 1026, the communication module 1024, and/or the GPS module 1025 may be contained or housed in the data acquisition and processing module 1020, which can be carried or worn by the user. The components of the system 1000 (including the optical components, the processing components, and the communications components) may be packaged or assembled in the data acquisition and processing module 1020 and may occupy a volume less than about 300 cubic inches, less than about 200 cubic inches, or less than about 100 cubic inches. In various embodiments, the components of the system 1000 (including the optical components, the processing components, and the communications components) may be packaged or assembled in the data acquisition and processing module 1020 and may occupy a volume greater than about 2 cubic inches, or greater than about 16 cubic inches. A power supply, including a battery and/or solar module may also be included among the components packaged or assembled in the data acquisition and processing module 1020 and fit into the above-referenced volumetric dimensions.

The data acquisition and processing module 1020 (with the system components mounted therein or thereon, including the imaging optics, focal plane array, and on board processing electronics may) may be sized and shaped to fit within a box-shaped boundary having dimensions X×Y×Z. For example, in some embodiments, the data acquisition and processing module 1020 (including the imaging optics, focal plane array, and on board processing electronics may) can be sized and shaped to fit within a box-shaped boundary smaller than 8 inches×6 inches×6 inches. In some embodiments, the data acquisition and processing module 1020 (including the imaging optics, focal plane array, and on board processing electronics may) can be sized and shaped to fit within a box-shaped boundary smaller than 7 inches×5 inches×5 inches. In some embodiments, the data acquisition and processing module 1020 (including the imaging optics, focal plane array, and on board processing electronics may) can be sized and shaped to fit within a box-shaped boundary smaller than 6 inches×4 inches×4 inches. In some embodiments, the data acquisition and processing module 1020 (including the imaging optics, focal plane array, and on board processing electronics may) can be sized and shaped to fit within a box-shaped boundary having dimensions larger than 4 inches by 2 inches×2 inches. In some embodiments, the data acquisition and processing module 1020 (including the imaging optics, focal plane array, and on board processing electronics may) can be sized and shaped to fit within a box-shaped boundary having dimensions larger than 2 inches by 1 inches×1 inches. A power supply, including a battery and/or solar module, a communications module, or both may be included in the data acquisition and processing module 1020 and fit into the above-referenced dimensions. It should be appreciated that the dimensions disclosed herein may not correspond to the directions shown in FIG. 11A with respect to X, Y, and Z. Moreover, the system 1000 can have a mass and weight sufficiently small so as to enable the user 1275 to easily carry or wear the data acquisition and processing module 1020 at the site.

Figure 13A:
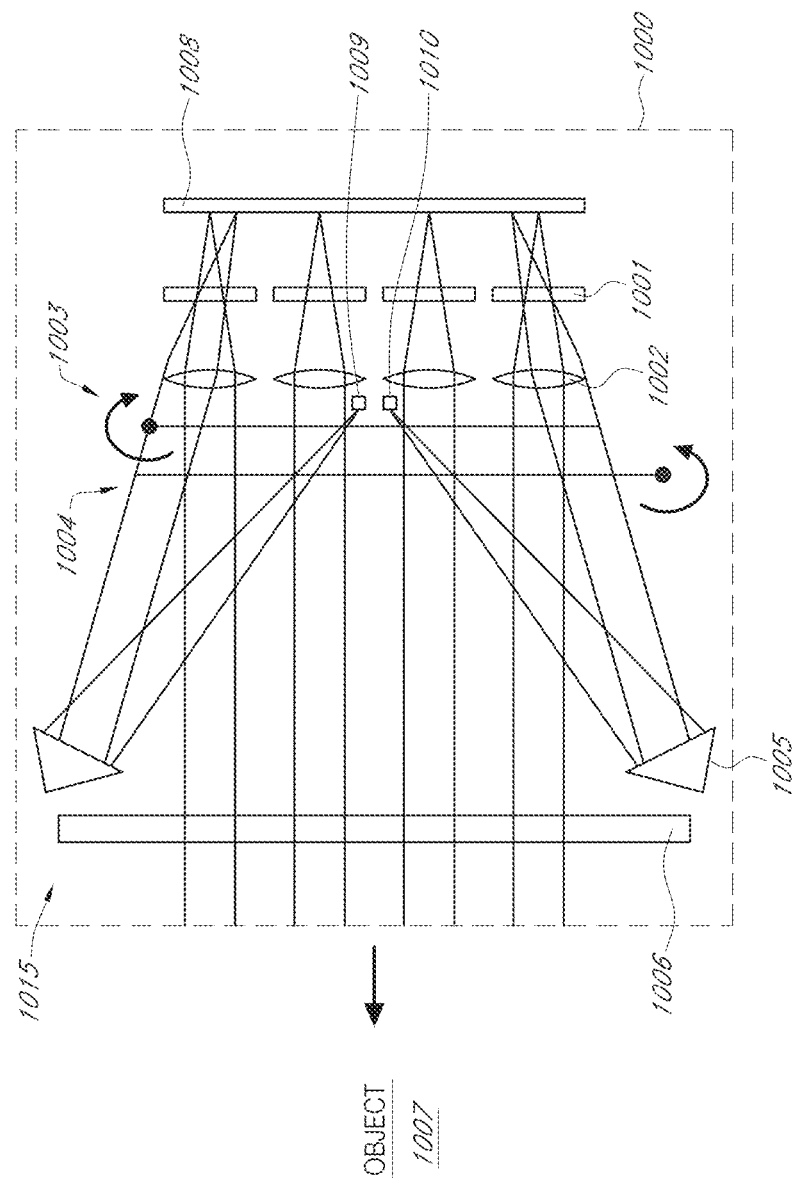
FIG. 13A is a schematic system diagram of an optical system configured to be used in the mobile infrared imaging systems disclosed herein, according to various embodiments.

FIG. 13A is a schematic system diagram of an optical system 1015 configured to be used in the mobile infrared imaging systems 1000 disclosed herein, according to various embodiments. As explained herein, the optical system 1015 shown in FIG. 13A can be provided in the data acquisition and processing module 1020 to be worn or carried by the user. The optical system 1015 can be configured to capture multispectral image data of an object 1007, such as a gas cloud, chemical spill, etc. The components of the optical system 1015 shown in FIG. 13A may be similar to or the same as the components of the optical systems and devices explained herein with respect to FIGS. 1-10C. The optical system 1015 can include a focal plane array (FPA) unit 1008 configured to record infrared image data captured by the system 1000. As shown in FIG. 13A, the FPA unit 1008 may advantageously be uncooled, e.g., devoid of a cooling system.

The optical system 1015 can include a front window 1006 through which light from the object 1007 passes. A first moveable blackbody source 1003 and a second moveable blackbody source 1004 can be provided to enable calibration of the optical system 1015. The moveable sources 1003, 1004 can be moved in front of the field of view such that the optics image these sources for calibration. For example, the first and second blackbody sources 1003, 1004 can be maintained at different known temperatures in a stable manner. For example, a heater and a temperature sensor can be attached to each blackbody source 1003, 1004 to provide feedback to create a stable and known temperature difference (e.g., at least 50 mK in some arrangements) between different spatial regions of the sources.

In addition, the optical system 1000 can include a dynamic calibration apparatus to dynamically calibrate the system 1000. As shown in FIG. 13A, one or more calibration sources 1009, 1010 can be provided. The calibration sources 1009, 1010 can comprise a thermal electrically controlled (TEC) material with a temperature sensor attached thereto. The calibration sources 1009, 1010 can be coated with a spectrally measured coating or paint. Light from the calibration sources 1009, 1010 can be reflected from one or more mirrors 1005 and directed through the lens array 1002 (described below) to be imaged on a portion of the FPA unit 1008 to assist in dynamically calibrating the system 1000 (e.g., while imaging of the target gas cloud is simultaneously being imaged).

The optical system 1000 can include a lens array 1002 to focus the incoming light onto the FPA unit 1008. As shown in FIG. 13A, each lens of the lens array 1002 can at least partially define or be included in an optical channel to be imaged by the FPA unit 1008. To improve the mobility and portability of the mobile imaging system 1000, the lens array 1002 can comprise an integrated unit formed from or assembled into a single unitary body. Such an integrated lens array 1002 can reduce the size of the imaging system 1015, and therefore, the size of the system 1000, to at least partially enable the system 1000 to be worn or carried by the user. The lens array 1002 can be monolithically formed in any suitable manner. For example, in various embodiments, the lens array 1002 can be formed by a diamond milling tool. In some embodiments, the lens array 1002 can comprise a monolithic piece of transparent material which has separate regions shaped into curved refractive surfaces for creating separate lenses. In some embodiments, the lenses can be inserted into an array of openings formed in a plate or substrate to create the lens array 1002.

The optical system 1000 can also include an array of infrared (IR) filters 1001 configured to filter wavelengths of infrared light in an appropriate manner. Examples of IR filters and filtering techniques are disclosed herein, for example, with respect to FIGS. 5A-6D. As shown in FIG. 13A, the IR filters 1001 can be disposed between the lens array 1002 and the FPA unit 1008. The IR filters 1001 can at least partially define the multiple optical channels to be imaged by the FPA unit 1008. In some embodiments, the IR filters 1001 can be positioned between the lens array 1002 and the first and second moveable blackbody sources 1009, 1010.

Figure 13B:
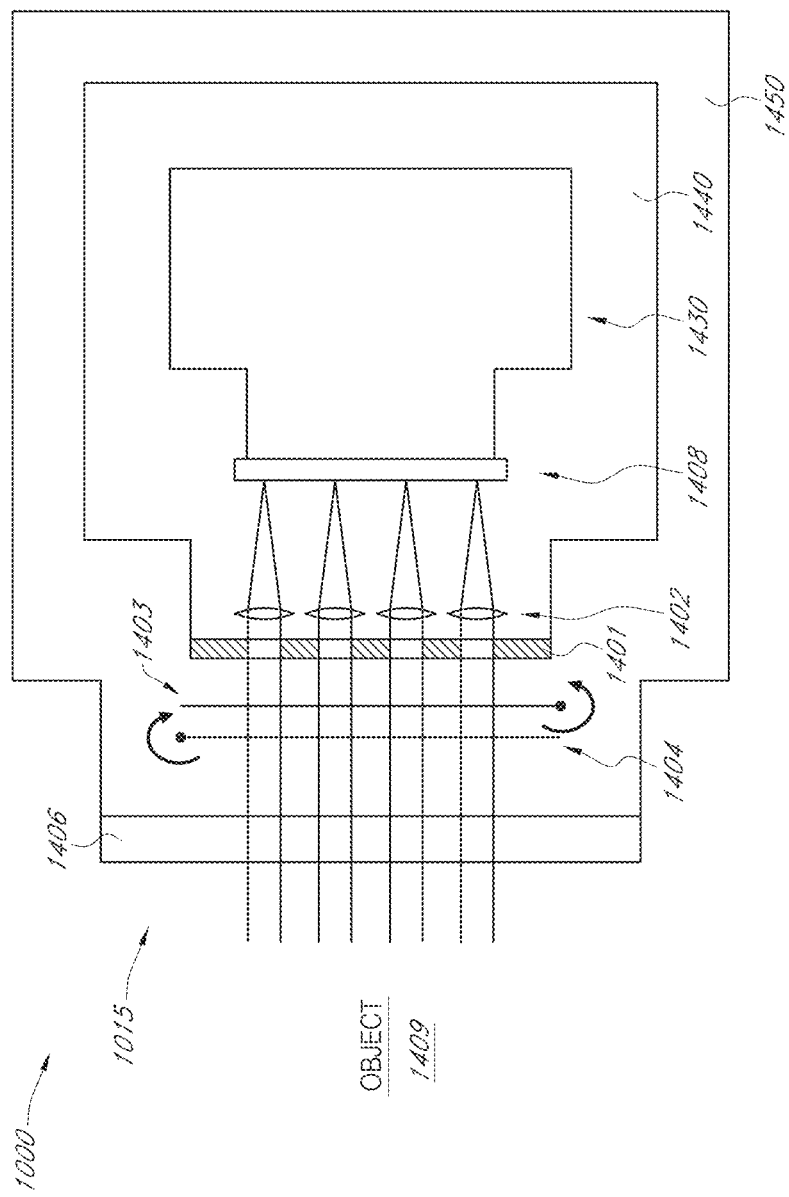
FIG. 13B is a schematic system diagram of an optical system configured to be used in the mobile infrared imaging systems disclosed herein, according to other embodiments.

FIG. 13B is a schematic system diagram of an optical system 1015 configured to be used in the mobile infrared imaging systems 1000 disclosed herein, according to various embodiments. As explained herein, the optical system 1015 shown in FIG. 13B can be provided in the data acquisition and processing module 1020 to be worn or carried by the user. The components of the optical system 1015 shown in FIG. 13B may be similar to or the same as the components of the optical systems and devices explained herein with respect to FIGS. 1-10C and 13A.

The optical system 1015 of FIG. 13B can include an FPA unit 1408 configured to image an object 1409, such as a gas cloud or chemical leak. As with the embodiment illustrated in FIG. 13A, the system 1015 of FIG. 13B can include a front window 1406 through which light from the object 1409 passes, first and second moveable blackbody sources 1403, 1404, an IR filter array 1401, and a lens array 1402. As with the embodiment of FIG. 13A, the lens array 1402 can comprise a unitary or monolithic body. In the embodiment of FIG. 13B, the lens array 1402 may be disposed between the filter array 1401 and the FPA unit 1408. In other arrangements, the filter array 1401 may be disposed between the lens array 1402 and the FPA unit 1408.

The optical system 1015 of FIG. 13B can include a cooling unit 1430 configured to cool the FPA unit 1408. The cooling unit 1430 can comprise a cooling finger configured to cryogenically cool the FPA array 1408 in various arrangements. As shown in FIG. 13B, the filter array 1401, the lens array 1402, and the FPA unit 1408 can be disposed in a cooled region 1440. The blackbody sources 1403, 1404 and front window 1406 can be disposed in an uncooled region 1450. Disposing the blackbody sources 1403, 1404 at uncooled temperatures and the filter array 1401, lens array 1402, and FPA unit 1408 at cooled temperatures can assist in the periodic calibration of the system 1000.

Figure 14A:
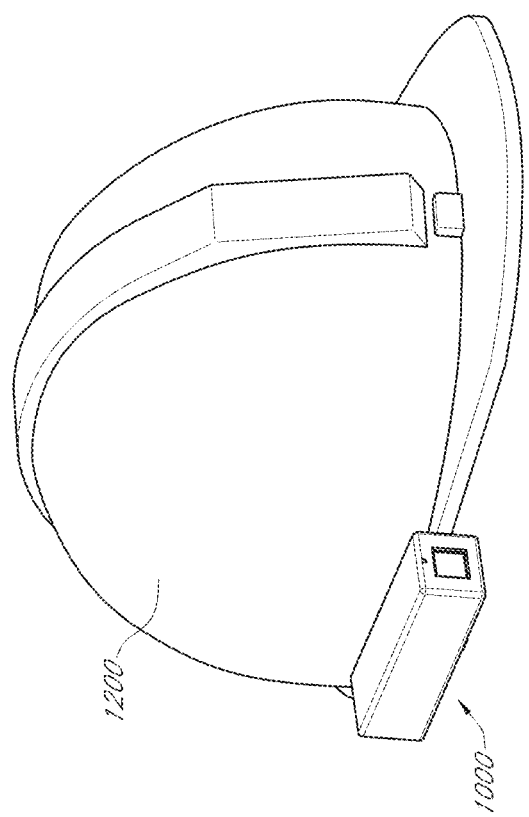
FIG. 14A is a schematic perspective view of a mobile infrared imaging system mounted to a helmet, according to various embodiments.
Figure 14B:
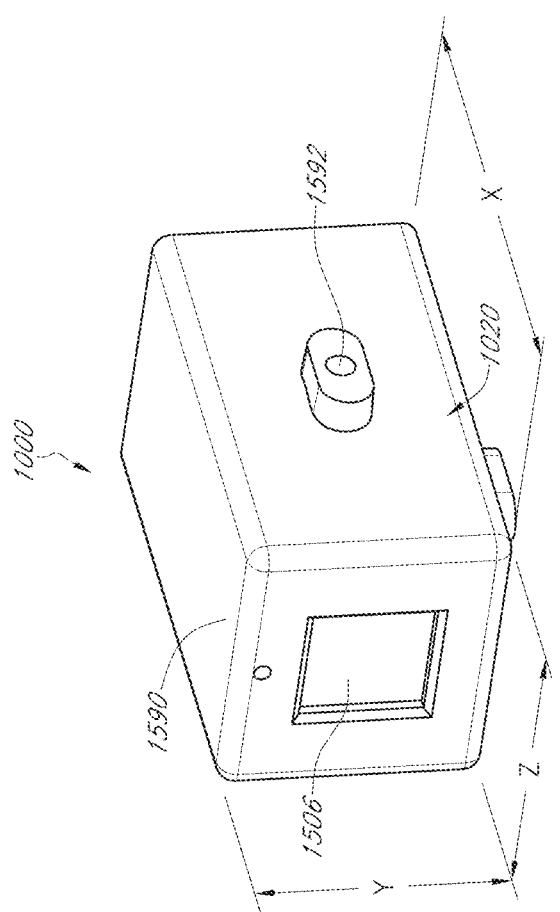
FIG. 14B is an enlarged schematic perspective view of the mobile infrared imaging system shown in FIG. 14A.

FIG. 14A is a schematic perspective view of a mobile infrared imaging system 1000 (e.g., mobile DAISI system) mounted to a helmet 1200, according to various embodiments. FIG. 14B is an enlarged schematic perspective view of the mobile infrared imaging system 1000 shown in FIG. 14A. The helmet 1200 can comprise a portion of a user's personal protective equipment and can also advantageously be used as a platform for the imaging system 1000. As explained above, the helmet 1200 can be worn by a user as the user visits a particular installation site to be monitored, such as an oil well site, a refinery, etc. The system 1000 can be activated to continuously monitor and analyze the sites that the user visits. The system 1000 can thereby continuously and actively search for gas leaks wherever the user visits and can initiate an alarm or other notification if a leak is detected.

In the embodiment illustrated in FIG. 14B, the imaging system 1000 can comprise a housing 1590, within or to which a data acquisition and processing module 1020 (see, e.g., FIG. 12 and associated description) is mounted or coupled. A support 1592 can be coupled to or formed with the housing 1590 and can be configured to attach to the helmet 1200 or to any other suitable platform. For example, in some embodiments, the support 1592 can include one or more mounting holes for attaching to the helmet 1200 by way of, e.g., screws, bolts, or other fasteners. In addition, as shown in FIG. 14B, a front window 1506 can be provided at a front end of the housing 1590. The front window 1506 can be transparent to IR radiation and can at least partially define the aperture of the system 1000. In some embodiments, the window 1506 comprises germanium. A diamond like coating (DLC) or other coating or layer can be disposed over the window 1506 to provide a durable surface.

As explained herein, the system 1000 can be configured to be worn or carried by a human user. Accordingly, the data acquisition and processing module 1020 can be suitably dimensioned such that a user can easily wear or carry the system 1000. For example, the data acquisition and processing module 1020 can be defined at least in part by dimensions X×Y×Z, as shown in FIGS. 14A and 14B.

Unlike other systems, in which the system components are bulky or are assembled over a large form factor, the mobile system 1000 can be sized and shaped in such a manner so as to be easily moved and manipulated when the user moves about the site. Indeed, it can be very challenging to integrate the various system components in a small form-factor. Advantageously, the systems 1000 disclosed herein can be worn or carried by a human user. For example, the components of the system 1000 can be contained together in the data acquisition and processing module 1020, which may include the housing 1590 to support the system components. The components of the system 1000 (including the optical or imaging components, the focal plane array, the on-board processing electronics, and the communications components) may be packaged or assembled in the data acquisition and processing module 1020 and may occupy a volume less than about 300 cubic inches, less than about 200 cubic inches, or less than about 100 cubic inches. In various embodiments, the components of the system 1000 (including the optical or imaging components, the focal plane array, the on-board processing electronics, and the communications components) may be packaged or assembled in the data acquisition and processing module 1020 and may occupy a volume greater than about 2 cubic inches, or greater than about 16 cubic inches. In some embodiments, the components of the system 1000 (including the optical or imaging components, the focal plane array, the on-board processing electronics, and the communications components) may be packaged or assembled in the data acquisition and processing module 1020 and may occupy a volume in a range of about 4 cubic inches to about 15 cubic inches. In some embodiments, the components of the system 1000 (including the optical or imaging components, the focal plane array, the on-board processing electronics, and the communications components) may be packaged or assembled in the data acquisition and processing module 1020 and may occupy a volume in a range of about 5 cubic inches to about 12 cubic inches. In some embodiments, the components of the system 1000 (including the optical or imaging components, the focal plane array, the on-board processing electronics, and the communications components) may be packaged or assembled in the data acquisition and processing module 1020 and may occupy a volume in a range of about 4 cubic inches to about 6.5 cubic inches, e.g., about 5.63 cubic inches in one embodiment. In some embodiments, the components of the system 1000 (including the optical or imaging components, the focal plane array, the on-board processing electronics, and the communications components) may be packaged or assembled in the data acquisition and processing module 1020 and may occupy a volume in a range of about 9 cubic inches to about 13 cubic inches, e.g., about 11.25 cubic inches in one embodiment. In some embodiments, the components of the system 1000 (including the optical or imaging components, the focal plane array, the on-board processing electronics, and the communications components) may be packaged or assembled in the data acquisition and processing module 1020 and may occupy a volume in a range of about 6 cubic inches to about 10 cubic inches.

The data acquisition and processing module 1020 (with the system components mounted therein or thereon) may be sized and shaped to fit within a box-shaped boundary having dimensions X×Y×Z. For example, the data acquisition and processing module 1020, including the imaging optics, focal plane array, and on board processing electronics may be included in a package that is sized and shaped to fit within the box-shaped boundary having dimensions X×Y×Z. This package may also contain a power supply, such as a battery and/or solar module. In some embodiments, the data acquisition and processing module 1020 (including the imaging optics, focal plane array, and on board processing electronics may) can be sized and shaped to fit within a box-shaped boundary smaller than 8 inches×6 inches×6 inches. In some embodiments, the data acquisition and processing module 1020 (including the imaging optics, focal plane array, and on board processing electronics may) can be sized and shaped to fit within a box-shaped boundary smaller than 7 inches×5 inches×5 inches. In some embodiments, the data acquisition and processing module 1020 (including the imaging optics, focal plane array, and on board processing electronics may) can be sized and shaped to fit within a box-shaped boundary smaller than 6 inches×4 inches×4 inches. In some embodiments, the data acquisition and processing module 1020 (including the imaging optics, focal plane array, and on board processing electronics may) can be sized and shaped to fit within a box-shaped boundary smaller than 6 inches×2 inches×2 inches. In some embodiments, the data acquisition and processing module 1020 (including the imaging optics, focal plane array, and on board processing electronics may) can be sized and shaped to fit within a box-shaped boundary having dimensions larger than 4 inches×2 inches×2 inches. In some embodiments, the data acquisition and processing module 1020 (including the imaging optics, focal plane array, and on board processing electronics may) can be sized and shaped to fit within a box-shaped boundary having dimensions larger than 2 inches×1 inches×1 inches. The data acquisition and processing module 1020 (including the imaging optics, focal plane array, and on board processing electronics may) can have dimensions less than 3 inches×2 inches×2 inches. The data acquisition and processing module 1020 (including the imaging optics, focal plane array, and on board processing electronics may) can have dimensions greater than 1 inches×0.5 inch×0.5 inch. The data acquisition and processing module 1020 (including the imaging optics, focal plane array, and on board processing electronics may) can have a volume less than 30 cubic inches. The data acquisition and processing module 1020 (including the imaging optics, focal plane array, and on board processing electronics may) can have a volume less than 20 cubic inches. The data acquisition and processing module 1020 (including the imaging optics, focal plane array, and on board processing electronics may) can have a volume less than 15 cubic inches. The data acquisition and processing module 1020 (including the imaging optics, focal plane array, and on board processing electronics may) can have a volume less than 10 cubic inches. The data acquisition and processing module 1020 (including the imaging optics, focal plane array, and on board processing electronics may) can have a volume more than 1 cubic inches. The data acquisition and processing module 1020 (including the imaging optics, focal plane array, and on board processing electronics may) can have a volume more than 4 cubic inches. The data acquisition and processing module 1020 (including the imaging optics, focal plane array, and on board processing electronics may) can have a volume more 5 cubic inches. The data acquisition and processing module 1020 (including the imaging optics, focal plane array, and on board processing electronics may) can have a volume more 10 cubic inches. This package may also contain a power supply, including a battery and/or solar module, a communications module, or both and fit into the above-referenced dimensions. It should be appreciated that the dimensions disclosed herein may not correspond to the directions shown in FIG. 11A with respect to X, Y, and Z. This package may also contain a power supply, including a battery and/or solar module, a communications module, or both and fit into the above-referenced dimensions. It should be appreciated that the dimensions disclosed herein may not correspond to the directions shown in FIG. 11A with respect to X, Y, and Z.

In some embodiments, the dimension X shown in FIG. 14B can be in a range of about 2 inches to about 7 inches, or more particularly, in a range of about 2 inches to about 4 inches, e.g., about 2.5 inches in one embodiment. In some embodiments, the dimension X shown in FIG. 14B can be in a range of about 4 inches to about 6 inches, e.g., about 5 inches in one embodiment. In some embodiments, the dimension Y shown in FIG. 14B can be in a range of about 1 inch to about 5 inches, or more particularly, in a range of about 1 inch to about 3 inches, e.g., about 1.5 inches in one embodiment. In some embodiments, the dimension Z shown in FIG. 14B can be in a range of about 1 inch to about 5 inches, or more particularly, in a range of about 1 inch to about 3 inches, e.g., about 1.5 inches in one embodiment.

Moreover, the system 1000 can have a mass and weight sufficiently small so as to enable the user 1275 to easily carry or wear the data acquisition and processing module 1020 at the site. For example, the system 1000 can have a weight in a range of about 0.5 pounds to 5 pounds, or more particularly, in a range of about 0.5 pounds to 2 pounds, or more particularly in a range of about 0.25 pounds to about 2 pounds, or more particularly, in a range of about 0.25 pounds to about 1.5 pounds. In one embodiment, for example, the system 1000 can weight about 1 pound. In another embodiment, for example, the system 1000 can weigh about 0.5 pounds. Thus, the embodiment shown in FIG. 11A can be sized and shaped and configured to have a mass that enables a human user to easily and effectively manipulate the system 1000.

Figure 14C:
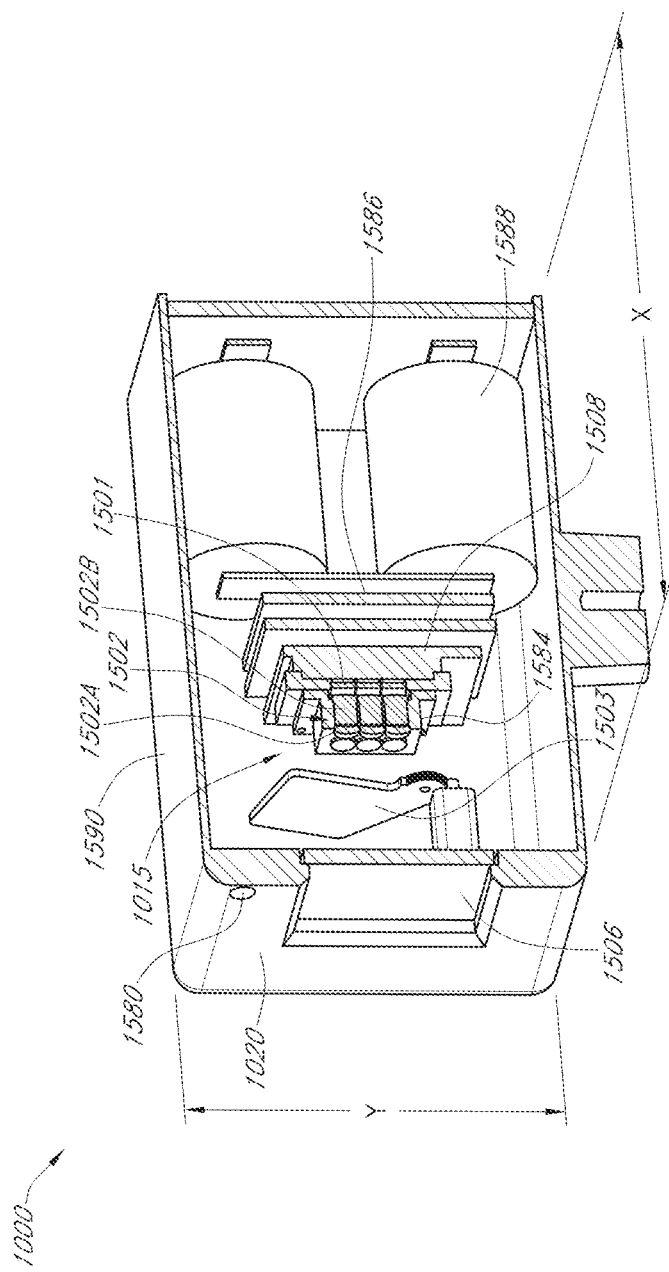
FIG. 14C is a perspective cross-sectional view of the mobile infrared imaging system shown in FIGS. 14A-14B.

FIG. 14C is a perspective cross-sectional view of the mobile infrared imaging system 1000 shown in FIGS. 14A-14B. The mobile infrared imaging system 1000 can include one or more movable shutters 1503 (e.g., two shutters) rear of the window 1506 and a lens assembly 1502 rear of the shutter(s) 1503. A filter array 1501 can be disposed rear (or forward) of the second lens array 1502B, and an optical focal plane array (FPA) unit 1508 can be disposed rear of the filter array 1501. The optical FPA unit 1508 can be mechanically and electrically coupled with one or more substrates 1586, which may comprise printed circuit board or PCB substrates. In various embodiments, the FPA unit 1508 comprises a single FPA or detector array. Additionally, as explained herein, the lens assembly 1502, filter array 1501, and optical FPA unit can at least partially define one or more optical channels that are spatially and spectrally different. A number of the optical channels can be at least 4, at least 5, at least 8, at least 9, at least 12, at least 13, or at least 20. In some embodiments, a number of the optical channels is between 4 and 50.

One or more batteries 1588 can supply power to the system 1000 by way of the substrate(s) 1586. In addition, a visible light imaging sensor 1580 can be disposed in the housing 1590 and can be configured to provide a visible light image of the scene being captured by the system 1000. The processed IR image data can be overlaid upon the visible light image. In various embodiments the visible light imaging sensor 1580 can be used for reduction of scene-motion-induced detection errors, for example, to detect a moving object that enters the field of view (such as an animal or person) and would interfere with the data being collected.

As explained herein, the movable shutter(s) 1503 can be configured to provide spectral-radiometric calibration for the system 1000. The shutter(s) 1503 can be configured to move in and out of the field of view of the lens assembly 1502 periodically, e.g., in a time period in a range of about 1 minute to about 15 minutes, or more particularly, in a range of about 3 minutes to about 7 minutes, e.g., about 5 minutes. Although one shutter 1503 is illustrated in FIG. 14C, it should be appreciated that two or more shutters may be provided. The shutter(s) 1503 can be used in static calibration procedures to provide the system with absolute temperature values. In some embodiments, only static calibration is performed, e.g., no dynamic calibration is performed. In some embodiments, both static and dynamic calibration procedures are performed.

The lens assembly 1502 can include a first lens array 1502A and a second lens array 1502B. In some embodiments, the lens assembly 1502 can comprise an array of two-part lenses denoted by the first and second arrays 1502A, 1502B. In some embodiments, the lens assembly 1502 can comprise an array of two separate lenses denoted by the first and second arrays 1502A, 1502B. Each of the lens arrays 1502A, 1502B can comprise a 4×3 array of lenses, each of which may correspond to a particular detector region in the FPA unit 1508 and can define an optical channel of the system 1000. The lenses used in the first lens array 1502A may be different from the lenses used in the second lens array 1502B. The lenses can be any suitable type of lens, including, e.g., spherical lenses, aspheric lenses, rod lenses, etc. or any combination thereof. For example, the lenses used in the first lens array 1502A can comprise aspheric lenses, and the lenses used in the second lens array 1502B can comprise rod lenses. Although the lens assembly 1502 shown in FIG. 14C includes two lens arrays, it should be appreciated that additional lens arrays may be used, e.g., three lens arrays, four lens arrays, five lens arrays, etc. In addition, to assist in enabling a small system size, the diameter of each lens in the assembly 1502 can be less than about 0.5", e.g., in a range of about 0.1" to about 0.5". The f-number of each lens can be less than about 2, e.g., in a range of about 0.2 to 2, or more particularly, in a range of about 0.5 to 2, or 1.0 to 2 or 1.1 to 2.

The first lens array 1502A and the second lens array 1502B can be coupled to one another by way of a mounting plate 1584 sized and shaped to support or receive each lens array 1502A, 1502B. For example, the first lens array 1502A can be mounted on one side of the mounting plate 1584, and the second lens array 1502B can be mounted on an opposite side of the mounting plate 1584. The mounting plate 1584 can be machined to have diameter tolerances of about +/−25 microns. The lenses of the arrays 1502A, 1502B can be secured to the mounting plate 1584 with a curable epoxy. For example, the lenses may fit into opposite sides of holes formed in the mounting plate 1584.

The optical FPA unit 1508 can comprise any suitable type of detector array that is configured to detect infrared radiation, for example, greater than 1 micron, or greater than 2 microns, or greater than 3 microns or greater than 5 microns, or greater than 6 microns and possibly lower than 20 microns, or 15 microns, or 13 microns, or 12 microns or 10 microns, in wavelength, and may be cooled or uncooled. In some embodiments the optical FPA unit 1508 comprises one or more microbolometer arrays, which may be uncooled. For example, an array of about 1000×1000 microbolometer arrays may be used in the embodiments disclosed herein. Microbolometer arrays such as those manufactured by DRS Technologies of Arlington, Va., and Sofradir EC, Inc., of Fairfield, N.J., may be suitable for the embodiments disclosed herein. For example, the DRS U8000 FPA manufactured by DRS Technologies may be used in some embodiments. In some arrangements, the microbolometer array may have a resolution of 1024×768 with a pixel pitch of 12 microns. The array of lenses can form separate channels having image detection regions that form part of the array. For example, 12 channels can be included in the 1024×768 pixel array on the detector array (microbolometer array) that are for example 250×250 pixels for each of the 12 channels. Detector arrays having more or less pixels may be employed. Similarly the number of channels be larger or smaller than 12 and the detection area on the detector array for a single channel may be larger or smaller than 250×250 pixels. For example, the detection region may comprise from between 100-200 pixels×100-200 pixels per detection region. For example, the detection region may comprise from between 100-200 pixels×100-200 pixels per detection region, from between 200-300 pixels×200-300 pixels per detection region, or from between 300-400 pixels×300-400 pixels or from between 400-500 pixels×400-500 pixels. Likewise the detection region for a channel may measure 100-200 pixels on a side, 200-300 pixels on a side, 300-400 pixels on a side, 400-500 pixels on side or larger or smaller.

In some arrangements, the spectral band of the microbolometer can be about 7.5 microns to 14 microns or can be about 3 microns to 14 microns or 3 to 8 microns. The microbolometer array can operate at a frame rate of about 30 Hz and can operate at operating temperatures of about −40° C. to +70° C. In various embodiments, the microbolometer array is an uncooled microbolometer that does not include a cooler. The sensitivity of the microbolometer at F/1 can be <about 40 mK. The systems 1000 disclosed herein can be used to detect wavelengths in a range of about 1 micron to about 20 microns. For example, the systems 1000 disclosed herein can be used to detect wavelengths above about 6 microns, e.g., in a range of about 6 microns to about 18 microns, in a range of about 3 microns to about 14 microns, or more particularly, in a range of about 7 microns to about 14 microns or 3 to 8 microns. In various embodiments, the individual detector elements of the microbolometer array can be spaced relatively close together to at least partially enable a small, compact system. For example, adjacent detector elements of the array can be spaced apart by a distance in a range of about 7 microns to about 15 microns, or more particularly in a range of about 9 microns to about 13 microns, e.g., about 11 microns. The individual lenses can be spaced apart by a distance in a range of about 20 mm to about 35 mm, e.g. in a range of about 24 mm to about 30 mm, e.g., about 27.5 mm. Likewise the spatially and spectrally spaced channels may be physically spaced apart by 20 to 35 mm, 24 mm to 30 mm, etc. Although various embodiments of the system are described as including an FPA comprising for example a microbolometer array, certain embodiments comprise a plurality of FPAs. In some embodiments, a single optical FPA is used. In some embodiments, detectors of the optical FPA are configured to detect radiation in the same band of IR wavelengths.

The on-board processing electronics of the data acquisition and processing module 1020 can process the IR optical data to detect and/or identify a target species from the IR radiation received at the optical FPA. For example, the module 1020 can be configured to acquire multispectral image data and analyze the acquired image data to identify the target species. For example, the mobile imaging systems 1000 disclosed herein can be configured to image a 10 m×10 m object area at a distance of about 17 m at a resolution of about 0.04 m. In this example, any gas leaks that generate a gas cloud of at least about 1.5 inches in size can be detected and/or identified by the system 1000. The detection and identification methods can be performed substantially in real-time such that the user can be alerted if any leaks are identified.

As explained above, the infrared image data captured by the system 1000 can be processed on board the data acquisition and processing module 1020 of the imaging system 1000. One way to provide a smaller system 1000 is to process the image data using one or more field-programmable gate arrays (FPGA) configured to execute methods used in the analysis of the images captured by the optical system 1015. In some embodiments, one or more Application Specific Integrated Circuits (ASICs) may be used instead of, or in addition to, the FPGAs. For example, an ASICs chip may include a FPGA. The FPGA(s) (and/or ASIC(s)) can be mounted to and electrically coupled with the substrate(s) 1586 shown in FIG. 14C and can be physically located proximate the optical system. For example, the FPGA can include logic gates and read access memory (RAM) blocks that are designed to quickly implement the computations used to detect the types of gases in a gas cloud. The small size/weight, and high performance characteristics of the FPGA can enable on board computation and analysis within the data acquisition and detection unit 1020 worn or carried by the user. The use of FPGA (or similar electronics) on board the system 1000 can reduce costs associated with using an off-site central server or larger computing device to conduct the image analysis computations. Advantageously, the embodiments disclosed herein can enable on-board computation even though it can be challenging to implement complex methods on the limited computing platform that FPGAs provide.

In addition, enabling computation with one or more FPGA devices on board the wearable system can also prevent or reduce communication bottlenecks associated with wirelessly transmitting large amounts of raw data from the system 1000 to a remote server or computer. For example, the infrared optical system 1015 disclosed herein may generate up to about 380 Mbps of raw image data at 30 frames per second, and the visible sensor 1580 may generate about 425 Mbps of raw image data at 30 frames per second. The resulting data rate of about 800 Mbps is faster than most conventional wireless technologies. While data compression and/or pre-processing may reduce the raw data rates for the visible and IR images, in some embodiments, the IR image data may only be compressed by a ratio of about 2:1. The resulting overall data rate of about 192 Mbps may not be transmitted effectively by conventional wireless communications devices. Accordingly, performing the image processing calculations on board the system 1000 (e.g., on the data acquisition and processing module 1020) can reduce the occurrence of or avoid bottlenecks generated by wirelessly communicating the raw image data to an off-site central server.

One challenge to implementing a mobile imaging system is the power requirements of each component of the system, including, e.g., the IR optical system 1015, the visible sensor 1580, the processing electronics, the wireless communications modules, etc. Advantageously, the mobile infrared imaging systems 1000 disclosed herein can be configured to operate by battery power for long periods of time without recharging or replacing the batteries 1588. In some arrangements the one or more batteries 1588 can comprise lithium ion batteries, which have relatively high energy densities. In addition, to help reduce power consumption within the system 1000, the FPGAs of the data acquisition and processing module 1020 can be advantageously programmed such that power consumption is lower than that used for other types of processing electronics.

The systems 1000 disclosed herein can advantageously operate for between 8 hours and 36 hours without recharging or replacing the batteries, or more particularly between about 10 hours and 24 hours without recharging or replacing the batteries. In some embodiments, the system 1000 can operate for at least about 12 hours without recharging or replacing the batteries. The components of the data acquisition and processing module 1020 (including the imaging optics, focal plane array, and on board processing electronics may) can be configured to operate at relatively low electrical power levels, e.g., at power levels in a range of about 3 W to about 10 W, or more particularly in a range of about 4 W to about 7 W, or in a range of about 4 W to about 6 W, e.g., about 5 W in some embodiments. The components of the data acquisition and processing module 1020 (including the imaging optics, focal plane array, and on board processing electronics may) can also be configured to operate at relatively low overall energy levels for a single charge of the batteries 1588, e.g., at energy levels in a range of about 60 Watt-hours (Wh) to about 100 Wh, or more particularly in a range of about 80 Wh to about 95 Wh, or in a range of about 85 Wh to about 90 Wh.

In addition, for each of the embodiments disclosed herein, various motion detection and/or compensation techniques can be implemented to account for relatively large-scale motions that are induced by the user moving his or her head during use. For example, when a user is visiting a well site or other installation, the user may be continuously walking and looking in different directions (e.g., by rotating his or her head). Additionally, vibration can be introduced by the user's natural unsteadiness. Such movement can continuously change the system's field of view at a relatively rapid rate, which can affect the accuracy of the methods used to determine the identity of species in a gas cloud or other object. Accordingly, it can be desirable to provide improved motion detection and/or compensation techniques to reduce errors associated with the movements of the user.

IV. Additional Examples of a Mobile DAISI System

Additional examples of mobile divided-aperture infrared spectral imaging (DAISI) systems are provided in this section. For example, the systems 1000 shown in FIGS. 15A-24D may be used with any of the embodiments disclosed above, including, e.g., the embodiments of the mobile DAISI systems 1000 shown in FIGS. 11A-14C. Moreover, the imaging components used in FIGS. 15A-24D may be used in conjunction with any of the embodiments of FIGS. 1-10C. Beneficially, the systems 1000 disclosed herein can provide various improvements that enable a multi-spectral, snapshot mode imaging system to be worn or carried by a person.

As with the above-referenced embodiments, the systems 1000 of FIGS. 15A-24D can comprise an optical focal plane array (FPA) and components that define at least two optical channels that are spatially and spectrally different from one another. The at least two optical channels can be positioned to transfer infrared (IR) radiation towards the FPA. A processing unit comprising a processor and/or processing electronics can acquire multispectral image data representing a target species from the received IR radiation. The optical system and the processing unit can be contained together in a data acquisition and processing module configured to be worn or carried by a person. In some embodiments disclosed in this section, the imaging system may be fixed at a desired location, such as at a petroleum refinery, an oil well site, etc.

A. System Overview

Figure 15B:
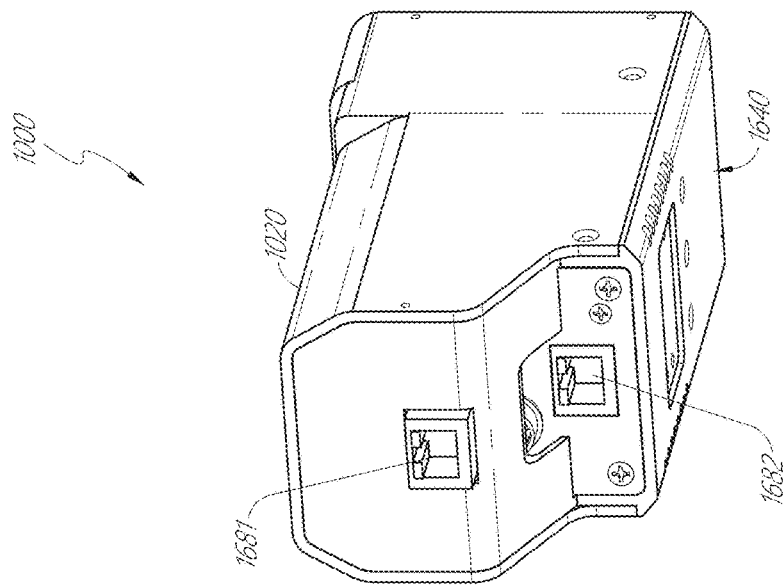
FIG. 15B is a schematic rear perspective view of the system shown in FIG. 15A.
Figure 15A:
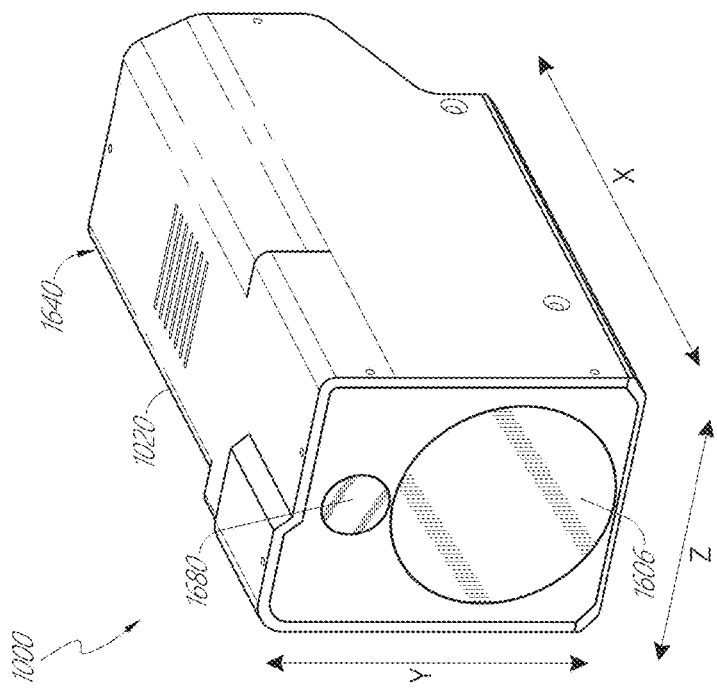
FIG. 15A is a schematic perspective view of a system, according to various embodiments.

FIG. 15A is a schematic perspective view of a system 1000, according to various embodiments. FIG. 15B is a schematic rear perspective view of the system 1000 shown in FIG. 15A. The system 1000 can comprise a data acquisition and processing module 1020, which may be similar to the data acquisition and processing module described above. For example, the data acquisition and processing module 1020 can comprise a housing 1640 within which the optical components of the system 1000 are housed. The system 1000 can include an optical window 1606 and a visible light imaging system 1680. The window 1606 can be configured to transmit infrared radiation from the object to the internal optical components within the housing 1640. In some embodiments, the window 1606 comprises germanium. The window 1606 and visible light imaging system 1680 may be the same as or similar to the window and visible light system described above.

As shown in FIG. 15B, the data acquisition and processing unit 1020 can comprise any suitable number of power and/or signal connections to a computing device. For example, the data acquisition and processing unit 1020 can comprise a data connector 1681 to provide data communication between the data acquisition and processing unit 1020 and a computing device. The data acquisition and processing unit 1020 can also comprise a power connector 1682 to provide electrical power to the data acquisition and processing unit 1020. In some arrangements, the data acquisition and processing unit 1020 can comprise a communication module 1024, which can provide wireless (and/or wired) data communication with an external computing device (such as a laptop computer, a tablet computer, a smartphone, etc.). In addition, the data acquisition and processing unit 1020 can comprise one or more batteries to provide power to the system 1000.

The data acquisition and processing unit 1020 can be configured to be worn or carried by a person. The combination of components described herein can advantageously enable the optical components and processing electronics to fit within a small form factor sufficient to be worn or carried by a person. For example, the data acquisition and processing unit 1020 can have dimensions and a weight (or mass) selected so as to be easily worn or carried by a human user to any suitable location, e.g., for conducting infrared imaging and monitoring of potential gas leaks at a petroleum installation. As shown in FIG. 15A, the data acquisition and processing unit 1020 can be sized and shaped to fit within a box-shaped boundary having dimensions length X×height Y×width Z. The volume of the data acquisition and processing unit 1020 can be in a range of 5 cubic inches to 40 cubic inches, in a range of 9 cubic inches to 30 cubic inches, in a range of 10 cubic inches to 30 cubic inches, in a range of 10 cubic inches to 25 cubic inches, in a range of 10 cubic inches to 20 cubic inches, or in a range of 10 cubic inches to 15 cubic inches. In some embodiments, the volume of the data acquisition and processing unit 1020 can be in a range of 15 cubic inches to 25 cubic inches, in a range of 17 cubic inches to 24 cubic inches, or in a range of 19 cubic inches to 23 cubic inches.

The length X can be in a range of 3 inches to 8 inches, in a range of 3.5 inches to 6 inches, in a range of 4 inches to 6 inches, or in a range of 5 inches to 6 inches. The height Y can be in a range of 1 inch to 5 inches, in a range of 1 inch to 3 inches, in a range of 1.5 inches to 2.5 inches, or in a range of 2 inches to 2.5 inches. The width Z can be in a range of 1 inch to 5 inches, in a range of 1 inch to 3 inches, in a range of 1 inch to 2.5 inches, or in a range of 1 inch to 2 inches. For example, the width Z can be in a range of 1.25 inches to 2 inches, in a range of 1.5 inches to 2 inches, or in a range of 1.6 inches to 1.9 inches.

The weight of the data acquisition and processing unit 1020 can be in a range of 0.5 pounds to 5 pounds, in a range of 0.5 pounds to 3 pounds, in a range of 0.75 pounds to 2.5 pounds, in a range of 1 pound to 2.5 pounds, in a range of 1 pound to 2 pounds, or in a range of 1.25 pounds to 1.75 pounds.

Figure 15C:
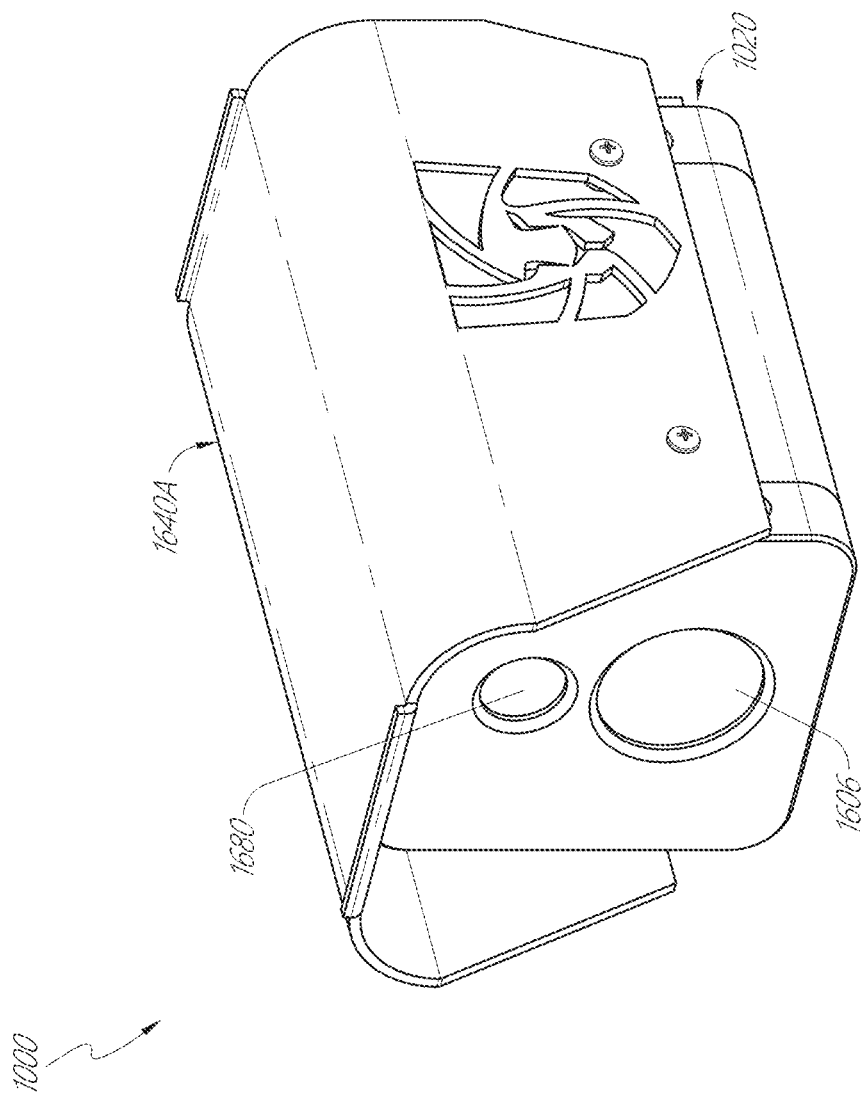
FIG. 15C is a schematic front perspective view of a system according to various embodiments.

FIG. 15C is a schematic front perspective view of a system 1000 according to various embodiments. The components of the system 1000 of FIG. 15C may be the same as the components of FIGS. 15A-15B. However, in the embodiment of FIG. 15C can comprise a housing 1640A that is configured for use in conjunction with locations classified in Class 1, Division 1 of the National Electrical Code (NEC), available at necconnect.org. For example, the housing 1640A of FIG. 15C can be sufficiently sealed so as to prevent gases from entering the housing 1640A. As another example, the housing 1640a of FIG. 15C can be of a type generally considered to be explosion proof. The processing electronics and other components within the data acquisition and processing unit 1020 can be passively cooled without requiring external airflow into the data acquisition and processing unit 1020 from the outside environs (e.g., ambient air). In some embodiments, the data acquisition and processing unit 1020 can be filled with a gas to cool the internal components. For example, in some embodiments, data acquisition and processing unit 1020 and the housing 1640A can be filled with nitrogen gas. The system 1000 shown in FIG. 15C can be fixed in a permanent location (e.g., an oil well site or other petroleum installation) or can be configured for mobile user (e.g., worn or carried by a user).

Figure 15D:
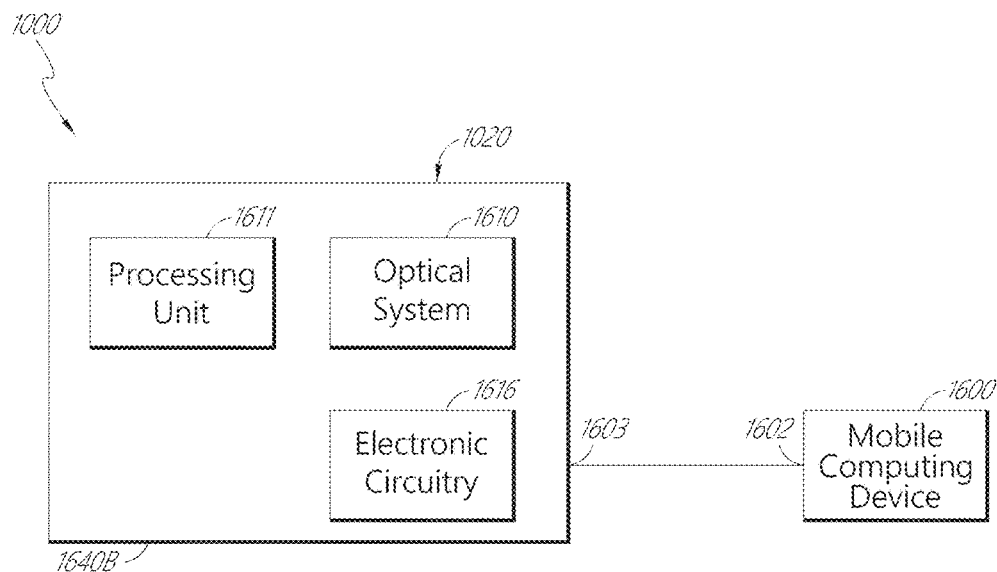
FIG. 15D is a schematic system diagram of a mobile computing device having a first port configured to electrically and physically couple with a divided-aperture infrared spectral imaging (DAISI) system, according to various embodiments.

FIG. 15D is a schematic system diagram of a mobile computing device 1600 having a first port 1602 configured to electrically and physically couple with a DAISI system 1000, such as any of the mobile DAISI systems disclosed herein. The mobile computing device 1600 can be any suitable type of mobile computing device, e.g., a computing device configured to be worn or carried by a person. For example, the mobile computing device 1600 can comprise a mobile smartphone, a tablet computing device, a laptop computer, etc.

The DAISI system 1000 can comprise a data acquisition and processing unit 1020 as described herein. The data acquisition and processing unit 1020 can be contained in and/or coupled with a housing 1640B. The DAISI system 1000 can comprise an optical system 1610 contained in the data acquisition and processing unit 1020 and/or the housing 1640B. The optical system 1610 can include the various optical components of the DAISI system that cooperate to acquire multispectral image data, including, e.g., optical filters, lenses, and the optical detector. For example, the optical system 1610 can include a plurality of spectrally and spatially different optical channels along which infrared radiation can be transferred to the detector.

In some embodiments, the data acquisition and processing unit 1020 and/or the housing 1640B can comprise a processing unit 1611 having processing circuitry configured to analyze the acquired image data to detect and/or identify the target species. In the illustrated embodiment, the processing unit 1611 which analyzes the acquired image data is disposed in and/or coupled with the data acquisition and processing unit 1020 and/or the housing 1640B. In other embodiments, however, the processing unit 1611 may be disposed in and may form part of the mobile computing device 1600.

The data acquisition and processing unit 1020 and/or the housing 1640B can comprise a second port 1603 configured to mate with the first port 1602 of the mobile computing device 1600. The ports 1602, 1603 can be any suitable type of data and/or power port. For example, the ports 1602, 1603 may comprise ports used as conventional power supply ports, audio ports, or other ports on mobile smartphones and/or tablet computing devices. In various embodiments, the ports 1602, 1603 can comply with various industry standards, such as the Universal Serial Bus (USB) standards (e.g., USB Type-C, USB 3.1, etc.), available at usb.org. As another example, ports 1602, 1603 may be wireless communication ports utilizing any desired wireless technology (e.g., by Bluetooth, WiFi, etc.) such the mobile computing device 1600 and the DAISI system 1000 can communicate even without physical connection.

Beneficially, the arrangement shown in FIG. 15D can enable the user to acquire a plug-and-play mobile DAISI system 1000, and can removably connect the system 1000 with his or her personal mobile computing device 1600. The system 1000 can be pre-loaded with software instructions that cooperate with the operating system of the mobile computing device 1600 to operate the optical and processing components of the mobile computing device 1600. In other arrangements, the user can download software to the mobile computing device 1600, and the downloaded software instructions can control the operation of the DAISI system 1000. In some embodiments, the DAISI system 1000 comprises both the optical components and the processing electronics (e.g., the data acquisition and processing unit 1020), such that the system 1000 can perform image acquisition and data processing to detect and/or identify the target species. The system 1000 can transmit data regarding the detected and/or identified species to the mobile computing device 1600, which can display the information to the user by way of a suitable user interface (e.g., a display and/or a speaker). In some embodiments, the DAISI system 1000 may include user interfaces (e.g., a display and/or a speaker) such that the system 1000 can directly alert the user to detected and/or identified species, even when the mobile computing device 1600 is not coupled to the DAISI system 1000. As just one example, the DAISI system 1000 may include a display such as a strobe light and/or a speaker that alerts the user (i.e., provides an alarm for the user) upon detection of one or more target species and/or upon detection of one or more targets species at greater than a predetermined threshold concentration.

In other embodiments, the DAISI system 1000 may include only the optical components (e.g., the optical window, a plurality of optical filters, a plurality of lenses, and an optical detector), and the processing electronics may be housed in the mobile computing device 1600. In such an arrangement, the DAISI system 1000 can be configured to acquire image data from the scene (with or without pre-processing techniques), and can transmit the acquired image data to the mobile computing device 1600. The processing electronics of the mobile computing device 1600 can be configured with software instructions that, when executed by the processing electronics, processes the acquired image data to detect and/or identify one or more target species. The detected and/or identified target species can be transmitted to the user by way of a user interface, e.g., a display and/or a speaker. In some embodiments, the housing can comprise the optical system and a processing unit having processing circuitry configured to analyze the acquired image data to detect and/or identify the target species.

Thus, in various embodiments, the DAISI system 1000 can comprise a housing 1640B in which the optical system 1610 is disposed. The optical system 1610 can comprise the optical components described herein, including, e.g., an optical detector and optical components defining a plurality of spectrally and spatially different optical channels (such as a plurality of filters and a plurality of lenses spaced from the filters). Each optical channel of the plurality of optical channels can be positioned to transfer IR radiation incident on the optical system 1610 towards the optical detector, as explained herein. The second port 1603 can be in data communication with the optical detector and configured to electrically and physically connect to the mobile computing device 1600 to transmit image data acquired by the optical detector to the mobile computing device 1600. In addition, the housing 1640B can comprise electronic circuitry 1616 in communication with the second port 1603. The electronic circuitry 1616 can be configured to receive an indication from, or to transmit an indication to, the mobile computing device 1600 indicating that the mobile computing device 1600 is electrically and physically connected with the port 1603, e.g., by way of the first port 1602.

The electronic circuitry 1616 of the housing can be configured to verify an identifier transmitted from the mobile computing device 1600 to authenticate that the mobile computing device 1600 is authorized to receive the acquired image data. For example, when the user connects the second port 1603 with the first port 1602, corresponding circuitry in the mobile computing device 1600 can send an identifier to the electronic circuitry of the housing to request access to the captured image data and to verify the authenticity of the user associated with the mobile computing device 1600. If the mobile computing device 1600 is verified by the electronic circuitry 1616, the electronic circuitry 1616 can comprise switching circuitry that permits the acquired image data to be transferred to the mobile computing device 1600 through the port. In some embodiments, the electronic circuitry 1616 may be part of the processing unit 1611.

The system 1000 illustrated in FIG. 15D can accordingly be sufficiently miniaturized so as to be usable with small mobile computing devices, such as mobile smartphones and tablet computers. In various embodiments, for example, the housing 1640B in which the optical system 1610 and processing unit 1611 are disposed may have a volume in a range of 0.25 cubic inches to 10 cubic inches, in a range of 0.25 cubic inches to 8 cubic inches, in a range of 0.5 cubic inches to 8 cubic inches, in a range of 0.5 cubic inches to 5 cubic inches, in a range of 0.5 cubic inches to 3 cubic inches, or in a range of 0.5 cubic inches to 2 cubic inches.

The system 1000 can be miniaturized in various ways. In some embodiments, the optical system and/or the processing unit can be fabricated using wafer-scale or chip-scale processing techniques. For example, as explained herein in Section IV.E.1, a filter array of the optical system can be patterned using semiconductor processing techniques, such as deposition, lithography, and etching. In some embodiments, the lens array and the detector array may also be manufactured using such wafer-scale or chip-scale techniques.

Figure 15E:
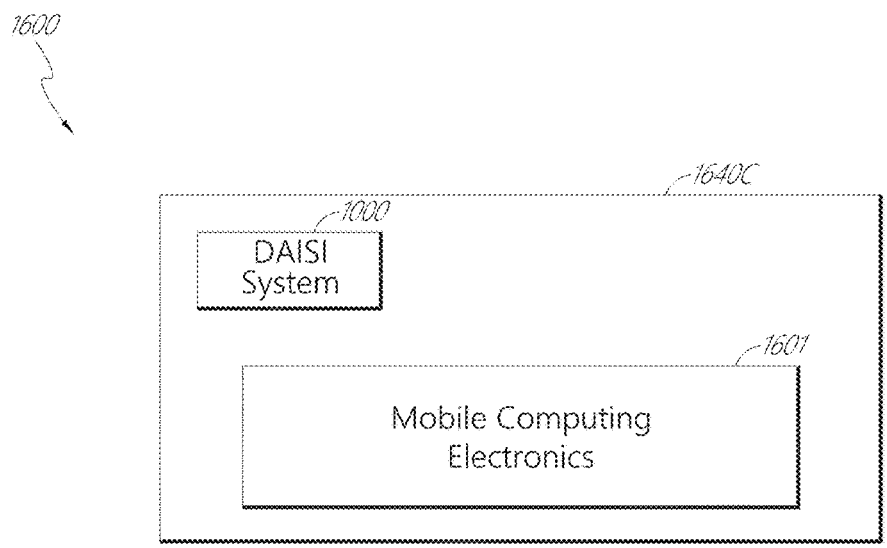
FIG. 15E is a schematic system diagram of a mobile computing device, according to various embodiments.

FIG. 15E is a schematic system diagram of a mobile computing device 1600, according to another embodiment. In FIG. 15E, the DAISI system 1000 is integrated within a housing 1640C that defines the body of the mobile computing device 1600. The mobile computing device 1600 of FIG. 15E can comprise any suitable type of mobile computing device, such as a mobile smartphone or a tablet computer. The DAISI system 1000 and mobile computing electronics 1601 may be disposed together within the housing 1640C of the mobile computing device 1600. The DAISI system 1000 may comprise any of the mobile DAISI systems disclosed herein. The mobile computing electronics 1601 can comprise processing electronics configured to control the operation of a conventional mobile computing device 1600. For example, the mobile computing electronics 1601 can comprise various communications platforms, including circuitry configured to transmit and receive cellular data (e.g., voice data and/or multimedia data), wireless data packets, etc. The mobile computing electronics 1601 can comprise various other applications used in mobile devices, such as mobile smartphones and/or tablet computers.

Figure 16A:
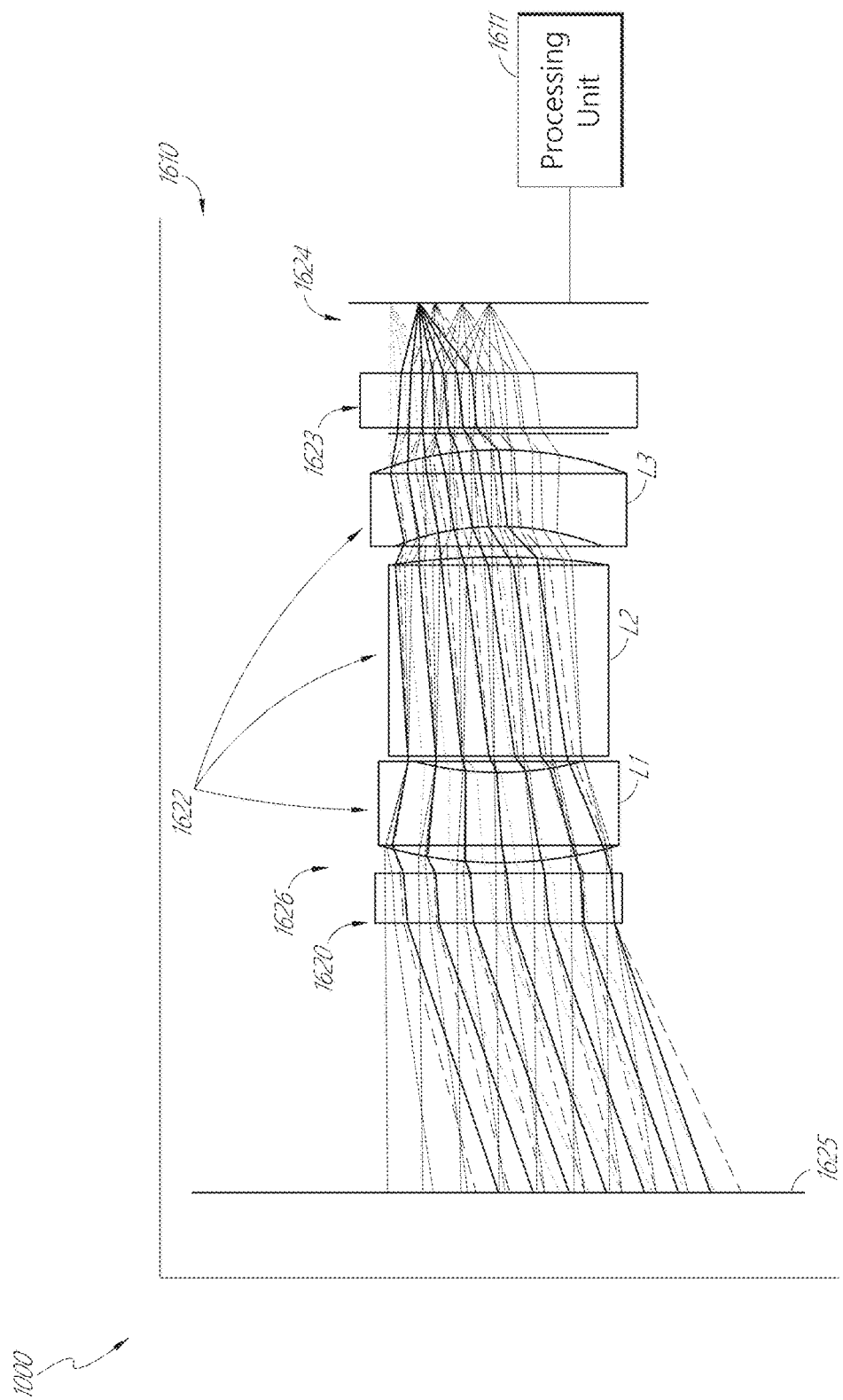
FIG. 16A is a schematic diagram of a DAISI system that can be used in accordance with any of the embodiments disclosed herein.

FIG. 16A is a schematic diagram of a DAISI system 1000 that can be used in accordance with any of the embodiments disclosed herein. The system 1000 of FIG. 16A can comprise the optical system 1610 in electrical communication with the processing unit 1611. FIG. 16A illustrates a single optical channel 1626; however, the system 1000 can include a plurality of optical channels 1626 that are spectrally and spatially different from one another, as explained herein. The optical system 1610 can include a filter 1620, a lens 1622 comprising a plurality of lens elements L1, L2, L3, an optical window 1623, and an optical detector 1624. The filter 1620 can comprise any of the filters described herein, which may be infrared filters. Although only a single filter 1620 is illustrated in FIG. 16A, the DAISI system 1000 can comprise a plurality of spatially and spectrally distinct filters which may be arranged in a two-dimensional array, as explained herein.

The lens 1622 of the illustrated optical channel 1626 can comprise a plurality of lens elements L1, L2, L3 that are disposed adjacent or with respect to one another along the optical axis, e.g., between an object 1625 (e.g., a gas cloud) and the detector 1624. As explained herein, the lens elements L1, L2, L3 can be selectively dimensioned so as to improve the sensitivity of the optical system 1610 and improve image quality. As with the filters 1620, a plurality of lenses 1622 can be arranged in a two-dimensional array and can be disposed with respect to or spaced from the filters 1620 along the optical axis. The optical window 1623 can be disposed rear of the lens 1622, and the detector 1624 can be disposed rear of the optical window 1623 and can be configured to transduce acquired infrared image data into electrical current. The detector 1624 can be any suitable type of detector including those disclosed herein, such as an optical focal plane array (FPA). As an example, the detector 1624 can comprise one or a plurality of microbolometers. The detector 1624 can be in electrical communication with the processing unit 1611. Variation in the optical design is possible. For example, additional elements may be included such as baffles and/or stops. Filters such as filters 1620 and other filters may be combined with the lenses and/or window.

Figure 16B:
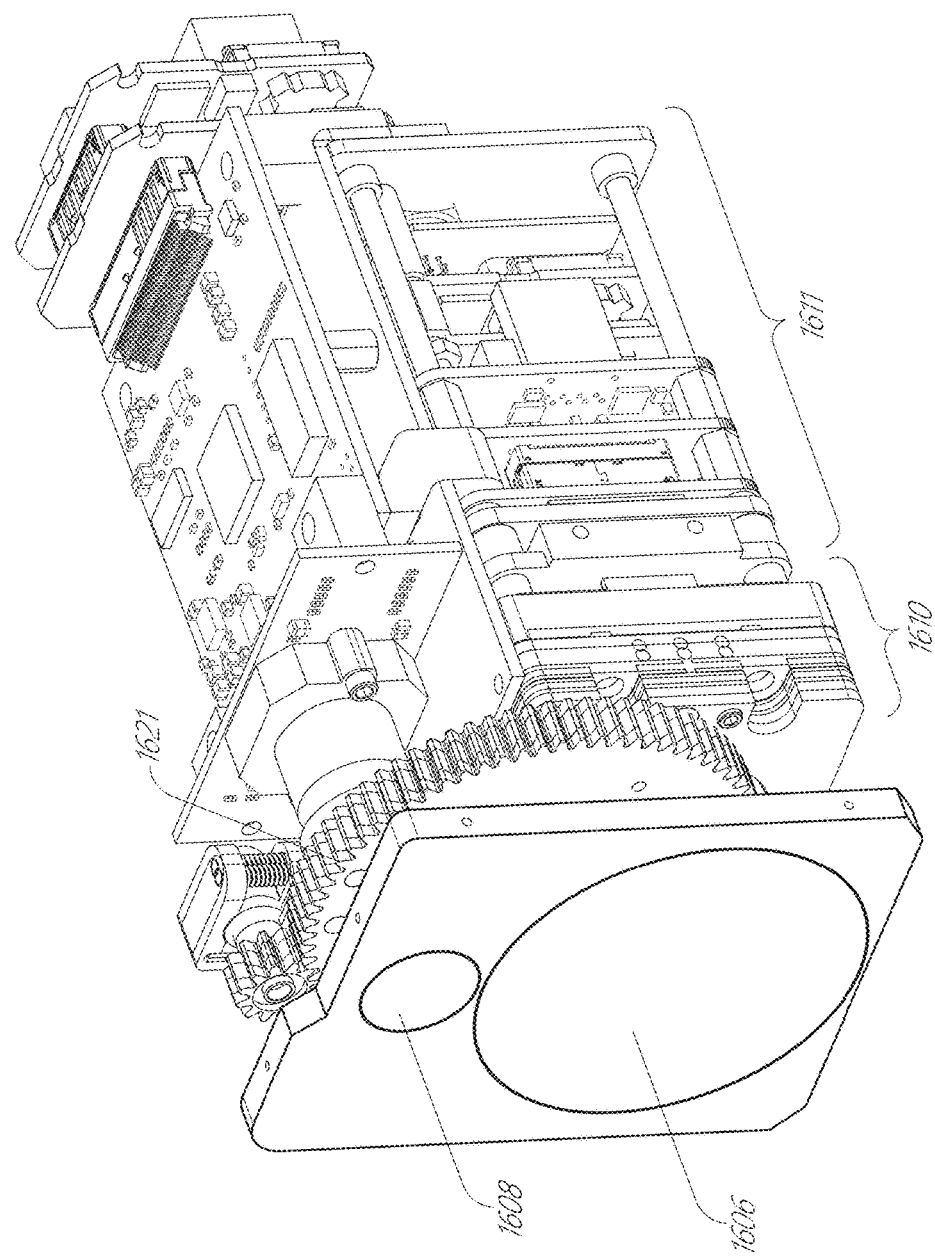
FIG. 16B is a schematic front perspective view of a DAISI system, according to various embodiments, with the housing removed for purposes of illustration only.
Figure 16C:
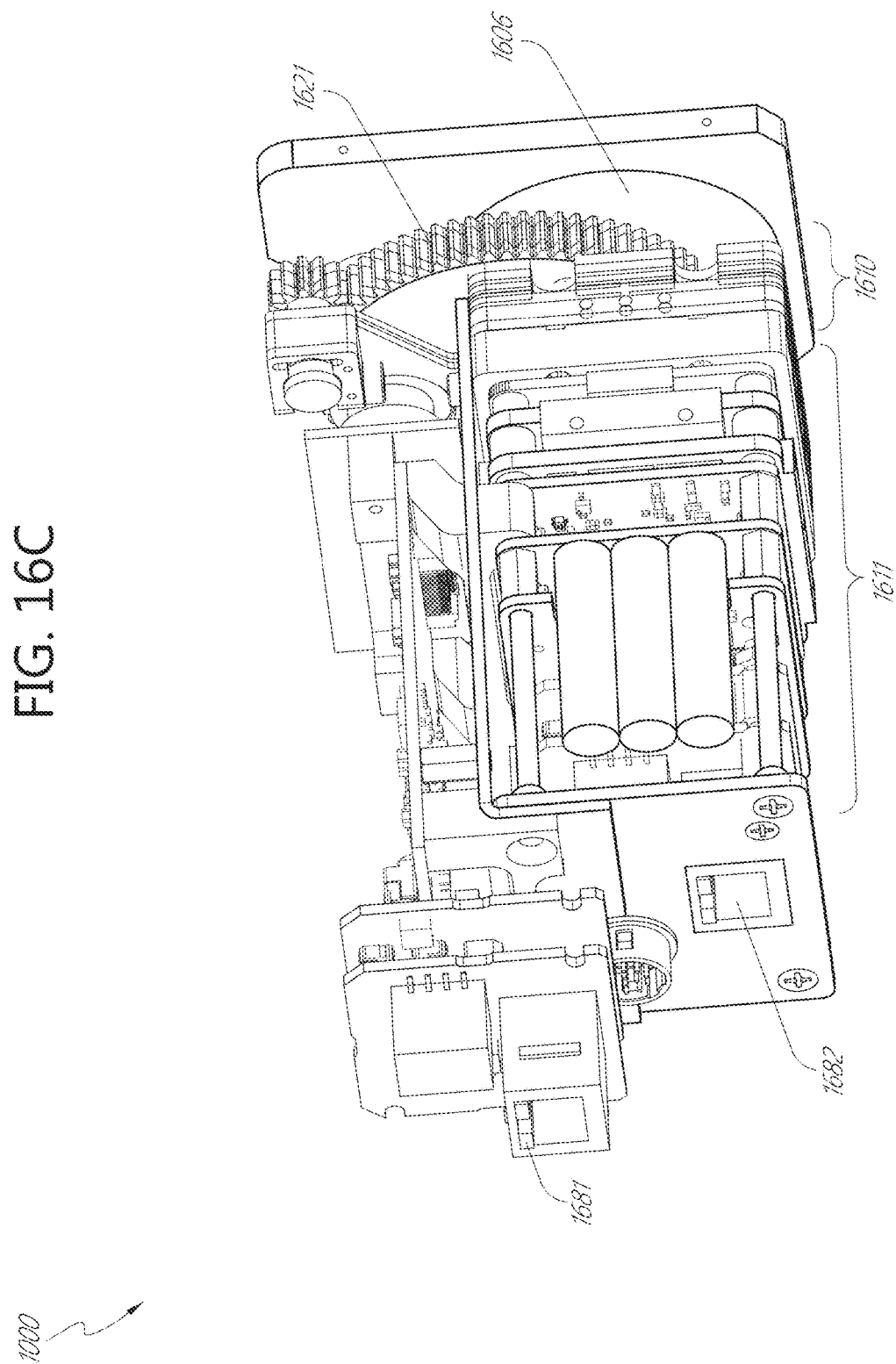
FIG. 16C is a schematic rear perspective view of the DAISI system of FIG. 16B.

FIG. 16B is a schematic front perspective view of the DAISI system 1000 with the housing removed for purposes of illustration only. FIG. 16C is a schematic rear perspective view of the system 1000 of FIG. 16B. As shown in FIGS. 16B and 16C, a shutter 1621 can be disposed rear of an optical window 1606. As explained below, the shutter 1621 can comprise a rotary shutter which rotates to switch between one or more calibration modes and an operational imaging mode. The optical system 1610 can be disposed rear of the shutter 1621, and the processing unit 1611 can be disposed rear of the optical system 1610. The optical system 1610 can include the optical components described herein that enable the acquisition of multispectral infrared image data. The processing unit 1611 comprises processing electronics that can be configured to process the acquired multispectral infrared image data to detect and/or identify a target species. For example, the processing unit 1611 can comprise or be similar to the processing unit 1021 of FIG. 12 and the associated disclosure.

In the examples of FIG. 16B and also FIG. 15C, visible light imaging system 1680 is illustrated as being closely positioned to (e.g., just above) a divided-aperture infrared spectral imaging (DAISI) system. If desired, other suitable arrangements may be provided. As an example, the visible light imaging system 1680 may be omitted entirely. As another example, housing 1640A (see FIG. 15C) may be divided into two or more sections, one of which may contain a visible light imaging system module and one of which may contain a DAISI system. Such an arrangement may facilitate servicing of system 1000, including replacing the visible light imaging system 1680 with another visible light imaging system depending on a user's needs and desires. As an example, system 1000 may be provided to enable a user swap out at least part of the visible light imaging system 1680 for one having a zoom lens. System 1000 may facilitate such a swap by providing visible light imaging system 1680 relatively separate from the DAISI system and/or contained in a separate section of housing 1640A.

Visible light imaging system 1680 may include any desired focal length lens including zoom lenses with varying focal lengths. A zoom lens in the visible light imaging system 1680 may include an actuator, motor, or other similar device that drives lens elements within the zoom lens to adjust the focal length (e.g., the magnification power) of the lens in response to control signals (generally locally by circuitry in system 1000 or remotely by external devices and received by system 1000 over a communications channel).

Figure 16D:
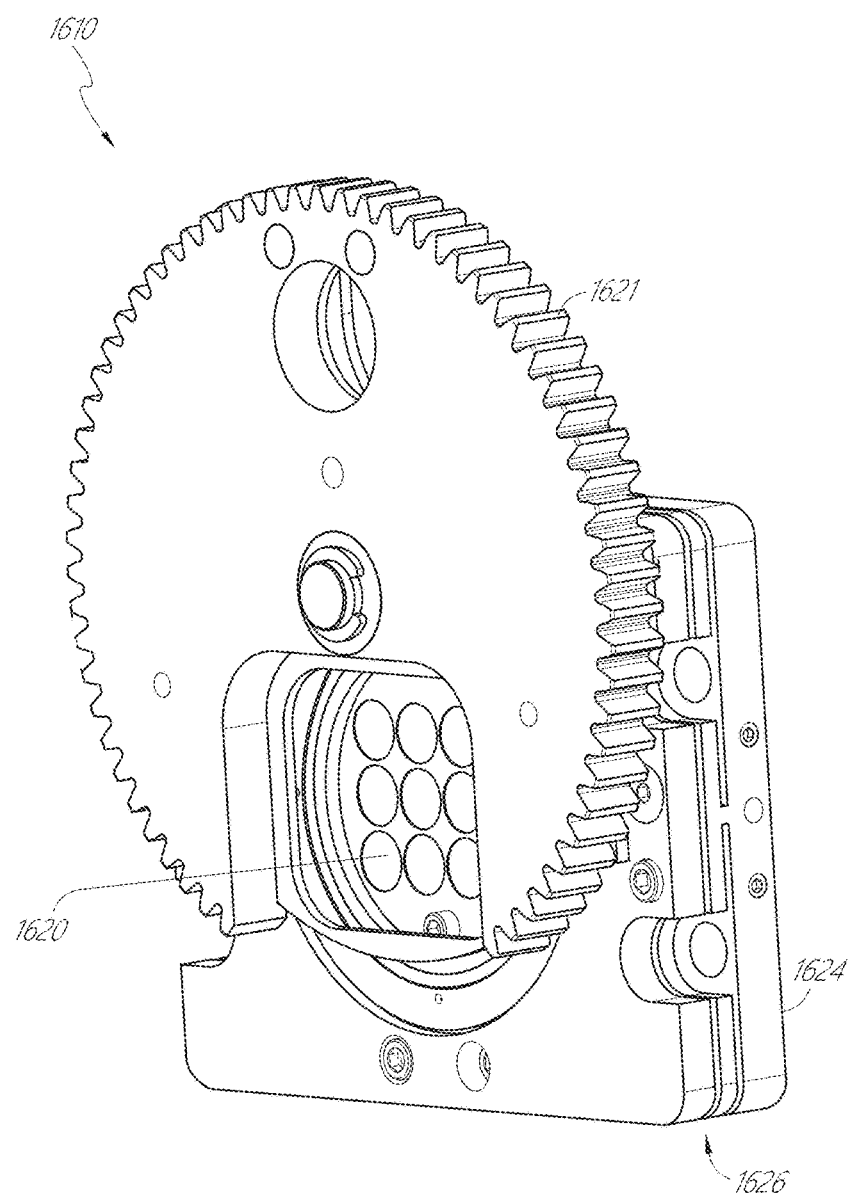
FIG. 16D is a schematic front perspective view of the optical system of the DAISI system of FIG. 16B.
Figure 16E:
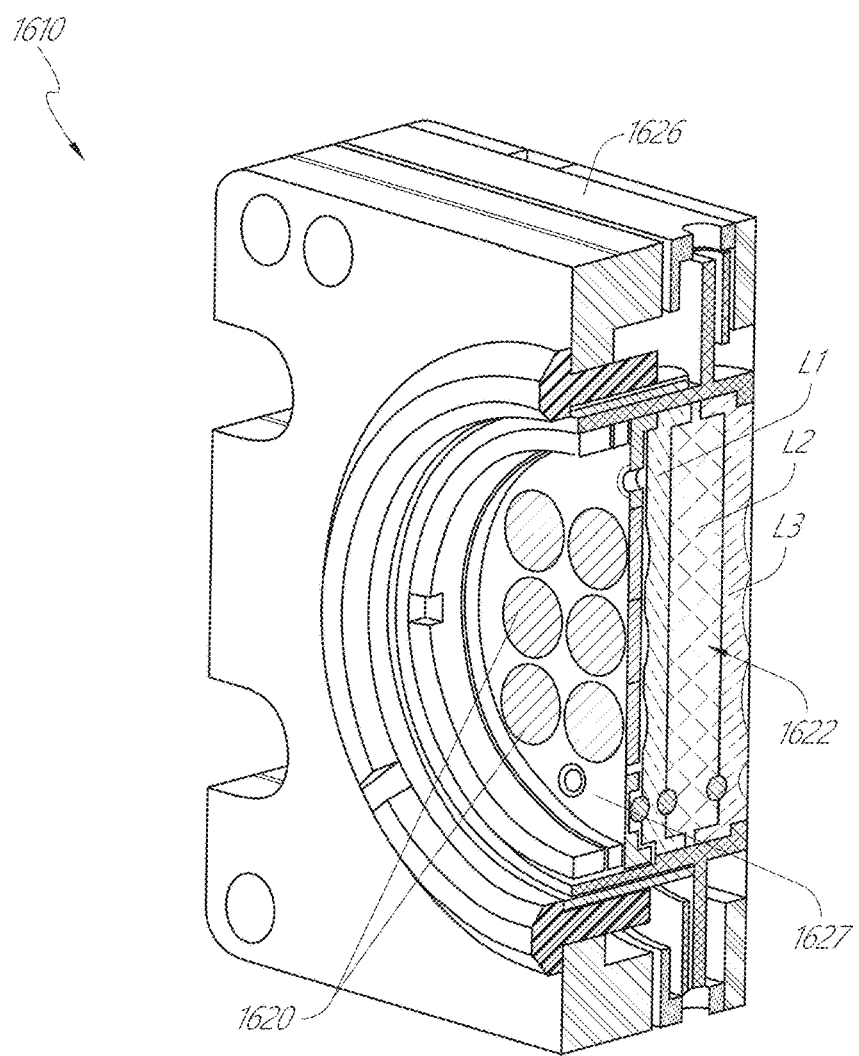
FIG. 16E is a schematic perspective cross-sectional view of the optical system of the DAISI system of FIG. 16B, with the shutter omitted for illustration purposes.

FIG. 16D is a schematic front perspective view of the optical system 1610. As shown in FIG. 16D, the optical system 1610 can comprise the shutter 1621, a support body 1626, and the optical detector 1624. In FIG. 16D, the optical components such as the filter 1620 and the lens 1622 can be disposed in the support body 1626. FIG. 16E is a schematic perspective cross-sectional view of the optical system 1610, with the shutter omitted for illustration purposes. FIG. 16E illustrates the array of filters 1620 and the lens elements L1, L2, L3 of the lenses 1622 being supported by the support body 1626. As shown in FIG. 16E, the array of filters 1620 can be fitted within apertures of a lens holder 1627. Additional features of the optical system 1610 are described in detail below.

As shown in FIG. 16E, the lens elements L1 may generally lie in a common plane. Similarly, the lens elements L2, L3 and the filters 1620 may generally lie in their own common planes. If desired, some or all of the optical components (e.g., lens elements L1, L2, and L3 and filters 1620) associated with one or more of the spectral channels may be offset from the optical components of the remaining spectral channels in a direction along the optical axis of system 1000 (i.e., in a direction normal to the common planes). In general, any of the channels may be offset in any direction (towards or away from the detector) and by any amount, as desired. As examples, the optical components of one or more channels may be offset closer to the detector 1624 by approximately 10 microns, by approximately 10-20 microns, approximately 20 microns, approximately 20-30 microns, approximately 30 microns, approximately 10-30 microns, approximately 10-50 microns, approximately 10-100 microns, more than approximately 100 microns, less than 100 microns, less than 50 microns, less than 30 microns, more than 30 microns, more than 50 microns, etc. The optical components of one or more channels may also be shifted away from detector 1624 by similar amounts.

In at least some arrangements, the position of filters 1620 relative to the lens elements L1, L2, and L3 may also be altered on a per-channel basis. As an example, a first set of filters 1620 may be behind one or more of lens elements L1, L2, and L3 for some channels and, in other channels, a second set of filters 1620 may be disposed in front of the lens elements L2, L2, and L3.

Shifting the optical elements of at least one spectral channel closer to (or farther from) detector 1624 may facilitate imaging of a wider or particular range of infrared wavelengths. In some embodiments, the lenses of one or more spectral channels may be towards detector 1624 by approximately 20 microns. A shift of lens position about 20 microns may enable those channels to properly focus incident IR radiation having wavelengths between 3 and 8 microns. The remaining (i.e., non-shifted) lenses may properly focus incident IR radiation have longer wavelengths of about 8 to 14 microns.

As an example, the lens elements L1, L2, and L3 of the four channels in the corners of system 1000 (channels 1, 4, 9, and 12 in the FIG. 19 perspective) may be offset from the other channels by approximately 20 microns towards the infrared detector 1624. The offset of the four channels in the corners may enable the offset channels to image objects having different (e.g., shorter) wavelengths than the remaining channels. In particular, the offset channels may propagate shorter wavelength light. The index of refraction of the material used in L1, L2, L3, may vary with wavelength. As a result, the focal length of the imaging optics in these channels may be shorter. Without reducing the distance between the imaging optics and the detector array, the image will be out of focus. Likewise, by reducing this distance to the detector array, the image may be more in focus. Accordingly, this distance may be reduce by moving the lenses (e.g., L1, L2, L3) closer to the detector array and thereby providing a better focus for shorter wavelengths such as those extending from 8 microns down to 3 microns (e.g., in comparison to wavelength 8 to 14 microns). Accordingly, the offset along the optical axis may provide increase focus for the different wavelengths of incident infrared radiation onto detector 1624. The offset along the optical axis may thus reduce differences in focus for channels operating in different wavelengths.

B. Rotary Shutter

As explained above with respect to FIGS. 1-4, it can be important to provide one or more reference surfaces for calibration of the DAISI system. For example, as explained above, in some embodiments, the systems disclosed herein can utilize one or more shutters that have a known and/or measured temperature. To calibrate the system, the one or more shutters (or other reference surface(s)) can be placed along the optical axis of the system, and the optical detector array can acquire infrared image data of the shutter. The measured value at the detector array can be used to estimate the gain and/or offset of the pixels so as to accurately estimate concentrations of objects (such as a gas cloud). In some embodiments, as explained above, the system can utilize a plurality of shutters or surfaces that are at a corresponding plurality of known and/or measured temperatures. The absolute difference in temperature between the shutters or surfaces can be measured at the detector array, and, as explained herein, the measured temperature difference can be utilized to measure temperatures at the object.

Figure 17A:
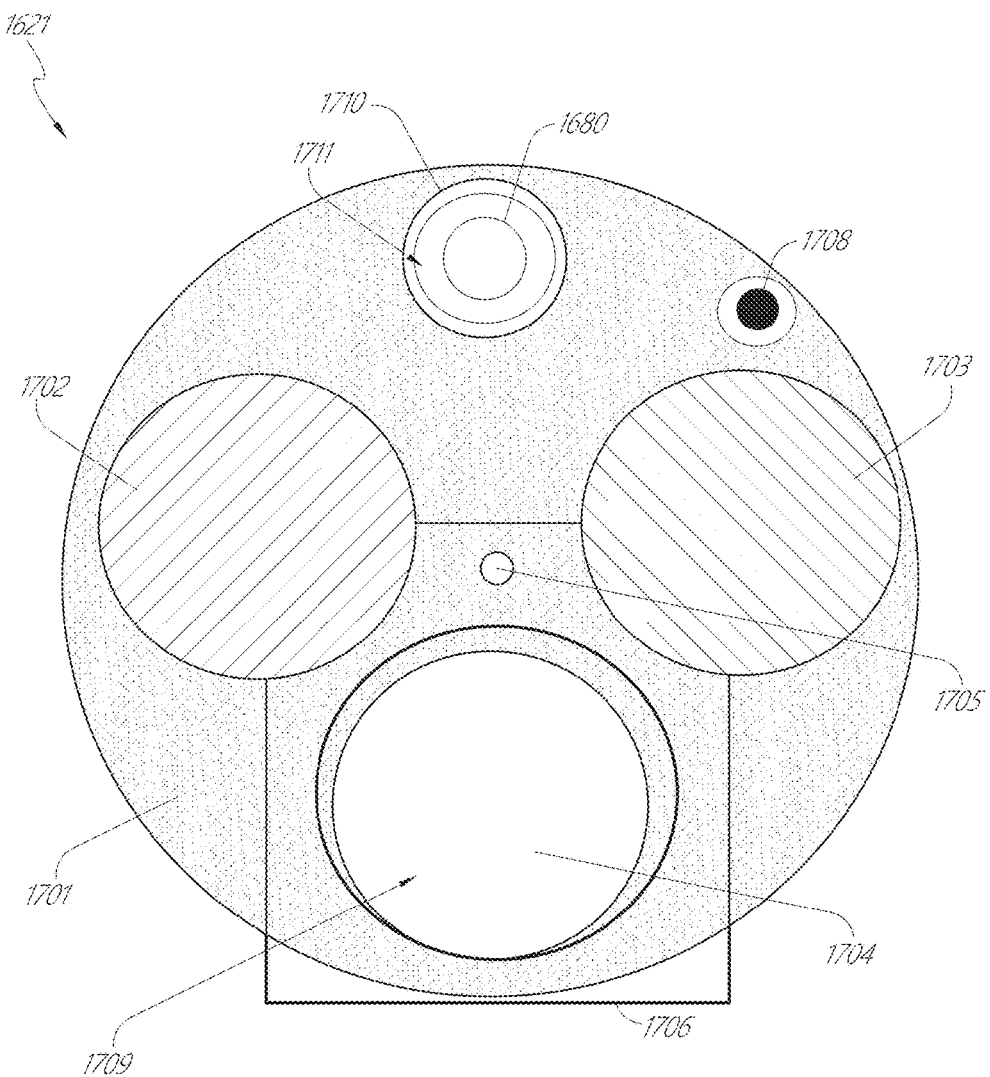
FIG. 17A is a front plan view of the shutter illustrated in FIGS. 16B and 16D, according to various embodiments.

FIG. 17A is a front plan view of the shutter 1621 illustrated in FIGS. 16B and 16D. The illustrated shutter 1621 can comprise a rotary shutter assembly configured to rotate about an axis parallel to the optical axis of the system. The shutter 1621 (or shutter assembly) can comprise a shutter frame 1706 and a shutter body 1701 rotatably mounted to the shutter frame 1706. For example, the shutter 1621 can comprise a shaft 1705 disposed within an aperture of the shutter frame 1706. A shutter drive system 1708 can be activated to cause the shaft 1705 to rotate about an axis parallel to the optical axis of the system. The drive system 1708 can comprise any suitable drive components for imparting rotation to the shaft 1705. For example, the drive system 1708 can comprise a drive motor and one or more gears (or other clutch mechanisms) to impart rotation to the shaft 1705. The shaft 1705 can be secured to the shutter body 1701 such that rotation of the shaft 1705 imparts rotation to the shutter body 1701.

The shutter body 1701 can comprise a plurality of separate and distinct regions 1702, 1703, 1704, 1710 spaced circumferentially from one another on the shutter body 1701. In the illustrated embodiment, for example, the shutter body 1701 can comprise a first reference region 1702, a second reference region 1703, an infrared imaging region 1704, and a visible imaging region 1710. In some embodiments, the first and/or second reference regions 1702, 1703 may be opaque to infrared radiation. The system 1000 can include an infrared imaging aperture 1709, which can correspond to the front aperture of the system 1000. For example, during operation of the system 1000, at least infrared radiation from the object can pass through the infrared imaging aperture 1709 and to the optical elements (e.g., the filters, lenses, etc.) of the system 1000. The system 1000 can also include a visible imaging aperture 1711 through which at least visible light from the object passes. The visible imaging aperture 1711 can be transparent to at least visible light such that visible light from the object passes through the aperture 1711 and to the visible light imaging system 1680, which may comprise a visible light sensor to capture visible light image data from the object.

Processing electronics can be provided in the processing unit 1611 to control the operation of the drive system 1708. The processing electronics can comprise one or more processors that are programmed to instruct the motor to rotate the shaft 1705 about its axis of rotation. Rotation of the shaft 1705 and shutter body 1701 causes the regions 1702, 1703, 1704, 1710 to also rotate. To calibrate the system 1000, the drive system 1708 can rotate the shutter body 1701 such that the first reference region 1702 is approximately aligned with the infrared imaging aperture 1709. The first reference region 1702 can be at a known or measured first temperature. For example, in some embodiments, the first reference region 1702 can be actively maintained at a predetermined temperature by one or more heating or cooling elements. In some embodiments, the first temperature of the first reference region 1702 can be monitored (with or without active heating or cooling) by one or more temperature sensors (e.g., thermocouples, etc.). Thus, the system 1000 can accurately measure or otherwise store the approximate temperature of the first reference region 1702. When the first reference region 1702 is aligned with the infrared imaging aperture 1709, the optical detector can acquire first calibration image data representative of the first temperature of the first reference region 1702.

Similarly, the drive system 1708 can be activated to cause the shutter body 1701 to rotate such that the second reference region 1703 is approximately aligned with the infrared imaging aperture 1709. As with the first reference region 1702, the second reference region 1703 can be actively maintained at a second predetermined temperature by one or more heating or cooling elements. In some embodiments, the second temperature of the second reference region 1703 can be monitored (with or without active heating or cooling) by one or more temperature sensors (e.g., thermocouples, etc.). Thus, the system 1000 can accurately measure or otherwise store the approximate temperature of the second reference region 1703. When the second reference region 1703 is aligned with the infrared imaging aperture 1709, the optical detector can acquire second calibration image data representative of the second temperature of the first reference region 1703, which may be different from the first temperature of the first reference region 1702 by a known and/or predetermined amount.

During operation (e.g., when the calibration is complete and the user wishes to acquire image data of an object), the drive system 1708 can cause the shutter body 1701 to rotate such that the infrared imaging region 1704 is approximately aligned with the infrared imaging aperture 1709 of the DAISI system 1000. The visible imaging region 1710 of the shutter body 1701 can be spaced relative to the infrared imaging region 1704 of the shutter body 1701 such that, when the infrared imaging region 1704 is aligned with the infrared imaging aperture 1709 of the system 1000, the visible imaging region 1710 is also aligned with the visible imaging aperture 1711 of the system 1000. When the infrared imaging region 1704 and the visible imaging region 1710 are aligned with the respective apertures 1709, 1711, infrared radiation from the object can pass through the infrared imaging region 1704 and the infrared imaging aperture 1709 and to the infrared imaging optics. Similarly, when the infrared imaging region 1704 and the visible imaging region 1710 are aligned with the respective apertures 1709, 1711, visible light radiation from the object can pass through the visible imaging region 1710 and the visible imaging aperture 1711 and to the visible light imaging system 1680.

The shutter body 1701 may comprise any suitable number of reference regions, and the reference regions may be disposed at any suitable position on the body 1701. Moreover, the shutter body 1701 may include embedded processing electronics for controlling the operation of various components, such as temperature sensor(s), the drive system 1708, active heating and/or cooling elements, etc. Advantageously, the embodiment of FIG. 17A enables the DAISI systems 1000 disclosed herein to efficiently calibrate the system by rotating a single rotary wheel shutter.

C. Dual Shutters

Figure 17B:
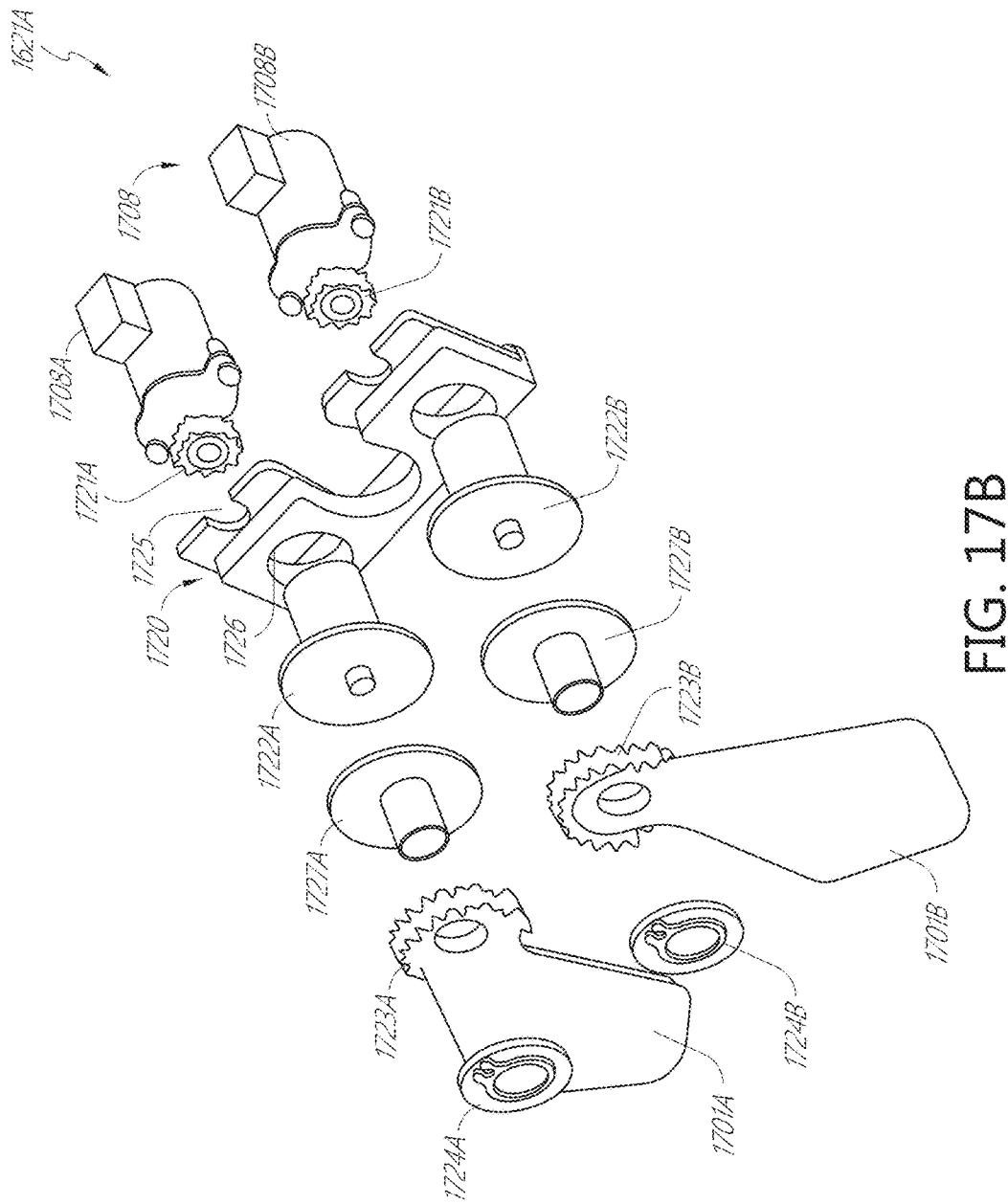
FIG. 17B is a schematic perspective exploded view of a shutter according to some embodiments.
Figure 17C:
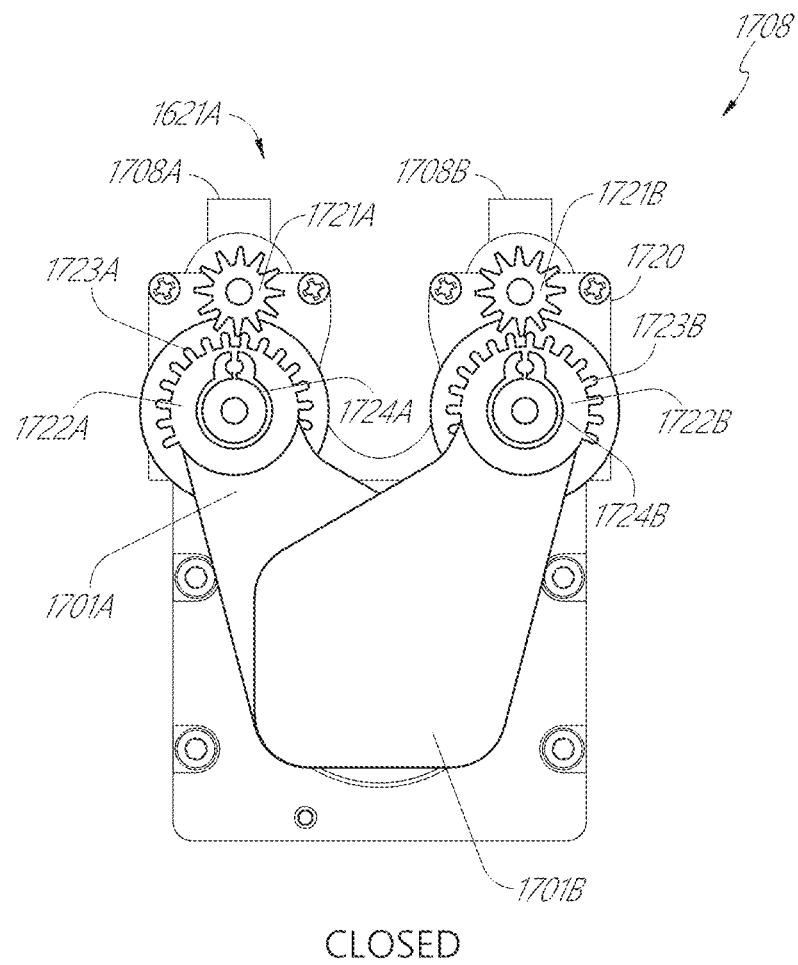
FIG. 17C is a front view of the shutter of FIG. 17B in a closed configuration.
Figure 17D:
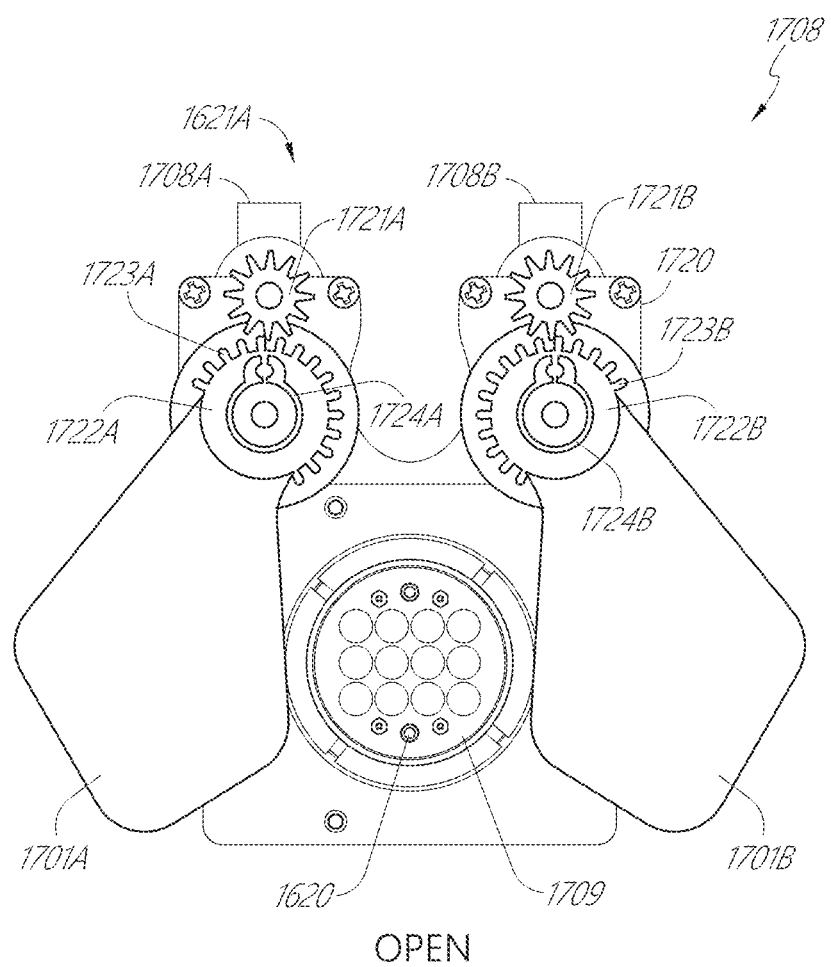
FIG. 17D is a front view of the shutter of FIGS. 17B and 17C in an open configuration.

FIG. 17B is a schematic perspective exploded view of a shutter 1621A according to some embodiments. FIG. 17C is a front view of the shutter 1621A in a closed configuration. FIG. 17D is a front view of the shutter 1621A in an open configuration. The shutter 1621A can be used with any of the DAISI systems 1000 disclosed herein.

The shutter 1621A can include a drive system 1708 comprising first and second drive elements 1708A, 1708B. The first and second drive elements 1708A, 1708B can comprise a motor configured to impart rotation to corresponding first and second shutter bodies 1701A, 1701B. The first and second drive elements 1708A, 1708B can be spaced from one another along a lateral direction. The first and second drive elements 1708A, 1708B can have drive shafts connected to respective drive gears 1721A, 1721B, each of which may have a plurality of gear teeth. The drive shafts (not shown) of the motor (to which the gears 1721A, 1721B are connected) can be disposed in corresponding recesses 1725 of a frame 1720. As shown in FIGS. 17C and 17D, drive gears 1721A, 1721B can be disposed above the shutter bodies 1701A, 1701B. The drive gears 1721A, 1721B can be separated from the drive elements 1708A, 1708B by the frame 1720.

Slip rings 1722A, 1722B can be disposed in corresponding holes 1726 of the frame 1720. The slip rings 1722A, 1722B can be configured to rotate within the holes 1726 in some embodiments. Respective gear shafts 1727A, 1727B can be mounted to corresponding flanges of the slip rings 1722A, 1722B. The first and second shutter bodies 1701A, 1701B can be secured to corresponding shutter gears 1723A, 1723B. Retaining washers 1724A, 1724B can be provided to secure the shutter bodies 1701A, 1701B and gears 1723A, 1723B to the gear shafts 1727A, 1727B.

As shown in FIGS. 17C and 17D, the drive gears 1721A, 1721B can be operably engaged with the shutter gears 1723A, 1723B. To rotate the shutter bodies 1701A, 1701B, the drive elements 1708A, 1708B can be activated to cause rotation of the drive gears 1721A, 1721B, which in turn can cause the shutter gears 1723A, 1723B to rotate. For example, gear teeth of the drive gears 1721A, 1721B can mesh or interleave with corresponding gear teeth of the shutter gears 1723A, 1723B. Rotation of the shutter gears 1723A, 1723B can cause the shutter bodies 1701A, 1701B to rotate about respective axes which are parallel to the optical axis of the DAISI system 1000. For example, rotation of the shutter bodies 1701A, 1701B can cause the slip rings 1722A, 1722B to rotate within the holes 1726 in some arrangements.

As with the embodiment of FIG. 17A, in the embodiment of FIGS. 17B-17D, the shutter 1621A can be used to calibrate the DAISI system 1000. For example, the first shutter body 1701A can be at a known or measured first temperature. For example, in some embodiments, the first shutter body 1701A can be actively maintained at a predetermined temperature by one or more heating or cooling elements. In some embodiments, the first temperature of the first shutter body 1701A can be monitored (with or without active heating or cooling) by one or more temperature sensors (e.g., thermocouples, etc.). Thus, the system 1000 can accurately measure or otherwise store the approximate temperature of the first shutter body 1701A. When the first shutter body 1701A is aligned with an infrared imaging aperture 1709, the optical detector can acquire first calibration image data representative of the first temperature of the first shutter body 1701A.

Similarly, the second shutter body 1701B can be at a known or measured second temperature. For example, in some embodiments, the second shutter body 1701B can be actively maintained at a predetermined temperature by one or more heating or cooling elements. In some embodiments, the second temperature of the second shutter body 1701B can be monitored (with or without active heating or cooling) by one or more temperature sensors (e.g., thermocouples, etc.). Thus, the system 1000 can accurately measure or otherwise store the approximate temperature of the second shutter body 1701B. When the second shutter body 1701B is aligned with an infrared imaging aperture 1709, the optical detector can acquire second calibration image data representative of the second temperature of the second shutter body 1701B.

In FIG. 17C, the shutter 1621A is illustrated in the closed configuration, in which one or more of the shutter bodies 1701A, 1701B are aligned with the infrared imaging aperture 1709. In the closed configuration, the shutter body 1701A can be disposed in a region laterally between the two axes of rotation along the lateral direction. In the illustrated arrangement, both shutter bodies 1701A, 1701B are aligned with the aperture 1709. In other arrangements, the drive system 1708 can independently align each of the shutter bodies 1701A, 1701B with the aperture 1709. For example, the system 1000 can rotate the first shutter body 1701A to be aligned with the aperture 1709 to acquire a first calibration measurement, as illustrated in FIG. 17D. At the same time, the system 1000 may rotate the second shutter body 1701B into its closed position (i.e., to be aligned with the aperture 1709) or may rotate the second shutter body 170B into its open position. To acquire a second calibration measurement, the system 1000 can rotate the first shutter body 1701A to expose the aperture 1709, and can rotate the second shutter body 1701B to be aligned with the aperture 1709. In its closed configuration, the shutter body 1701B can be disposed in the region laterally between the two axes of rotation along the lateral direction. When calibration is complete, the drive system 1708 can rotate both shutter bodies 1701A, 1701B into their respective open positions to expose the infrared imaging aperture 1709, as illustrated in FIG. 17D. As explained above, infrared radiation from the object (such as a gas cloud) can enter the aperture 1709 and impinge upon the imaging optics, such as the filters 1620, lenses, etc.

D. Lens Arrays

The divided-aperture infrared spectral imaging (DAISI) systems described herein, including the DAISI systems disclosed in Section II above and the mobile DAISI systems disclosed in Section III above, may include features such as arrays of lenses formed with monolithic lens substrates, arrays of lenses formed with individual lens substrates, patterned optical filters, arrays of individual optical filters, and cooling modules coupled to components such as an optical focal plane array (FPA) unit and a lens assembly.

As described herein, DAISI systems may include a lens assembly 1502 including a lens array 1002. As disclosed in connection with FIG. 18A, each lens of the lens array 1002 can at least partially define or be included in an optical channel to be imaged by the FPA unit 1008.

In at least some embodiments, a baffle 2500 may be provided (e.g., in mounting plate 1584) to reduce or block stray light. Baffle 2500 may reduce or block light that enters via one optical channel (which may be associated with one lens) from exiting the lens assembly 1502 via another optical channel (which may be associated with another lens). Baffle 2500 may be formed of any desired materials and using any desired techniques. As one example, baffle 2500 may include a metal sheet with lens openings formed by mechanical or laser cutting. If desired, baffle 2500 may be formed with a material having a coefficient of thermal expansion (CTE) that is similar to or that matches the CTE of substrate 2501. By having similar or matching CTE's, baffle 2500 and substrate 2501 may maintain optical performance across a wide range of temperatures.

1. Monolithic Substrates for Lenses

Figure 18A:
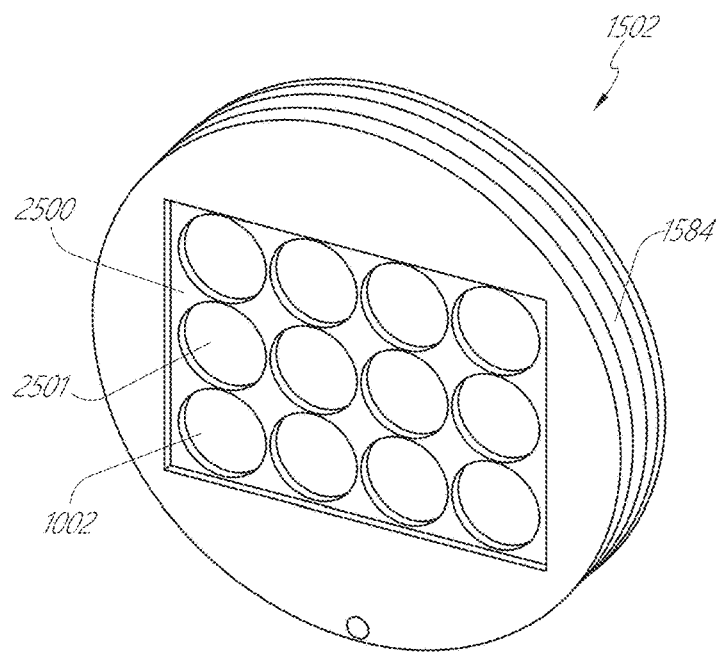
FIGS. 18A and 18B show an embodiment of an imaging system including an array of lenses formed with monolithic lens substrates, according to various embodiments.
Figure 18B:
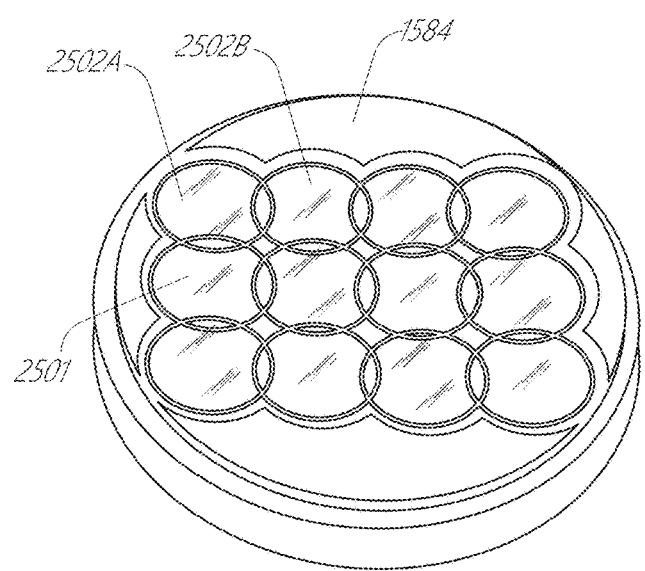

As illustrated in FIGS. 18A and 18B, lens array 1002 may be formed from one or more monolithic substrates 2501. In other words, multiple lenses (i.e., some or all of the lenses) in lens array 1002 may share a single common substrate. A monolithic substrate may be formed in such a manner as to provide lenses associated with multiple optical channels. As shown in FIG. 18B, all of the lenses of lens array 1002 may be formed from a single monolithic substrate 2501. In this manner, monolithic lens substrate 2501 may include portions corresponding to a lens for each of the optical channels in a DAISI system. For example, monolithic substrate 2501 may include a lens portion 2502A corresponding to a first optical channel, lens portion 2502B corresponding to a second optical channel, etc.

While FIG. 18B illustrates monolithic lens substrate 2501 as having multiple lens portions formed from respective shaped (e.g., spherical) portions of the substrate, monolithic lens substrate 2501 may also be a gradient-index-based optical substrate (i.e., lens substrate 2501 may form GRIN lenses). In such arrangements, monolithic substrate 2501 may be formed with flat surfaces, but have variations of refractive index of the substrate material that forms the lenses, in a manner that focuses lights through each of the lens portions 2502A, 2502B, etc. in the same manner as conventionally shaped lens. Lens substrates such as monolithic substrate 2501 may also be formed with a combination of lens-forming shaped portions and lens-forming variations of refractive index of the substrate material.

Lens substrate 2501 may be formed from any suitable materials including, but not limited to, silicon, germanium, chalcogenide glass, calcium fluoride, zinc selenide, zinc sulfide, gallium arsenide, cadmium telluride, BLACK DIAMOND-2™ (a chalcogenide made of an amorphous mixture of germanium, antimony, and selenium), AMTIR™ (amorphous material transmitting infrared radiation), thallium bromoiodide, IR fused silica, sodium chloride, potassium bromide, potassium chloride, sapphire, crystal quarts, UV fused silica, barium fluoride, calcium fluoride, magnesium fluoride, lithium fluoride, etc. Lens substrate 2501 may preferably be formed of materials that are transparent to infrared wavelengths and/or other wavelengths that system 1000 is configured to detect and may be formed from glass substances, crystal substances, and/or other suitable substances.

Lens substrate 2501 may be molded into desired shapes (i.e., individual lens portions 2502A, 2502B, etc. may be formed by molding processes). Molding process may be particularly suitable when lens substrate 2501 is formed from glass or other amorphous materials. Lens substrate 2501 may also be ground or cut into desired shapes (i.e., individual lens portions 2502A, 2502B, etc. may be formed by diamond cutting or other methods). Grinding and cutting processes may be particularly suitable when lens substrate 2501 is formed from crystalline or other similar substances. In general, combinations of molding, grinding, cutting, and other similar processes may be used to shape lens substrate 2501, regardless of whether lens substrate 2501 is formed from amorphous, crystalline, or other substances.

2. Individual Lens Substrates

Figure 18C:
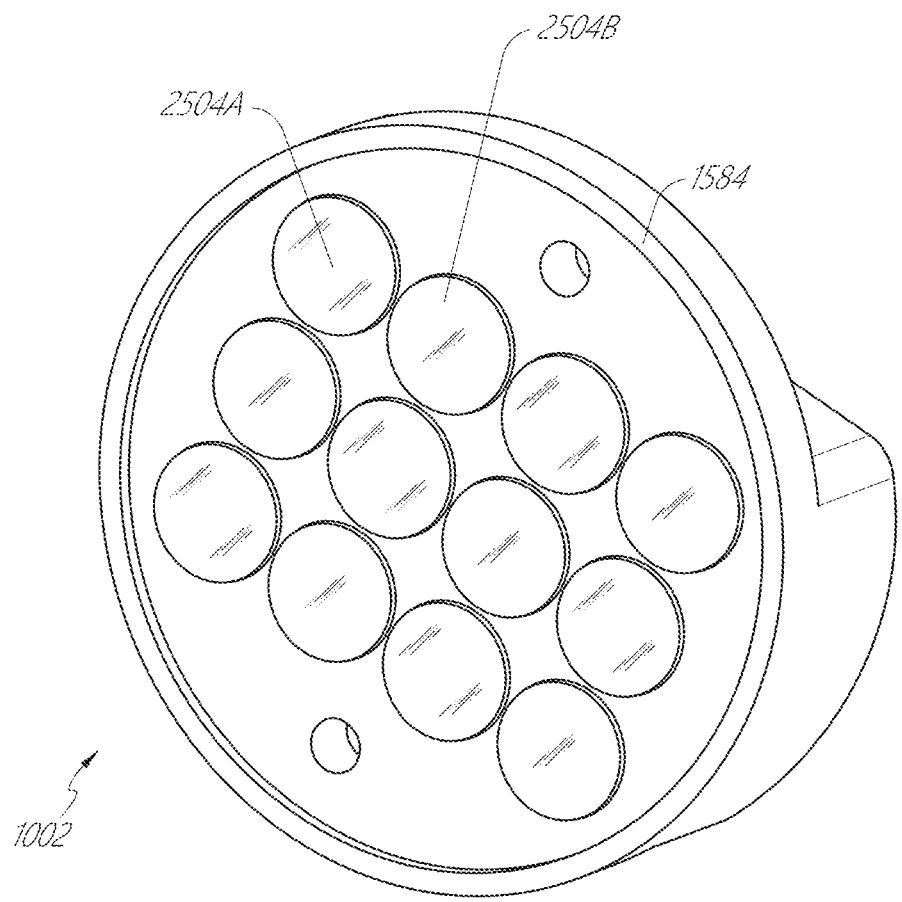
FIG. 18C shows an embodiment of an imaging system including an array of lenses formed with individual lens substrates, according to various embodiments.
Figure 18D:
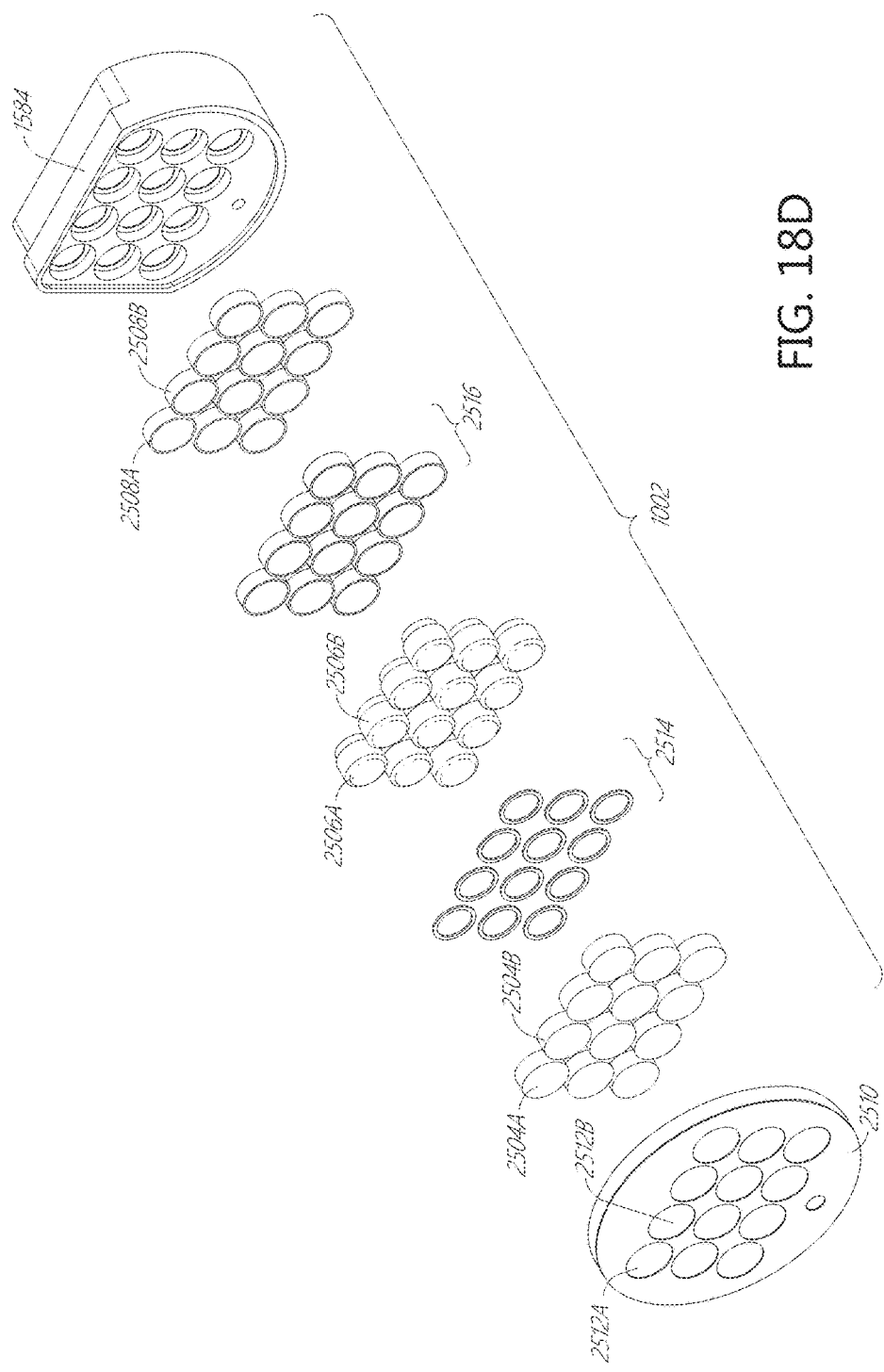
FIG. 18D is an exploded perspective of the imaging system having an array of lenses formed with individual lens substrates shown in FIG. 18C.
Figure 18E:
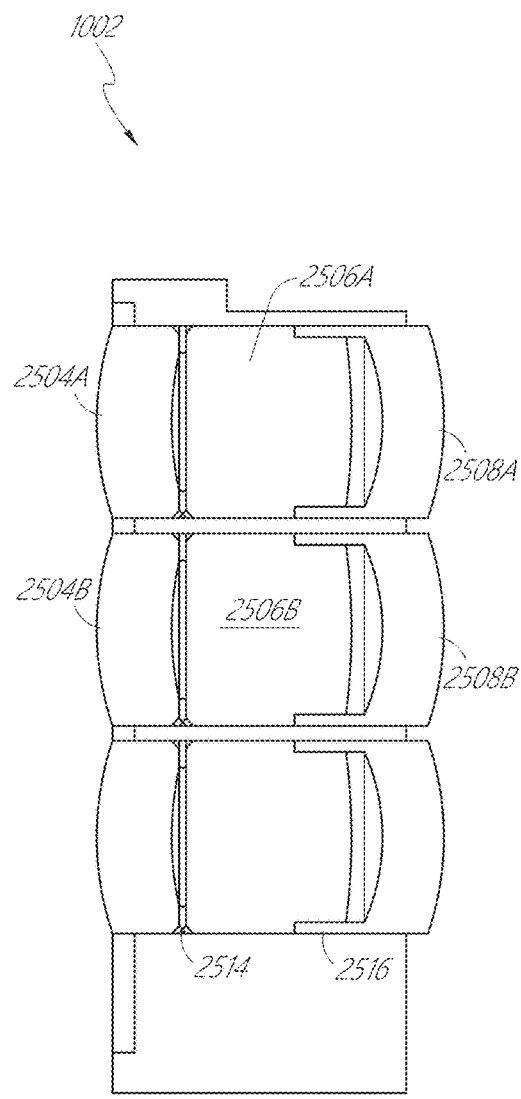
FIG. 18E is a cross-sectional view of a lens assembly formed from individual lens substrates of the type shown in FIGS. 18C and 18D.

As shown in FIG. 18C as well as FIGS. 18D-18E, lens array 1002 may be formed from an array of individual lens substrates such as lens substrates 2504A, 2504B, etc. (also referred to herein as individual lenses). By forming lens array 1002 from an array of individual lenses, fabrication of the lens array 1002 may be simplified (i.e., in at least some scenarios, it may be simpler to produce multiple individual lenses than a monolithic substrate including multiple lens portions). The individual lenses 2504A, 2504B, etc. in lens array 1002 may be formed from any suitable materials including those described herein in connection with monolithic lens substrate 2501. The individual lenses 2504A, 2504B, etc. in lens array 1002 may be formed using any suitable techniques including those described herein in connection with monolithic lens substrate 2501.

Lens array 1002, whether formed from individual lens substrates or a monolithic lens substrates, may be mounted in lens holder 1584 (also referred to herein as a mounting plate). Lens holder 1584 may be formed from any desired materials and using any desired techniques. As one example, lens holder 1584 may be formed from metal with lens openings formed by mechanical or laser cutting. In at least some embodiments, lens holder 1584 may be formed with a material having a coefficient of thermal expansion (CTE) that is similar to or that matches the CTE of the lenses in lens array 1002. By having similar or matching CTE's, lens holder 1584 and the lenses in lens array 1002 may maintain optical performance across a wide range of temperatures. In other words and by having similar or matching CTE's, the lens holder is able to maintain optical alignment of lens portions 2502A, 2502B, etc. or individual lenses 2504A, 2504B, etc. even if the temperature of the overall system is varied. As a specific example, lens holder 1584 may be formed from KOVAR® (a nickel-cobalt ferrous alloy having substantially similar CTE characteristics as germanium). KOVAR® may have a CTE of approximately $5.5 \times 10^{-6}$/degree K (at temperatures below 200 degrees C.), whereas borosilicate glass may have a CTE of between approximately 3 to $6 \times 10^{-6}$/degree K (at temperatures below 200 degrees C.).

FIG. 18D shows an exploded perspective view of the imaging system of FIG. 18C. FIG. 18E shows a cross-sectional view of the imaging system of FIG. 18C. As shown in FIGS. 18D and 18E, lens array 1002 may include multiple optical layers such as front lenses 2504A, 2504B, etc.; middle lenses 2506A, 2506B, etc.; and rear lenses 2508a, 2508B, etc. Additionally, lens array 1002 may include washers or other mounting structures 2514 and 2516 that hold the front, middle, and rear lenses together when lens array 1002 is assembled with lens holder 1584. Furthermore, the imaging system may include a filter housing 2510 including an array of filters 2512A, 2512B, each of which corresponds to a particular optical channel and respective set of front, middle, and rear lenses. In at least some embodiments, the front, middle, and rear lenses may be recessed into the front of lens holder 1584 and secured by filter housing 2510. The arrangement of FIG. 18D may reduce the possibility of stray light (i.e., light that enters a first optical channel and crosses over into a second optical channel). In other words, lens holder 1584 may operate as a stray light blocking baffle when the lenses are recessed within lens holder 1584.

The middle and rear lenses 2506 and 2508 illustrated in FIG. 18D may be formed using materials similar to those described herein in connection with lenses 2504. In addition, the middle and rear lenses 2506 and 2508 may be formed using manufacturing techniques similar to those described herein in connection with lenses 2504. In at least some embodiments, middle lenses 2506 may have relatively flat front and rear surfaces, while the front and rear lenses 2504 and 2508 have curved front and rear surfaces. In at least some other embodiments some or all of the front, middle, and rear lenses are formed from GRIN lenses.

E. Filter Arrays

Figure 19:
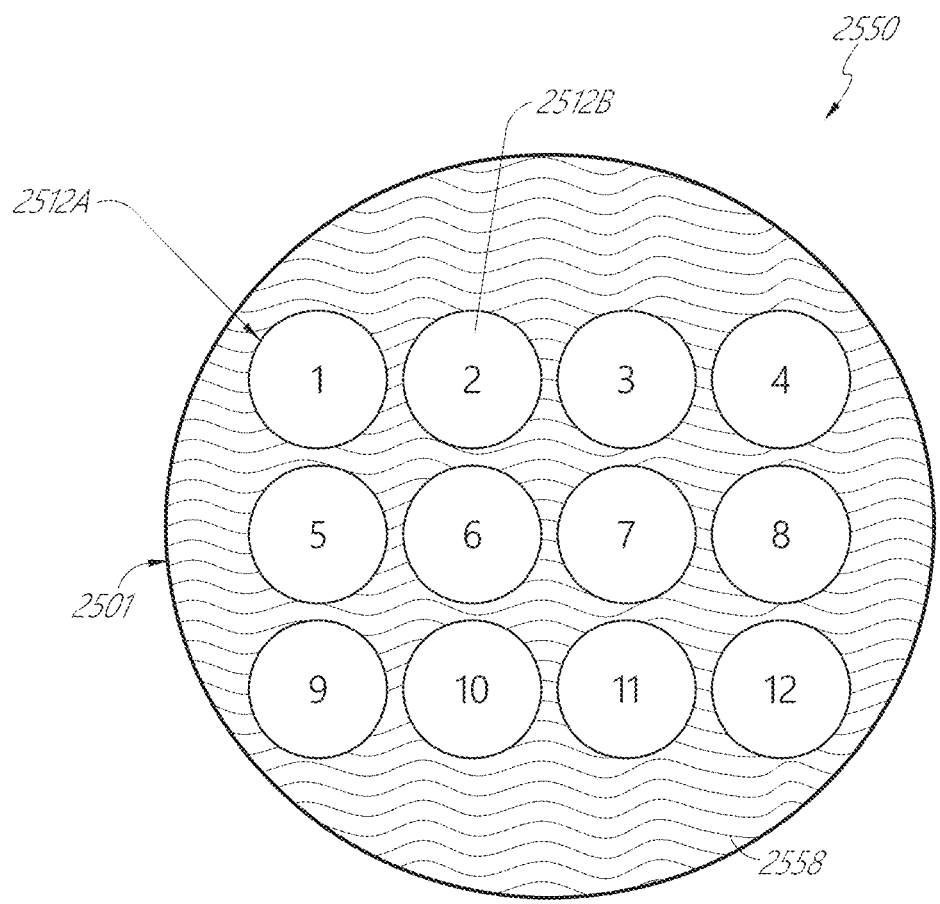
FIG. 19 is a schematic diagram of a patterned array of optical filters that may be used in an imaging system having divided apertures, according to various embodiments.

As discussed herein, gas and chemical imaging systems may include an array 2550 of optical filters, such as array 2550 illustrated in FIG. 19, that define spectrally-distinct sub-images. These optical filters may each pass a distinct wavelength or wavelength range or band or set of wavelengths or set of wavelength ranges or bands of incident light. In at least some embodiments, some or all of the optical filters comprise filters that pass a distinct wavelength or set of wavelengths of incident light in an infrared range (e.g., extending generally from approximately 1 micron to approximately 20 microns in wavelength). Theoretical plots of the transmission characteristics of optical filters usable in gas and chemical imaging systems of the type described herein are shown and described in connection with FIGS. 6A, 6B, 6C, and 6D. The optical filters shown and described in connection with FIGS. 6A, 6B, 6C, and 6D are merely illustrative.

While the filters and filter array 2550 are generally described herein as being separate from the optical lens array 1002 (and lenses 2502, 2504, 2506, or 2508), the filters may, if desired, be incorporated into or on some or all of the lenses of the optical lens array 1002. In particular, the filter array 2550 may be provided as coatings on some or all the lenses of lens array 1002. In arrangements in which lens array 1002 is formed from a monolithic substrate, the filter array 2550 may be formed from a patterned filter array (as described herein) coated onto or integrated within the monolithic substrate. In arrangements in which lens array 1002 is formed from individual lenses, the filter array 2550 may be formed from individual filters coated onto or integrated within some or all of the individual lenses.

1. Patterned Filter Arrays

As illustrated in FIG. 19, a filter array 2550 may be provided that includes a substrate 2501 patterned to form individual optical filters 2512A, 2512B, etc. (also labeled 1, 2, ... 12 in FIG. 19) and with infrared blocking material 2558 disposed between the individual optical filters. Filter array 2550 may also be referred to herein as filter array 454. Each individual optical filter 2512A, 2512B, etc. may pass only the desired infrared radiation for its respective optical channel and for its respective infrared detector. In at least some embodiments, the individual optical filters selectively pass at least one wavelength or wavelength range or band or set of wavelengths or set of wavelength ranges or bands in the infrared range of approximately 1 to 20 microns wavelength, in the infrared range of approximately 7-14 microns, or in the infrared range of approximately 3-14 microns or 3-8.5 microns. As an example, one of more spectral channels in system 1000 may have an infrared filter (which may be formed from multiple filters) that passes infrared light in both a 3 micron to 4 micron range and a 6 to 8 micron range (or a 7 micron to 8.5 micron range, or a 7 to 8 micron range, or other suitable range). In other words, the system 1000 may include a dual-notch infrared filter in at least one spectral channel. Such a dual-notch filter may be particularly useful in detecting a particular gas's infrared signature (such as methane) even without information from other spectral channels in system 1000. A notch filter may generally attenuate wavelengths that fall outside their pass range. As an example, a dual-notch filter that passes infrared light in both a 3 to 4 micron and a 6 to 8.5 micron range may attenuate wavelengths shorter than 3 microns, wavelengths between 4 and 6 microns, and wavelengths longer than 8.5 microns. Infrared blocking material 2258 may help to reduce optical crosstalk or stray light, in which infrared light entered a first optical channel but undesirably crosses over to a second optical channel.

Individual optical filters 2512A, 2512B, etc. may be formed on substrate 2501 using any suitable technique or combination of techniques. As examples, the optical transmission characteristics of individual optical filters may be tuned by varying the type of material or materials deposited at the location of each optical filter, the thickness of the material or materials formed at the location of each optical filter, the number of layers of material or materials at the location of each optical filter, etc. In at least some embodiments, the optical filters may be interference filters and may be bandpass, high-pass, low-pass, or band-rejection filters. The optical filters may, in at least some embodiments, be formed from one or more thin film layers that determine the optical transmission characteristics of the filters. Interference coating with different designs (e.g., having different number or arrangement of layers, different materials, different thickness layers, etc.) may be used. Forming the individual optical filters 2512A, 2512B, etc. can involve processing steps such as masking, etching, depositing, planarizing, doping, stripping mask materials, etc. In this manner, one or more optical filters can be selectively processed while one or more other optical filters are protected).

Infrared blocking material 2558 may serve as a baffle, aperture stop, or field stop and may be patterned onto substrate 2501 in the spaces between the filters 2512. Infrared blocking material 2558 may be formed from any suitable material, such as chrome, that blocks light including stray light between the filters 2512. In at least some embodiments, infrared blocking material 2558 may be formed to implement apodization (i.e., a smoothly varying transmission profile, a transmission profile that smoothly varies as a function of position in the filter array, etc.). In particular, infrared blocking material 2558 may provide a slowly varying gradient baffle, aperture stop, or field stop that has maximum transmissivity near the centers of the filters, minimal or zero transmissivity in the spaces between the filters, and some intermediate transmissivity near the edges of the filters. Infrared blocking material 2258 may be formed in such a manner using suitable patterning and processing techniques.

2. Individual or Diced Filters

Figure 20A:
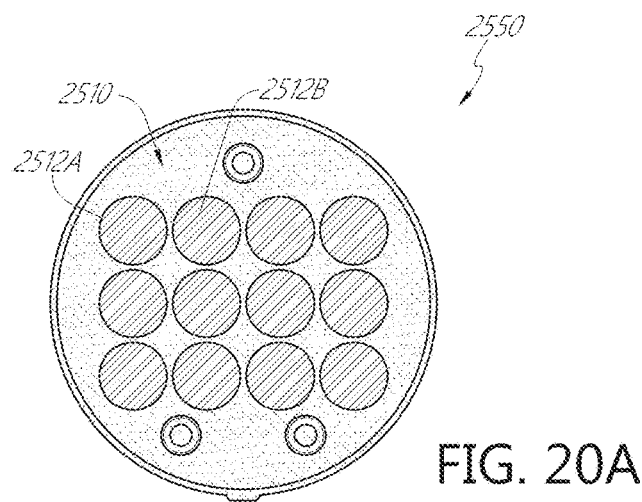
FIGS. 20A-20C illustrate a filter body and an array of individual optical filters that may be used in an imaging system having divided apertures, according to various embodiments.
Figure 20B:
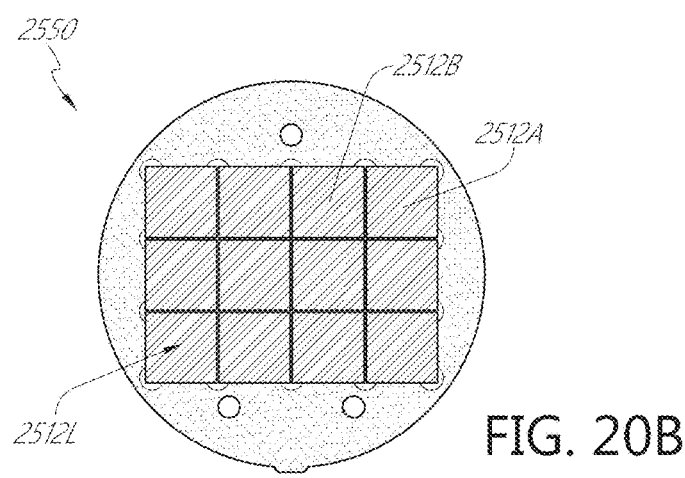
Figure 20C:
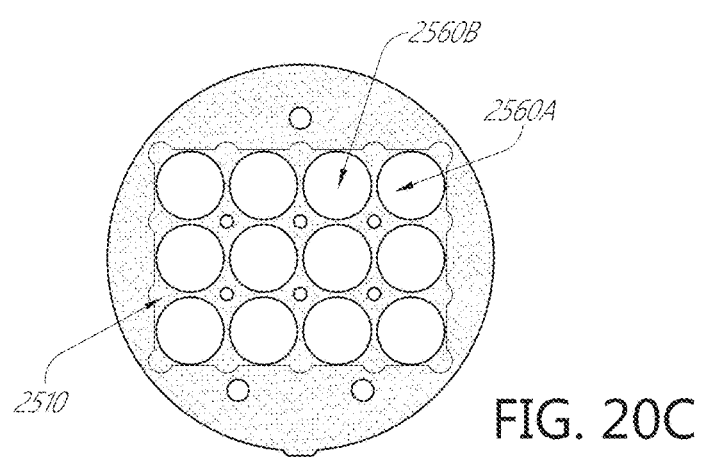

FIGS. 20A-20C illustrate an alternative arrangement for filter array 2550 in which the filter array 2550 is formed from individual filters. In this arrangement, batches of filters are created using suitable processing steps (as described in connection with patterned filters herein). Each batch may include multiple copies of a particular filter (i.e., one of filter 2512A, 2512B, etc.). After forming a batch, the multiple copies of that particular filter may be separated, or diced, to create individual copies of that particular filter. Individual copies of each of the filters that form filter array 2550 that have been separated or diced from their respective batches may then be assembled into filter array 2550. With arrangements of this type, processing each batch may be somewhat simplified, as each substrate being processed includes only a single type of filter. The benefits of simplified batch processing may outweigh any additional complexity involved in the separation, or dicing, and subsequent assembly of individual filters into filter array 2550.

As shown in the rear views of FIGS. 20B and 20C, filter housing 2510 may include alignment structures 2560A, 2560B, etc. in which individual filters 2512A, 2512B, etc. are mounted and aligned. The alignment structures 2560A, 2560B may be formed from recesses, registration features, posts, other suitable elements, or a combination of these and other elements in filter housing 2510. In at least some embodiments, individual filters may be secured to housing 2510 by pressure, when assembled onto mounting plate 1584. If desired, individual filters may also or alternatively be secured to housing 2510 by pressure (i.e., by snapping into place in recessed portions of housing 2510), adhesive, screws, clips, or other fastening elements.

F. Detector Arrays

As discussed herein, gas and chemical imaging systems may include a detector such as optical focal plane array (FPA) 1508. The FPA 1508 may receive light from a plurality of optical channels that are spatially separated and, for example, by virtue of filter array 2550, and this light may be spectrally different. In at least some embodiments, FPA 1508 may be formed from one or more arrays of microbolometers configured to detect infrared radiation, as discussed in more detail herein. In at least some embodiments, the individual lenses 2502, 2504, etc. and filters 2512 can be laterally spaced apart by a distance in a range of about 2 mm to about 20 mm, in a range of about 3 mm to about 10 mm, in a range of about 4 mm to about 8 mm, about 4.3 mm, or some other suitable distance. Likewise, the spatially and spectrally spaced channels of FPA 1508 may be physically spaced about by 2 to 20 mm, 3 to 10 mm, 4 to 8 mm, about 4.3 mm, etc.

Figure 21:
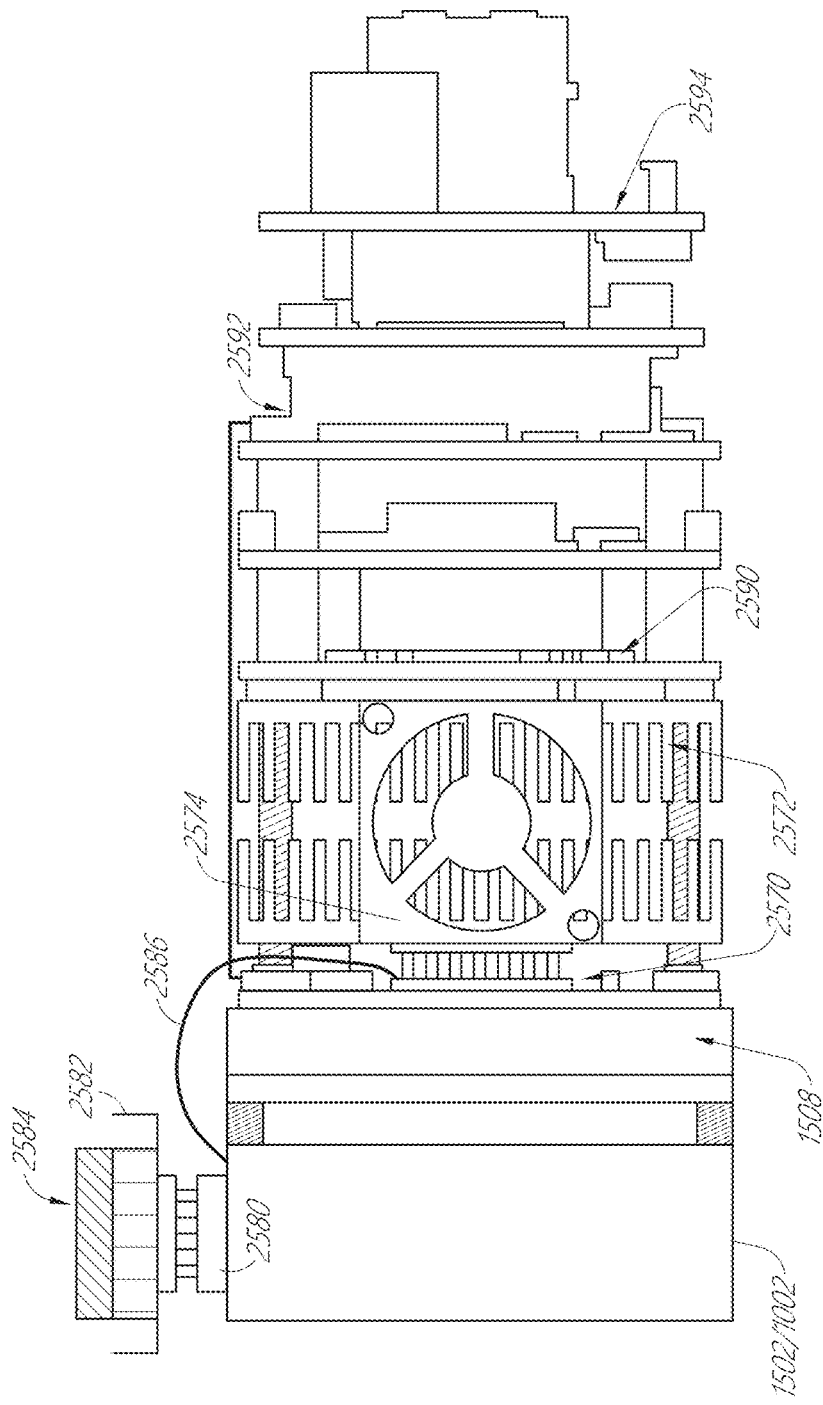
FIG. 21 shows a schematic system diagram of a mobile infrared imaging system including one or more optional cooling systems, according to various embodiments.

FIG. 21 also illustrates that the imaging system may include components such as an FPGA board 2590, a signal conditioning board 2592, and a data communication board 2594. FPGA board 2590 and the signal conditioning board 2592 may be configured to execute methods used in the analysis of the images captured by the optical system as discussed herein (see, e.g., the discussion of processing unit 1021 of FIG. 12). The data communication board 2594 can be configured to communication with at least one device physically separate from the imaging system (e.g., over a wired or wireless connection) as discussed herein (see, e.g., the discussion of communication module 1024 of FIG. 12).

1. TEC Cooling

As shown in FIG. 21, FPA 1508 may be actively cooled, heated, temperature-stabilized, and/or actively thermally controlled using a thermoelectric cooling (TEC) device 2570 (which may also be operable as a heater) utilizing the Peltier effect or using another cooling and/or heating device. TEC device 2570 may be coupled to heat sinks 2572 and heat sink fan 2574. In operation, TEC device 2570 may convey thermal energy from FPA 1508 to heat sink 2572 and heat sink fan 2574 may transfer the thermal energy into the surrounding environment. If desired, heat sinks 2572 may be cooled by liquid cooling in addition to or instead of heat sink fan 2574. The imaging system may include a temperature sensor thermally coupled to FPA 1508 or TEC device 2570. The temperature sensor may be integrated into FPA 1508, integrated into TEC device 2570, or may be a separate device. TEC device 2570 may be configured to monitor the temperature of FPA 1508 using the temperature sensor and, in response, maintain FPA 1508 at a target temperature. By holding the temperature of FPA 1508 relatively constant, the calibration of FPA 1508 can be improved or optimized. In particular, FPA 1508 may be calibrated after TEC device 2570 cools FPA 1508 to a desired operating temperature, and then TEC device 2570 may hold FPA 1508 at the operating temperature to maintain the calibration. TEC device 2570 may, alternatively, operate at a maximum or other preset cooling power to maintain as low a temperature of FPA 1508 as possible. TEC 2570 may, alternatively, maintain the temperature of FPA 1508 in some desired range, e.g., below a first temperature, above a second temperature, etc. In some embodiments, TEC 2570 may cryogenically cool FPA 1508. In other embodiments, TEC 2570 may cool FPA 1508 to a non-cryogenic temperature such as ambient temperature, 10 degrees C. below ambient, 20 degrees C. below ambient, 30 degrees C. below ambient, etc. or a temperature independent of ambient such as −10 degrees C., −5 degrees C., 0 degrees C., 5 degrees C., 10 degrees C., 15 degrees C., 20 degrees C., 25 degrees C., 30 degrees C., etc. and any range within any combination of these temperatures. TEC device 2570 may be a single stage TEC cooler or may include multiple stages (e.g., a first TEC stage having a "hot side" cooled by a larger second TEC stage, which itself has a hot side cooled by a radiator). The temperature to which TEC unit 2570 cools FPA 1508 (whether an absolute temperature or a temperature relative to ambient) may be preconfigured, may be set by a user, or may be determined as part of a calibration process. As an example, a calibration process may involve determining that FPA 1508 needs to be cooled to a certain temperature (whether an absolute temperature or a temperature relative to ambient) for a desired level of performance. In response, a cooling controller in the imaging system may configure itself based on the results of the calibration to maintain FPA 1508 at that temperature. In this manner, the accuracy of the gas and chemical detection of FPA 1508 may be improved.

The imaging system may include one or more controllers that control the operation of cooling units such as TEC units 2570 and 2580. The controllers may receive inputs from thermometers (i.e., temperature sensors) coupled to elements being cooled, thermometers that determine the ambient temperature, other processors and controllers in the imaging system, feedback from the TEC units or other cooling units, etc. The controllers may adjust the operation of TEC units in real time, in order to maintain cooling performance and desired temperatures of the elements being cooled.

2. TEC Cooling of Optics

If desired, lens assembly 1502 including elements such as lens array 1002, mounting plate 1584 and filter housing 2510 may be actively cooled and/or heated using a thermoelectric cooling (TEC) device 2580 utilizing the Peltier effect or using another cooling and/or heating device. TEC device 2580 may be coupled to heat sinks 2582 and heat sink fan 2584. In operation, TEC device 2580 may convey thermal energy from lens assembly 1502 to heat sink 2582 and heat sink fan 2584 may transfer the thermal energy into the surrounding environment. If desired, heat sinks 2582 may be cooled by liquid cooling in addition to or instead of heat sink fan 2584. TEC device 2580 may be provided with any of the features and operated using any of the techniques discussed herein in connection with TEC device 2570. As examples, TEC device 2580 may actively cool lens assembly 1502 to cryogenic or non-cryogenic temperatures, may utilize a thermometer to monitor the temperature of lens assembly 1502, may be a single or multi-stage TEC device, may facilitate calibration and maintenance of calibrated performance, etc. By actively cooling lens assembly 1502, the accuracy of the gas and chemical detection of FPA 1508 may be improved.

As shown schematically by thermal connection 2586, lens assembly 1502 may optionally be actively cooled by TEC device 2570. Thermal connection 2586 may be a heat pipe 2582 or other device. In other words, TEC device 2570 may provide primary cooling to FPA 1508 and secondary cooling to lens assembly 1502 through a heat pipe 2586, through the mounting of lens assembly 1502 to FPA 1508 and/or TEC device 2570, or via other devices.

G. Reduction of Crosstalk

A DAISI system (whether installed at a fixed location or a mobile DAIS' system) may include a lens array for imaging an object (such as a gas cloud) by an optical detector. For example, as described herein in connection to FIGS. 18A-18E, a DAISI system can comprise a lens assembly 1502 including lens arrays 2504, 2506, and 2508 that at least partially define or are included in an optical channel to be imaged by an FPA unit 1008. In some implementations described throughout the present application, the DAISI system is configured as an infrared (IR) imaging system for imaging an object. FPAs configured to image IR radiation may be costly, thus to increase or maximize the usable area of the FPA unit 1008, it may be advantageous to position the optical channels close together or possibly as close together as physically possible. However, positioning the optical channels close together may result in undesired stray light rays from one optical channel crossing over into a neighboring optical channel, also referred hereinto as "optical crosstalk." In various embodiments, the lenses may be spaced apart edge-to-edge by a distance in a range of 0 mm to 2 mm, in a range of 0 mm to 1 mm, in a range of 0 mm to 0.5 mm, or in a range of 0.05 mm to 0.5 mm, e g about 0.1 mm.

Figure 22A:
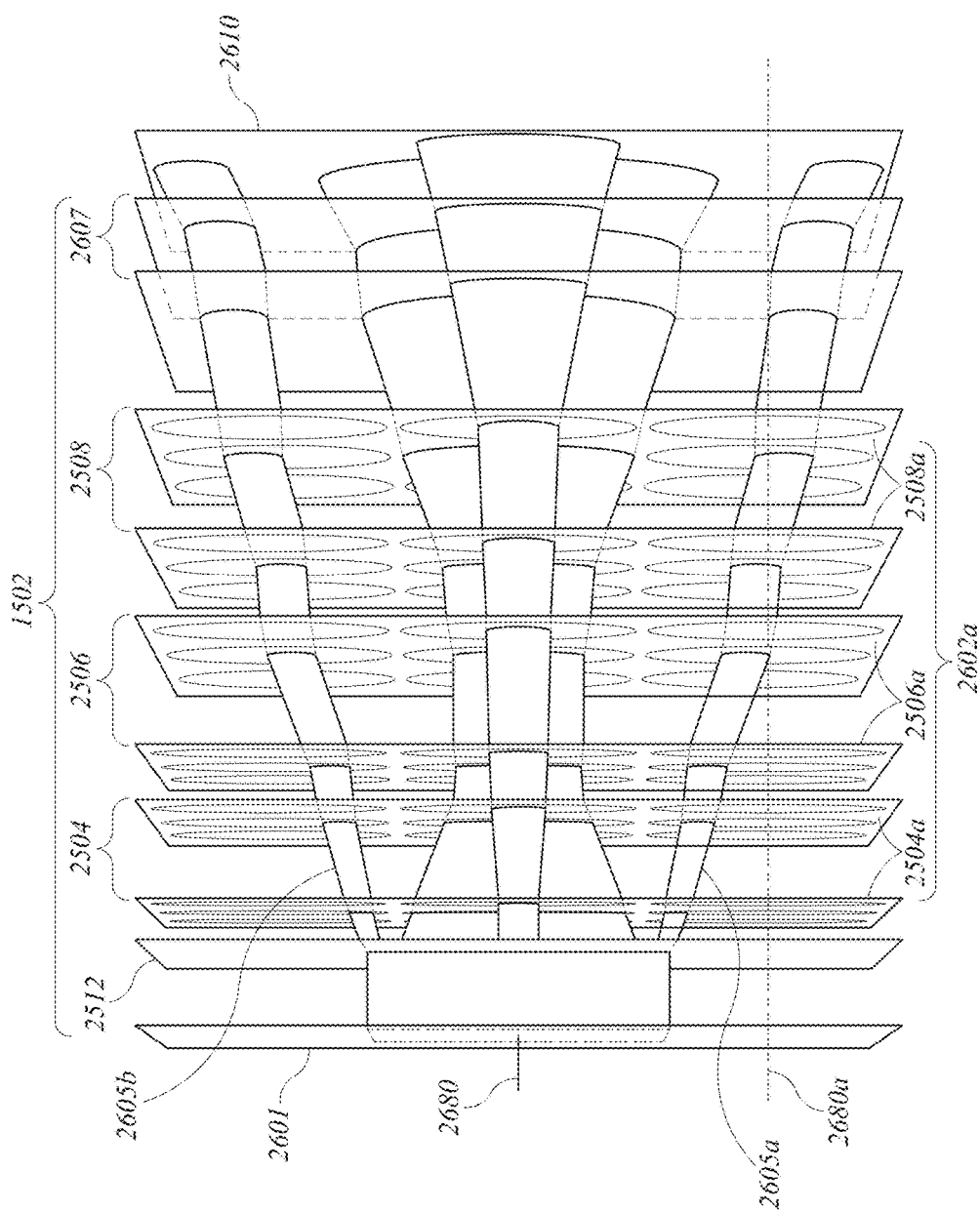
FIG. 22A is a ray trace diagram illustrating one example of optical crosstalk between the optical channels of lens assembly of FIG. 18D, according to various embodiments.

For example, FIG. 22A is a ray trace diagram illustrating one example of optical crosstalk between the optical channels of lens assembly 1502 of FIG. 18D. Unless otherwise noted, like reference numerals in FIG. 22A represent components that are the same as or similar to like numbered components in FIGS. 18A-18E. FIG. 22A illustrates the various optical elements described in connection to FIGS. 18A-18E as a collection of optical surfaces (represented as planes in FIG. 22A). For example, the lens assembly 1502 can include lenses 2504, lenses 2506, lenses 2508, filters 2512, and an optical window 2607. (FIG. 22A schematically illustrated front and rear surfaces of each of lenses 2504, 2506, and 2508 as well as optical window 2607.) The lens assembly 1502 can be used to image an object 2601 that is spaced from the lens assembly 1502 along an axis 2680 of an optical detector 2610. FIG. 22A depicts lenses 2504A, 2506A, and 2508A that correspond to an optical channel 2602A disposed along the axis 2680A. Although FIG. 22A depicts 9 distinct optical channels 2602, any number (two, three, four, five, six, seven, eight, nine, twelve, or greater) of optical channels 2602 are possible.

Each optical channel 2602 is configured to collect light from the object 2601 and transfer light along its corresponding axis 2680 toward the optical detector 2610 (represented as light rays 2605). The optical detector 2610 may generate data representing an image corresponding to the light received for each optical channel 2602. However, as illustrated in FIG. 22A, some of the light may cross between the neighboring optical channels because of the angle of incidence of the light on the optical surfaces and the refractive nature of the lenses. For example, light rays 2605A and 2605B are refracted by lenses 2504 into neighboring optical channels and out of the desired optical channel 2605 (in the FIG. 22A, the central optical channel). Thus, a portion of the light incident on one optical channel may cross into neighboring optical channels (e.g., optical channel 2602A) and be added to the light from the object 2601 as transferred by the neighboring optical channels to the optical detector 2610. The additional light from a neighboring optical channel may distort, corrupt, or otherwise interfere with the data corresponding to a given optical channel 2602.

Therefore, controlling stray light rays is important in a DAISI system comprising a lens array of closely packed optical channels. Various embodiments disclosed herein employ various techniques that can provide such control to increase, improve, or optimize the illumination of the optical detector while reducing the effects of stray light on the resulting image. For example, a DAISI system may be configured to provide vignetting of the image of the optical channel at the optical detector to remove or at least partially reduce optical crosstalk between the optical channels. The DAISI system may induce the vignetting by at least a partial reduction of the brightness or illumination of the light at the periphery or edges of an optical channel. For example, the DAISI system may include one or more baffles or aperture elements configured to at least partially block stray light from crossing between the optical channels, while permitting the optical channels to transfer light that is incident on that optical channel. The one or more baffles or aperture elements may also be configured to at least partially block stray light that has crossed between the optical channels from reaching the optical detector. Reduction of optical crosstalk between the optical channels may be important in tightly packed lens array systems because, as the optical channels are placed closer together, the optical crosstalk between the optical channels may increase, thereby degrading the quality of the data obtained.

In various embodiments, each of the systems disclosed herein can be used to monitor potential gas leaks in any suitable installation site, including, without limitation, drilling rigs, refineries, pipelines, transportations systems, ships or other vessels (such as off-shore oil rigs, trains, tanker trucks, petro-chemical plants, chemical plants, etc.). Furthermore, each of the systems disclosed herein can also be used with any mobile DAISI systems, including, without limitations, systems worn or carried by a user. In addition, each of the embodiments and aspects disclosed and illustrated herein, e.g., with respect to FIGS. 22A-22G can be used in combination with any or any combination of the features disclosed and illustrated through the present application.

Figure 22B:
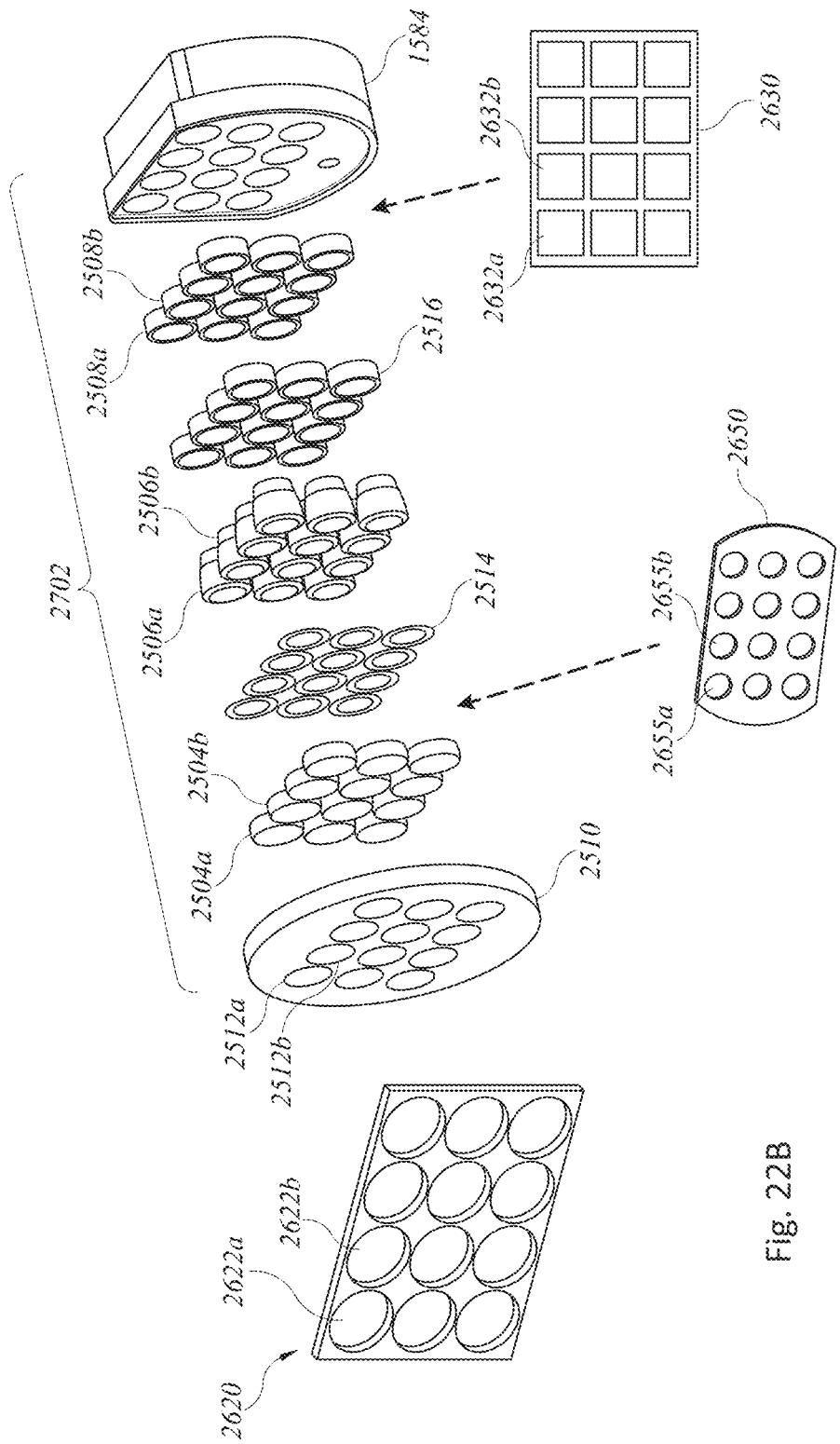
FIG. 22B is an exploded perspective view of a lens assembly configured to at least partially reduce optical crosstalk, which can be used in conjunction with a DAISI system, according to various embodiments.

FIG. 22B is an exploded perspective view of a lens assembly 2702 configured to at least partially reduce optical crosstalk, which can be used in conjunction with a DAISI system. The lens assembly 2702 is substantially similar to the lens assembly 1502 of FIGS. 18A-18E. Unless otherwise noted, like reference numerals in FIG. 22B represent components that are the same as or similar to like numbered components in FIGS. 18A-18E. Although the lens assembly 2702 is described in connection with lens assembly 1502, various features described herein can be used in conjunction with any other suitable type of optical system. For example, the various lenses and lens arrays and components illustrated in FIG. 22B are described in connection to FIGS. 18A-18E. However, the lens assembly 2702 can include any number or combination of lenses and optical elements, which may correspond to a plurality of spatially and spectrally different optical channels as described herein.

The lens assembly 2702 can be designed to block stray light rays that have crossed between one optical channel into another optical channel. In some implementations, the lens assembly 2702 can also be configured to permit light rays incident on a given optical channel to be transferred by that optical channel to the corresponding region of the optical detector (e.g., a detection region as described in connection to FIG. 22D below). In various embodiments, the optical detector can comprise a single focal plane array. In various other embodiments, the optical detector can comprise a plurality of focal plane arrays. For example, the lens assembly 2702 may comprise at least one baffle 2630, configured to control stray light to provide at least partially vignetting of the image at the optical detector. In some embodiments the lens assembly 2702 may include two baffles 2620 and 2630. Unless otherwise stated, the baffles 2620 and 2630 may be substantially similar to baffle 2500 of FIGS. 18A-18E and configured to at least partially block light from crossing between the optical channels. The baffles 2620 and 2630 may be configured to at least partially block stray light that has crossed from neighboring optical channels from being transferred to the optical detector. In various implementations, the baffles are configured to substantially vignette the image at optical detector array or portions thereof.

For example, the baffle 2620 may be configured to reduce or at least partially block light that enters via one optical channel from exiting the lens assembly 2702 via another optical channel. In some embodiments, the baffle 2620 is configured to substantially reduce light from crossing between the optical channels. The baffle 2620 may be positioned at the front of the optical channel 2602. In some embodiments, the baffle 2620 may be disposed adjacent to the lenses 2504 and/or between the lenses 2504 and the object (not shown in FIG. 22B). In another embodiment, alternatively or in combination, the baffle 2620 may be disposed between the filter housing 2510 and the object. In some embodiments, the baffle 2620 may be formed as part of the filter housing 2510 or integrated into a recess of the filter housing 2510 (illustrated in FIG. 18D). In one implementation, the baffle 2620 is disposed as close as possible to the filter housing 2510, within manufacturing tolerances.

As described in connection to FIGS. 18A-18E, the baffle 2620 may comprise an light attenuating or light blocking surface e.g., a sheet or plate comprising light attenuating or blocking material, e.g., metal or plastic, with a plurality of openings 2622 (e.g., also referred to as apertures) formed, for example, by mechanical or laser cutting. Each opening 2622a, 2622b, etc. may be disposed along an axis (e.g., axis 2680 of FIG. 22A) of a respective optical channel. The openings 2622 may be configured to control light rays incident on the optical channel by modifying the light path entering the optical channel. For example, each opening 2622 may be configured to block stray light rays that would otherwise be incident at the outer edge of the corresponding optical channel. The openings 2622 can also be configured to permit light rays incident at a central region of the optical channel to be transferred to the optical detector (not shown in FIG. 22B) via the optical channel on which the light is incident. Thus, the light rays are at least partially or substantially blocked such that stray light does not cross into a neighboring optical channel.

Although the plurality of openings 2622 are illustrated in FIG. 22B as having a circular shape, it should be appreciated that the openings 2622 may have any suitable shape (e.g., ovular, rectangular, square, etc.) so as to vignette the image at the optical detector. The shape, dimensions, and position of the openings 2622 may be based on the optical properties and arrangement of the elements in the lens assembly 2702. For example, the lens assembly 2702 may comprise an optical stop layer 2650 comprising a plurality of optical stops 2655a, 2655b, etc. corresponding to each optical channel. In one embodiment, the optical stop layer 2650 may be disposed between the lens 2504 and 2506. The dimensions of the plurality of openings 2622 may be based, at least in part, on the position of the optical stop layer 2650 within the lens assembly 2702. For example, for the embodiment illustrated in FIG. 22B, each opening 2622 has a lateral size (e.g., diameter, side, etc.) in a range of 3 mm to 6 mm, or in a range of 4 mm to 5 mm, e.g., dimensions of about 4.4 millimeters, with a tolerance of about +/−0.010. A thickness of the baffles can be in a range of 0.05 mm to 0.5 mm, in a range of 0.1 mm to 0.3 mm, e.g., about 0.2 mm. Although the openings 2622 are described herein as each having the same dimensions, it should be appreciated that this is not intended to be limiting and each opening 2622 may have different dimensions and/or shapes. In some embodiments, the structure and location of the baffles 2620 may be based on an optical system that has been optimized for any suitable application.

In some embodiments, the baffle 2630 is provided which may be similar to baffle 2620 and also configured to provide at least partially vignetting of the image of the object. The baffle 2630 may be positioned at the back of the optical channel closer to the optical detector array than to the front element of the lens assembly. In some embodiments, the baffle 2630 may be disposed adjacent to the lenses 2508 and between the lenses 2508 and the optical detector. In another embodiment, alternatively or in combination, the baffle 2630 may be disposed between the lenses 2508 and the lens holder 1584 of FIG. 18D. In some embodiments, the baffle 2630 may be formed as part of the lens holder 1584 or attached therein. In one implementation, the baffle 2630 is disposed as close as possible to the optical detector, within manufacturing tolerances.

Similar to baffle 2620, the baffle 2630 may comprise an light attenuating or light blocking surface such as a metal or plastic sheet or plate with a plurality of openings 2632 formed, for example, by mechanical or laser cutting. Each opening 2632a, 2632b, etc. (e.g., also referred to as field stops) may be disposed along an axis of an optical channel of the lens assembly 2702. The openings 2632 may be configured to control light rays transferred through the optical channel by modifying the light path to the optical channel. For example, each opening 2632 may be configured to block stray light rays that have crossed between optical channels such that these stray light rays are not transferred to the optical detector. The openings 2632 can also be configured to permit light rays incident on a given optical channel to be transferred by the given optical channel to reach the associated optical detector. For example, the baffle 2630 may not affect light rays that are incident at a central region of a given optical channel and/or have an angle of incidence that permits the light ray to be transferred through the given optical channel. Thus, the light rays are blocked such that they do not interfere with the image formed by neighboring optical channels.

Although the plurality of openings 2632 are illustrated in FIG. 22B as having a rectangular shape, it should be appreciated that the opening 2632 may have any suitable shape (e.g., ovular, circular, square, etc.) so as to vignette the image at the optical detector. As described above in connection to baffle 2620, the shape, dimensions, and position of the openings 2632 may be based on the optical properties and arrangement of the optical elements in the lens assembly 2702. Accordingly, the dimensions of the plurality of openings 2632 may be based, at least in part, on the position and dimensions of the optical stop layer 2650. For example, for the embodiment illustrated in FIG. 22B, each opening 2632 has a lateral dimension (e.g., diameter, side, etc.) of 1 mm to 5 mm, in a range of 2 mm to 5 mm, or in a range of 3 mm to 4 mm, e.g., about 3.2 mm. The openings 2632 can be polygonal (e.g., square or rectangular) or rounded (e.g., elliptical or circular), in various arrangements. Although the openings 2632 are described herein as each having the same dimensions, this is not intended to be limiting and each opening 2632 may have different dimensions and/or shapes. In some embodiments, the baffles 2630 may be configured for an optical system designed or optimized for any suitable application and have a design based on the components that of the optical system.

The lens assembly 2702 can be used in conjunction with an optical system that comprises any suitable optical arrangement, such as one or more lenses (e.g., a plurality of lenses) and/or one or more filters (e.g., a plurality of filters) that transfer light to the optical detector. The lens assembly 2702 is one embodiment of a design described in connection with various DAISI systems that may vary in design characteristics (e.g., the DAISI system may be mobile or fixed). However, the optical components and the positions within the lens assembly 2702 can be modified as desired in conjunction with any suitable type of imaging application. For example, the lens assembly 2702 can be used with any suitable type of infrared imaging system or camera to control stray light to maintain the optical performance of the system. Based on the desired application, the lens assembly 2702 may be optimized for any particular application having any combination or arrangement of elements. Accordingly, the various optical elements of the lens assembly 2702 may be modified, moved, removed, etc, for any suitable application. For example, the position of the optical stop 2650 may be changed or the optical powers and/or position of the lenses 2504, 2506, and/or 2508 may be modified, for example, for a particular application.

In some embodiments, controlling the stray light and increasing the sensitivity of the lens assembly 2702 for a given application may be inversely related (e.g., blocking light beams may inversely affect the overall amount of light received at the optical detector). Accordingly, in some implementations it may be advantageous to design the lens assembly 2702 such that the baffles are configured to block or reduce the light at the edges of an image to approximately 0.1% of the amount of light incident on the optical detector at the center of an image (e.g., as described below in connection to FIGS. 22F and 22G). In another implementation, alternatively or in combination, it may be advantageous to configure the lens assembly 2702 such that at least about 50% or at least about 60% of the light from the object is transferred to the optical detector (e.g., as described below in connection to FIG. 22G). Although the lens assembly 2702 is described as comprising two baffles 2620 and 2630, it should be appreciated that the lens assembly 2702 can comprise any number of baffles suitable to vignette an image at the optical detector for a suitable application.

FIG. 22C is a forward facing schematic diagram of the optical detector 2610 depicting another example of optical crosstalk between neighboring optical channels, and a potential resulting non-uniformity in usable image size due to the crosstalk. The detector 2610 can comprise a plurality of illumination regions 2616, each of which may correspond to an optical channel 2602 and associated components (such as the lenses or lens elements 2504, 2506, 2508). For example, each illumination region 2616 can represent the area of the detector 2610 upon which light that enters the first element of the associated optical channel 2602 is incident. In some embodiments, the width of the optical channels 2602 at different locations (e.g., the lenses) may be smaller than the corresponding width of the illumination region 2616. In the arrangement shown in FIG. 22C, the optical channels 2602 (including, e.g., the lenses of the lens array) may be spaced in a two-dimensional array at a generally uniform spacing. For example, the spacing between adjacent optical channels in the vertical direction may be approximately uniform, and the spacing between adjacent optical channels in the horizontal direction may also be approximately uniform.

Due to the spacing of the optical channels in FIG. 22C, the illuminated regions 2616 may overlap, illustrated as overlapping regions 2618 in FIG. 22C. The overlapping regions 2618 may occur since the image produced by the lenses in the illumination regions 2616 is typically larger than the corresponding area of the associated lenses and other optical elements of the optical channels. The overlapping regions 2618 may be indicative of the optical crosstalk between neighboring optical channels, and may introduce non-uniform image regions that reduce the effective size of the usable image that is not contaminated by cross-talk from other channels. For example, FIG. 22C depicts rectangular regions of different sizes, with the overlapping regions 2618 disposed about each rectangular region. The rectangular regions may define a usable image region 2615 for imaging an object (such as a gas cloud).

For example, a first optical channel transfers light to a portion of the optical detector 2610 corresponding to the illumination region 2616A. The neighboring optical channels also transfer light within the corresponding illumination regions 2616B, 2616C, 2616D. However, because the optical channels are spaced close together, the light of at least the illumination regions 2616B and 2616D may enter the neighboring illumination region 2616A, and vice versa. This produces the plurality of overlapping regions 2618 shown in FIG. 22C.

In the arrangement illustrated in FIG. 22C, each optical channel 2602 also defines a detection region 2612 of the optical detector 2610. Each of the detections regions 2612 comprises a square that may have its center coincident with the optical axis or central axis through the lens assembly corresponding to the optical channel. The detection region 2612 can comprise a plurality of pixels and can be spatially separate from one another. For example, in the illustrated arrangement, the detection regions 2612 can be separated by approximately 0.136 millimeters and can have dimensions of 4.25 millimeters by 4.25 millimeters. The illumination regions 2616 can have a diameter of 6.01 millimeters in some embodiments.

Accordingly, the illumination regions 2616 of a particular channel can extend beyond the detection region 2612 for that channel and into detection regions 2612 of neighboring channels, thereby generating the overlapping regions 2618. The overlapping regions 2618 may therefore be indicative of the optical crosstalk between the optical channels 2602. While specific example dimensions have been described above, these dimensions are not intended to be limiting and are merely one example of the optical detector 2610. For example, the detection regions 2612 may have a width or height in a range of approximately 3 mm to approximately 6 mm, or in a range of 3.5 mm to 5 mm, e.g., about 4.250 mm in the illustrated embodiment. The usable image region 2615 may have a height in a range of approximately 2 millimeters to 6 millimeters, e.g., in a range of 2 mm to 5 mm, or in a range of 2 mm to 4 mm. The usable image region 2615 can have a width in a range of approximately 2 millimeters to 5 millimeters, e.g., in a range of 2 mm to 4 mm. However, the design of the lens assembly 2702 may be modified to provide larger (or smaller) surface areas for each usable regions 2615.

As shown in FIG. 22C, in some arrangements, the usable image area 2615 may be non-uniform at the detector 2610. For example, for illumination regions 2616 in an interior region of the detector 2610 (such as illumination region 2616A), the overlapping regions 2618 may reduce the usable image area 2615A to a greater extent than neighboring usable image areas 2615B, 2615C, 2615D. That is, the image areas 2615B-2615D may be larger than the image area 2615A. Moreover, the image area 2615C may be larger than image areas 2615B, 2615D, because the image area 2615C is disposed in a corner of the detector 2610 such that there is image overlap 2618 on only two sides of the detection region 2612. By contrast, the image areas 2615B, 2615D are reduced in size by image overlap 2618 on three sides of the detection region 2612, and the image area 2615A is reduced in size by image overlap 2618 on four sides of the detection region 2612.

Accordingly, the different shapes and profiles of the image areas 2615A-2615D creates non-uniform image areas at the detector 2610. In the arrangement of FIG. 22C, the maximum image size at the detector 2610 may be limited by the smallest usable image area 2615 on the detector 2610, e.g., the image area 2615A in of the detector 2610. For example, in the illustrated arrangement, the usable image area 2615A may be 162 pixels along the x-direction and 162 pixels along the y-direction, which may represent the largest usable area for imaging on the detector 2610. It can be important to increase the usable image area 2515 of the detector 2610 in order to improve image quality and the gas detection capabilities of the system 1000.

Figure 22D:
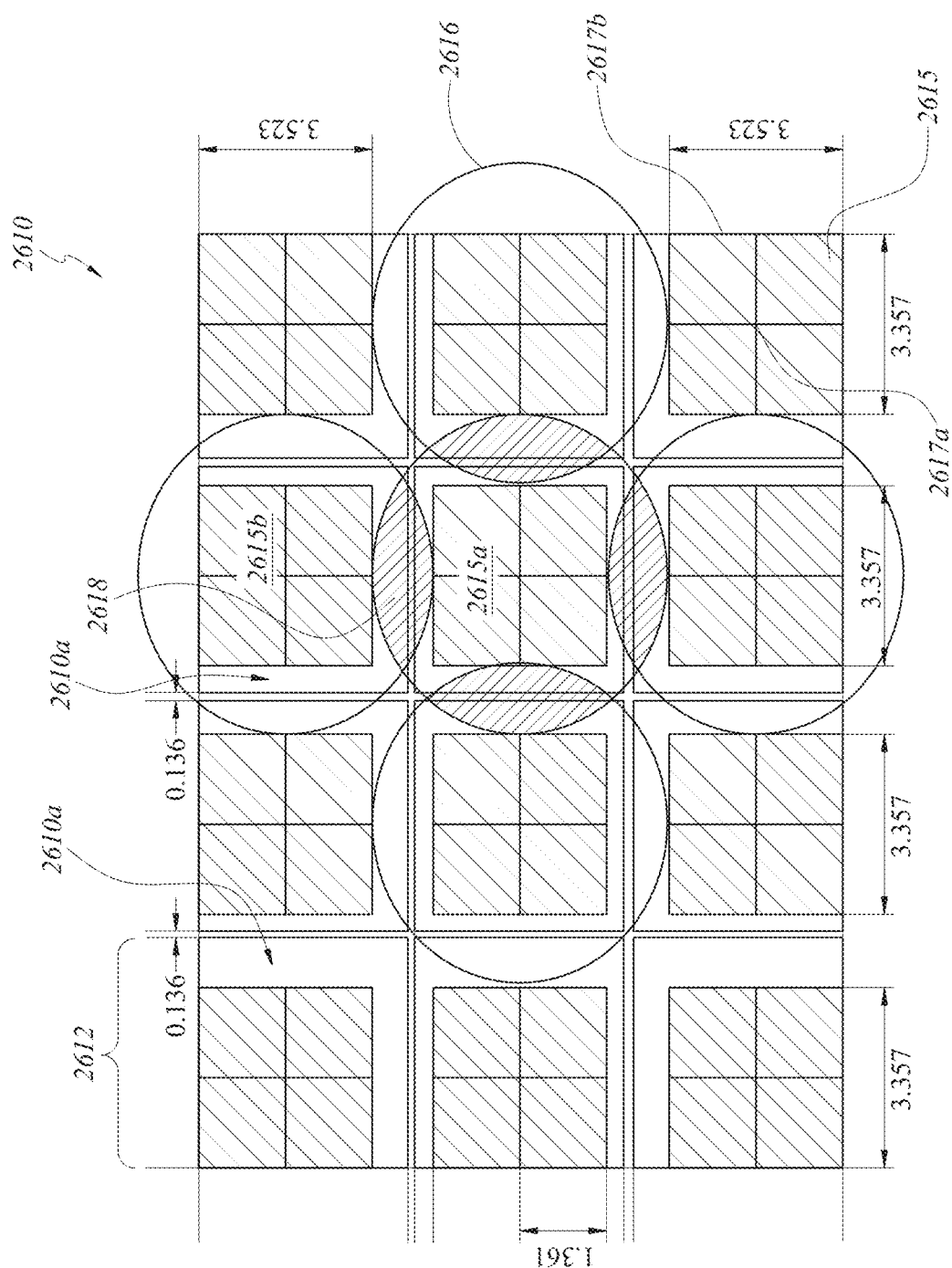
FIG. 22D depicts illumination regions indicative of light transferred from the object to the optical detector, in which the lens assembly may be configured to increase the usable image area at the optical detector with reduced vignetting, according to various embodiments.
Figure 22E:
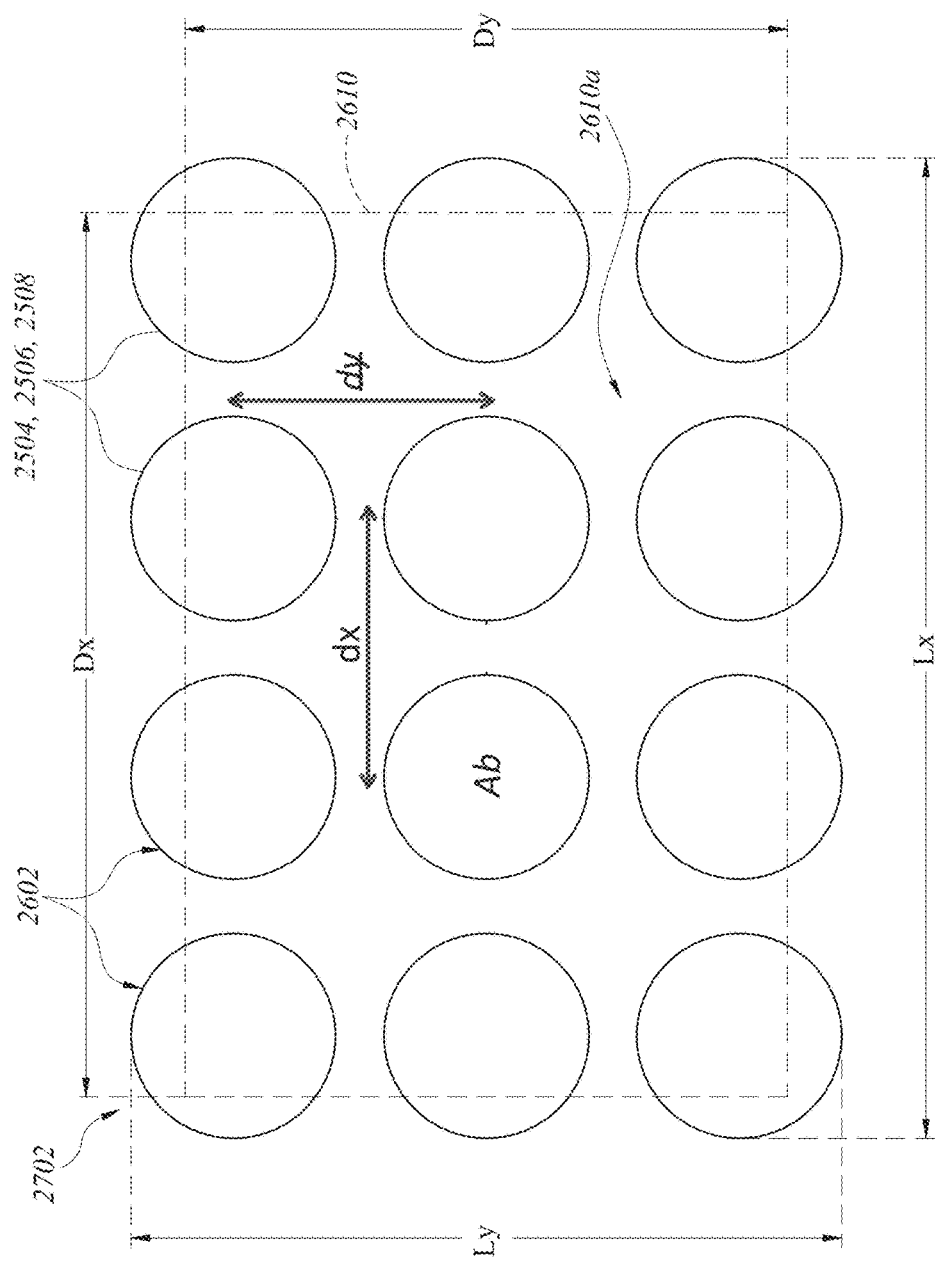
FIG. 22E is a front plan view of an example lens assembly that is dimensioned so as to transfer radiation to the illumination regions illustrated in FIG. 22D.

FIG. 22D depicts illumination regions 2616 indicative of light transferred from the object to the optical detector, in which the lens assembly may be configured to increase the usable image area at the optical detector 2610 with reduced vignetting. FIG. 22E is a front plan view of an example lens assembly 2702 that is dimensioned so as to transfer radiation to the illumination regions 2616 illustrated in FIG. 22D. As with the arrangement of FIG. 22C, each illumination region 2616 of FIG. 22D may represent an area receiving the light from the respective optical channel and associated lenses at the optical detector 2610. The illumination regions 2616 may be larger than the corresponding lens in the optical channel 2602. As explained above, due to the spacing of the optical channels 2602, the illuminated regions 2616 overlap, illustrated as overlapping regions 2618. The overlapping regions 2618 may be indicative of the optical crosstalk between neighboring optical channels. As with FIG. 22C, the overlapping regions 2618 may define usable image regions 2615, which are rectangular (e.g., approximately square) in FIG. 22D. In the embodiments shown in FIG. 22D, these usable image regions 2615 are the generally the same size unlike in the embodiment shown in FIG. 22C where the more detections regions toward the center of the focal plane array are smaller than the detection regions at the periphery of the focal plane array.

In the embodiment of FIGS. 22D and 22E, the lens assembly 2702 can be designed so as to increase the usable image area 2615, as compared with the arrangement of FIG. 22C. The optical properties and positions of the various optical elements in the lens assembly 2702 impact each other and have an effect on the resulting usable region 2615. For example, as compared with the optical channels 2602 that form the usable image areas 2615 in FIG. 22C, the optical channels 2602 (e.g., the lenses 2504, 2506, 2508) in FIG. 22E may be spaced farther apart. For example, a horizontal (center-to-center) spacing dx between adjacent lenses in the lens assembly 2702 may be in a range of 2 mm to 6 mm. A vertical (center-to-center) spacing dy between adjacent lenses in the lens assembly 2702 may be in a range of 2 mm to 6 mm. The horizontal spacing dx may be the same as or different from the vertical spacing dy. In some embodiments, the spacings dx, dy, may be smaller near the center of the detector 2610, and may be progressively larger near the edges of the detector 2610. Such an arrangement may shift the usable image areas 2615 farther apart so as to reduce optical crosstalk and increase the area of each usable area 2615. In other arrangements, the spacings dx, dy may be generally uniform across the lens assembly 2702. In still other arrangements, the spacings dx, dy may be larger near the center of the detector 2610 and progressively smaller near the edges of the detector 2610, which may reduce optical crosstalk and/or increase the area of each usable area 2615. The usable image area 2615 of FIG. 22D can have a width in a range of 2.5 mm to 5 mm, in a range of 3 mm to 4 mm, in a range of 3 mm to 3.5 mm, e.g., about 3.357 mm. The usable image area 2615 of FIG. 22D can have a height in a range of 3 mm to 4 mm, e.g., about 3.523 mm. The image area 2615 of FIG. 22D can be in a range of 9 mm$^2$ to 16 mm$^2$, or in a range of 9 mm$^2$ to 13 mm$^2$.

Moreover, the optical detector 2610 can comprise an active imaging region 2610A that includes the active imaging elements or pixels that are used to acquire image data from IR radiation transferred to the detector 2610. For example, the active imaging region 2610A can comprise the region on the detector 2610 that includes active pixels used to sense the image that is processed by the processing electronics to detect a target species. In some embodiments, the active imaging region 2610A can comprise all or substantially all the area of the detector 2610. In other embodiments, the active imaging region 2610A can be substantially smaller than the total area of the front face of the detector 2610. In the embodiment shown in FIG. 22E, the active imaging region 2610A of the detector can comprise a total active imaging area $A_I$ that may be defined by a horizontal width $D_x$ and a vertical height $D_y$ of the active imaging region 2610A (e.g., $A_I=D_x*D_y$). Similarly, the lens assembly 2702 can define an optical footprint area $A_O$ that represents the approximate lateral footprint of the lens assembly 2702. In the illustrated embodiment, the optical footprint area $A_O$ can be defined by the horizontal footprint $L_x$ and the vertical footprint $L_y$ of the lens assembly 2702 (e.g., $A_O=L_x*L_y$). The horizontal footprint $L_x$ can be defined based on the lateral outermost extent of the lens assembly 2702, as shown in FIG. 22E. Similarly, the vertical footprint $L_y$ can be defined based on the vertical outermost extent of the lens assembly 2702, as shown in FIG. 22E.

In the embodiment of FIG. 22E, the optical footprint area $A_O$ can be larger than the active imaging area $A_I$. Moreover, the lens assembly 2702 can define N optical channels 2602, each channel 2602 imaging a beam or spot size area $A_b$ on the detector 2610 that may be slightly larger than the diameter or lateral dimension of the associated lens. In FIG. 22E, the spot size area $A_b$ is illustrated as being co-extensive with the optical channel 2602, but it should be appreciated that the spot size area $A_b$ may differ due, e.g., to diffraction. The total beam area $A_T$ of light impinging on the detector can be calculated based on the portions of each beam or channel that impinges on the active area of the detector 2610. The total beam area $A_T$ can be less than the active imaging area $A_I$. In other words, there may be regions of the active imaging area $A_I$ that do not receive light from the lens assembly 2702. The total beam area $A_T$ can be less than 98% of the total active imaging area $A_I$. In various embodiments, the total beam area $A_T$ can be less than 95% of the total active imaging area $A_I$, less than 90% of the total active imaging area $A_I$, or less than 75% of the total active imaging area $A_I$. In some embodiments, the total beam area $A_T$ can be in a range of 50% to 98% of the total active imaging area $A_I$, in a range of 55% to 75% of the total active imaging area $A_I$, or in a range of 57% to 67% of the total active imaging area, e.g., about 62% of the total active imaging area $A_I$. In some embodiments, the active imaging area $A_I$ can be less than 98% of the optical footprint area $A_O$, less than 95% of the optical footprint area $A_O$, less than 90% of the optical footprint area $A_O$, less than 85% of the optical footprint area $A_O$, less than 80% of the optical footprint area $A_O$, or less than 75% of the optical footprint area $A_O$. In some embodiments, the active imaging area $A_I$ can be in a range of 50% to 98% of the optical footprint area $A_O$, in a range of 65% to 95% of the optical footprint area $A_O$, or in a range of 55% to 65% (e.g., about 62%) of the optical footprint area $A_O$.

In the embodiment illustrated in FIGS. 22D and 22E, the optical channels are spaced apart such that the detector regions 2612 are spatially close together (e.g., approximately 0.136 millimeters apart in some embodiments) while also increasing or maximizing the size of the usable regions 2615. As shown in FIGS. 22D and 22E, the optical channels 2602 may be configured such that the usable regions 2615 are spaced apart in a non-uniform spatial arrangement, but with a generally uniform size. For example, from a central usable region 2615A, the usable regions 2615 may be designed to be increasingly closer to one or more edges of its detector region 2612 and increasingly further away from a neighboring usable region 2615. Beneficially, the sizing of the lens assembly 2702 in FIG. 22E can increase the effective usable imaging region 2615, by reducing overlapping regions 2618 and crosstalk.

For example, based on the position of each usable region 2615 and/or positioning the baffles 2620 and 2630 as described above, the usable regions 2615 may have widths and lengths in a range of about 3 mm to 4 mm, e.g., about 3.523 millimeters by 3.357 millimeters as illustrated in the embodiment of FIG. 22D. This may correspond to a number of usable pixels within each usable region 2615, for example, 207 pixels by 197 pixels, which is about 55% larger than the usable region 2615 of FIG. 22C. Although a specific example of the usable regions 2615 and the lens assembly 2702 has been described herein, the usable regions 2615 and lens assembly 2702 can be modified and/or optimized for any suitable application. The above described lens assembly 2702 is merely one embodiment, and the optical properties of the components within the lens assembly 2702 can be modified as desired in conjunction with any other suitable type of imaging application.

Figure 22F:
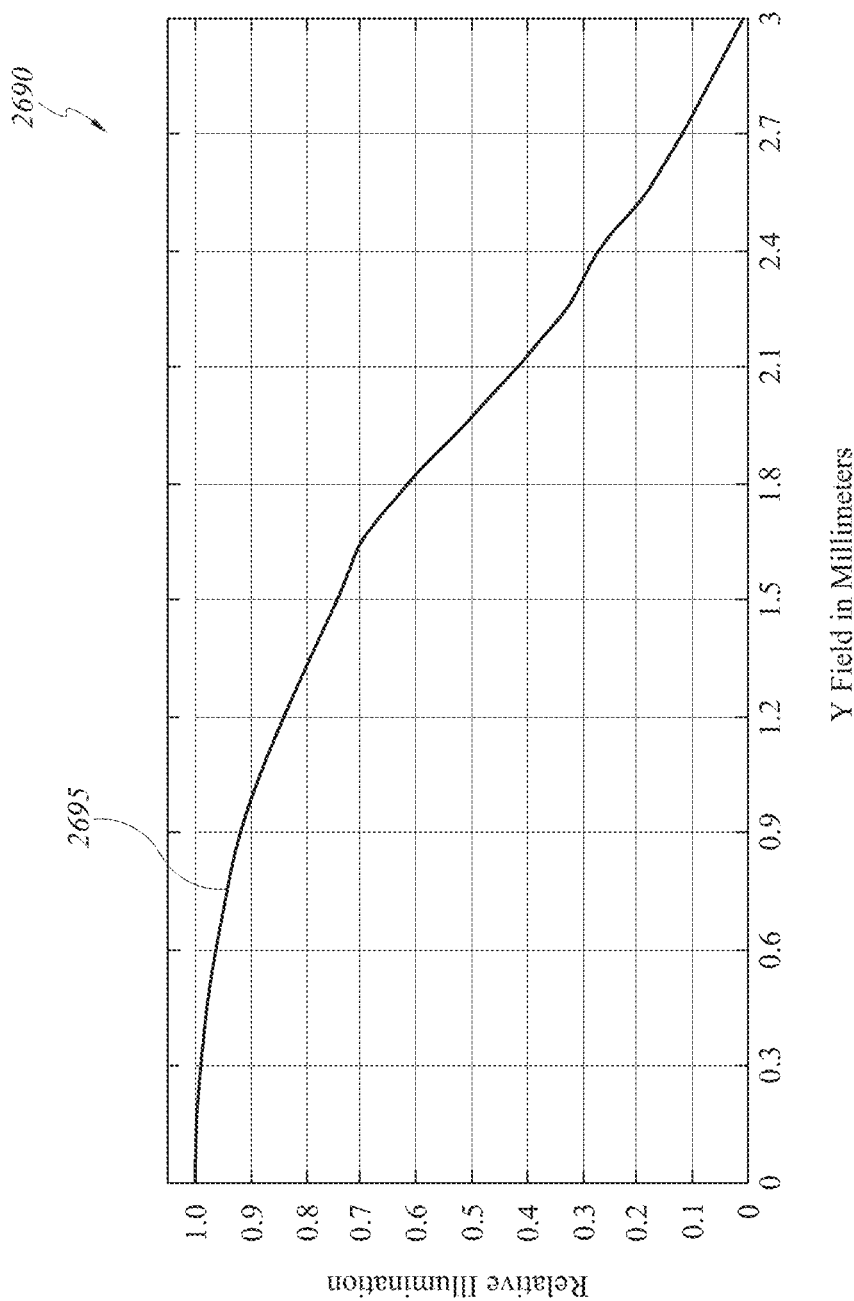
FIG. 22F is an example simulation of the intensity roll-off across the usable region of FIG. 22D.

In some implementations, it may be advantageous to include the baffles 2620 and 2630 (as described above in connection to FIG. 22B) that may be based, at least in part, on the usable region 2615 of FIG. 22D. For example, the baffles 2620 and 2630 may be configured such that light is transferred to the optical detector 2610 within the usable region 2615, while substantially blocking stray light that would otherwise be transferred to the optical detector within the overlapping regions 2618. In various embodiments, the baffles 2620, 2630 can remove light in the overlapping regions such that the irradiance at or near the edge of the image region approaches zero (or is otherwise negligible). In various embodiments, the baffles may define the overlapping regions. For example, the baffles 2620 and 2630 may be configured such that the amount of light received at a center 2617A (see FIG. 22D) of the usable region 2615 is relatively more than the amount received at the edge 2617B (see FIG. 22D). Accordingly, the baffles 2620 and 2630, may be configured to cause the relative intensity of the light on the usable region 2615 to decrease as a function of distance from the center 2617A (e.g., as illustrated in FIG. 22F), hereinafter an "intensity roll-off". In some embodiments, the intensity roll-off may be a relative roll-off, where the amount of light at the edge 2617B is controlled relative to the amount at the center 2617A. For example, the amount of light at the center may be considered to be 100% and amount of light at the edge 2617B may be designed to rolls-off to approximately 0%. Accordingly, each usable region 2615 may be indicative of an image corresponding to an optical channel that is substantially independent or unaffected by light crossing between the neighboring optical channels.

In various embodiments, the optical detector 2601 can comprise a detector array, including a single FPA or an array of FPAs. In various embodiments, the optical detector 2601 can include a plurality of photo-sensitive devices. In some embodiments, the plurality of photo-sensitive devices may comprise a two-dimensional imaging sensor array that is sensitive to radiation having wavelengths between 1 μm and 20 μm (for example, in near infrared wavelength range, mid infra-red wavelength range, or long infra-red wavelength range). In various embodiments, the plurality of photo-sensitive devices can include CCD or CMOS sensors, bolometers, microbolometers or other detectors that are sensitive to infrared radiation.

Although a specific embodiment of the lens assembly 2702 has been described in connection to FIGS. 22B-22G, it should be appreciated that the lens assembly 2702 can be designed for any suitable application. The lens assembly 2702 and the usable regions 2615 created therefrom are one embodiment described in connection with various DAISI systems (e.g., the DAISI system may be mobile or fixed). However, the optical components and the positions of such within the lens assembly 2702 (for example, the number, size, and position of the apertures and stops) can be modified as desired in conjunction with any other suitable type of imaging application. For example, the lens assembly 2702 can be used with any suitable type of infrared imaging system or camera to control stray light to maintain the optical performance of the system. Based on the desired application, the lens assembly may be configured or optimized for any particular application having any desired elements.

FIG. 22F is an example simulation of the intensity roll-off across the usable region 2615 of FIG. 22D. FIG. 22F shows the relative illumination (e.g., intensity) at the optical detector 2610 as a function of location on a usable region 2615 (represented as line 2695). For example, the horizontal axis represents a position from the center 2617A in millimeters. The line 2695 may represent any line extending between the center 2617A and an edge 2617B (e.g., a position along a horizontal or vertical line or along a line at some angle therefrom). In some embodiments, the line 2695 represents an intensity roll-off based on vignetting the image at the optical detector 2610. In some embodiments, vignetting of the image may be induced via the baffles 2620 and/or 2630 in the lens assembly 2702. The simulation results can be obtained by optical simulation software (for example, FRED™ Software).

FIG. 22F illustrates, for the embodiment described above in connection to FIGS. 22D and 22E, the light received at the edge of the usable region 2615 drops to 0 relative to the largest detected intensity or illumination. For example, at the center 2617A of the usable region 2615A (position 0 millimeters on the graph 2690) an amount of light is received by the optical detector 2610. The amount of light maybe normalized to provide a maximum value of 1.0 (or 100%). While the example shown in FIG. 22F depicts the maximum value at the center 2617A, the normalization need not be located at the center 2617A and may be located elsewhere on the usable region 2615.

As described above, the simulation measures the amount of light received across the usable are 2615 relative to the amount received at the center 2617A. FIG. 22F illustrates that the amount of light received at the edges 2617B can be reduced to approximately 0.01 (or 0.1%) of the light received at the center 2617A. The reduction of stray light at the edge 2617B may be based on implementing one or more of the baffles 2620 and/or 2630 and optimizing the lens assembly 2702 as described above in connection to FIGS. 22D and 22C. For example, a figure of merit may be evaluated as the various parameters of the lens assembly, including the selection of curvature of lens surfaces, position of lens, thickness of lenses, as well as the number, size and position of aperture(s)/stop(s), are varied to determine a suitable design with appropriate vignetting. The figure of merit, may for example, take into account the vignetting and/or affects thereof. In some implementations, stray light may be substantially blocked from crossing between optical channels based at least in part on the baffles 2620 and/or 2630.

Figure 22G:
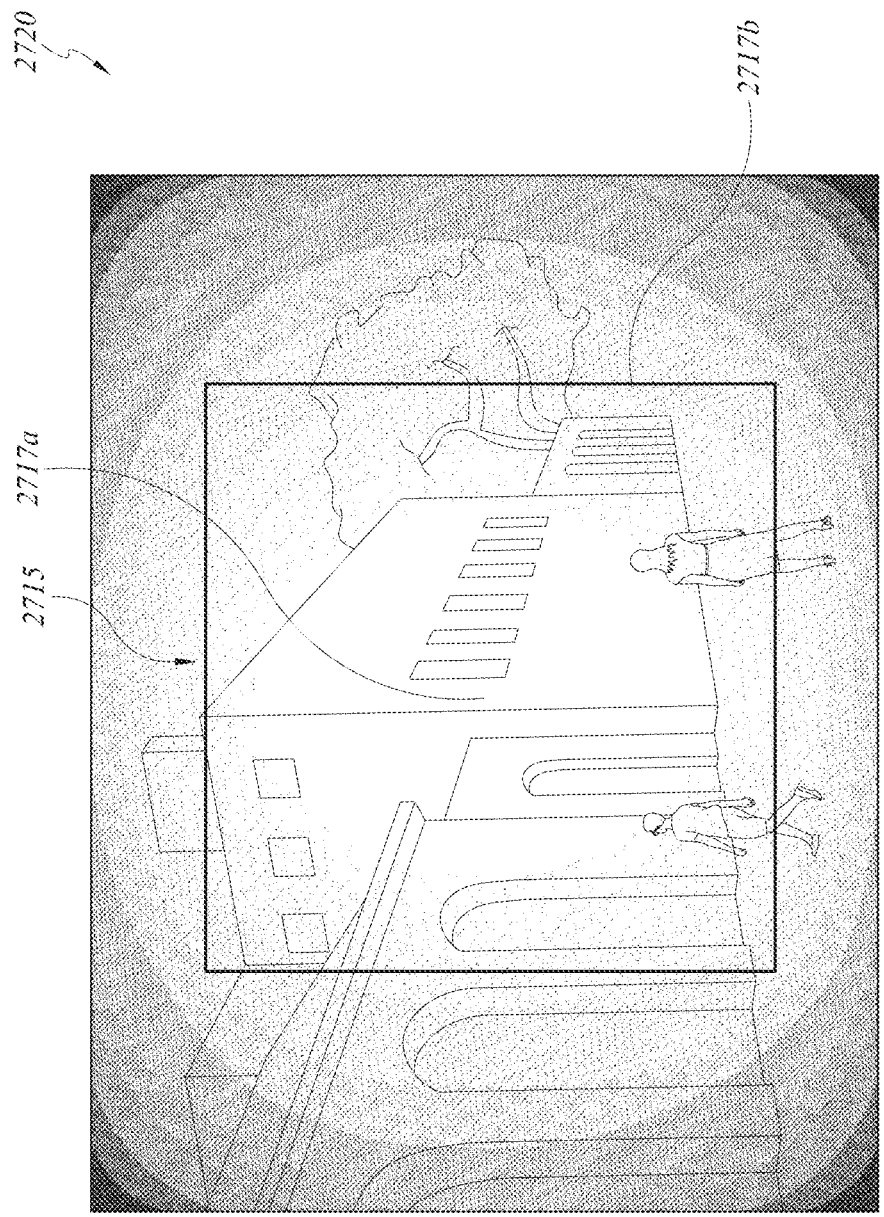
FIG. 22G illustrates an example vignetting of an image of a scene, according to various embodiments.

FIG. 22G illustrates an example vignetting of an image of a scene 2720. FIG. 22G shows a simulated usable region 2715 (represented as a square) that is substantially similar to the usable region 2615 of FIGS. 22D-22E. As shown in FIG. 22G, the image contained within the usable region appears more vibrant and clear, while the portion of the image 2720 outside of the useable region 2715 is darker. The darkening of the image 2720 at the edges is indicative of vignetting the image to reduce or block the light received at the edges 2715b of images without sacrificing the clarity or performance of the lens assembly 2702 at the center 2715a of the image 2720.

In the embodiments disclosed herein, the lenses or lens elements 2504, 2506, 2508 (see FIG. 18D herein) of the lens assembly 2702 can be fabricated to meet precise tolerances, which can significantly improve the performance of the system 1000. The lens assemblies disclosed herein can advantageously be designed by selecting tolerances for each individual lens in the assembly, and by selecting tolerances that consider the lens assembly 2702 as a whole (e.g., by considering lens fabrication errors, baffle size errors, etc.). For example, the embodiments disclosed herein can utilize one or more of root sum of squares (RSS) and Monte Carlo techniques to select the lens tolerances. The tolerances can be selected so that greater than or equal to 90% of the root-mean-square (rms) spot size is less than the diffraction-limited Airy disk for the imaged spot. Such a relatively conservative criterion can ensure improved system performance that is also manufacturable according to the manufacturing techniques disclosed herein.

The lens assembly 2702 disclosed herein can be designed and manufactured to have very low f-number (f/#) for each optical channel. The low f-number systems disclosed herein can advantageously improve the sensitivity of the system significantly (e.g., by at least about 44%) for each optical channel. In some embodiments, for example, the lenses can be designed for the system 1000 to achieve f/1 for each channel, in which the focal length is approximately the same as the width of the effective system aperture. In various embodiments, the lens assembly 2702 can be designed to achieve an f-number in a range of f/1 to f/3, in a range of f/1 to f/2, in a range of f/1 to f/1.5, or in a range of f/1 to f/1.2. Such low f-numbers can beneficially enable the detection of low concentrations of target species, such as methane. For example, at a wind velocity (e.g., approximating little or no wind conditions) of zero miles per hour, the system 1000 disclosed herein can have a sensitivity to methane having minimum flow or leak rates in a range of 0.00001 ft$^3$/hr to 0.0006 ft$^3$/hr, in a range of 0.00005 ft$^3$/hr to 0.0006 ft$^3$/hr, in a range of 0.00005 ft$^3$/hr to 0.0004 ft$^3$/hr, in a range of 0.0001 ft$^3$/hr to 0.0005 ft$^3$/hr, in a range of 0.0001 ft$^3$/hr to 0.0004 ft$^3$/hr, in a range of 0.0002 ft$^3$/hr to 0.0006 ft$^3$/hr, or in a range of 0.0002 ft$^3$/hr to 0.0004 ft$^3$/hr. As an another example, at a wind velocity of 15 mph, the system 1000 disclosed herein can have a sensitivity to methane having minimum flow or leak rates in a range of 0.01 ft$^3$/hr to 0.3 ft$^3$/hr, in a range of 0.05 ft$^3$/hr to 0.25 ft$^3$/hr, in a range of 0.1 ft$^3$/hr to 0.25 ft$^3$/hr, in a range of 0.2 ft$^3$/hr to 0.2 ft$^3$/hr, or in a range of 0.14 ft$^3$/hr to 0.22 ft$^3$/hr.

The relatively low f-numbers provided by the embodiments disclosed herein can enable minimum detection levels of methane in a range of 100 ppm-m to 400 ppm-m, in a range of 200 ppm-m to 300 ppm-m, e.g., a minimum detection level of about 250 ppm-m, where ppm-m is provided in parts per million—meter. The relatively low f-numbers provided by the embodiments disclosed herein can enable minimum detection levels of acetic acid in a range of 100 ppm-m to 200 ppm-m, e.g., a minimum detection level of about 180 ppm-m. The relatively low f-numbers provided by the embodiments disclosed herein can enable minimum detection levels of ammonia in a range of 5 ppm-m to 20 ppm-m, e.g., a minimum detection level of about 13.5 ppm-m. The relatively low f-numbers provided by the embodiments disclosed herein can enable minimum detection levels of benzene in a range of 100 ppm-m to 150 ppm-m, e.g., a minimum detection level of about 125 ppm-m. The relatively low f-numbers provided by the embodiments disclosed herein can enable minimum detection levels of butadiene in a range of 100 ppm-m to 150 ppm-m, e.g., a minimum detection level of about 125 ppm-m. The relatively low f-numbers provided by the embodiments disclosed herein can enable minimum detection levels of butane in a range of 200 ppm-m to 300 ppm-m, e.g., a minimum detection level of about 250 ppm-m. The relatively low f-numbers provided by the embodiments disclosed herein can enable minimum detection levels of carbon dioxide in a range of 1050 ppm-m to 1100 ppm-m, e.g., a minimum detection level of about 1079 ppm-m. The relatively low f-numbers provided by the embodiments disclosed herein can enable minimum detection levels of chlorobenzene in a range of 10 ppm-m to 40 ppm-m, e.g., a minimum detection level of about 25 ppm-m. The relatively low f-numbers provided by the embodiments disclosed herein can enable minimum detection levels of dichlorobenzene in a range of 25 ppm-m to 75 ppm-m, e.g., a minimum detection level of about 50 ppm-m. The relatively low f-numbers provided by the embodiments disclosed herein can enable minimum detection levels of 1,2 dichloroethane in a range of 100 ppm-m to 150 ppm-m, e.g., a minimum detection level of about 125 ppm-m. The relatively low f-numbers provided by the embodiments disclosed herein can enable minimum detection levels of ethane in a range of 200 ppm-m to 300 ppm-m, e.g., a minimum detection level of about 250 ppm-m. The relatively low f-numbers provided by the embodiments disclosed herein can enable minimum detection levels of ethanol in a range of 5 ppm-m to 25 ppm-m, e.g., a minimum detection level of about 15 ppm-m. The relatively low f-numbers provided by the embodiments disclosed herein can enable minimum detection levels of ethylene in a range of 200 ppm-m to 300 ppm-m, e.g., a minimum detection level of about 250 ppm-m. The relatively low f-numbers provided by the embodiments disclosed herein can enable minimum detection levels of hydrazine in a range of 100 ppm-m to 150 ppm-m, e.g., a minimum detection level of about 125 ppm-m. The relatively low f-numbers provided by the embodiments disclosed herein can enable minimum detection levels of isobutylene in a range of 100 ppm-m to 150 ppm-m, e.g., a minimum detection level of about 125 ppm-m. The relatively low f-numbers provided by the embodiments disclosed herein can enable minimum detection levels of isopentane in a range of 30 ppm-m to 50 ppm-m, e.g., a minimum detection level of about 40 ppm-m. The relatively low f-numbers provided by the embodiments disclosed herein can enable minimum detection levels of methanol in a range of 5 ppm-m to 20 ppm-m, e.g., a minimum detection level of about 10 ppm-m. The relatively low f-numbers provided by the embodiments disclosed herein can enable minimum detection levels of N-pentane in a range of 10 ppm-m to 30 ppm-m, e.g., a minimum detection level of about 20 ppm-m. The relatively low f-numbers provided by the embodiments disclosed herein can enable minimum detection levels of propane in a range of 400 ppm-m to 600 ppm-m, e.g., a minimum detection level of about 500 ppm-m. The relatively low f-numbers provided by the embodiments disclosed herein can enable minimum detection levels of propylene in a range of 100 ppm-m to 150 ppm-m, e.g., a minimum detection level of about 125 ppm-m. The relatively low f-numbers provided by the embodiments disclosed herein can enable minimum detection levels of propylene oxide in a range of 150 ppm-m to 250 ppm-m, e.g., a minimum detection level of about 200 ppm-m. The relatively low f-numbers provided by the embodiments disclosed herein can enable minimum detection levels of sulfur dioxide in a range of 10 ppm-m to 30 ppm-m, e.g., a minimum detection level of about 20 ppm-m. The relatively low f-numbers provided by the embodiments disclosed herein can enable minimum detection levels of sulfur hexafluoride in a range of 4 ppm-m to 12 ppm-m, e.g., a minimum detection level of about 7 ppm-m. The relatively low f-numbers provided by the embodiments disclosed herein can enable minimum detection levels of toluene in a range of 100 ppm-m to 200 ppm-m, e.g., a minimum detection level of about 150 ppm-m. The relatively low f-numbers provided by the embodiments disclosed herein can enable minimum detection levels of vinyl chloride in a range of 1 ppm-m to 5 ppm-m, e.g., a minimum detection level of about 2.5 ppm-m. The relatively low f-numbers provided by the embodiments disclosed herein can enable minimum detection levels of p- or m-xylene in a range of 10 ppm-m to 30 ppm-m, e.g., a minimum detection level of about 20 ppm-m. The above ranges are for gas clouds having a lateral size of 1 m or less. Gas clouds larger than 1 m may be detected at lower detection levels (e.g., a 10 m methane cloud can be detected at a concentration of 25 ppm-m).

The dimensions of the lenses 2504, 2506, and 2508 can be selected to achieve the low f-numbers associated with this improved gas detection performance. For example, each lens 2504, 2506, 2508 can have a first surface S1 that faces the object and a second surface S2 that faces the detector 2610. Each surface S1, S2 of each lens 2504, 2506, 2508 can have an associated surface curvature which can appreciably affect the performance of the lens assembly 2702. The surface S1 is positioned to face the object, and the surface S2 is positioned to face the detector.

For example, the curvature of surface S1 (i.e., the radius of curvature) of the lens 2504 can be in a range of 5.5 mm to 7.5 mm, in a range of 6 mm to 7 mm, in a range of 6.25 mm to 6.75 mm, in a range of 6.4 mm to 6.5 mm, or in a range of 6.41 mm to 6.44 mm (e.g., 6.429 mm in some embodiments). The tolerance of the curvature of surface S1 of the lens 2504 can be in a range of ±0.005 mm to ±0.015 mm or in a range of ±0.008 mm to ±0.012 mm, e.g., about ±0.010 mm. The curvature of surface S2 of the lens 2504 can be in a range of 6.5 mm to 8.5 mm, in a range of 7 mm to 8 mm, in a range of 7.25 mm to 7.75 mm, in a range of 7.5 mm to 7.6 mm, or in a range of 7.55 mm to 7.65 mm (e.g., 7.562 mm in some embodiments). The tolerance of the curvature of surface S2 of the lens 2504 can be in a range of ±0.005 mm to ±0.015 mm or in a range of ±0.008 mm to ±0.012 mm, e.g., about ±0.010 mm.

The curvature of surface S1 of the lens 2506 (i.e., the radius of curvature) can be in a range of −30 mm to −36 mm, in a range of −31 mm to −35 mm, in a range of −32 mm to −34 mm, in a range of −32.5 mm to −33.8 mm, or in a range of −33 mm to −33.7 mm (e.g., −33.374 mm in some embodiments). The tolerance of the curvature of surface S1 of the lens 2506 can be in a range of ±0.1 mm to ±0.5 mm or in a range of ±0.25 mm to ±0.35 mm, e.g., about ±0.300 mm. The curvature of surface S2 of the lens 2506 can be in a range of −9 mm to −17 mm, in a range of −10 mm to −16 mm, in a range of −11 mm to −15 mm, in a range of −12 mm to −14 mm, in a range of −12.5 mm to −13.5 mm, or in a range of −12.8 mm to −13.2 mm (e.g., −13.026 mm in some embodiments). The tolerance of the curvature of surface S2 of the lens 2506 can be in a range of ±0.03 mm to ±0.07 mm or in a range of ±0.04 mm to ±0.06 mm, e.g., about ±0.050 mm.

The curvature of surface S1 of the lens 2508 (i.e., radius of curvature) can be in a range of −3 mm to −7 mm, in a range of −4 mm to −6 mm, in a range of −4.5 mm to −5.5 mm, in a range of −4.9 mm to −5.15 mm, or in a range of −5 mm to −5.1 mm (e.g., −5.060 mm in some embodiments). The tolerance of the curvature of surface S1 of the lens 2508 can be in a range of ±0.01 mm to ±0.02 mm or in a range of ±0.013 mm to ±0.0.017 mm, e.g., about ±0.015 mm. The curvature of surface S2 of the lens 2508 can be in a range of −3 mm to −7 mm, in a range of −4 mm to −6 mm, in a range of −4.5 mm to −5.5 mm, in a range of −4.9 mm to −5.15 mm, or in a range of −5 mm to −5.1 mm (e.g., −5.068 mm in some embodiments). The tolerance of the curvature of surface S2 of the lens 2508 can be in a range of ±0.005 mm to ±0.015 mm or in a range of ±0.008 mm to ±0.012 mm, e.g., about ±0.010 mm. In various embodiments, one or more surfaces can be planar or flat.

The system (including the lenses and lens elements) may have other features that contribute to the improved system performance. For example, the effective focal length or focal length of the lens that defines each channel (e.g., the focal length of the combined lens defined by lens elements 2504, 2506, 2508) can be in a range of 1 mm to 10 mm, in a range of 1.5 mm to 7 mm, or in a range of 3 mm to 6 mm, e.g., about 4 mm. The spectral region imaged by the system may be in a range of 7.5 microns to 14 microns or may be in a range of 3 microns to 14 microns, e.g., within the infrared imaging band. The full horizontal system field of view can be in a range of 40 degrees to 60 degrees, in a range of 45 degrees to 55 degrees, in a range of 46 degrees to 40 degrees, e.g., about 48 degrees. The full vertical system field of view can be in a range of 40 degrees to 60 degrees, in a range of 42 degrees to 55 degrees, or in a range of 44 degrees to 50 degrees, e.g., about 46 degrees. The diameter of each lens can be in a range of 1 mm to 10 mm, in a range of 1 mm to 8 mm, in a range of 2 mm to 6 mm, or in a range of 3.5 mm to 5 mm, e.g., about 4.4 mm. The length of the lens (e.g., the length as defined by the lens elements 2504, 2506, 2508) can be in a range of 5 mm to 25 mm, in a range of 5 mm to 15 mm, in a range of 6 mm to 14 mm, in a range of 8 mm to 14 mm, or in a range of 9 mm to 13 mm, e.g., about 12 mm.

The overall image distortion may be less than 10%, less than 5%, or less than 1%. The stray light between images can be less than 5%, less than 2%, less than 1%, less than 0.5%, or less than 0.1%. In various embodiments, the root-mean-square (rms) spot size of the image can be less than 1 pixel. Accordingly, the lenses and the other system parameters can be suitably selected so as to improve system performance.

H. Athermal Imaging Features

A DAISI system (whether installed at a fixed location or a mobile DAISI system) may be operated during day or night under extreme weather conditions at different locations as stated herein. Accordingly, it can be advantageous to provide a DAISI system configured to operate under a wide range of temperatures, such as between −40° C. to +80° C. For example, a DAISI system may be installed at some locations on a long-term basis, such as oil well sites. An oil well site can be in the desert which experiences a wide range of temperature differences between day and night. Optical elements distort due to environmental temperature fluctuations that can cause the optical elements to expand, contract, or otherwise change dimensions. Furthermore, for mobile or portable DAISI systems, the user may wear or carry the imaging system into different environments over time, which also experience temperature fluctuations.

Therefore, optothermal stability is important in a changing thermal environment. Various embodiments disclosed herein employ various athermalization features that can provide such optothermal stability to maintain and/or improve the performance of the optical system. Athermalization (or an "athermal system") can reduce the sensitivity of the optical system to environmental or other thermal changes, i.e., that the performance of the optical system does not appreciably degrade when used at different temperatures. Athermalization may be particularly important in an infrared imaging system because the change in refractive index with temperature (dn/dT) of most IR materials is orders of magnitude higher than materials used for visible light, creating large changes in the refractive index. An athermal system can depend on the Coefficient of Thermal Expansion (CTE) of the materials used, including housing materials and/or the materials of the optical elements, and the change in refractive index with temperature (dn/dT). Accordingly, it can be desirable to provide an athermal DAISI system to achieve optothermal stability. For example, an athermal DAISI system can ensure normal operation of the system under extreme temperature fluctuations at different remote installation locations, and/or at different locations to which a user with a mobile DAISI system may travel.

As discussed above, various systems disclosed herein can be used to monitor potential gas leaks in any suitable installation site, including, without limitation, drilling rigs, refineries, pipelines, transportations systems, ships or other vessels (such as off-shore oil rigs, trains, tanker trucks, petro-chemical plants, chemical plants, etc. Furthermore, systems disclosed herein can also be used with mobile DAISI systems, including, without limitations, systems worn or carried by a user. In addition, various of the embodiments and aspects disclosed and illustrated herein can be used in combination with each of the athermalization features disclosed and illustrated herein with respect to FIGS. 23A-23D.

An athermal system can depend on the Coefficient of Thermal Expansion (CTE) of the materials and the change in refractive index with temperature (dn/dT). The expansion and contraction of a material due to temperature changes is governed by the material's CTE, $\alpha$, which has units of ppm/° C. (or $10^{-6}$ m/° C.). The change in length ($\Delta L$) of the material due to a temperature change ($\Delta T$) can be expressed as:

$$\Delta L = \alpha L \Delta T$$

Thermal defocus ($\Delta f$) is the change in the focal position with temperature changes ($\Delta T$) due to the variation of the index of refraction with temperature (dn/dT) and the expansion of the material. The equation quantifying the change in focal length (f) of a lens in air with temperature can be expressed as:

$$\Delta f = \beta f \Delta T$$

where $\beta$ is the thermo-optic coefficient of the optical lens, which can be expressed as:

$$\beta = \alpha_g - 1/(n-1) dn/dT,$$

where $\alpha_g$ is the CTE of the glass. A term for changes in the air index of refraction with temperature is not included in the above equation since the value is relatively small.

Figure 23A:
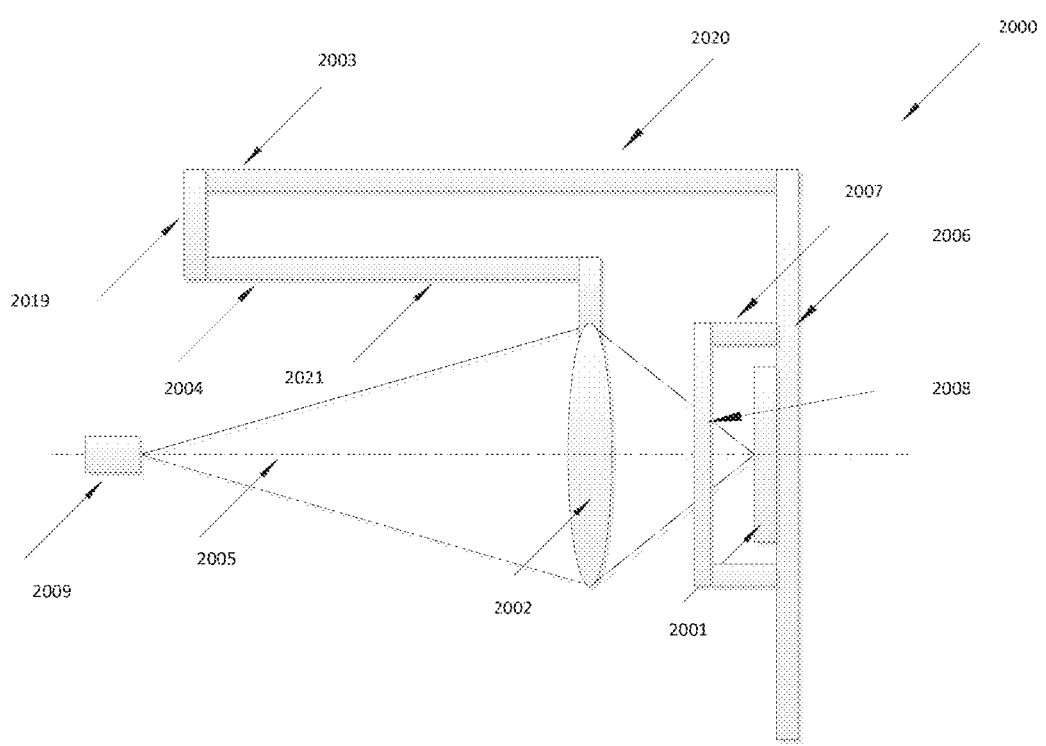
FIGS. 23A-23D are schematic side views of an athermalization system, according to various embodiments.

FIG. 23A is a schematic side view of an athermalization system 2000, which can be used in conjunction with a DAISI system. The optical athermalization system 2000 of FIG. 23A can be configured to maintain optothermal stability, i.e., to maintain optical performance at different temperatures. The system 2000 can include an optical detector 2001, an optical lens 2002, a first thermal element 2003, a second thermal element 2004, a base structure 2006, a housing element 2007, and an optical window 2008. The system 2000 can be used to image an object 2009 (such as a gas cloud) that is spaced from the lens 2002 and detector 2001 along an axis 2005. The system 2000 can be designed to be operated under a wide range of temperatures while reducing the likelihood that the light transferred to the detector 2001 does not appreciably defocus relative to the detector 2001. The system 2000 can be used in conjunction with an optical system that comprises any suitable optical arrangement, such as one or more lenses (e.g., a plurality of lenses) and/or one or more filters (e.g., a plurality of filters)

that transfer light to the detector 2001. Although the athermalization system 2000 is described in connection with various DAISI systems (e.g., whether the DAISI system is mobile or fixed), the athermalization system 2000 can be used in conjunction with any other suitable type of optical system. For example, the athermalization system 2000 can be used with any suitable type of infrared imaging system or camera to maintain the focusing characteristics and optical performance of the system.

The optical lens 2002, shown in FIG. 23A is a single objective lens. In various embodiments; however, the optical lens 2002 can include a plurality of lenses, which may correspond to a plurality of spatially and spectrally different optical channels as described herein.

Figure 23B:
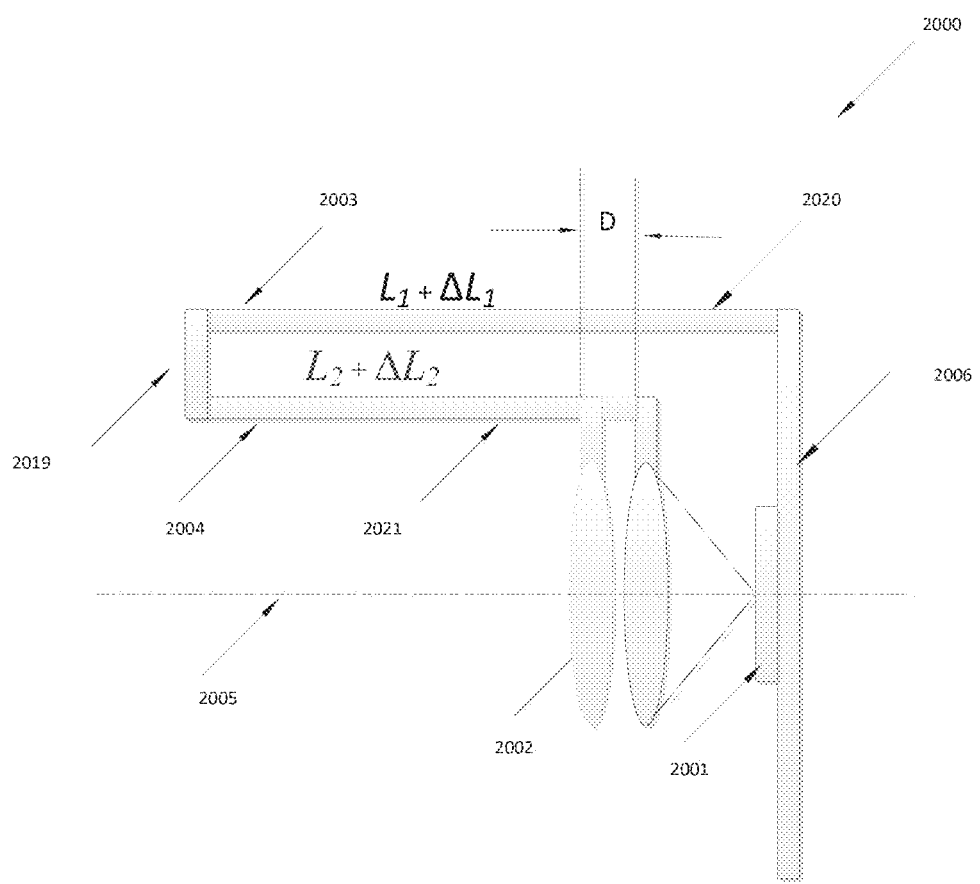

The first thermal element 2003 can be disposed along a first thermal arm 2020, and the second thermal element 2004 can be disposed along a second thermal arm 2021. In the embodiment of FIGS. 23A-B, only one thermal element is provided per thermal arm 2020, 2021. However, in other arrangements, each thermal arm 2020, 2021 may have one or a plurality of thermal elements. The thermal arms 2020, 2021 may be spaced apart from one another along a direction transverse to the axis 2005, and may be connected by way of a transverse connector 2019 that serves to mechanically connect the arms 2020, 2021.

For example, the second thermal element 2004 can be mechanically and thermally coupled to the transverse connector 2019 (and thereby connected to the first thermal element 2003) at a first end portion and coupled to the lens 2002 at a second end portion. The first thermal element 2003 can be mechanically and thermally coupled to the transverse connector 2019 (and thereby connected to the second thermal element 2004) at a first end portion and coupled to the base structure 2006 at a second end portion. The first and second thermal arms 2020, 2021 (and hence the first and second thermal elements 2003, 2004, respectively) may be disposed generally parallel to one another in some arrangements. Thus, the position of the lens 2002 may be determined based on length changes of the first thermal arm 2020 and length changes of the second thermal arm 2021, which are coupled together by way of the common intervening transverse connector 2019.

Beneficially, the first thermal element 2003 can have a first CTE that is different from a second CTE of the second thermal element 2004. In the illustrated embodiment, the first CTE is less than the second CTE. As explained herein, such an arrangement can allow the second thermal element 2004 to compensate for length changes induced in the first thermal element 2003, which can advantageously compensate for changes in the focal plane of the optical system. In various arrangements, the first thermal element 2003 can have a first CTE in a range of 10 ppm/° C. to 60 ppm/° C., or more particularly in a range of 15 ppm/° C. to 30 ppm/° C., e.g., in a range of 20 ppm/° C. to 25 ppm/° C. In the illustrated embodiment, the first thermal element 2003 can comprise aluminum (e.g., Al or an aluminum alloy) with a CTE of about 23 ppm/° C. The second thermal element 2004 can have a second CTE in a range of 75 ppm/° C. to 200 ppm/° C., or more particularly in a range of 95 ppm/° C. to 180 ppm/° C., e.g., in a range of 110 ppm/° C. to 130 ppm/° C. For example, in the illustrated embodiment, the second thermal element 2004 can comprise Delrin® with a CTE of about 120 ppm/° C. In various embodiments, the first thermal element and the second thermal element can be different materials with the second CTE being greater than the first CTE.

The optical lens 2002 may collect light from the object 2009 and transfer light to the detector 2001. In various embodiments, the detector 2001 can comprise a detector array, including a single FPA or an array of FPAs. In various embodiments, the detector 2001 can include a plurality of photo-sensitive devices. In some embodiments, the plurality of photo-sensitive devices may comprise a two-dimensional imaging sensor array that is sensitive to radiation having wavelengths between 1 μm and 20 μm (for example, in near infrared wavelength range, mid infra-red wavelength range, or long infra-red wavelength range,). In various embodiments, the plurality of photo-sensitive devices can include CCD or CMOS sensors, bolometers, microbolometers or other detectors that are sensitive to infrared radiation.

The detector 2002, show in FIG. 23A, can be mounted to the base structure 2006. In some embodiments, the base structure 2006 can comprise ceramic. The detector 2002 can be further enclosed in a cavity defined at least in part by the housing element 2007 and the optical window 2008. In some embodiments, the optical window 2008 can comprise a germanium window. The housing element 2007 can comprise a Kovar® housing. Kovar® is a well characterized metal injection modeling material which is widely used in optoelectronic applications for hermetically sealed packages. Kovar®'s CTE, about 5.5 ppm/° C., is comparable to germanium's CTE, which is about 5.7 ppm/° C. Kovar®'s thermal expansion characteristics may generally match those of borosilicate glass enabling its use for metal-glass or metal ceramic interfaces. In various embodiments, the housing element 2007 can be made of other materials with similar CTE of Kovar® in a range of 1 ppm/° C. to 20 ppm/° C. and the optical window 2008 can be made of other materials with similar CTE to germanium in a range of 1 ppm/° C. to 20 ppm/° C.

As shown in FIG. 23B, the optical lens 2002 may collect light from the object 2009 and transfer light to the detector 2001. When the temperature of an environment changes or if the user of a mobile DAISI system moves to a location at a different temperature, the focal length of the optical lens 2002 may change in response to the temperature changes. For example, if the temperature of the DAISI system 200 increases, the focal length of the lens 2002 may be shorter, and may accordingly focus closer to the lens 2002 along the axis 2005, which can lead to defocus and reduced performance of the imaging system. The change in length ($\Delta L_1$) of the first thermal element due to the temperature change ($\Delta T$) is $\Delta L_1 = \alpha_1 L_1 \Delta T$, while the change in length ($\Delta L_2$) of the second thermal element due to the temperature change ($\Delta T$) is $\Delta L_2 = \alpha_2 L_2 \Delta T$. Since $\alpha_2$ is greater than $\alpha_1$, and $L_2$ is comparable to $L_1$, $\Delta L_2$ is greater than $\Delta L_1$. Due to the difference between $\Delta L_2$ and $\Delta L_1$ i.e., the expansion of the second thermal element 2004 is greater than the expansion of the first thermal element 2003, the optical lens 2001 moves closer to the detector 2002 when the temperature increases (illustrated as moving from left to right in FIG. 23B). In particular, the optical lens 2001 moves closer to the detector by a distance D, as labeled in FIG. 23B, which is approximately equal to ($\Delta L_2 - \Delta L_1$). Vice versa, the optical lens 2001 may move away from the detector 2002, with a distance D which is equal to ($\Delta L_2 \Delta L_1$), when the temperature decreases. Thermal defocus ($\Delta f$) of the optical lens 2001 due to the temperature change ($\Delta T$) can be expressed as: $\Delta f = \beta f \Delta T$, where $\beta$ is the thermo-optic coefficient of the optical lens 2001, which can be expressed as: $\beta = \alpha_g - 1/(n-1) \, dn/dT$, where $\alpha_g$ is the CTE of the glass. When the difference between $\Delta L_2$ of the second thermal element 2004 and $\Delta L_1$ of the first thermal element 2003 ($\Delta L_2 \Delta L_1$), is about the same as the change in focal length of the optical lens 2002 (Δf), the degree of defocus may be reduced or effectively eliminated in the presence of the temperature change.

Figure 23C:
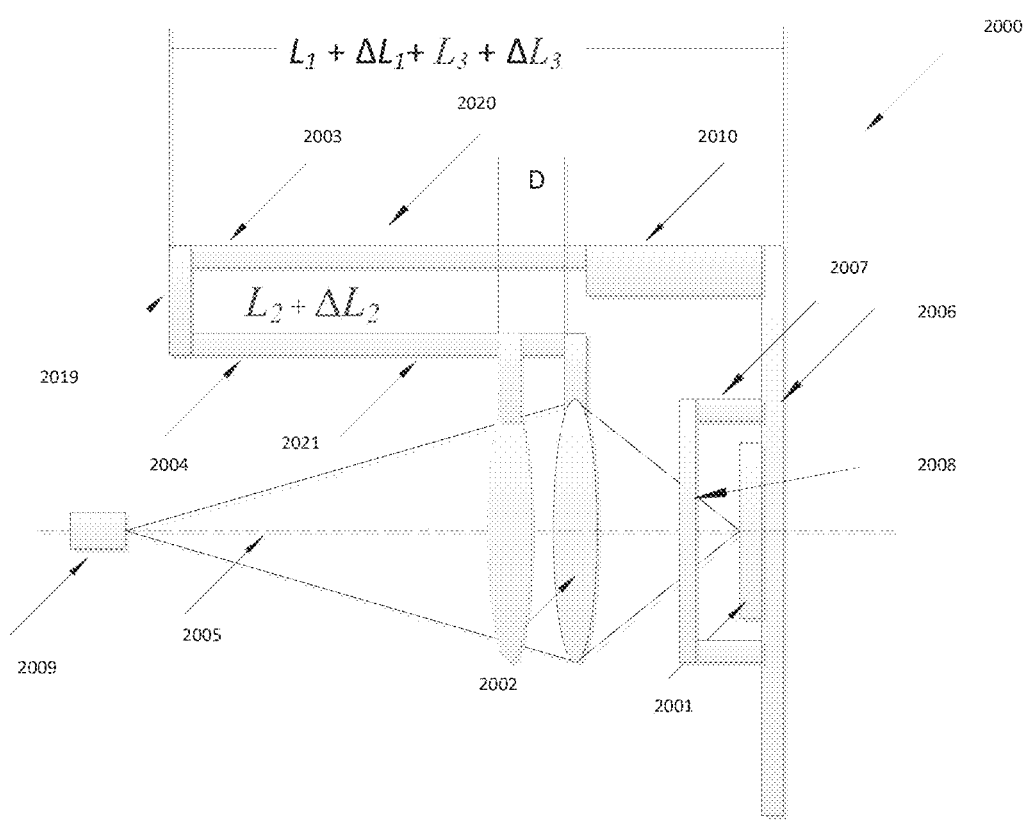

FIG. 23C is a side view of another embodiment of the athermalization system 2000. As with the embodiment of FIGS. 23A-B, the system of FIG. 23C can be used in conjunction with a DAISI system, or with any other suitable optical system. Unless otherwise noted, like reference numerals in FIG. 23C represent components that are the same as or similar to like numbered components in FIGS. 23A-B. Unlike FIGS. 23A-B, a third thermal element 2010 can be disposed between the first thermal element 2003 and the base structure 2006 along the first arm 2020. For example, the third thermal element 2010 can be disposed generally linearly between the first thermal element 2003 and the base structure 2006, such that linear deformation of the first and third thermal elements 2003, 2010 causes the first and third thermal elements 2003, 2010 to deform along the same direction.

As with FIG. 23B, the second arm 2021 can include the second thermal element 2004. In FIG. 23C, the first thermal element 2003 indirectly couples to the base structure 2006 by way of the intervening third thermal element 2010. For example, the first thermal element 2003 can be coupled to the third thermal element 2010 at a first end of portion of the third thermal element 2010. The third thermal element 2010 can be coupled to the base structure 2006 at a second end portion of the third thermal element 2010. Beneficially, the third thermal element 2010 can have a third CTE that is different from (e.g., greater than) the first CTE of the first thermal element 2003. For example, in some embodiments, the third CTE can be equal to or generally similar to the second CTE of the second thermal element 2004. Such an arrangement can allow the second thermal element 2004 to compensate for length changes induced in the first thermal element 2003 and the third thermal element 2010, which can advantageously compensate for temperature-induced changes in the focal plane of the optical system.

The change in length (ΔL) of the first thermal element due to the temperature change (ΔT) is $\Delta L_1 = \alpha_1 L_1 \Delta T$, the change in length ($\Delta L_2$) of the second thermal element due to the temperature change (ΔT) is $\Delta L_2 = \alpha_2 L_2 \Delta T$, and, the change in length ($\Delta L_3$) of the third thermal element due to the temperature change (ΔT) is $\Delta L_3 = \alpha_3 L_3 \Delta T$ when the temperature increases, the optical lens 2001 moves closer to the detector with a distance D, as labeled in FIG. 23C, which is equal to ($\Delta L_2 - \Delta L_1 - \Delta L_3$). Vice versa, the optical lens 2001 may move further away from the detector 2002, with a distance D which is equal to ($\Delta L_2 - \Delta L_1 - \Delta L_3$), when the temperature decreases. Thermal defocus (Δf) of the optical lens 2001 due to the temperature change (ΔT) is expressed as: $\Delta f = \beta f \Delta T$, where β is the thermo-optic coefficient of the optical lens 2001, which can be expressed as: $\beta = \alpha_g - 1/(n-1) \, dn/dT$, where a, is the CTE of the glass.

By adjusting the length of each thermal element and selecting a thermal material with a desired CTE for each thermal element, the combination of the first, the second, and the third elements 2003, 2004, 2010 can be adjusted to compensate for the different degrees of defocus of the optical lens 2001 due to different materials used in the optical lens 2001 and different ranges of the temperature changes. For example, the third thermal element 2010 may be incorporated in the system to counterbalance the relatively large movements provided by the second thermal element 2004. If, for example, the lens 2002 is positioned sufficiently close to the window 2008, excessive temperature increases may force the lens 2002 into the window 2008 in the absence of the third thermal element 2010. The third thermal element 2010 may compensate for such large movements by reducing the movement of the second thermal element 2004 and the lens 2002.

In various arrangements, the third thermal element 2010 can have a third CTE in a range of 75 ppm/° C. to 200 ppm/° C., or more particularly in a range of 95 ppm/° C. to 180 ppm/° C., e.g., in a range of 110 ppm/° C. to 130 ppm/° C. For example, in the illustrated embodiment, the third thermal element 2010 can comprise Delrin® with a CTE of about 120 ppm/° C. In various embodiments, the third thermal element and the second thermal element can be the same or a similar material with similar CTEs.

Although three thermal elements 2003, 2004, 2010 are illustrated in FIG. 23C, any suitable number of thermal elements may be included. For example, additional thermal elements may be provided along the first arm 2020 and/or the second arm 2021. Indeed, each thermal arm 2020, 2021 may include any suitable number of thermal elements of any suitable material, CTE, and length. Advantageously, the thermal arms 2020, 2021 can be selected so as to provide precise, passive position control of the lens 2002 to accommodate for defocus due to temperature changes.

Figure 23D:
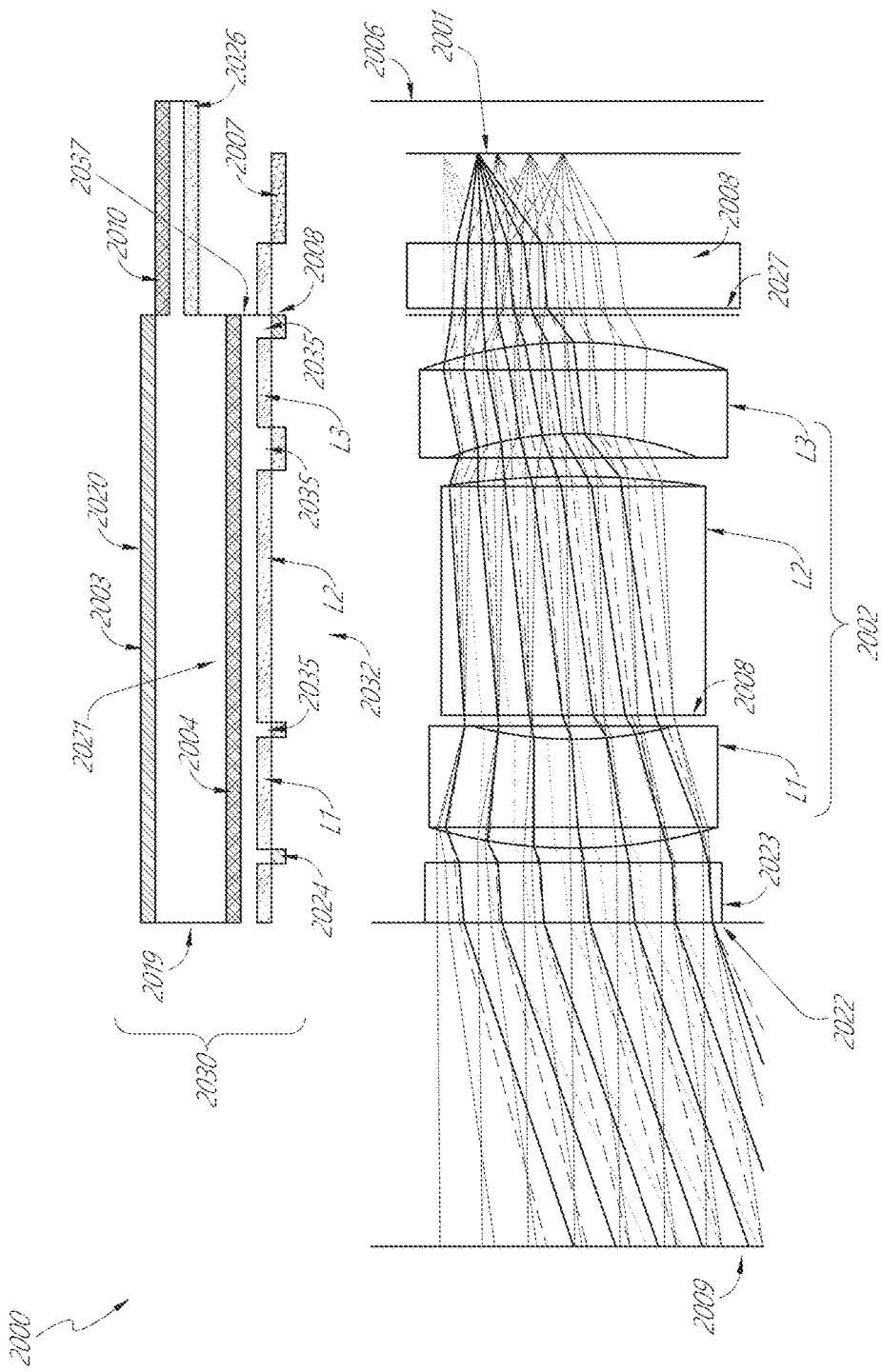

FIG. 23D is a side view of another embodiment of the athermalization system 2000. In FIG. 23D, a thermal model 2030 of the system 2000 is illustrated above the optical components. Unless otherwise noted, like reference numerals in FIG. 23D represent components that are the same as or similar to like numbered components in FIGS. 23A-C. Unlike the system 2000 of FIGS. 23A-C, the optical lens 2001 of FIG. 23D can comprise a plurality (e.g., three) of lens elements L1, L2, L3. The system can also include a front aperture 2022, one or more filters 2023, a stop 2028, and a field stop 2027. Additional details of these components are described herein.

As with the embodiments of FIGS. 23A-C, the system 2000 can include first and second thermal arms 2020, 2021, which form part of the illustrated thermal model 2030. The first thermal arm 2020 can comprise the first and third thermal elements 2003, 2010. The second thermal arm 2021 can comprise the second thermal element 2004. The optical components (e.g., the filter 2023, a filter holder 2024, the lens elements L1-L3, a lens holder 2035 that support the lens elements L1-L3, the optical window 2008, and the housing 2007) can be disposed along a third arm 2032. An air gap 2026 can be disposed between the first and second thermal arms 2020, 2021. The third arm can 2032 be spaced apart from and can be disposed generally parallel to the first and second thermal arms 2020, 2021. As shown in FIG. 23D, a second transverse connector 2037 can connect the second thermal arm 2021 with the lens 2002 (e.g., the lens elements L1-L3), such that length changes in the second thermal arm 2021 (e.g., the second thermal element 2004) can cause the lens 2002 to move closer to or farther away from the detector 2006. In the illustrated arrangement, the base of the detector 2006 can act as a common connection point, relative to which the other components move. For example, the lenses can be physically mounted to the edges of the detector 2006 by way of the third thermal element 2010, which can comprise a Delrin clip which can be screwed onto the edges of the base of the detector 2006. The window 2008 can also be mounted to the base of the detector 2006 and can move as temperature changes. As with the embodiments of FIGS. 23A-C, the first and second thermal arms 2020, 2021 can cooperate to reduce or eliminate thermally-induced defocus of the lens 2002.

Accordingly, the system 2000 shown in the embodiments of FIGS. 23A-D may be considered to be thermally compensated as a generally athermal system, as used herein. The system 2000 disclosed herein can beneficially reduce the degree of defocus in the presence of temperature changes. For example, the system 2000 may be operated at temperatures in a range of −60° C. to 100° C., or more particularly, in a range of −50° C. to 80° C., e.g., in a range of −40° C. to 60° C. When operated in environments at any temperature in these ranges, the system 2000 can reduce the amount of image defocus such that the effective focal length changes by an amount in a range of 1 micron to 100 microns, or more particularly, in a range of 1 micron to 50 microns. When operated in environments at any temperature in these ranges, the system 2000 can yield root-mean-square (RMS) spot sizes that are less than 10 times the Airy disk spot size, e.g., less than 5 times the Airy disk spot size for the system, or less than 5 waves of aberration.

I. Motion Compensation Techniques

As explained herein, mobile DAISI systems can be sized and configured to be worn or carried by a human user. While the system 1000 is being worn or carried by the user, the user may remain generally stationary or may move. The systems 1000 disclosed herein may be configured to compensate for the movement of the user so as to maintain the accuracy of the system 1000 for target species detection and identification across various degrees of movement. In general, without being limited by theory, relatively large user movements may reduce the accuracy of species detection to a greater extent, as compared with relatively small user movements. It can be important to provide motion compensation techniques that automatically compensate for movement of the user and/or the system 1000.

Figure 24A:
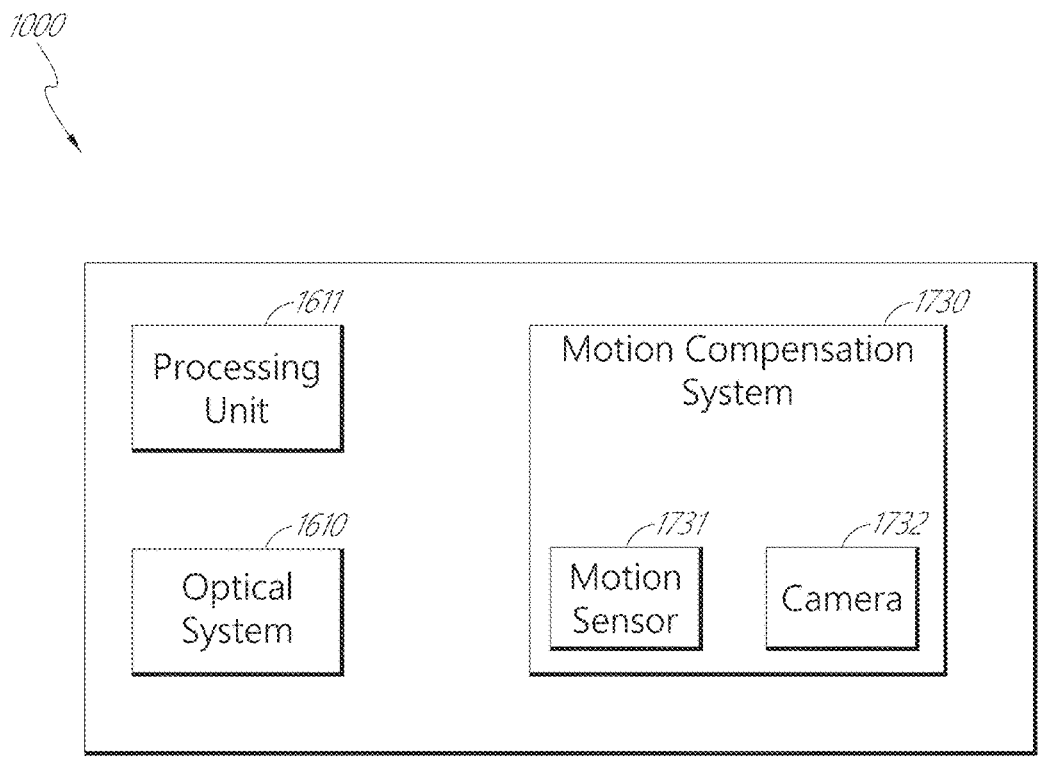
FIG. 24A is a schematic system diagram of a DAISI system that can include a motion compensation system, according to various embodiments.

FIG. 24A is a schematic system diagram of a DAISI system 1000 (such as a mobile DAISI system) that can include a motion compensation system 1730. In some embodiments, the motion compensation system 1730 can communicate with the processing unit 1611 and/or the optical system 1610. In the illustrated embodiment, the motion compensation system can include a motion sensor 1731 and a camera 1732. The motion sensor 1731 can comprise one or a plurality of motion sensors. In some embodiments, for example, the motion sensor 1731 can comprise one or more of a gyroscope, an accelerometer, a compass, etc. For example, the motion sensor 1731 can comprise a nine-axis motion sensor in some implementations. The camera 1732 can comprise a visible light camera in some embodiments. In some embodiments, the camera 1732 can form part of the visible light imaging system 1680 described herein. In some embodiments, the camera 1732 can be separate from the visible light imaging system 1680. In some embodiments, the motion compensation system 1730 can comprise its own dedicated processing electronics configured to estimate the amount of motion per frame. In some embodiments, the motion compensation system 1730 can utilize processing electronics of the processing unit 1611 to estimate the amount of motion per frame. In some embodiments, the motion compensation system 1730 can be contained with the processing unit 1611 and the optical system 1610 in the data acquisition and processing module 1020, which can be configured to be worn or carried by a person.

When the motion compensation system 1730 detects and/or estimates the degree of movement of the system 1000 per frame, the processing unit 1611 can comprise circuitry configured to re-align the acquired image data to compensate for the estimated motion. For example, based on the estimated system motion, the processing unit 1611 can shift and/or rotate pixel data based on the estimated system motion. Alignment of the acquired image data can be accomplished to within two pixels or less.

In some embodiments, the system 1000 can have an activated mode, in which the system 1000 operates to detect and/or identify a target species, and a de-activated mode, in which the system 1000 is not actively operated to detect and/or identify a target species. In some embodiments, it may be desirable to place the system 1000 in the activated mode when the user is generally stationary or moving by a relatively small amount and/or at a small rate. Similarly, it may be desirable in some instances to place the system 1000 in the de-activated mode when the user is moving by a relatively large amount and/or at a large rate. Beneficially, the detection and/or identification of target species can be improved at stationary and/or relatively small movements and power consumption may be reduced by disabling detection and/or identification of target species during times of relatively large amounts or rates of movement of system 1000.

In some embodiments, the motion compensation system 1730 can be configured to automatically determine whether the user and/or the system 1000 are moving by an amount and/or rate that are below a threshold. If the user and/or the system 1000 are moving by an amount and/or rate below the threshold, then the system 1000 may be placed in, or maintained at, the activated mode in which the system 1000 is operational to detect a target species. If the user and/or the system 1000 are moving by an amount and/or rate above the threshold, then the system 1000 may be placed in, or maintained at, the de-activated mode in which the system 1000 is not operational to detect a target species. In various embodiments, the motion compensation techniques disclosed herein can compensate for large and/or small scale motions.

Figure 24B:
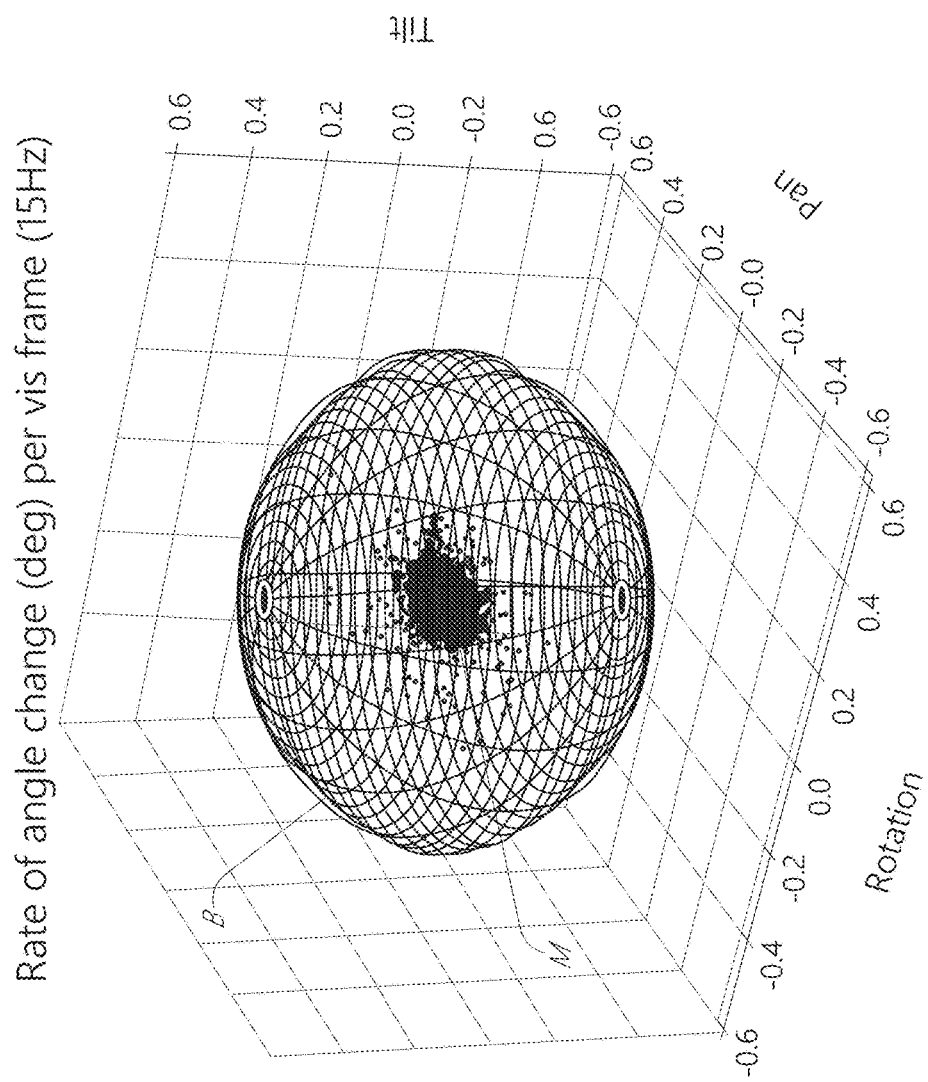
FIG. 24B is a plot illustrating an example set of motion thresholds that may be used by the DAISI system of FIG. 24A to activate itself only when the motion of the DAISI system is less than the motion thresholds.

FIG. 24B is a plot illustrating a boundary B which can be used to define the aforementioned threshold. The boundary B can be estimated based on empirical and/or theoretical motion values at which the system 1000 can accurately re-align the image data and/or otherwise compensate for system motion. For example, in the illustrated embodiment, a sample of human users wearing an example motion compensation system 1730 remained relatively stationary. The users wore the motion compensation system 1730 on a helmet in the illustrated example. In the example, the users breathed normally with minimal or no head movement. The motion sensor 1731 monitored the motion of the users wearing the example motion compensation system 1730. In particular, the rate of angular change of the user's head from frame-to-frame was measured for tilt (T), pan (P), and rotation (R), in degrees. The sampling frame rate used for the example of FIG. 24B was 15 Hz, but it should be appreciated that other suitable frame rates may be used. The measured values of the users' motion M is plotted as a scatterplot in FIG. 24B.

The boundary B illustrated in FIG. 24B is the smallest sphere within which all the measured motions M can be disposed. In the illustrated embodiment, the boundary B can be represented by $T^2+P^2+R^2 \leq B$. In the illustrated embodiment B is approximately 0.25. In various embodiments, B can be in a range of 0.1 to 1, in a range of 0.1 to 0.8, in a range of 0.1 to 0.5, or in a range of 0.15 to 0.3. The boundary B determined during this example calibration can be used to place the system 1000 in the activated or de-activated modes. As another example, a boundary B used in determining whether to place the system 1000 in the activated or de-activated mode may be based off of user's walking through a site. In other words, motion compensation system 1730 may place the system 1000 in the activated mode as long the motion of system 1000 does not exceed the amount and/or rates of motion associated with typical users walking through typical sites.

Figure 24C:
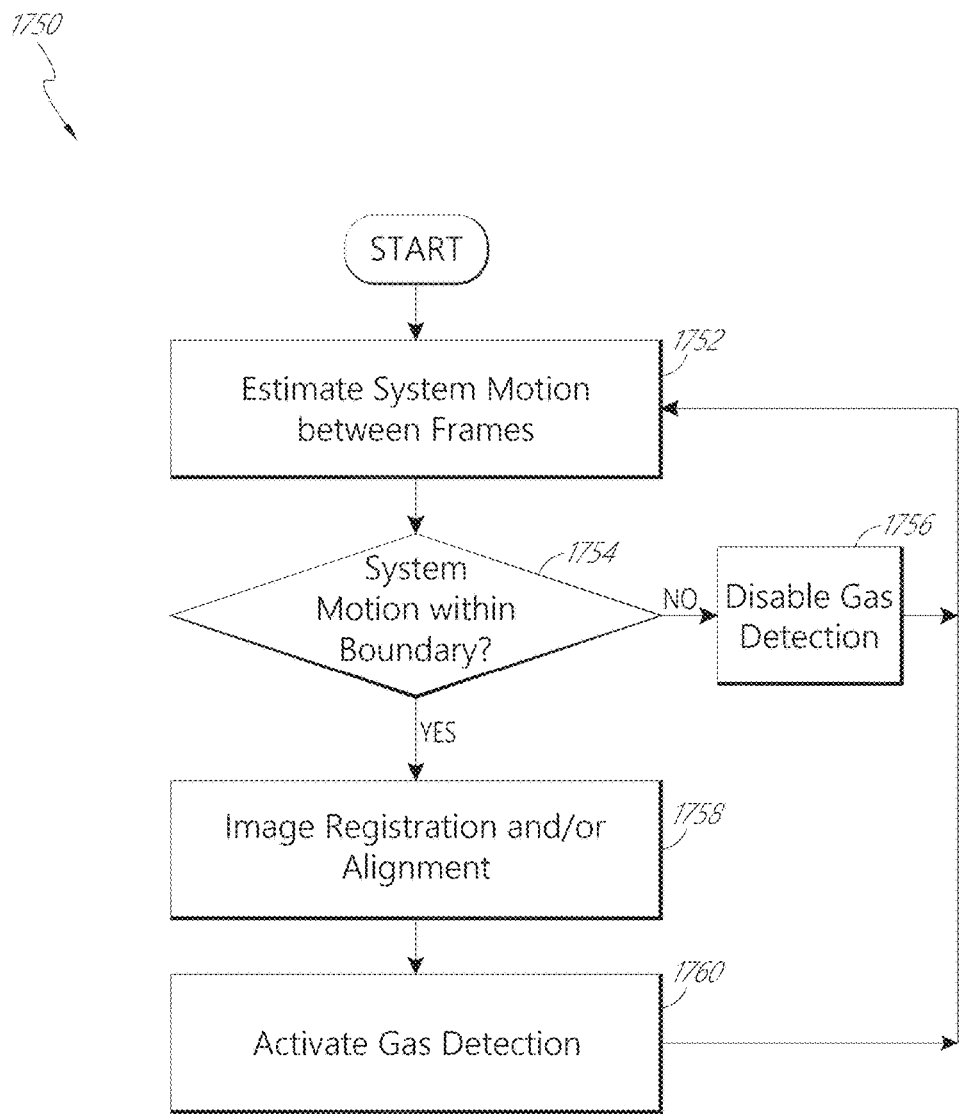
FIG. 24C is a flowchart illustrating an example method for compensating for motion of a DAISI system, according to various embodiments.

FIG. 24C is a flowchart illustrating an example method 1750 for compensating for motion of a DAISI system 1000. The method 1750 can begin in a block 1752 to estimate system motion between frames, e.g., from one frame to a subsequent frame. In other arrangements, the system can estimate system motion within a portion of a particular frame. The motion sensor 1731 can estimate the movements of the system 1000 and/or the user using any suitable type of sensor. For example, the motion sensor 1731 can estimate the amount of rotation, tilt, and/or pan of the system 1000 from one frame to another. In other arrangements, other motion components (such as linear position, linear velocity, linear acceleration, etc.) can be measured. Estimating system motion in block 1752 may also or alternatively involve analyzing images from visible light imaging system 1680 and/or optical system 1610 (e.g., some or all of the infrared detector 1624) to measure the amount and/or rate of motion of system 1000.

Moving to a block 1754, a decision can be made regarding whether the estimated system motion is within a predefined boundary, such as the boundary B. The boundary B can represent the maximum or desired amount of motion for which the system 1000 can be adequately compensated. For example, the system 1000 can accurately detect and/or identify a target species when the system motion is within the boundary B. If the system motion is not within the boundary, e.g., if the overall system movement exceeds the predetermined boundary B or threshold, then the method 1750 moves to a block 1756, in which the system 1000 is placed in the de-activated mode in which gas detection and/or identification is disabled. For the subsequent frame, the method 1750 can return to the block 1752 to estimate the system motion between frames. The system 1000 can remain disabled until the amount or extent of motion is within the system motion boundary B. System 1000 may consume less power while disabled, thereby preserving and increasing battery life in mobile DAISI systems.

If a decision in block 1754 is made that the system motion is within the boundary B, then the method 1750 moves to a block 1758, in which processing electronics performs image registration and/or alignment. For example, the processing unit 1611 can translate and/or rotate pixel image data appropriately to compensate for the system motion.

Moving to a block 1760, the system 1000 can be placed in the activated mode to activate the gas detection and/or identification capabilities of the system 1000. The system 1000 can accurately detect and/or identify a target species, based on the motion compensated and aligned image data. For the subsequent frame, the system motion can be estimated and the method 1750 can be repeated. In some arrangements, the amount of system motion may be measured across a collection of multiple frames, as opposed to between each adjacent frame. For example, in some embodiments, the amount of motion can be estimated across an average of N frames.

Figure 24D:
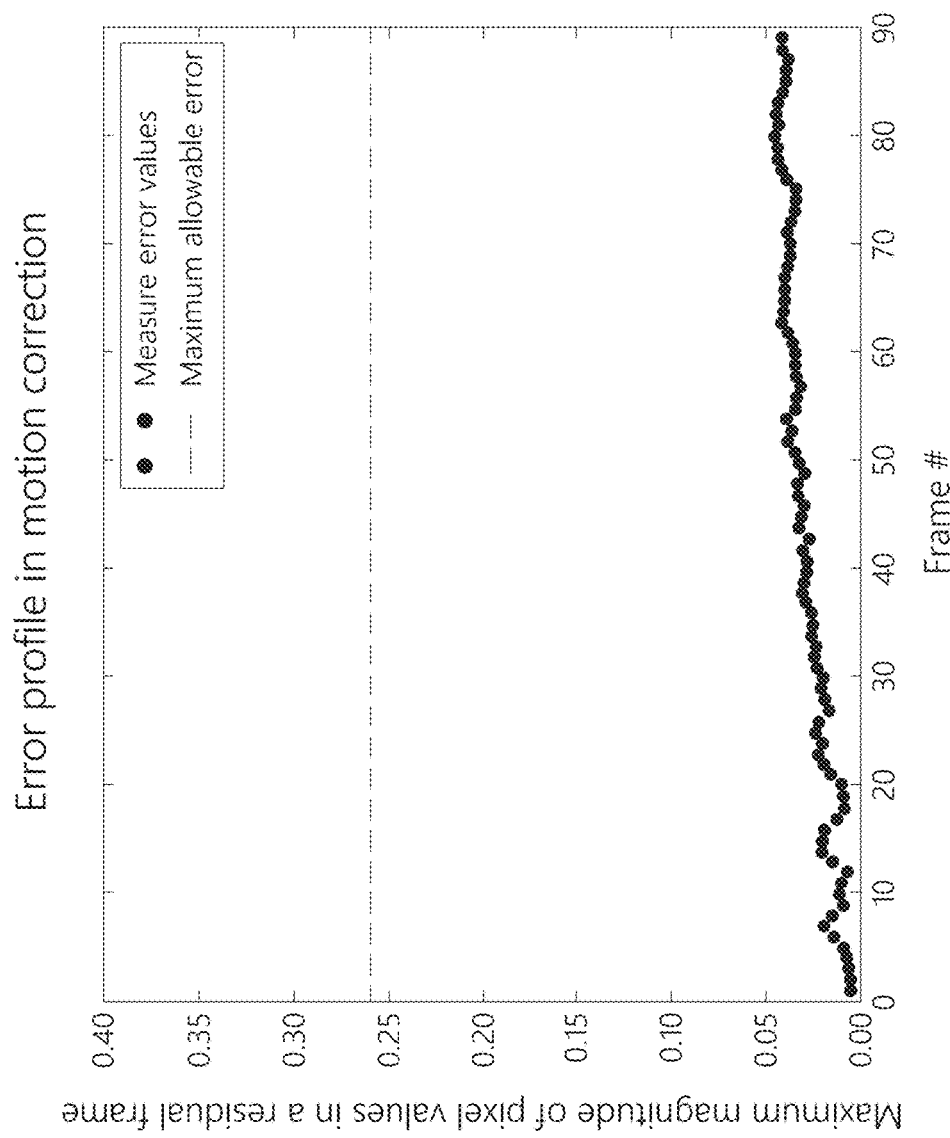
FIG. 24D is a plot of the error profile of the motion compensation systems and methods described herein, according to various embodiments.

FIG. 24D is a plot of the error profile of the motion compensation systems and methods described herein. In particular, the vertical axis of FIG. 24D is the maximum magnitude of pixel values in a residual frame. The horizontal axis of FIG. 24D is the frame number. As shown in FIG. 24D, the disclosed motion compensation systems and methods can beneficially maintain the measured error values below the maximum allowable error. Maintaining such reduced error values can beneficially improve the overall system performance and the identification of target species.

Each of the embodiments disclosed herein can be used to estimate various characteristics of gases present in a gas leak imaged by the infrared imaging systems disclosed herein.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

In the drawings like numbers are used to represent the same or similar elements wherever possible. The depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

Moreover, if the schematic flow chart diagram is included, it is generally set forth as a logical flow-chart diagram. As such, the depicted order and labeled steps of the logical flow are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Without loss of generality, the order in which processing steps or particular methods occur may or may not strictly adhere to the order of the corresponding steps shown.

The features recited in claims appended to this disclosure are intended to be assessed in light of the disclosure as a whole.

At least some elements of a device of the invention can be controlled—and at least some steps of a method of the invention can be effectuated, in operation—with a programmable processor governed by instructions stored in a memory. The memory may be random access memory (RAM), read-only memory (ROM), flash memory or any other memory, or combination thereof, suitable for storing control software or other instructions and data. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While examples of embodiments of the system and method of the invention have been discussed in reference to the gas-cloud detection, monitoring, and quantification (including but not limited to greenhouse gases such as Carbon Dioxide, Carbon Monoxide, Nitrogen Oxide as well as hydrocarbon gases such as Methane, Ethane, Propane, n-Butane, iso-Butane, n-Pentane, iso-Pentane, neo-Pentane, Hydrogen Sulfide, Sulfur Hexafluoride, Ammonia, Benzene, p- and m-Xylene, Vinyl chloride, Toluene, Propylene oxide, Propylene, Methanol, Hydrazine, Ethanol, 1,2-dichloroethane, 1,1-dichloroethane, Dichlorobenzene, Chlorobenzene, to name just a few), embodiments of the invention can be readily adapted for other chemical detection applications. For example, detection of liquid and solid chemical spills, biological weapons, tracking targets based on their chemical composition, identification of satellites and space debris, ophthalmological imaging, microscopy and cellular imaging, endoscopy, mold detection, fire and flame detection, and pesticide detection are within the scope of the invention.

As used herein, a phrase referring to "at least one of" a list of items refers to any combination of those items, including single members. As an example, "at least one of: a, b, or c" is intended to cover: a, b, c, a-b, a-c, b-c, and a-b-c.

If implemented in software, the functions may be stored on or transmitted over as one or more instructions or code on a computer-readable medium. The steps of a method or algorithm disclosed herein may be implemented in a processor-executable software module which may reside on a computer-readable medium.

Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above also may be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:
1. An infrared (IR) imaging system comprising:
an optical detector having a total active imaging area comprising pixels capable of sensing IR light;
a plurality of spatially and spectrally distinct optical channels spaced from the optical detector along an optical axis, the plurality of optical channels arranged to transfer IR radiation from an object to the optical detector, where IR light input into the optical channels is directed by the optical channels onto the optical detector; and
processing electronics configured to process image data from the optical detector representative of the IR radiation to detect a target species,
wherein the processing electronics processes image data from a plurality of usable portions of the total active imaging area corresponding to respective optical channels of the plurality of optical channels, said usable portions corresponding to the respective plurality of optical channels being uniformly sized or uniformly shaped, wherein the usable portions of the total active imaging area comprise portions of the total active imaging area that receive light from only one optical channel and wherein the usable portions of the total active imaging area comprise approximately square regions.

2. The infrared imaging system of claim 1, wherein the usable portions of the total active imaging area comprise approximately square regions having widths in the range of 3 mm to 4 mm.

3. The infrared imaging system of claim 2, wherein the usable portions of the total active imaging area are surrounded by respective overlapping regions that receive light from at least two optical channels.

4. The infrared imaging system of claim 1, wherein the usable portions of the total active imaging area comprise square regions having heights in the range of 3 mm to 4 mm.

5. The system of claim 1, wherein the useable portions comprise square regions.

6. The system of claim 1, wherein the optical detector comprises an infrared focal plane array (FPA).

* * * * *